United States Patent
Ting et al.

(10) Patent No.: US 9,296,827 B2
(45) Date of Patent: *Mar. 29, 2016

(54) METHODS AND COMPOSITIONS FOR MODULATING T CELL AND/OR B CELL ACTIVATION

(71) Applicant: University of North Carolina at Chapel Hill, Chapel Hill, NC (US)

(72) Inventors: Jenny P.-Y. Ting, Chapel Hill, NC (US); Brian P. O'Connor, Denver, CO (US); So-Young Eun, San Diego, CA (US); Zhengmao Ye, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 13 days.

This patent is subject to a terminal disclaimer.

(21) Appl. No.: 13/933,555

(22) Filed: Jul. 2, 2013

(65) Prior Publication Data

US 2014/0050726 A1 Feb. 20, 2014

Related U.S. Application Data

(63) Continuation of application No. 13/284,341, filed on Oct. 28, 2011, now Pat. No. 8,501,677, which is a continuation of application No. 12/293,913, filed as application No. PCT/US2007/007331 on Mar. 23, 2007, now abandoned.

(60) Provisional application No. 60/785,310, filed on Mar. 23, 2006.

(51) Int. Cl.
| | |
|---|---|
| *C07K 16/46* | (2006.01) |
| *C07K 14/705* | (2006.01) |
| *A61K 38/16* | (2006.01) |
| *C07H 21/00* | (2006.01) |
| *C07K 16/28* | (2006.01) |

(52) U.S. Cl.
CPC ............... *C07K 16/46* (2013.01); *A61K 38/16* (2013.01); *C07K 14/705* (2013.01); *C07K 16/28* (2013.01)

(58) Field of Classification Search
None
See application file for complete search history.

(56) References Cited

U.S. PATENT DOCUMENTS

| | | | |
|---|---|---|---|
| 5,866,341 A * | 2/1999 | Spinella et al. ............ 506/9 |
| 8,501,677 B2 * | 8/2013 | Ting et al. ............ 514/1.1 |
| 2004/0018977 A1 * | 1/2004 | Alvarez et al. ............ 514/12 |
| 2007/0099209 A1 | 5/2007 | Clarke et al. |

OTHER PUBLICATIONS

Castellani and Rougon. "Control of Semaphorin Signaling" *Curr Opin Neurobiol* 12:532-541 (2002).
Catalano et al. "Semaphorin-3A is Expressed by Tumor Cells and Alters T-Cell Signal Transduction and Function" *Blood* 107:3321-3329 (2006).
El Behi et al. "New Insights into Cell Responses Involved in Experimental Autoimmune Encephalomyelitis and Multiple Sclerosis" *Immunology Letters* 96:11-26 (2005).
Eun et al. "Cutting Edge: Rho Activation and Actin Polarization are Dependent on Plexin-A1 in Dendritic Cells" *The Journal of Immunology* 177:4271-4275 (2006).
Feldmann and Steinman. "Design of Effective Immunotherapy for Human Autoimmunity" *Nature* 435:612-619 (2005).
Freshney. *Culture of Animal Cells*, A Manual of Basic Technique, Alan R. Liss, Inc., New York (4 pages)(1983).
Girvin et al. "A Critical Role for B7/CD28 Costimulation in Experimental Autoimmune Encephalomyelitis: A Comparative Study Using Costimulatory Molecule-Deficient Mice and Monoclonal Antibody Blockade" *J Immunol* 164:136-143 (2000).
Gold et al. "Understanding Pathogenesis and Therapy of Multiple Sclerosis via Animal Models: 70 Years of Merits and Culprits in Experimental Autoimmune Encephalomyelitis Research" *Brain* 129:1953-1971 (2006).
Greenwald et al. "The B7 Family Revisited" *Ann Rev Immunol* 23:515-548 (2005).
Gura. "Systems for Identifying New Drugs are Often Faulty" *Science* 278:1041-1042 (1997).
International Search Report and Written Opinion of International Application No. PCT/US07/07331, mailed Aug. 8, 2008 (10 pages).
Janeway et al. *Immunobiology: The Immune System in Health and Disease*, Chapter 1: The Components of the Immune System, 5th ed., New York, Garland Science (18 pages)(2001).
Kaiser. "First Pass at Cancer Genome Reveals Complex Landscape" *Science* 313:1370 (2006).
Keir and Sharpe. "The B7/CD28 Costimulatory Family in Autoimmunity" *Immunol Rev* 204:128-143 (2005).
Kikutani and Kumanogoh. "Semaphorins in Interactions Between T Cells and Antigen-Presenting Cells" *Nat Rev Immunol* 3:159-164 (2003).
Kumanogoh and Kitutani. "Immune Semaphorins: A New Area of Semaphorin Research" *J Cell Sci* 116:3463-3470 (2003).
Liu and Strittmatter. "Semaphorin-Mediated Axonal Guidance Via Rho-Related G Proteins" *Curr Opin Cell Biol* 13:619-626 (2001).
Miller "Antigen Presentation in the CNS by Myeloid Dendritic Cells Drives Progression of Relapsing Experimental Autoimmune Encephalomyelitis" *Ann. N. Y. Acad. Sci.* 1103: 179-191 (2007).
O'Connor et al. "Semaphorin 6D Regulates the Late Phase of CD4+ T Cell Primary Immune Responses" *PNAS* 105(35):13015-13020 (2008).
Qu et al. "Identification, Characterization, and Functional Study of the Two Novel Human Members of the Semaphorin Gene Family" *The Journal of Biological Chemistry* 277(38):35574-35585 (2002).
Quezada et al. "CD40/CD154 Interactions at the Interface of Tolerance and Immunity" *Annu Rev Immunol* 22:307-328 (2004).
Salomon and Bluestone. "Complexities of CD28/B7: CTLA-4 Costimulatory Pathways in Autoimmunity and Transplantation" *Annu Rev Immunol* 19:225-252 (2001).

(Continued)

*Primary Examiner* — Peter J Reddig
(74) *Attorney, Agent, or Firm* — Myers Bigel Sibley, P.A.

(57) ABSTRACT

The present invention provides methods of reducing or enhancing T cell activation and/or B cell activation in a subject, comprising administering to a subject an effective amount of an inhibitor or enhancer, respectively, of Semaphorin 6D (Sema6D) activity on T cells and/or B cells.

6 Claims, 1 Drawing Sheet

(56) References Cited

OTHER PUBLICATIONS

Steinman et al. "Virtues and Pitfalls of EAE for the Development of Therapies for Multiple Sclerosis" *Trends in Immunology* 26(11):565-571 (2005).

Su et al. "PKC-β Controls IχB Kinase Lipid Raft Recruitment and Activation in Response to BCR Signaling" *Nature Immunology* 3(8):780-786 (2002).

Tamagnone and Comoglio. "To Move or Not to Move? Semaphorin Signalling in Cell Migration" *EMBO Reports* 5:356-361 (2004).

Tamagnone et al. "Plexins are a Large Family of Receptors for Transmembrane, Secreted, and GPI-Anchored Semaphorins in Vertebrates" *Cell* 99:71-80 (1999).

Toyofuku et al. "Dual Roles of Sema6D in Cardiac Morphogenesis Through Region-Specific Association of its Receptors, Plexin-A1, with Off-Track and Vascular Endothelial Growth Factor Receptor Type 2" *Genes Dev* 18:435-447 (2004).

Toyofuku et al. "Guidance of Myocardial Patterning in Cardiac Development by Sema6D Reverse Signalling" *Nat Cell Biol* 6:1204-1217 (2004).

Turner et al. "The Activity of the Plexin-A1 Receptor is Regulated by Rac" *The Journal of Biological Chemistry* 279(32):33199-33205 (2004).

Watts. "TNF/TNFR Family Members in Costimulation of T Cell Responses" *Annu Rev Immunol* 23:23-68 (2005).

Wong et al. "CIITA-Regulated Plexin-A1 Affects T-Cell-Dendritic Cell Interactions" *Nature Immunology* 4:891-898 (2003).

Zanata et al. "Antagonistic Effects of Rnd1 and RhoD GTPases Regulate Receptor Activity in Semaphorin 3A-Induced Cytoskeletal Collapse" *The Journal of Neuroscience* 22(2):471-477 (2002).

Zhang et al. "Monoclonal Antibody Therapy in Experimental Allergic Encephalomyelitis and Multiple Sclerosis" *Immunologic Research* 28(1):61-78 (2003).

Zipfel et al. "Requirement for Abl Kinases in T Cell Receptor Signaling" *Current Biology* 14:1222-1231 (2004).

Zips et al. "New Anticancer Agents: In Vitro and In Vivo Evaluation" *In vivo* 19:1-7 (2005).

\* cited by examiner

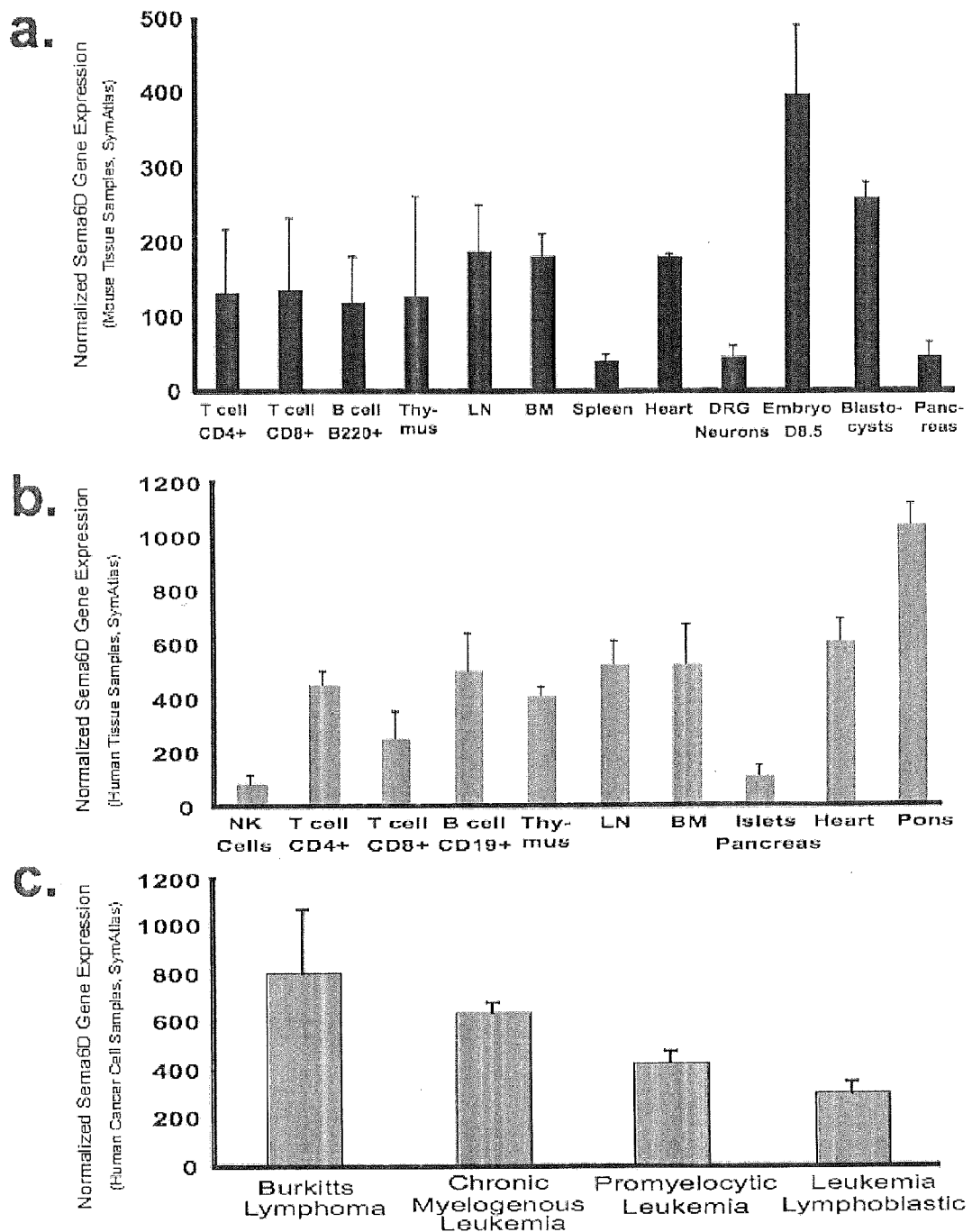

SEQUENCE LISTING

<160> NUMBER OF SEQ ID NOS: 58

<210> SEQ ID NO 1
<211> LENGTH: 2668
<212> TYPE: DNA
<213> ORGANISM: Artificial
<220> FEATURE:
<223> OTHER INFORMATION: Murine Sema6D-Ig fusion nucleotide sequence
<220> FEATURE:
<221> NAME/KEY: CDS
<222> LOCATION: (8)..(2665)

<400> SEQUENCE: 1

```
gccaccc atg ggg ttc ctt ctg ctt tgg ttc tgc gtg ctg ttc ctt ctg      49
        Met Gly Phe Leu Leu Leu Trp Phe Cys Val Leu Phe Leu Leu
        1               5                  10 gtc tcc agg tta cgg gcg gtc agc ttc cca gaa gac gat gag ccc ctc      97
Val Ser Arg Leu Arg Ala Val Ser Phe Pro Glu Asp Asp Glu Pro Leu
15                  20                  25                  30 aac acg gtt gac tat cac tat tca agg caa tat ccg gtt ttt aga gga     145
Asn Thr Val Asp Tyr His Tyr Ser Arg Gln Tyr Pro Val Phe Arg Gly
                35                  40                  45 cgc cct tca ggc aac gaa tcg cag cac agg ctg gac ttt cag ctg atg     193
Arg Pro Ser Gly Asn Glu Ser Gln His Arg Leu Asp Phe Gln Leu Met
            50                  55                  60 ttg aaa att cga gac aca ctt tat att gct ggc agg gat caa gtc tat     241
Leu Lys Ile Arg Asp Thr Leu Tyr Ile Ala Gly Arg Asp Gln Val Tyr
        65                  70                  75 aca gtg aac tta aat gaa atc ccc caa aca gag gtg ata cca agc aag     289
```

|     |     |     |     |     |     |     |     |     |     |     |     |     |     |
| --- | --- | --- | --- | --- | --- | --- | --- | --- | --- | --- | --- | --- | --- |
| Thr | Val | Asn | Leu | Asn | Glu | Ile | Pro | Gln | Thr | Glu | Val | Ile | Pro | Ser | Lys |
|     | 80  |     |     |     | 85  |     |     |     |     | 90  |     |     |     |     |     |

```
aag ctg acg tgg agg tcc aga cag cag gat cga gaa aat tgt gct atg      337
Lys Leu Thr Trp Arg Ser Arg Gln Gln Asp Arg Glu Asn Cys Ala Met
 95             100                 105                 110 aaa ggc aag cat aaa gat gaa tgc cac aac ttc atc aaa gtc ttt gtc      385
Lys Gly Lys His Lys Asp Glu Cys His Asn Phe Ile Lys Val Phe Val
                115                 120                 125 cca aga aat gat gag atg gtt ttt gtc tgt ggt acc aat gct ttc aac      433
Pro Arg Asn Asp Glu Met Val Phe Val Cys Gly Thr Asn Ala Phe Asn
                130                 135                 140 ccg atg tgc aga tac tat agg ttg aga acg tta gag tat gat ggg gaa      481
Pro Met Cys Arg Tyr Tyr Arg Leu Arg Thr Leu Glu Tyr Asp Gly Glu
            145                 150                 155 gaa att agt ggc ctg gca cga tgc ccg ttt gat gcc cga caa acc aat      529
Glu Ile Ser Gly Leu Ala Arg Cys Pro Phe Asp Ala Arg Gln Thr Asn
        160                 165                 170 gtc gcc ctc ttt gct gat gga aaa ctc tat tct gcc aca gtg gct gat      577
Val Ala Leu Phe Ala Asp Gly Lys Leu Tyr Ser Ala Thr Val Ala Asp
175                 180                 185                 190 ttc ctg gcc agt gat gct gtc att tac aga agc atg gga gat gga tct      625
Phe Leu Ala Ser Asp Ala Val Ile Tyr Arg Ser Met Gly Asp Gly Ser
                195                 200                 205 gcc ctt cgc aca ata aaa tac gat tcc aag tgg atc aaa gaa cca cac      673
Ala Leu Arg Thr Ile Lys Tyr Asp Ser Lys Trp Ile Lys Glu Pro His
                210                 215                 220 ttc ctt cat gcc ata gaa tat gga aac tat gtc tat ttc ttc aga          721
Phe Leu His Ala Ile Glu Tyr Gly Asn Tyr Val Tyr Phe Phe Arg
            225                 230                 235 gaa atc gcc gtg gaa cat aat aac tta ggc aag gct gtg tat tcc cgc      769
Glu Ile Ala Val Glu His Asn Asn Leu Gly Lys Ala Val Tyr Ser Arg
240                 245                 250 gtg gct cgc att tgt aaa aac gac atg ggt ggc tca cag cgg gtc ctg      817
Val Ala Arg Ile Cys Lys Asn Asp Met Gly Gly Ser Gln Arg Val Leu
255                 260                 265                 270 gag aaa cac tgg act tcc ttc ctt aag gct cgg ctg aac tgc tcc gtt      865
Glu Lys His Trp Thr Ser Phe Leu Lys Ala Arg Leu Asn Cys Ser Val
                275                 280                 285 cct gga gat tcc ttt ttc tac ttc gac gtc ctg cag tct ata aca gac      913
Pro Gly Asp Ser Phe Phe Tyr Phe Asp Val Leu Gln Ser Ile Thr Asp
                290                 295                 300 ata atc caa atc aat ggc atc ccc act gtg gtt ggg gtc ttc acc aca      961
Ile Ile Gln Ile Asn Gly Ile Pro Thr Val Val Gly Val Phe Thr Thr
                305                 310                 315 cag ctc aac agc att cct ggt tct gca gtc tgt gcc ttt agc atg gac     1009
Gln Leu Asn Ser Ile Pro Gly Ser Ala Val Cys Ala Phe Ser Met Asp
                320                 325                 330 gac att gag aaa gtg ttc aaa ggg cgg ttc aaa gag cag aaa acc cca     1057
Asp Ile Glu Lys Val Phe Lys Gly Arg Phe Lys Glu Gln Lys Thr Pro
335                 340                 345                 350 gac tct gtt tgg aca gca gtt ccc gaa gac aaa gta cca aaa cca agg     1105
Asp Ser Val Trp Thr Ala Val Pro Glu Asp Lys Val Pro Lys Pro Arg
                355                 360                 365 cct ggc tgt tgt gcc aaa cac ggc ctc gca gaa gct tac aag acc tcc     1153
Pro Gly Cys Cys Ala Lys His Gly Leu Ala Glu Ala Tyr Lys Thr Ser
                370                 375                 380 atc gac ttt cca gat gac acc ctg gct ttc atc aag tcc cac ccg ctg     1201
Ile Asp Phe Pro Asp Asp Thr Leu Ala Phe Ile Lys Ser His Pro Leu
                385                 390                 395
```

```
atg gac tct gcc gtc cca ccc att gcc gat gag ccc tgg ttc aca aag    1249
Met Asp Ser Ala Val Pro Pro Ile Ala Asp Glu Pro Trp Phe Thr Lys
    400             405                 410 aca cgg gtc agg tac agg ttg aca gcc atc gaa gtg gac cgt tca gca    1297
Thr Arg Val Arg Tyr Arg Leu Thr Ala Ile Glu Val Asp Arg Ser Ala
415             420                 425                 430 ggg cca tac caa aac tac aca gtc atc ttt gtt ggc tct gaa gct ggc    1345
Gly Pro Tyr Gln Asn Tyr Thr Val Ile Phe Val Gly Ser Glu Ala Gly
                435                 440                 445 gtg gta ctt aaa gtt ttg gca aag acc agt cct ttc tct ctg aat gac    1393
Val Val Leu Lys Val Leu Ala Lys Thr Ser Pro Phe Ser Leu Asn Asp
            450                 455                 460 agt gta tta ctc gaa gag att gaa gct tat aac cca gcc aag tgc agc    1441
Ser Val Leu Leu Glu Glu Ile Glu Ala Tyr Asn Pro Ala Lys Cys Ser
465             470                 475 gcc gag agt gag gag gac aga aag gtg gtc tca tta cag ctg gac aag    1489
Ala Glu Ser Glu Glu Asp Arg Lys Val Val Ser Leu Gln Leu Asp Lys
    480             485                 490 gat cac cat gct tta tac gtg gcc ttc tct agc tgc gtg gtc cgc atc    1537
Asp His His Ala Leu Tyr Val Ala Phe Ser Ser Cys Val Val Arg Ile
495             500                 505                 510 ccc ctc agc cgc tgt gag cgc tac gga tcg tgt aaa aag tct tgc att    1585
Pro Leu Ser Arg Cys Glu Arg Tyr Gly Ser Cys Lys Lys Ser Cys Ile
                515                 520                 525 gca tca cgt gac ccg tac tgt ggt tgg tta agc cag gga gtt tgt gag    1633
Ala Ser Arg Asp Pro Tyr Cys Gly Trp Leu Ser Gln Gly Val Cys Glu
            530                 535                 540 aga gtg acc cta ggg atg ctc cct gga gga tat gag cag gac acg gag    1681
Arg Val Thr Leu Gly Met Leu Pro Gly Gly Tyr Glu Gln Asp Thr Glu
545             550                 555 tac ggc aac aca gcc cac cta ggg gac tgc cac gac atg gag gta tcc    1729
Tyr Gly Asn Thr Ala His Leu Gly Asp Cys His Asp Met Glu Val Ser
    560             565                 570 tca tct tct gtt acc act gtg gca agt agc cca gaa att aca tct aaa    1777
Ser Ser Ser Val Thr Thr Val Ala Ser Ser Pro Glu Ile Thr Ser Lys
575             580                 585                 590 gtg att gat acc tgg aga cct aaa ctg acg agc tcc cgg aaa ttt gta    1825
Val Ile Asp Thr Trp Arg Pro Lys Leu Thr Ser Ser Arg Lys Phe Val
                595                 600                 605 gtt caa gat gac cca aat act tct gat ttt act gat act ata tca ggt    1873
Val Gln Asp Asp Pro Asn Thr Ser Asp Phe Thr Asp Thr Ile Ser Gly
            610                 615                 620 atc cca aag ggt gta cgg tgg gaa gtc cag tct gga gaa tcc aat cag    1921
Ile Pro Lys Gly Val Arg Trp Glu Val Gln Ser Gly Glu Ser Asn Gln
625             630                 635 atg gtc cac atg aat gtc ctc atc acc tgc gtg ttt gcc gct gga tcc    1969
Met Val His Met Asn Val Leu Ile Thr Cys Val Phe Ala Ala Gly Ser
    640             645                 650 gag ccc aaa tct tgt gac aaa act cac aca tgc cca ccg tgc cca gca    2017
Glu Pro Lys Ser Cys Asp Lys Thr His Thr Cys Pro Pro Cys Pro Ala
655             660                 665                 670 cct gaa ctc ctg ggg gga ccg tca gtc ttc ctc ttc ccc cca aaa ccc    2065
Pro Glu Leu Leu Gly Gly Pro Ser Val Phe Leu Phe Pro Pro Lys Pro
                675                 680                 685 aag gac acc ctc atg atc tcc cgg acc cct gag gtc aca tgc gtg gtg    2113
Lys Asp Thr Leu Met Ile Ser Arg Thr Pro Glu Val Thr Cys Val Val
            690                 695                 700 gtg gac gtg agc cac gaa gac cct gag gtc aag ttc aac tgg tac gtg    2161
Val Asp Val Ser His Glu Asp Pro Glu Val Lys Phe Asn Trp Tyr Val
705                 710                 715
```

```
gac ggc gtg gag gtg cat aat gcc aag aca aag ccg cgg gag gag cag       2209
Asp Gly Val Glu Val His Asn Ala Lys Thr Lys Pro Arg Glu Glu Gln
            720                 725                 730 tac aac agc acg tac cgt gtg gtc agc gtc ctc acc gtc ctg cac cag       2257
Tyr Asn Ser Thr Tyr Arg Val Val Ser Val Leu Thr Val Leu His Gln
735                 740                 745                 750 gac tgg ctg aat ggc aag gag tac aag tgc aag gtc tcc aac aaa gcc       2305
Asp Trp Leu Asn Gly Lys Glu Tyr Lys Cys Lys Val Ser Asn Lys Ala
                755                 760                 765 ctc cca gcc ccc atc gag aaa acc atc tcc aaa gcc aaa ggg cag ccc       2353
Leu Pro Ala Pro Ile Glu Lys Thr Ile Ser Lys Ala Lys Gly Gln Pro
            770                 775                 780 cga gaa cca cag gtg tac acc ctg ccc cca tcc cgg gat gag ctg acc       2401
Arg Glu Pro Gln Val Tyr Thr Leu Pro Pro Ser Arg Asp Glu Leu Thr
785                 790                 795 aag aac cag gtc agc ctg acc tgc ctg gtc aaa ggc ttc tat ccc agc       2449
Lys Asn Gln Val Ser Leu Thr Cys Leu Val Lys Gly Phe Tyr Pro Ser
                800                 805                 810 gac atc gcc gtg gag tgg gag agc aat ggg cag ccg gag aac aac tac       2497
Asp Ile Ala Val Glu Trp Glu Ser Asn Gly Gln Pro Glu Asn Asn Tyr
815                 820                 825                 830 aag acc acg cct ccc gtg ctg gac tcc gac ggc tcc ttc ttc ctc tac       2545
Lys Thr Thr Pro Pro Val Leu Asp Ser Asp Gly Ser Phe Phe Leu Tyr
                835                 840                 845 agc aag ctc acc gtg gac aag agc agg tgg cag cag ggg aac gtc ttc       2593
Ser Lys Leu Thr Val Asp Lys Ser Arg Trp Gln Gln Gly Asn Val Phe
            850                 855                 860 tca tgc tcc gtg atg cat gag gct ctg cac aac cac tac acg cag aag       2641
Ser Cys Ser Val Met His Glu Ala Leu His Asn His Tyr Thr Gln Lys
865                 870                 875 agc ctc tcc ctg tct ccg ggt aaa tga                                   2668
Ser Leu Ser Leu Ser Pro Gly Lys
            880                 885

<210> SEQ ID NO 2
<211> LENGTH: 886
<212> TYPE: PRT
<213> ORGANISM: Artificial
<220> FEATURE:
<223> OTHER INFORMATION: Synthetic Construct

<400> SEQUENCE: 2

Met Gly Phe Leu Leu Leu Trp Phe Cys Val Leu Phe Leu Leu Val Ser
1               5                   10                  15

Arg Leu Arg Ala Val Ser Phe Pro Glu Asp Asp Glu Pro Leu Asn Thr
            20                  25                  30

Val Asp Tyr His Tyr Ser Arg Gln Tyr Pro Val Phe Arg Gly Arg Pro
        35                  40                  45

Ser Gly Asn Glu Ser Gln His Arg Leu Asp Phe Gln Leu Met Leu Lys
    50                  55                  60

Ile Arg Asp Thr Leu Tyr Ile Ala Gly Arg Asp Gln Val Tyr Thr Val
65                  70                  75                  80

Asn Leu Asn Glu Ile Pro Gln Thr Glu Val Ile Pro Ser Lys Lys Leu
                85                  90                  95

Thr Trp Arg Ser Arg Gln Gln Asp Arg Glu Asn Cys Ala Met Lys Gly
            100                 105                 110

Lys His Lys Asp Glu Cys His Asn Phe Ile Lys Val Phe Val Pro Arg
        115                 120                 125
```

```
Asn Asp Glu Met Val Phe Val Cys Gly Thr Asn Ala Phe Asn Pro Met
130                 135                 140

Cys Arg Tyr Tyr Arg Leu Arg Thr Leu Glu Tyr Asp Gly Glu Ile
145                 150                 155                 160

Ser Gly Leu Ala Arg Cys Pro Phe Asp Ala Arg Gln Thr Asn Val Ala
                165                 170                 175

Leu Phe Ala Asp Gly Lys Leu Tyr Ser Ala Thr Val Ala Asp Phe Leu
            180                 185                 190

Ala Ser Asp Ala Val Ile Tyr Arg Ser Met Gly Asp Gly Ser Ala Leu
        195                 200                 205

Arg Thr Ile Lys Tyr Asp Ser Lys Trp Ile Lys Glu Pro His Phe Leu
    210                 215                 220

His Ala Ile Glu Tyr Gly Asn Tyr Val Tyr Phe Phe Arg Glu Ile
225                 230                 235                 240

Ala Val Glu His Asn Asn Leu Gly Lys Ala Val Tyr Ser Arg Val Ala
                245                 250                 255

Arg Ile Cys Lys Asn Asp Met Gly Gly Ser Gln Arg Val Leu Glu Lys
            260                 265                 270

His Trp Thr Ser Phe Leu Lys Ala Arg Leu Asn Cys Ser Val Pro Gly
        275                 280                 285

Asp Ser Phe Tyr Phe Asp Val Leu Gln Ser Ile Thr Asp Ile Ile
    290                 295                 300

Gln Ile Asn Gly Ile Pro Thr Val Val Gly Val Phe Thr Thr Gln Leu
305                 310                 315                 320

Asn Ser Ile Pro Gly Ser Ala Val Cys Ala Phe Ser Met Asp Asp Ile
                325                 330                 335

Glu Lys Val Phe Lys Gly Arg Phe Lys Glu Gln Lys Thr Pro Asp Ser
            340                 345                 350

Val Trp Thr Ala Val Pro Glu Asp Lys Val Pro Lys Pro Arg Pro Gly
        355                 360                 365

Cys Cys Ala Lys His Gly Leu Ala Glu Ala Tyr Lys Thr Ser Ile Asp
    370                 375                 380

Phe Pro Asp Asp Thr Leu Ala Phe Ile Lys Ser His Pro Leu Met Asp
385                 390                 395                 400

Ser Ala Val Pro Pro Ile Ala Asp Glu Pro Trp Phe Thr Lys Thr Arg
                405                 410                 415

Val Arg Tyr Arg Leu Thr Ala Ile Glu Val Asp Arg Ser Ala Gly Pro
            420                 425                 430

Tyr Gln Asn Tyr Thr Val Ile Phe Val Gly Ser Glu Ala Gly Val Val
        435                 440                 445

Leu Lys Val Leu Ala Lys Thr Ser Pro Phe Ser Leu Asn Asp Ser Val
    450                 455                 460

Leu Leu Glu Glu Ile Glu Ala Tyr Asn Pro Ala Lys Cys Ser Ala Glu
465                 470                 475                 480

Ser Glu Glu Asp Arg Lys Val Ser Leu Gln Leu Asp Lys Asp His
                485                 490                 495

His Ala Leu Tyr Val Ala Phe Ser Ser Cys Val Val Arg Ile Pro Leu
            500                 505                 510

Ser Arg Cys Glu Arg Tyr Gly Ser Cys Lys Lys Ser Cys Ile Ala Ser
        515                 520                 525

Arg Asp Pro Tyr Cys Gly Trp Leu Ser Gln Gly Val Cys Glu Arg Val
    530                 535                 540

Thr Leu Gly Met Leu Pro Gly Gly Tyr Glu Gln Asp Thr Glu Tyr Gly
```

```
545                 550                 555                 560
Asn Thr Ala His Leu Gly Asp Cys His Asp Met Glu Val Ser Ser Ser
                565                 570                 575

Ser Val Thr Thr Val Ala Ser Ser Pro Glu Ile Thr Ser Lys Val Ile
                580                 585                 590

Asp Thr Trp Arg Pro Lys Leu Thr Ser Ser Arg Lys Phe Val Val Gln
                595                 600                 605

Asp Asp Pro Asn Thr Ser Asp Phe Thr Asp Thr Ile Ser Gly Ile Pro
610                 615                 620

Lys Gly Val Arg Trp Glu Val Gln Ser Gly Glu Ser Asn Gln Met Val
625                 630                 635                 640

His Met Asn Val Leu Ile Thr Cys Val Phe Ala Ala Gly Ser Glu Pro
                645                 650                 655

Lys Ser Cys Asp Lys Thr His Thr Cys Pro Pro Cys Pro Ala Pro Glu
                660                 665                 670

Leu Leu Gly Gly Pro Ser Val Phe Leu Phe Pro Pro Lys Pro Lys Asp
                675                 680                 685

Thr Leu Met Ile Ser Arg Thr Pro Glu Val Thr Cys Val Val Val Asp
                690                 695                 700

Val Ser His Glu Asp Pro Glu Val Lys Phe Asn Trp Tyr Val Asp Gly
705                 710                 715                 720

Val Glu Val His Asn Ala Lys Thr Lys Pro Arg Glu Glu Gln Tyr Asn
                725                 730                 735

Ser Thr Tyr Arg Val Val Ser Val Leu Thr Val Leu His Gln Asp Trp
                740                 745                 750

Leu Asn Gly Lys Glu Tyr Lys Cys Lys Val Ser Asn Lys Ala Leu Pro
                755                 760                 765

Ala Pro Ile Glu Lys Thr Ile Ser Lys Ala Lys Gly Gln Pro Arg Glu
                770                 775                 780

Pro Gln Val Tyr Thr Leu Pro Pro Ser Arg Asp Glu Leu Thr Lys Asn
785                 790                 795                 800

Gln Val Ser Leu Thr Cys Leu Val Lys Gly Phe Tyr Pro Ser Asp Ile
                805                 810                 815

Ala Val Glu Trp Glu Ser Asn Gly Gln Pro Glu Asn Asn Tyr Lys Thr
                820                 825                 830

Thr Pro Pro Val Leu Asp Ser Asp Gly Ser Phe Phe Leu Tyr Ser Lys
                835                 840                 845

Leu Thr Val Asp Lys Ser Arg Trp Gln Gln Gly Asn Val Phe Ser Cys
                850                 855                 860

Ser Val Met His Glu Ala Leu His Asn His Tyr Thr Gln Lys Ser Leu
865                 870                 875                 880

Ser Leu Ser Pro Gly Lys
                885

<210> SEQ ID NO 3
<211> LENGTH: 20
<212> TYPE: DNA
<213> ORGANISM: Artificial
<220> FEATURE:
<223> OTHER INFORMATION: PCR primer

<400> SEQUENCE: 3
agggctatgc tctccctcac                                               20

<210> SEQ ID NO 4
```

```
<211> LENGTH: 20
<212> TYPE: DNA
<213> ORGANISM: Artificial
<220> FEATURE:
<223> OTHER INFORMATION: PCR primer

<400> SEQUENCE: 4
ctctcagctg tggtggtgaa                                                    20

<210> SEQ ID NO 5
<211> LENGTH: 20
<212> TYPE: DNA
<213> ORGANISM: Artificial
<220> FEATURE:
<223> OTHER INFORMATION: PCR primer

<400> SEQUENCE: 5
cagaagcatg ggagatggat                                                    20

<210> SEQ ID NO 6
<211> LENGTH: 20
<212> TYPE: DNA
<213> ORGANISM: Artificial
<220> FEATURE:
<223> OTHER INFORMATION: PCR primer

<400> SEQUENCE: 6
gccacccatg tcgtttttac                                                    20

<210> SEQ ID NO 7
<211> LENGTH: 23
<212> TYPE: DNA
<213> ORGANISM: Artificial
<220> FEATURE:
<223> OTHER INFORMATION: PCR primer

<400> SEQUENCE: 7
atggggttcc ttctgctttg gtt                                                23

<210> SEQ ID NO 8
<211> LENGTH: 28
<212> TYPE: DNA
<213> ORGANISM: Artificial
<220> FEATURE:
<223> OTHER INFORMATION: PCR primer

<400> SEQUENCE: 8
ctagtacgtg tacttgttca gtggtctg                                           28

<210> SEQ ID NO 9
<211> LENGTH: 41
<212> TYPE: DNA
<213> ORGANISM: Artificial
<220> FEATURE:
<223> OTHER INFORMATION: PCR primer

<400> SEQUENCE: 9
gcggatatcg ccacccatgg ggttccttct gctttggttc t                            41

<210> SEQ ID NO 10
<211> LENGTH: 35
<212> TYPE: DNA
<213> ORGANISM: Artificial
<220> FEATURE:
<223> OTHER INFORMATION: PCR primer

<400> SEQUENCE: 10
```

-continued gcgggatcca gcggcaaaca cgcaggtgat gagga          35

<210> SEQ ID NO 11
<211> LENGTH: 20
<212> TYPE: DNA
<213> ORGANISM: Artificial
<220> FEATURE:
<223> OTHER INFORMATION: PCR primer

<400> SEQUENCE: 11
cgggacttcg ctatcttcag          20

<210> SEQ ID NO 12
<211> LENGTH: 20
<212> TYPE: DNA
<213> ORGANISM: Artificial
<220> FEATURE:
<223> OTHER INFORMATION: PCR primer

<400> SEQUENCE: 12
agcatgagtg gcttttccag          20

<210> SEQ ID NO 13
<211> LENGTH: 20
<212> TYPE: DNA
<213> ORGANISM: Artificial
<220> FEATURE:
<223> OTHER INFORMATION: PCR primer

<400> SEQUENCE: 13
gctgtcttct ccacctccag          20

<210> SEQ ID NO 14
<211> LENGTH: 20
<212> TYPE: DNA
<213> ORGANISM: Artificial
<220> FEATURE:
<223> OTHER INFORMATION: PCR primer

<400> SEQUENCE: 14
ggttccgacc aaactggata          20

<210> SEQ ID NO 15
<211> LENGTH: 20
<212> TYPE: DNA
<213> ORGANISM: Artificial
<220> FEATURE:
<223> OTHER INFORMATION: PCR primer

<400> SEQUENCE: 15
tcggcagtgt gtgtgtatca          20

<210> SEQ ID NO 16
<211> LENGTH: 20
<212> TYPE: DNA
<213> ORGANISM: Artificial
<220> FEATURE:
<223> OTHER INFORMATION: PCR primer

<400> SEQUENCE: 16
ccttctgtgg atggggtaga          20

<210> SEQ ID NO 17
<211> LENGTH: 20
<212> TYPE: DNA

```
<213> ORGANISM: Artificial
<220> FEATURE:
<223> OTHER INFORMATION: PCR primer

<400> SEQUENCE: 17
atggctgata tccgagcagt                                                      20

<210> SEQ ID NO 18
<211> LENGTH: 20
<212> TYPE: DNA
<213> ORGANISM: Artificial
<220> FEATURE:
<223> OTHER INFORMATION: PCR primer

<400> SEQUENCE: 18
ttctcttgaa ggtcggtgct                                                      20

<210> SEQ ID NO 19
<211> LENGTH: 20
<212> TYPE: DNA
<213> ORGANISM: Artificial
<220> FEATURE:
<223> OTHER INFORMATION: PCR primer

<400> SEQUENCE: 19
gaggccatgc tgtatgtgtg                                                      20

<210> SEQ ID NO 20
<211> LENGTH: 20
<212> TYPE: DNA
<213> ORGANISM: Artificial
<220> FEATURE:
<223> OTHER INFORMATION: PCR primer

<400> SEQUENCE: 20
cgtcatcggg taatctttgg                                                      20

<210> SEQ ID NO 21
<211> LENGTH: 5923
<212> TYPE: DNA
<213> ORGANISM: Homo sapiens
<220> FEATURE:
<221> NAME/KEY: CDS
<222> LOCATION: (440)..(3472)

<400> SEQUENCE: 21
gcggccgctt cccaccgtcc ctctcccctt actggcagag cgcgctgcgg gcggactccc           60
gggcccggag cagcccaccg gccaccccac cgcccacccg gctcccggtg tctcctcccg          120
gccgctctac ccagcaactt tccgtgcttt gttccccgac tggaaatgct ttacggaagc          180
gtcttggaca gggtctccgc caggcgacaa gagctcggtg ctgagatgtg ttacgttctc          240
atctccccat caattatgga tggaaacaaa taaggaagag tcaattttgc tgagccccct          300
ctccggcaac gagaggcgtt ctgcagccgg gaggagccg ccgctcgcgc cggcagccgc           360
tggcaggggc atggtgagga ggaaggtagc tcagtggcat ttctgagcag ggccaccct           420 gacttcacct tggcccacc atg agg gtc ttc ctg ctt tgt gcc tac ata ctg           472
                     Met Arg Val Phe Leu Leu Cys Ala Tyr Ile Leu
                      1               5                  10 ctg ctg atg gtt tcc cag ttg agg gca gtc agc ttt cct gaa gat gat            520
Leu Leu Met Val Ser Gln Leu Arg Ala Val Ser Phe Pro Glu Asp Asp
            15                  20                  25 gaa ccc ctt aat act gtc gac tat cac tat tca agg caa tat ccg gtt            568
Glu Pro Leu Asn Thr Val Asp Tyr His Tyr Ser Arg Gln Tyr Pro Val
```

```
                      30                  35                  40
ttt aga gga cgc cct tca ggc aat gaa tcg cag cac agg ctg gac ttt      616
Phe Arg Gly Arg Pro Ser Gly Asn Glu Ser Gln His Arg Leu Asp Phe
         45                  50                  55 cag ctg atg ttg aaa att cga gac aca ctt tat att gct ggc agg gat      664
Gln Leu Met Leu Lys Ile Arg Asp Thr Leu Tyr Ile Ala Gly Arg Asp
 60                  65                  70                  75 caa gtt tat aca gta aac tta aat gaa atg ccc aaa aca gaa gta ata      712
Gln Val Tyr Thr Val Asn Leu Asn Glu Met Pro Lys Thr Glu Val Ile
                 80                  85                  90 ccc aac aag aaa ctg aca tgg cga tca aga caa cag gat cga gaa aac      760
Pro Asn Lys Lys Leu Thr Trp Arg Ser Arg Gln Gln Asp Arg Glu Asn
             95                 100                 105 tgt gct atg aaa ggc aag cat aaa gat gaa tgc cac aac ttt atc aaa      808
Cys Ala Met Lys Gly Lys His Lys Asp Glu Cys His Asn Phe Ile Lys
         110                 115                 120 gta ttt gtt cca aga aac gat gag atg gtt ttt gtt tgt ggt acc aat      856
Val Phe Val Pro Arg Asn Asp Glu Met Val Phe Val Cys Gly Thr Asn
     125                 130                 135 gca ttc aat ccc atg tgt aga tac tac agg ttg agt acc tta gaa tat      904
Ala Phe Asn Pro Met Cys Arg Tyr Tyr Arg Leu Ser Thr Leu Glu Tyr
140                 145                 150                 155 gat ggg gaa gaa att agt ggc ctg gca aga tgc cca ttt gat gcc aga      952
Asp Gly Glu Glu Ile Ser Gly Leu Ala Arg Cys Pro Phe Asp Ala Arg
                 160                 165                 170 caa acc aat gtt gcc ctc ttt gct gat ggg aag ctg tat tct gcc aca     1000
Gln Thr Asn Val Ala Leu Phe Ala Asp Gly Lys Leu Tyr Ser Ala Thr
             175                 180                 185 gtg gct gac ttc ttg gcc agc gat gcc gtt att tat cga agc atg ggt     1048
Val Ala Asp Phe Leu Ala Ser Asp Ala Val Ile Tyr Arg Ser Met Gly
         190                 195                 200 gat gga tct gcc ctt cgc aca ata aaa tat gat tcc aaa tgg ata aaa     1096
Asp Gly Ser Ala Leu Arg Thr Ile Lys Tyr Asp Ser Lys Trp Ile Lys
     205                 210                 215 gag cca cac ttt ctt cat gcc ata gaa tat gga aac tat gtc tat ttc     1144
Glu Pro His Phe Leu His Ala Ile Glu Tyr Gly Asn Tyr Val Tyr Phe
220                 225                 230                 235 ttc ttt cga gaa atc gct gtc gaa cat aat aat tta ggc aag gct gtg     1192
Phe Phe Arg Glu Ile Ala Val Glu His Asn Asn Leu Gly Lys Ala Val
                 240                 245                 250 tat tcc cgc gtg gcc cgc ata tgt aaa aac gac atg ggt ggt tcc cag     1240
Tyr Ser Arg Val Ala Arg Ile Cys Lys Asn Asp Met Gly Gly Ser Gln
             255                 260                 265 cgg gtc ctg gag aaa cac tgg act tca ttt cta aag gct cgg ctg aac     1288
Arg Val Leu Glu Lys His Trp Thr Ser Phe Leu Lys Ala Arg Leu Asn
         270                 275                 280 tgt tct gtc cct gga gat tcg ttt ttc tac ttt gat gtt ctg cag tct     1336
Cys Ser Val Pro Gly Asp Ser Phe Phe Tyr Phe Asp Val Leu Gln Ser
     285                 290                 295 att aca gac ata ata caa atc aat ggc atc ccc act gtg gtc ggg gtg     1384
Ile Thr Asp Ile Ile Gln Ile Asn Gly Ile Pro Thr Val Val Gly Val
300                 305                 310                 315 ttt acc acg cag ctc aat agc atc cct ggt tct gct gtc tgt gca ttt     1432
Phe Thr Thr Gln Leu Asn Ser Ile Pro Gly Ser Ala Val Cys Ala Phe
                 320                 325                 330 agc atg gat gac att gaa aaa gta ttc aaa gga cgg ttt aag gaa cag     1480
Ser Met Asp Asp Ile Glu Lys Val Phe Lys Gly Arg Phe Lys Glu Gln
             335                 340                 345 aaa act cca gat tct gtt tgg aca gca gtt ccc gaa gac aaa gtg cca     1528
```

```
Lys Thr Pro Asp Ser Val Trp Thr Ala Val Pro Glu Asp Lys Val Pro
            350                 355                 360 aag cca agg cct ggc tgt tgt gca aaa cac ggc ctt gcc gaa gct tat     1576
Lys Pro Arg Pro Gly Cys Cys Ala Lys His Gly Leu Ala Glu Ala Tyr
    365                 370                 375 aaa acc tcc atc gat ttc ccg gat gaa act ctg tca ttc atc aaa tct     1624
Lys Thr Ser Ile Asp Phe Pro Asp Glu Thr Leu Ser Phe Ile Lys Ser
380                 385                 390                 395 cat ccc ctg atg gac tct gcc gtt cca ccc att gcc gat gag ccc tgg     1672
His Pro Leu Met Asp Ser Ala Val Pro Pro Ile Ala Asp Glu Pro Trp
                400                 405                 410 ttc aca aag act cgg gtc agg tac aga ctg acg gcc atc tca gtg gac     1720
Phe Thr Lys Thr Arg Val Arg Tyr Arg Leu Thr Ala Ile Ser Val Asp
            415                 420                 425 cat tca gcc gga ccc tac cag aac tac aca gtc atc ttt gtt ggc tct     1768
His Ser Ala Gly Pro Tyr Gln Asn Tyr Thr Val Ile Phe Val Gly Ser
        430                 435                 440 gaa gct ggc atg gta ctt aaa gtt ctg gca aag acc agt cct ttc tct     1816
Glu Ala Gly Met Val Leu Lys Val Leu Ala Lys Thr Ser Pro Phe Ser
    445                 450                 455 ttg aac gac agc gta tta ctg gaa gag att gaa gcc tac aac cat gca     1864
Leu Asn Asp Ser Val Leu Leu Glu Glu Ile Glu Ala Tyr Asn His Ala
460                 465                 470                 475 aag tgc agt gct gag aat gag gaa gac aaa aag gtc atc tca tta cag     1912
Lys Cys Ser Ala Glu Asn Glu Glu Asp Lys Lys Val Ile Ser Leu Gln
                480                 485                 490 ttg gat aaa gat cac cac gct tta tat gtg gcg ttc tct agc tgc att     1960
Leu Asp Lys Asp His His Ala Leu Tyr Val Ala Phe Ser Ser Cys Ile
            495                 500                 505 atc cgc atc ccc ctc agt cgc tgt gag cgt tat gga tca tgt aaa aag     2008
Ile Arg Ile Pro Leu Ser Arg Cys Glu Arg Tyr Gly Ser Cys Lys Lys
        510                 515                 520 tct tgt att gca tct cgt gac ccg tat tgt ggc tgg tta agc cag gga     2056
Ser Cys Ile Ala Ser Arg Asp Pro Tyr Cys Gly Trp Leu Ser Gln Gly
    525                 530                 535 tcc tgt ggt aga gtg acc cca ggg atg ctg ctg tta acc gaa gac ttc     2104
Ser Cys Gly Arg Val Thr Pro Gly Met Leu Leu Leu Thr Glu Asp Phe
540                 545                 550                 555 ttt gct ttc cat aac cac agt gct gaa gga tat gaa caa gac aca gaa     2152
Phe Ala Phe His Asn His Ser Ala Glu Gly Tyr Glu Gln Asp Thr Glu
                560                 565                 570 ttc ggc aac aca gct cat cta ggg gac tgc cat ggt gta cga tgg gaa     2200
Phe Gly Asn Thr Ala His Leu Gly Asp Cys His Gly Val Arg Trp Glu
            575                 580                 585 gtc cag tct gga gag tcc aac cag atg gtc cac atg aat gtc ctc atc     2248
Val Gln Ser Gly Glu Ser Asn Gln Met Val His Met Asn Val Leu Ile
        590                 595                 600 acc tgt gtc ttt gct gct ttt gtt ttg ggg gca ttc att gca ggt gtg     2296
Thr Cys Val Phe Ala Ala Phe Val Leu Gly Ala Phe Ile Ala Gly Val
    605                 610                 615 gca gta tac tgc tat cga gac atg ttt gtt cgg aaa aac aga aag atc     2344
Ala Val Tyr Cys Tyr Arg Asp Met Phe Val Arg Lys Asn Arg Lys Ile
620                 625                 630                 635 cat aaa gat gca gag tcc gcc cag tca tgc aca gac tcc agt gga agt     2392
His Lys Asp Ala Glu Ser Ala Gln Ser Cys Thr Asp Ser Ser Gly Ser
                640                 645                 650 ttt gcc aaa ctg aat ggt ctc ttt gac agc cct gtc aag gaa tac caa     2440
Phe Ala Lys Leu Asn Gly Leu Phe Asp Ser Pro Val Lys Glu Tyr Gln
            655                 660                 665
```

```
                                    -continued cag aat att gat tct cct aaa ctg tat agt aac ctg cta acc agt cgg    2488
Gln Asn Ile Asp Ser Pro Lys Leu Tyr Ser Asn Leu Leu Thr Ser Arg
        670                 675                 680 aaa gag cta cca ccc aat gga gat act aaa tcc atg gta atg gac cat    2536
Lys Glu Leu Pro Pro Asn Gly Asp Thr Lys Ser Met Val Met Asp His
685                 690                 695 cga ggg caa cct cca gag ttg gct gct ctt cct act cct gag tct aca    2584
Arg Gly Gln Pro Pro Glu Leu Ala Ala Leu Pro Thr Pro Glu Ser Thr
700                 705                 710                 715 ccc gtg ctt cac cag aag acc ctg cag gcc atg aag agc cac tca gaa    2632
Pro Val Leu His Gln Lys Thr Leu Gln Ala Met Lys Ser His Ser Glu
            720                 725                 730 aag gcc cat ggc cat gga gct tca agg aaa gaa acc cct cag ttt ttt    2680
Lys Ala His Gly His Gly Ala Ser Arg Lys Glu Thr Pro Gln Phe Phe
        735                 740                 745 ccg tct agt ccg cca cct cat tcc cca tta agt cat ggg cat atc ccc    2728
Pro Ser Ser Pro Pro Pro His Ser Pro Leu Ser His Gly His Ile Pro
    750                 755                 760 agt gcc att gtt ctt cca aat gct acc cat gac tac aac acg tct ttc    2776
Ser Ala Ile Val Leu Pro Asn Ala Thr His Asp Tyr Asn Thr Ser Phe
765                 770                 775 tca aac tcc aat gct cac aaa gct gaa aag aag ctt caa aac att gat    2824
Ser Asn Ser Asn Ala His Lys Ala Glu Lys Lys Leu Gln Asn Ile Asp
780                 785                 790                 795 cac cct ctc aca aag tca tcc agt aag aga gat cac cgg cgt tct gtt    2872
His Pro Leu Thr Lys Ser Ser Ser Lys Arg Asp His Arg Arg Ser Val
            800                 805                 810 gat tcc aga aat acc ctc aat gat ctc ctg aag cat ctg aat gac cca    2920
Asp Ser Arg Asn Thr Leu Asn Asp Leu Leu Lys His Leu Asn Asp Pro
        815                 820                 825 aat agt aac ccc aaa gcc atc atg gga gac atc cag atg gca cac cag    2968
Asn Ser Asn Pro Lys Ala Ile Met Gly Asp Ile Gln Met Ala His Gln
    830                 835                 840 aac tta atg ctg gat ccc atg gga tcg atg tct gag gtc cca cct aaa    3016
Asn Leu Met Leu Asp Pro Met Gly Ser Met Ser Glu Val Pro Pro Lys
845                 850                 855 gtc cct aac cgg gag gca tcg cta tac tcc cct cct tca act ctc ccc    3064
Val Pro Asn Arg Glu Ala Ser Leu Tyr Ser Pro Pro Ser Thr Leu Pro
860                 865                 870                 875 aga aat agc cca acc aag cga gtg gat gtc ccc acc act cct gga gtc    3112
Arg Asn Ser Pro Thr Lys Arg Val Asp Val Pro Thr Thr Pro Gly Val
            880                 885                 890 cca atg act tct ctg gaa aga caa aga ggt tat cac aaa aat tcc tcc    3160
Pro Met Thr Ser Leu Glu Arg Gln Arg Gly Tyr His Lys Asn Ser Ser
        895                 900                 905 cag agg cac tct ata tct gct atg cct aaa aac tta aac tca cca aat    3208
Gln Arg His Ser Ile Ser Ala Met Pro Lys Asn Leu Asn Ser Pro Asn
    910                 915                 920 ggt gtt ttg tta tcc aga cag cct agt atg aac cgt gga gga tat atg    3256
Gly Val Leu Leu Ser Arg Gln Pro Ser Met Asn Arg Gly Gly Tyr Met
925                 930                 935 ccc acc ccc act ggg gcg aag gtg gac tat att cag gga aca cca gtg    3304
Pro Thr Pro Thr Gly Ala Lys Val Asp Tyr Ile Gln Gly Thr Pro Val
940                 945                 950                 955 agt gtt cat ctg cag cct tcc ctc tcc aga cag agc agc tac acc agt    3352
Ser Val His Leu Gln Pro Ser Leu Ser Arg Gln Ser Ser Tyr Thr Ser
            960                 965                 970 aat ggc act ctt cct agg acg gga cta aag agg acg ccg tcc tta aaa    3400
Asn Gly Thr Leu Pro Arg Thr Gly Leu Lys Arg Thr Pro Ser Leu Lys
        975                 980                 985
```

```
cct gac gtg cca cca aag cct tcc ttt gtt cct caa acc cca tct gtc    3448
Pro Asp Val Pro Pro Lys Pro Ser Phe Val Pro Gln Thr Pro Ser Val
        990             995                 1000 aga cca ctg aac aaa tac aca tac taggcctcaa gtgtgctatt              3492
Arg Pro Leu Asn Lys Tyr Thr Tyr
    1005                1010 cccatgtggc tttatcctgt ccgtgttgtt gagaggatga tgttgtaagg gtaccttaaa   3552
acaagagact cgcttgtatt ttaagagaac caagtggcca agaaactct ttctaacttt    3612 ggcaacatca gaacttgcca catgtagcta ctgcagcaag gcttctgtgt acttgcctga   3672
aaacaaagga aggtgctggt cattccattt cttttgtttg aagctaaaga gatgtgtagc   3732
tcacaggggc taccttacca gtataaagag ctgataacag tactcagaag aatctgtgaa   3792
caaatacttg aaaatgggtt caatgtagac tgccattatg tgtggtcttc ccattaaatg   3852
tgaacatttt aatatgtatg cattcacctt gcctcttgca caaatgtcaa aaaaaagatg   3912
gtaatatctc aaagaaatga acttgtagat taccaagcag tttgctaaaa attcaatctt   3972
tgacccaagc tgtagcattt ttttttcatg tgtggcatct tttcatgcc accaacaaac    4032 ttgttgtgtg tgtgcgtgtg tgtgtgtgtg tgtgtgtgtg tgtgtgtgtt ctgtacccac   4092
taggatttgt ttaggtgccc attgcatctt tttgtgctat ggagttgttt acattaagca   4152
tgaccgaacg agagacaata ctatttccca caggagtcca ttgggttcag ctttgaaaga   4212
ggaatagaat cgaggctcct ttgaccatca aaatgatgaa ctttacttat gtggtaccca   4272
atgccagaat gtaagagttg caagtgattt tgtgctgcta ttcattaaaa cttgtattcc   4332
agtcttgcca gcttaaggag atcaagatat taagaggtat ccttgattta ttttccagta   4392
ttcagtagta aaattttcct gtccactgtg aatcaaagcc tgagtcactc tatttaacct   4452
tggacacact aataaggttt tattttgatt gtgttcgttt ccccccccc aatagtaaaa    4512 tttctcctcc tttaactcct cctaccccc aaggtaagaa acaaaaaaca aacaaacaaa    4572
caaaaataga agacaaaaga aagacatatg aaaggaattg taattggctt aacagaaaca   4632
gtctgtaaaa acctaacagt ggtgcaatca tgttgtctgt gttgtgttat gtgagaattt   4692
tctcctaagt catgcaggta atgacaatat actgtaaata ccacatgtga gtttacctga   4752
atctgtgcat tttgtgcctt attcatgaga atgatagaag tactaaaatc tgtcaagtgt   4812
tttcagtata gcacattatt tactgagtgc cagttgtaaa tgttttttcaa ccagcaccta  4872 aaaagactct tttcaaaaaa tcacagaaac aacctaggac aattatttgt tacataatcc   4932
gacctcatag cagcattaca ttctttgccg tgataaacat tccactcctg ctttcctaag   4992
gatgaaacag tgataatgtg aactcaaatg aggtttcctg ggtaatgtga cacctgcaga   5052
aactatagag cgtcatttat acgtagtttg gcagaaacca cttacggctg atgatgcgca   5112
accctgctga ctgtttcagt taatatgctg cacaccacac acttgtttag tgaaccaaat   5172
ctagaaagta ccaaggcaga ggtatgctcc tgctgtaatc aggcaaatga gttcaactgg   5232 atttctttg acaatactgt tggtacctat tacttggggg aggacatgtt gcagaagacc    5292
agatcatttt tatacagaat gtgaaatact gatacagtta ttcttttttt taagaaacat   5352
tgttttataa agaacgtgat ttccagtgat ctctggaagc gctaaagcta aaatttctgt   5412
tcttgaaaca cttcagcttt gcaactaaaa tattacagat taataataaa ttaaaccaac   5472
caatgataaa cactactcag tccaccaaca acaaacgtgt ttgaattcac cttaccaata   5532
ttaatcccag cgtgtgtaaa acagaacagt aactctatgt gaccccagat aacatttgt    5592
```

```
aacattgtgc ttccttgtag tttgtaatgt gagttcaatc agtatttatg ttgaaatttc   5652
taacattaaa tctagtctct atcctgttaa tttaatttt aaatgcttta tccatttgtg    5712
caaaggtaaa cgcagattgt atcttttta atggtacggc ataaaaagta accctcaagt    5772
gaagtgtctc tatactgttt tatagagtac tttaacatga atagatacct tgtaaacttg   5832
tattgtggat gtgtaaataa tatgtacttt gggttttaa caccgcatgt aaagtcaaaa    5892
taaaatatac aaatcattat aaaaaaaaaa a                                  5923
```

<210> SEQ ID NO 22
<211> LENGTH: 1011
<212> TYPE: PRT
<213> ORGANISM: Homo sapiens

<400> SEQUENCE: 22

```
Met Arg Val Phe Leu Leu Cys Ala Tyr Ile Leu Leu Met Val Ser
1               5                   10                  15

Gln Leu Arg Ala Val Ser Phe Pro Glu Asp Glu Pro Leu Asn Thr
            20                  25                  30

Val Asp Tyr His Tyr Ser Arg Gln Tyr Pro Val Phe Arg Gly Arg Pro
        35                  40                  45

Ser Gly Asn Glu Ser Gln His Arg Leu Asp Phe Gln Leu Met Leu Lys
    50                  55                  60

Ile Arg Asp Thr Leu Tyr Ile Ala Gly Arg Asp Gln Val Tyr Thr Val
65                  70                  75                  80

Asn Leu Asn Glu Met Pro Lys Thr Glu Val Ile Pro Asn Lys Lys Leu
                85                  90                  95

Thr Trp Arg Ser Arg Gln Gln Asp Arg Glu Asn Cys Ala Met Lys Gly
            100                 105                 110

Lys His Lys Asp Glu Cys His Asn Phe Ile Lys Val Phe Val Pro Arg
        115                 120                 125

Asn Asp Glu Met Val Phe Val Cys Gly Thr Asn Ala Phe Asn Pro Met
    130                 135                 140

Cys Arg Tyr Tyr Arg Leu Ser Thr Leu Glu Tyr Asp Gly Glu Glu Ile
145                 150                 155                 160

Ser Gly Leu Ala Arg Cys Pro Phe Asp Ala Arg Gln Thr Asn Val Ala
                165                 170                 175

Leu Phe Ala Asp Gly Lys Leu Tyr Ser Ala Thr Val Ala Asp Phe Leu
            180                 185                 190

Ala Ser Asp Ala Val Ile Tyr Arg Ser Met Gly Asp Gly Ser Ala Leu
        195                 200                 205

Arg Thr Ile Lys Tyr Asp Ser Lys Trp Ile Lys Glu Pro His Phe Leu
    210                 215                 220

His Ala Ile Glu Tyr Gly Asn Tyr Val Tyr Phe Phe Arg Glu Ile
225                 230                 235                 240

Ala Val Glu His Asn Asn Leu Gly Lys Ala Val Tyr Ser Arg Val Ala
                245                 250                 255

Arg Ile Cys Lys Asn Asp Met Gly Gly Ser Gln Arg Val Leu Glu Lys
            260                 265                 270

His Trp Thr Ser Phe Leu Lys Ala Arg Leu Asn Cys Ser Val Pro Gly
        275                 280                 285

Asp Ser Phe Phe Tyr Phe Asp Val Leu Gln Ser Ile Thr Asp Ile Ile
    290                 295                 300

Gln Ile Asn Gly Ile Pro Thr Val Val Gly Val Phe Thr Thr Gln Leu
305                 310                 315                 320
```

```
Asn Ser Ile Pro Gly Ser Ala Val Cys Ala Phe Ser Met Asp Asp Ile
            325                 330                 335

Glu Lys Val Phe Lys Gly Arg Phe Lys Glu Gln Lys Thr Pro Asp Ser
            340                 345                 350

Val Trp Thr Ala Val Pro Glu Asp Lys Val Pro Lys Pro Arg Pro Gly
            355                 360                 365

Cys Cys Ala Lys His Gly Leu Ala Glu Ala Tyr Lys Thr Ser Ile Asp
            370                 375                 380

Phe Pro Asp Glu Thr Leu Ser Phe Ile Lys Ser His Pro Leu Met Asp
385                 390                 395                 400

Ser Ala Val Pro Pro Ile Ala Asp Glu Pro Trp Phe Thr Lys Thr Arg
            405                 410                 415

Val Arg Tyr Arg Leu Thr Ala Ile Ser Val Asp His Ser Ala Gly Pro
            420                 425                 430

Tyr Gln Asn Tyr Thr Val Ile Phe Val Gly Ser Glu Ala Gly Met Val
            435                 440                 445

Leu Lys Val Leu Ala Lys Thr Ser Pro Phe Ser Leu Asn Asp Ser Val
            450                 455                 460

Leu Leu Glu Glu Ile Glu Ala Tyr Asn His Ala Lys Cys Ser Ala Glu
465                 470                 475                 480

Asn Glu Glu Asp Lys Lys Val Ile Ser Leu Gln Leu Asp Lys Asp His
            485                 490                 495

His Ala Leu Tyr Val Ala Phe Ser Ser Cys Ile Ile Arg Ile Pro Leu
            500                 505                 510

Ser Arg Cys Glu Arg Tyr Gly Ser Cys Lys Lys Ser Cys Ile Ala Ser
            515                 520                 525

Arg Asp Pro Tyr Cys Gly Trp Leu Ser Gln Gly Ser Cys Gly Arg Val
            530                 535                 540

Thr Pro Gly Met Leu Leu Leu Thr Glu Asp Phe Phe Ala Phe His Asn
545                 550                 555                 560

His Ser Ala Glu Gly Tyr Glu Gln Asp Thr Glu Phe Gly Asn Thr Ala
            565                 570                 575

His Leu Gly Asp Cys His Gly Val Arg Trp Glu Val Gln Ser Gly Glu
            580                 585                 590

Ser Asn Gln Met Val His Met Asn Val Leu Ile Thr Cys Val Phe Ala
            595                 600                 605

Ala Phe Val Leu Gly Ala Phe Ile Ala Gly Val Ala Val Tyr Cys Tyr
            610                 615                 620

Arg Asp Met Phe Val Arg Lys Asn Arg Lys Ile His Lys Asp Ala Glu
625                 630                 635                 640

Ser Ala Gln Ser Cys Thr Asp Ser Ser Gly Ser Phe Ala Lys Leu Asn
            645                 650                 655

Gly Leu Phe Asp Ser Pro Val Lys Glu Tyr Gln Gln Asn Ile Asp Ser
            660                 665                 670

Pro Lys Leu Tyr Ser Asn Leu Leu Thr Ser Arg Lys Glu Leu Pro Pro
            675                 680                 685

Asn Gly Asp Thr Lys Ser Met Val Met Asp His Arg Gly Gln Pro Pro
            690                 695                 700

Glu Leu Ala Ala Leu Pro Thr Pro Glu Ser Thr Pro Val Leu His Gln
705                 710                 715                 720

Lys Thr Leu Gln Ala Met Lys Ser His Ser Glu Lys Ala His Gly His
            725                 730                 735
```

```
Gly Ala Ser Arg Lys Glu Thr Pro Gln Phe Phe Pro Ser Ser Pro Pro
                740                 745                 750

Pro His Ser Pro Leu Ser His Gly His Ile Pro Ser Ala Ile Val Leu
            755                 760                 765

Pro Asn Ala Thr His Asp Tyr Asn Thr Ser Phe Ser Asn Ser Asn Ala
        770                 775                 780

His Lys Ala Glu Lys Lys Leu Gln Asn Ile Asp His Pro Leu Thr Lys
785                 790                 795                 800

Ser Ser Ser Lys Arg Asp His Arg Arg Ser Val Asp Ser Arg Asn Thr
                805                 810                 815

Leu Asn Asp Leu Leu Lys His Leu Asn Asp Pro Asn Ser Asn Pro Lys
            820                 825                 830

Ala Ile Met Gly Asp Ile Gln Met Ala His Gln Asn Leu Met Leu Asp
        835                 840                 845

Pro Met Gly Ser Met Ser Glu Val Pro Pro Lys Val Pro Asn Arg Glu
850                 855                 860

Ala Ser Leu Tyr Ser Pro Pro Ser Thr Leu Pro Arg Asn Ser Pro Thr
865                 870                 875                 880

Lys Arg Val Asp Val Pro Thr Thr Pro Gly Val Pro Met Thr Ser Leu
                885                 890                 895

Glu Arg Gln Arg Gly Tyr His Lys Asn Ser Ser Gln Arg His Ser Ile
            900                 905                 910

Ser Ala Met Pro Lys Asn Leu Asn Ser Pro Asn Gly Val Leu Leu Ser
        915                 920                 925

Arg Gln Pro Ser Met Asn Arg Gly Gly Tyr Met Pro Thr Pro Thr Gly
930                 935                 940

Ala Lys Val Asp Tyr Ile Gln Gly Thr Pro Val Ser Val His Leu Gln
945                 950                 955                 960

Pro Ser Leu Ser Arg Gln Ser Ser Tyr Thr Ser Asn Gly Thr Leu Pro
                965                 970                 975

Arg Thr Gly Leu Lys Arg Thr Pro Ser Leu Lys Pro Asp Val Pro Pro
            980                 985                 990

Lys Pro Ser Phe Val Pro Gln Thr  Pro Ser Val Arg Pro Leu Asn Lys
        995                 1000                1005

Tyr Thr Tyr
    1010

<210> SEQ ID NO 23
<211> LENGTH: 5884
<212> TYPE: DNA
<213> ORGANISM: Homo sapiens
<220> FEATURE:
<221> NAME/KEY: CDS
<222> LOCATION: (440)..(3433)

<400> SEQUENCE: 23
gcggccgctt cccaccgtcc ctctcccctt actggcagag cgcgctgcgg gcggactccc      60
gggcccggag cagcccaccg gccaccccac cgcccacccg gctcccggtg tctcctcccg     120
gccgctctac ccagcaactt tccgtgcttt gttccccgac tggaaatgct ttacggaagc     180
gtcttggaca gggtctccgc caggcgacaa gagctcggtg ctgagatgtg ttacgttctc     240
atctccccat caattatgga tggaaacaaa taaggaagag tcaattttgc tgagccccttt    300 ctccggcaac gagaggcgtt ctgcagccgg gagggagccg ccgctcgcgc cggcagccgc    360
tggcaggggc atggtgagga ggaaggtagc tcagtggcat ttctgagcag gggccaccct    420
```

```
gacttcacct tggcccacc atg agg gtc ttc ctg ctt tgt gcc tac ata ctg        472
                    Met Arg Val Phe Leu Leu Cys Ala Tyr Ile Leu
                     1               5                      10 ctg ctg atg gtt tcc cag ttg agg gca gtc agc ttt cct gaa gat gat        520
Leu Leu Met Val Ser Gln Leu Arg Ala Val Ser Phe Pro Glu Asp Asp
             15                  20                  25 gaa ccc ctt aat act gtc gac tat cac tat tca agg caa tat ccg gtt        568
Glu Pro Leu Asn Thr Val Asp Tyr His Tyr Ser Arg Gln Tyr Pro Val
         30                  35                  40 ttt aga gga cgc cct tca ggc aat gaa tcg cag cac agg ctg gac ttt        616
Phe Arg Gly Arg Pro Ser Gly Asn Glu Ser Gln His Arg Leu Asp Phe
     45                  50                  55 cag ctg atg ttg aaa att cga gac aca ctt tat att gct ggc agg gat        664
Gln Leu Met Leu Lys Ile Arg Asp Thr Leu Tyr Ile Ala Gly Arg Asp
 60              65                  70                  75 caa gtt tat aca gta aac tta aat gaa atg ccc aaa aca gaa gta ata        712
Gln Val Tyr Thr Val Asn Leu Asn Glu Met Pro Lys Thr Glu Val Ile
             80                  85                  90 ccc aac aag aaa ctg aca tgg cga tca aga caa cag gat cga gaa aac        760
Pro Asn Lys Lys Leu Thr Trp Arg Ser Arg Gln Gln Asp Arg Glu Asn
         95                  100                 105 tgt gct atg aaa ggc aag cat aaa gat gaa tgc cac aac ttt atc aaa        808
Cys Ala Met Lys Gly Lys His Lys Asp Glu Cys His Asn Phe Ile Lys
     110                 115                 120 gta ttt gtt cca aga aac gat gag atg gtt ttt gtt tgt ggt acc aat        856
Val Phe Val Pro Arg Asn Asp Glu Met Val Phe Val Cys Gly Thr Asn
125                 130                 135 gca ttc aat ccc atg tgt aga tac tac agg ttg agt acc tta gaa tat        904
Ala Phe Asn Pro Met Cys Arg Tyr Tyr Arg Leu Ser Thr Leu Glu Tyr
140                 145                 150                 155 gat ggg gaa gaa att agt ggc ctg gca aga tgc cca ttt gat gcc aga        952
Asp Gly Glu Glu Ile Ser Gly Leu Ala Arg Cys Pro Phe Asp Ala Arg
                160                 165                 170 caa acc aat gtt gcc ctc ttt gct gat ggg aag ctg tat tct gcc aca       1000
Gln Thr Asn Val Ala Leu Phe Ala Asp Gly Lys Leu Tyr Ser Ala Thr
             175                 180                 185 gtg gct gac ttc ttg gcc agc gat gcc gtt att tat cga agc atg ggt       1048
Val Ala Asp Phe Leu Ala Ser Asp Ala Val Ile Tyr Arg Ser Met Gly
         190                 195                 200 gat gga tct gcc ctt cgc aca ata aaa tat gat tcc aaa tgg ata aaa       1096
Asp Gly Ser Ala Leu Arg Thr Ile Lys Tyr Asp Ser Lys Trp Ile Lys
     205                 210                 215 gag cca cac ttt ctt cat gcc ata gaa tat gga aac tat gtc tat ttc       1144
Glu Pro His Phe Leu His Ala Ile Glu Tyr Gly Asn Tyr Val Tyr Phe
220                 225                 230                 235 ttc ttt cga gaa atc gct gtc gaa cat aat aat tta ggc aag gct gtg       1192
Phe Phe Arg Glu Ile Ala Val Glu His Asn Asn Leu Gly Lys Ala Val
                240                 245                 250 tat tcc cgc gtg gcc cgc ata tgt aaa aac gac atg ggt ggt tcc cag       1240
Tyr Ser Arg Val Ala Arg Ile Cys Lys Asn Asp Met Gly Gly Ser Gln
             255                 260                 265 cgg gtc ctg gag aaa cac tgg act tca ttt cta aag gct cgg ctg aac       1288
Arg Val Leu Glu Lys His Trp Thr Ser Phe Leu Lys Ala Arg Leu Asn
         270                 275                 280 tgt tct gtc cct gga gat tcg ttt ttc tac ttt gat gtt ctg cag tct       1336
Cys Ser Val Pro Gly Asp Ser Phe Phe Tyr Phe Asp Val Leu Gln Ser
     285                 290                 295 att aca gac ata ata caa atc aat ggc atc ccc act gtg gtc ggg gtg       1384
Ile Thr Asp Ile Ile Gln Ile Asn Gly Ile Pro Thr Val Val Gly Val
300                 305                 310                 315
```

```
ttt acc acg cag ctc aat agc atc cct ggt tct gct gtc tgt gca ttt      1432
Phe Thr Thr Gln Leu Asn Ser Ile Pro Gly Ser Ala Val Cys Ala Phe
                320                 325                 330 agc atg gat gac att gaa aaa gta ttc aaa gga cgg ttt aag gaa cag      1480
Ser Met Asp Asp Ile Glu Lys Val Phe Lys Gly Arg Phe Lys Glu Gln
            335                 340                 345 aaa act cca gat tct gtt tgg aca gca gtt ccc gaa gac aaa gtg cca      1528
Lys Thr Pro Asp Ser Val Trp Thr Ala Val Pro Glu Asp Lys Val Pro
        350                 355                 360 aag cca agg cct ggc tgt tgt gca aaa cac ggc ctt gcc gaa gct tat      1576
Lys Pro Arg Pro Gly Cys Cys Ala Lys His Gly Leu Ala Glu Ala Tyr
    365                 370                 375 aaa acc tcc atc gat ttc ccg gat gaa act ctg tca ttc atc aaa tct      1624
Lys Thr Ser Ile Asp Phe Pro Asp Glu Thr Leu Ser Phe Ile Lys Ser
380                 385                 390                 395 cat ccc ctg atg gac tct gcc gtt cca ccc att gcc gat gag ccc tgg      1672
His Pro Leu Met Asp Ser Ala Val Pro Pro Ile Ala Asp Glu Pro Trp
                400                 405                 410 ttc aca aag act cgg gtc agg tac aga ctg acg gcc atc tca gtg gac      1720
Phe Thr Lys Thr Arg Val Arg Tyr Arg Leu Thr Ala Ile Ser Val Asp
            415                 420                 425 cat tca gcc gga ccc tac cag aac tac aca gtc atc ttt gtt ggc tct      1768
His Ser Ala Gly Pro Tyr Gln Asn Tyr Thr Val Ile Phe Val Gly Ser
        430                 435                 440 gaa gct ggc atg gta ctt aaa gtt ctg gca aag acc agt cct ttc tct      1816
Glu Ala Gly Met Val Leu Lys Val Leu Ala Lys Thr Ser Pro Phe Ser
    445                 450                 455 ttg aac gac agc gta tta ctg gaa gag att gaa gcc tac aac cat gca      1864
Leu Asn Asp Ser Val Leu Leu Glu Glu Ile Glu Ala Tyr Asn His Ala
460                 465                 470                 475 aag tgc agt gct gag aat gag gaa gac aaa aag gtc atc tca tta cag      1912
Lys Cys Ser Ala Glu Asn Glu Glu Asp Lys Lys Val Ile Ser Leu Gln
                480                 485                 490 ttg gat aaa gat cac cac gct tta tat gtg gcg ttc tct agc tgc att      1960
Leu Asp Lys Asp His His Ala Leu Tyr Val Ala Phe Ser Ser Cys Ile
            495                 500                 505 atc cgc atc ccc ctc agt cgc tgt gag cgt tat gga tca tgt aaa aag      2008
Ile Arg Ile Pro Leu Ser Arg Cys Glu Arg Tyr Gly Ser Cys Lys Lys
        510                 515                 520 tct tgt att gca tct cgt gac ccg tat tgt ggc tgg tta agc cag gga      2056
Ser Cys Ile Ala Ser Arg Asp Pro Tyr Cys Gly Trp Leu Ser Gln Gly
    525                 530                 535 tcc tgt ggt aga gtg acc cca ggg atg ctt gct gaa gga tat gaa caa      2104
Ser Cys Gly Arg Val Thr Pro Gly Met Leu Ala Glu Gly Tyr Glu Gln
540                 545                 550                 555 gac aca gaa ttc ggc aac aca gct cat cta ggg gac tgc cat ggt gta      2152
Asp Thr Glu Phe Gly Asn Thr Ala His Leu Gly Asp Cys His Gly Val
                560                 565                 570 cga tgg gaa gtc cag tct gga gag tcc aac cag atg gtc cac atg aat      2200
Arg Trp Glu Val Gln Ser Gly Glu Ser Asn Gln Met Val His Met Asn
            575                 580                 585 gtc ctc atc acc tgt gtc ttt gct gct ttt gtt tgg ggg gca ttc att      2248
Val Leu Ile Thr Cys Val Phe Ala Ala Phe Val Leu Gly Ala Phe Ile
        590                 595                 600 gca ggt gtg gca gta tac tgc tat cga gac atg ttt gtt cgg aaa aac      2296
Ala Gly Val Ala Val Tyr Cys Tyr Arg Asp Met Phe Val Arg Lys Asn
    605                 610                 615 aga aag atc cat aaa gat gca gag tcc gcc cag tca tgc aca gac tcc      2344
Arg Lys Ile His Lys Asp Ala Glu Ser Ala Gln Ser Cys Thr Asp Ser
```

-continued

| | | | | | | | | | | | | | | | |
|---|---|---|---|---|---|---|---|---|---|---|---|---|---|---|---|
|620| | | | |625| | | | |630| | | | |635| agt gga agt ttt gcc aaa ctg aat ggt ctc ttt gac agc cct gtc aag  2392
Ser Gly Ser Phe Ala Lys Leu Asn Gly Leu Phe Asp Ser Pro Val Lys
                640                 645                 650 gaa tac caa cag aat att gat tct cct aaa ctg tat agt aac ctg cta  2440
Glu Tyr Gln Gln Asn Ile Asp Ser Pro Lys Leu Tyr Ser Asn Leu Leu
        655                 660                 665 acc agt cgg aaa gag cta cca ccc aat gga gat act aaa tcc atg gta  2488
Thr Ser Arg Lys Glu Leu Pro Pro Asn Gly Asp Thr Lys Ser Met Val
    670                 675                 680 atg gac cat cga ggg caa cct cca gag ttg gct gct ctt cct act cct  2536
Met Asp His Arg Gly Gln Pro Pro Glu Leu Ala Ala Leu Pro Thr Pro
685                 690                 695 gag tct aca ccc gtg ctt cac cag aag acc ctg cag gcc atg aag agc  2584
Glu Ser Thr Pro Val Leu His Gln Lys Thr Leu Gln Ala Met Lys Ser
700                 705                 710                 715 cac tca gaa aag gcc cat ggc cat gga gct tca agg aaa gaa acc cct  2632
His Ser Glu Lys Ala His Gly His Gly Ala Ser Arg Lys Glu Thr Pro
                720                 725                 730 cag ttt ttt ccg tct agt ccg cca cct cat tcc cca tta agt cat ggg  2680
Gln Phe Phe Pro Ser Ser Pro Pro Pro His Ser Pro Leu Ser His Gly
        735                 740                 745 cat atc ccc agt gcc att gtt ctt cca aat gct acc cat gac tac aac  2728
His Ile Pro Ser Ala Ile Val Leu Pro Asn Ala Thr His Asp Tyr Asn
    750                 755                 760 acg tct ttc tca aac tcc aat gct cac aaa gct gaa aag aag ctt caa  2776
Thr Ser Phe Ser Asn Ser Asn Ala His Lys Ala Glu Lys Lys Leu Gln
765                 770                 775 aac att gat cac cct ctc aca aag tca tcc agt aag aga gat cac cgg  2824
Asn Ile Asp His Pro Leu Thr Lys Ser Ser Ser Lys Arg Asp His Arg
780                 785                 790                 795 cgt tct gtt gat tcc aga aat acc ctc aat gat ctc ctg aag cat ctg  2872
Arg Ser Val Asp Ser Arg Asn Thr Leu Asn Asp Leu Leu Lys His Leu
                800                 805                 810 aat gac cca aat agt aac ccc aaa gcc atc atg gga gac atc cag atg  2920
Asn Asp Pro Asn Ser Asn Pro Lys Ala Ile Met Gly Asp Ile Gln Met
        815                 820                 825 gca cac cag aac tta atg ctg gat ccc atg gga tcg atg tct gag gtc  2968
Ala His Gln Asn Leu Met Leu Asp Pro Met Gly Ser Met Ser Glu Val
    830                 835                 840 cca cct aaa gtc cct aac cgg gag gca tcg cta tac tcc cct cct tca  3016
Pro Pro Lys Val Pro Asn Arg Glu Ala Ser Leu Tyr Ser Pro Pro Ser
845                 850                 855 act ctc ccc aga aat agc cca acc aag cga gtg gat gtc ccc acc act  3064
Thr Leu Pro Arg Asn Ser Pro Thr Lys Arg Val Asp Val Pro Thr Thr
860                 865                 870                 875 cct gga gtc cca atg act tct ctg gaa aga caa aga ggt tat cac aaa  3112
Pro Gly Val Pro Met Thr Ser Leu Glu Arg Gln Arg Gly Tyr His Lys
                880                 885                 890 aat tcc tcc cag agg cac tct ata tct gct atg cct aaa aac tta aac  3160
Asn Ser Ser Gln Arg His Ser Ile Ser Ala Met Pro Lys Asn Leu Asn
        895                 900                 905 tca cca aat ggt gtt ttg tta tcc aga cag cct agt atg aac cgt gga  3208
Ser Pro Asn Gly Val Leu Leu Ser Arg Gln Pro Ser Met Asn Arg Gly
    910                 915                 920 gga tat atg ccc acc ccc act ggg gcg aag gtg gac tat att cag gga  3256
Gly Tyr Met Pro Thr Pro Thr Gly Ala Lys Val Asp Tyr Ile Gln Gly
925                 930                 935 aca cca gtg agt gtt cat ctg cag cct tcc ctc tcc aga cag agc agc  3304

```
Thr Pro Val Ser Val His Leu Gln Pro Ser Leu Ser Arg Gln Ser Ser
940                 945                 950                 955 tac acc agt aat ggc act ctt cct agg acg gga cta aag agg acg ccg    3352
Tyr Thr Ser Asn Gly Thr Leu Pro Arg Thr Gly Leu Lys Arg Thr Pro
                960                 965                 970 tcc tta aaa cct gac gtg cca cca aag cct tcc ttt gtt cct caa acc    3400
Ser Leu Lys Pro Asp Val Pro Pro Lys Pro Ser Phe Val Pro Gln Thr
            975                 980                 985 cca tct gtc aga cca ctg aac aaa tac aca tac taggcctcaa gtgtgctatt  3453
Pro Ser Val Arg Pro Leu Asn Lys Tyr Thr Tyr
        990                 995
```

| | |
|---|---|
| cccatgtggc tttatcctgt ccgtgttgtt gagaggatga tgttgtaagg gtaccttaaa | 3513 |
| acaagagact cgcttgtatt ttaagagaac caagtggcca agaaactct ttctaacttt | 3573 |
| ggcaacatca gaacttgcca catgtagcta ctgcagcaag gcttctgtgt acttgcctga | 3633 |
| aaacaaagga aggtgctggt cattccattt cttttgtttg aagctaaaga gatgtgtagc | 3693 |
| tcacaggggc taccttacca gtataaagag ctgataacag tactcagaag aatctgtgaa | 3753 |
| caaatacttg aaaatgggtt caatgtagac tgccattatg tgtggtcttc ccattaaatg | 3813 |
| tgaacatttt aatatgtatg cattcacctt gcctcttgca caaatgtcaa aaaaagatg | 3873 |
| gtaatatctc aaagaaatga acttgtagat taccaagcag tttgctaaaa attcaatctt | 3933 |
| tgacccaagc tgtagcattt ttttttcatg tgtggcatct ttttcatgcc accaacaaac | 3993 |
| ttgttgtgtg tgtgcgtgtg tgtgtgtgtg tgtgtgtgtt ctgtacccac | 4053 |
| taggatttgt ttaggtgccc attgcatctt tttgtgctat ggagttgttt acattaagca | 4113 |
| tgaccgaacg agagacaata ctatttccca caggagtcca ttgggttcag cttttgaaaga | 4173 |
| ggaatagaat cgaggctcct ttgaccatca aatgatgaa cttttacttat gtggtaccca | 4233 |
| atgccagaat gtaagagttg caagtgattt tgtgctgcta ttcattaaaa cttgtattcc | 4293 |
| agtcttgcca gcttaaggag atcaagatat taagaggtat ccttgattta ttttccagta | 4353 |
| ttcagtagta aaatttttcct gtccactgtg aatcaaagcc tgagtcactc tatttaacct | 4413 |
| tggacacact aataaggttt tattttgatt gtgttcgttt ccccccccccc aatagtaaaa | 4473 |
| tttctcctcc tttaactcct cctaccccccc aaggtaagaa acaaaaaaca aacaaacaaa | 4533 |
| caaaaataga agacaaaaga aagacatatg aaaggaattg taattggctt aacagaaaca | 4593 |
| gtctgtaaaa acctaacagt ggtgcaatca tgttgtctgt gttgtgttat gtgagaattt | 4653 |
| tctcctaagt catgcaggta atgacaatat actgtaaata ccacatgtga gtttacctga | 4713 |
| atctgtgcat tttgtgcctt attcatgaga atgatagaag tactaaaatc tgtcaagtgt | 4773 |
| tttcagtata gcacattatt tactgagtgc cagttgtaaa tgttttttcaa ccagcaccta | 4833 |
| aaaagactct tttcaaaaaa tcacagaaac aacctaggac aattatttgt tacataatcc | 4893 |
| gacctcatag cagcattaca ttctttgccg tgataaacat tccactcctg ctttcctaag | 4953 |
| gatgaaacag tgataatgtg aactcaaatg aggtttcctg ggtaatgtga cacctgcaga | 5013 |
| aactatagag cgtcatttat acgtagtttg gcagaaacca cttacggctg atgatgcgca | 5073 |
| accctgctga ctgtttcagt taatatgctg cacaccacac acttgtttag tgaaccaaat | 5133 |
| ctagaaagta ccaaggcaga ggtatgctcc tgctgtaatc aggcaaatga gttcaactgg | 5193 |
| atttctttg acaatactgt tggtacctat tacttggggg aggacatgtt gcagaagacc | 5253 |
| agatcatttt tatacagaat gtgaaatact gatacagtta ttcttttttt taagaacat | 5313 |
| tgttttataa agaacgtgat ttccagtgat ctctggaagc gctaaagcta aaatttctgt | 5373 |

```
tcttgaaaca cttcagcttt gcaactaaaa tattacagat taataataaa ttaaaccaac    5433
caatgataaa cactactcag tccaccaaca acaaacgtgt ttgaattcac cttaccaata    5493
ttaatcccag cgtgtgtaaa acagaacagt aactctatgt gaccccagat aacattttgt    5553
aacattgtgc ttccttgtag tttgtaatgt gagttcaatc agtatttatg ttgaaatttc    5613
taacattaaa tctagtctct atcctgttaa tttaattttt aaatgcttta tccatttgtg    5673
caaaggtaaa cgcagattgt atcttttta atggtacggc ataaaaagta accctcaagt     5733
gaagtgtctc tatactgttt tatagagtac tttaacatga atagatacct tgtaaacttg    5793
tattgtggat gtgtaaataa tatgtacttt gggtttttaa caccgcatgt aaagtcaaaa    5853
taaaatatac aaatcattat aaaaaaaaaa a                                   5884
```

<210> SEQ ID NO 24
<211> LENGTH: 998
<212> TYPE: PRT
<213> ORGANISM: Homo sapiens

<400> SEQUENCE: 24

```
Met Arg Val Phe Leu Leu Cys Ala Tyr Ile Leu Leu Met Val Ser
1               5                   10                  15

Gln Leu Arg Ala Val Ser Phe Pro Glu Asp Asp Glu Pro Leu Asn Thr
            20                  25                  30

Val Asp Tyr His Tyr Ser Arg Gln Tyr Pro Val Phe Arg Gly Arg Pro
        35                  40                  45

Ser Gly Asn Glu Ser Gln His Arg Leu Asp Phe Gln Leu Met Leu Lys
    50                  55                  60

Ile Arg Asp Thr Leu Tyr Ile Ala Gly Arg Asp Gln Val Tyr Thr Val
65                  70                  75                  80

Asn Leu Asn Glu Met Pro Lys Thr Glu Val Ile Pro Asn Lys Lys Leu
                85                  90                  95

Thr Trp Arg Ser Arg Gln Gln Asp Arg Glu Asn Cys Ala Met Lys Gly
            100                 105                 110

Lys His Lys Asp Glu Cys His Asn Phe Ile Lys Val Phe Val Pro Arg
        115                 120                 125

Asn Asp Glu Met Val Phe Val Cys Gly Thr Asn Ala Phe Asn Pro Met
    130                 135                 140

Cys Arg Tyr Tyr Arg Leu Ser Thr Leu Glu Tyr Asp Gly Glu Glu Ile
145                 150                 155                 160

Ser Gly Leu Ala Arg Cys Pro Phe Asp Ala Arg Gln Thr Asn Val Ala
                165                 170                 175

Leu Phe Ala Asp Gly Lys Leu Tyr Ser Ala Thr Val Ala Asp Phe Leu
            180                 185                 190

Ala Ser Asp Ala Val Ile Tyr Arg Ser Met Gly Asp Gly Ser Ala Leu
        195                 200                 205

Arg Thr Ile Lys Tyr Asp Ser Lys Trp Ile Lys Glu Pro His Phe Leu
    210                 215                 220

His Ala Ile Glu Tyr Gly Asn Tyr Val Tyr Phe Phe Phe Arg Glu Ile
225                 230                 235                 240

Ala Val Glu His Asn Asn Leu Gly Lys Ala Val Tyr Ser Arg Val Ala
                245                 250                 255

Arg Ile Cys Lys Asn Asp Met Gly Gly Ser Gln Arg Val Leu Glu Lys
            260                 265                 270

His Trp Thr Ser Phe Leu Lys Ala Arg Leu Asn Cys Ser Val Pro Gly
        275                 280                 285
```

```
Asp Ser Phe Phe Tyr Phe Asp Val Leu Gln Ser Ile Thr Asp Ile Ile
    290                 295                 300
Gln Ile Asn Gly Ile Pro Thr Val Val Gly Val Phe Thr Thr Gln Leu
305                 310                 315                 320
Asn Ser Ile Pro Gly Ser Ala Val Cys Ala Phe Ser Met Asp Asp Ile
                325                 330                 335
Glu Lys Val Phe Lys Gly Arg Phe Lys Glu Gln Lys Thr Pro Asp Ser
                340                 345                 350
Val Trp Thr Ala Val Pro Glu Asp Lys Val Pro Lys Pro Arg Pro Gly
            355                 360                 365
Cys Cys Ala Lys His Gly Leu Ala Glu Ala Tyr Lys Thr Ser Ile Asp
    370                 375                 380
Phe Pro Asp Glu Thr Leu Ser Phe Ile Lys Ser His Pro Leu Met Asp
385                 390                 395                 400
Ser Ala Val Pro Pro Ile Ala Asp Glu Pro Trp Phe Thr Lys Thr Arg
                405                 410                 415
Val Arg Tyr Arg Leu Thr Ala Ile Ser Val Asp His Ser Ala Gly Pro
                420                 425                 430
Tyr Gln Asn Tyr Thr Val Ile Phe Val Gly Ser Glu Ala Gly Met Val
            435                 440                 445
Leu Lys Val Leu Ala Lys Thr Ser Pro Phe Ser Leu Asn Asp Ser Val
450                 455                 460
Leu Leu Glu Glu Ile Glu Ala Tyr Asn His Ala Lys Cys Ser Ala Glu
465                 470                 475                 480
Asn Glu Glu Asp Lys Lys Val Ile Ser Leu Gln Leu Asp Lys Asp His
                485                 490                 495
His Ala Leu Tyr Val Ala Phe Ser Ser Cys Ile Ile Arg Ile Pro Leu
            500                 505                 510
Ser Arg Cys Glu Arg Tyr Gly Ser Cys Lys Lys Ser Cys Ile Ala Ser
                515                 520                 525
Arg Asp Pro Tyr Cys Gly Trp Leu Ser Gln Gly Ser Cys Gly Arg Val
            530                 535                 540
Thr Pro Gly Met Leu Ala Glu Gly Tyr Glu Gln Asp Thr Glu Phe Gly
545                 550                 555                 560
Asn Thr Ala His Leu Gly Asp Cys His Gly Val Arg Trp Glu Val Gln
                565                 570                 575
Ser Gly Glu Ser Asn Gln Met Val His Met Asn Val Leu Ile Thr Cys
            580                 585                 590
Val Phe Ala Ala Phe Val Leu Gly Ala Phe Ile Ala Gly Val Ala Val
            595                 600                 605
Tyr Cys Tyr Arg Asp Met Phe Val Arg Lys Asn Arg Lys Ile His Lys
            610                 615                 620
Asp Ala Glu Ser Ala Gln Ser Cys Thr Asp Ser Ser Gly Ser Phe Ala
625                 630                 635                 640
Lys Leu Asn Gly Leu Phe Asp Ser Pro Val Lys Glu Tyr Gln Gln Asn
                645                 650                 655
Ile Asp Ser Pro Lys Leu Tyr Ser Asn Leu Leu Thr Ser Arg Lys Glu
                660                 665                 670
Leu Pro Pro Asn Gly Asp Thr Lys Ser Met Val Met Asp His Arg Gly
            675                 680                 685
Gln Pro Pro Glu Leu Ala Ala Leu Pro Thr Pro Glu Ser Thr Pro Val
        690                 695                 700
```

| Leu | His | Gln | Lys | Thr | Leu | Gln | Ala | Met | Lys | Ser | His | Ser | Glu | Lys | Ala |
| 705 | | | | 710 | | | | | 715 | | | | | 720 | |

| His | Gly | His | Gly | Ala | Ser | Arg | Lys | Glu | Thr | Pro | Gln | Phe | Phe | Pro | Ser |
| | | | | 725 | | | | | 730 | | | | | 735 | |

| Ser | Pro | Pro | His | Ser | Pro | Leu | Ser | His | Gly | His | Ile | Pro | Ser | Ala |
| | | 740 | | | | | 745 | | | | | 750 | | |

| Ile | Val | Leu | Pro | Asn | Ala | Thr | His | Asp | Tyr | Asn | Thr | Ser | Phe | Ser | Asn |
| | | 755 | | | | | 760 | | | | | 765 | | | |

| Ser | Asn | Ala | His | Lys | Ala | Glu | Lys | Lys | Leu | Gln | Asn | Ile | Asp | His | Pro |
| 770 | | | | | 775 | | | | | 780 | | | | | |

| Leu | Thr | Lys | Ser | Ser | Lys | Arg | Asp | His | Arg | Arg | Ser | Val | Asp | Ser |
| 785 | | | | 790 | | | | | 795 | | | | | 800 |

| Arg | Asn | Thr | Leu | Asn | Asp | Leu | Leu | Lys | His | Leu | Asn | Asp | Pro | Asn | Ser |
| | | | 805 | | | | | 810 | | | | | 815 | | |

| Asn | Pro | Lys | Ala | Ile | Met | Gly | Asp | Ile | Gln | Met | Ala | His | Gln | Asn | Leu |
| | | 820 | | | | | 825 | | | | | 830 | | | |

| Met | Leu | Asp | Pro | Met | Gly | Ser | Met | Ser | Glu | Val | Pro | Pro | Lys | Val | Pro |
| 835 | | | | | 840 | | | | | 845 | | | | | |

| Asn | Arg | Glu | Ala | Ser | Leu | Tyr | Ser | Pro | Ser | Thr | Leu | Pro | Arg | Asn |
| 850 | | | | | 855 | | | | | 860 | | | | | |

| Ser | Pro | Thr | Lys | Arg | Val | Asp | Val | Pro | Thr | Thr | Pro | Gly | Val | Pro | Met |
| 865 | | | | 870 | | | | | 875 | | | | | 880 | |

| Thr | Ser | Leu | Glu | Arg | Gln | Arg | Gly | Tyr | His | Lys | Asn | Ser | Ser | Gln | Arg |
| | | | | 885 | | | | | 890 | | | | | 895 | |

| His | Ser | Ile | Ser | Ala | Met | Pro | Lys | Asn | Leu | Asn | Ser | Pro | Asn | Gly | Val |
| | | | 900 | | | | | 905 | | | | | 910 | | |

| Leu | Leu | Ser | Arg | Gln | Pro | Ser | Met | Asn | Arg | Gly | Gly | Tyr | Met | Pro | Thr |
| | 915 | | | | | 920 | | | | | 925 | | | | |

| Pro | Thr | Gly | Ala | Lys | Val | Asp | Tyr | Ile | Gln | Gly | Thr | Pro | Val | Ser | Val |
| | 930 | | | | | 935 | | | | | 940 | | | | |

| His | Leu | Gln | Pro | Ser | Leu | Ser | Arg | Gln | Ser | Ser | Tyr | Thr | Ser | Asn | Gly |
| 945 | | | | | 950 | | | | | 955 | | | | | 960 |

| Thr | Leu | Pro | Arg | Thr | Gly | Leu | Lys | Arg | Thr | Pro | Ser | Leu | Lys | Pro | Asp |
| | | | | 965 | | | | | 970 | | | | | 975 | |

| Val | Pro | Pro | Lys | Pro | Ser | Phe | Val | Pro | Gln | Thr | Pro | Ser | Val | Arg | Pro |
| | | 980 | | | | | 985 | | | | | 990 | | | |

| Leu | Asn | Lys | Tyr | Thr | Tyr |
| | | 995 | | | |

<210> SEQ ID NO 25
<211> LENGTH: 5941
<212> TYPE: DNA
<213> ORGANISM: Homo sapiens
<220> FEATURE:
<221> NAME/KEY: CDS
<222> LOCATION: (440)..(3490)

<400> SEQUENCE: 25

```
gcggccgctt cccaccgtcc ctctcccctt actggcagag cgcgctgcgg gcggactccc      60
gggcccggag cagcccaccg gccaccccac cgcccacccg gctcccggtg tctcctcccg     120
gccgctctac ccagcaactt tccgtgcttt gttccccgac tggaaatgct ttacggaagc     180
gtcttggaca gggtctccgc caggcgacaa gagctcggtg ctgagatgtg ttacgttctc     240
atctccccat caattatgga tggaaacaaa taaggaagag tcaattttgc tgagccccct     300
ctccggcaac gagaggcgtt ctgcagccgg gagggagccg ccgctcgcgc cggcagccgc     360
```

```
tggcaggggc atggtgagga ggaaggtagc tcagtggcat ttctgagcag gggccaccct    420
gacttcacct tggcccacc atg agg gtc ttc ctg ctt tgt gcc tac ata ctg    472
                      Met Arg Val Phe Leu Leu Cys Ala Tyr Ile Leu
                       1               5                   10 ctg ctg atg gtt tcc cag ttg agg gca gtc agc ttt cct gaa gat gat    520
Leu Leu Met Val Ser Gln Leu Arg Ala Val Ser Phe Pro Glu Asp Asp
            15                  20                  25 gaa ccc ctt aat act gtc gac tat cac tat tca agg caa tat ccg gtt    568
Glu Pro Leu Asn Thr Val Asp Tyr His Tyr Ser Arg Gln Tyr Pro Val
        30                  35                  40 ttt aga gga cgc cct tca ggc aat gaa tcg cag cac agg ctg gac ttt    616
Phe Arg Gly Arg Pro Ser Gly Asn Glu Ser Gln His Arg Leu Asp Phe
    45                  50                  55 cag ctg atg ttg aaa att cga gac aca ctt tat att gct ggc agg gat    664
Gln Leu Met Leu Lys Ile Arg Asp Thr Leu Tyr Ile Ala Gly Arg Asp
60                  65                  70                  75 caa gtt tat aca gta aac tta aat gaa atg ccc aaa aca gaa gta ata    712
Gln Val Tyr Thr Val Asn Leu Asn Glu Met Pro Lys Thr Glu Val Ile
            80                  85                  90 ccc aac aag aaa ctg aca tgg cga tca aga caa cag gat cga gaa aac    760
Pro Asn Lys Lys Leu Thr Trp Arg Ser Arg Gln Gln Asp Arg Glu Asn
        95                  100                 105 tgt gct atg aaa ggc aag cat aaa gat gaa tgc cac aac ttt atc aaa    808
Cys Ala Met Lys Gly Lys His Lys Asp Glu Cys His Asn Phe Ile Lys
    110                 115                 120 gta ttt gtt cca aga aac gat gag atg gtt ttt gtt tgt ggt acc aat    856
Val Phe Val Pro Arg Asn Asp Glu Met Val Phe Val Cys Gly Thr Asn
125                 130                 135 gca ttc aat ccc atg tgt aga tac tac agg ttg agt acc tta gaa tat    904
Ala Phe Asn Pro Met Cys Arg Tyr Tyr Arg Leu Ser Thr Leu Glu Tyr
140                 145                 150                 155 gat ggg gaa gaa att agt ggc ctg gca aga tgc cca ttt gat gcc aga    952
Asp Gly Glu Glu Ile Ser Gly Leu Ala Arg Cys Pro Phe Asp Ala Arg
            160                 165                 170 caa acc aat gtt gcc ctc ttt gct gat ggg aag ctg tat tct gcc aca    1000
Gln Thr Asn Val Ala Leu Phe Ala Asp Gly Lys Leu Tyr Ser Ala Thr
        175                 180                 185 gtg gct gac ttc ttg gcc agc gat gcc gtt att tat cga agc atg ggt    1048
Val Ala Asp Phe Leu Ala Ser Asp Ala Val Ile Tyr Arg Ser Met Gly
    190                 195                 200 gat gga tct gcc ctt cgc aca ata aaa tat gat tcc aaa tgg ata aaa    1096
Asp Gly Ser Ala Leu Arg Thr Ile Lys Tyr Asp Ser Lys Trp Ile Lys
205                 210                 215 gag cca cac ttt ctt cat gcc ata gaa tat gga aac tat gtc tat ttc    1144
Glu Pro His Phe Leu His Ala Ile Glu Tyr Gly Asn Tyr Val Tyr Phe
220                 225                 230                 235 ttc ttt cga gaa atc gct gtc gaa cat aat aat tta ggc aag gct gtg    1192
Phe Phe Arg Glu Ile Ala Val Glu His Asn Asn Leu Gly Lys Ala Val
            240                 245                 250 tat tcc cgc gtg gcc cgc ata tgt aaa aac gac atg ggt ggt tcc cag    1240
Tyr Ser Arg Val Ala Arg Ile Cys Lys Asn Asp Met Gly Gly Ser Gln
        255                 260                 265 cgg gtc ctg gag aaa cac tgg act tca ttt cta aag gct cgg ctg aac    1288
Arg Val Leu Glu Lys His Trp Thr Ser Phe Leu Lys Ala Arg Leu Asn
    270                 275                 280 tgt tct gtc cct gga gat tcg ttt ttc tac ttt gat gtt ctg cag tct    1336
Cys Ser Val Pro Gly Asp Ser Phe Phe Tyr Phe Asp Val Leu Gln Ser
285                 290                 295
```

```
att aca gac ata ata caa atc aat ggc atc ccc act gtg gtc ggg gtg    1384
Ile Thr Asp Ile Ile Gln Ile Asn Gly Ile Pro Thr Val Val Gly Val
300                 305                 310                 315 ttt acc acg cag ctc aat agc atc cct ggt tct gct gtc tgt gca ttt    1432
Phe Thr Thr Gln Leu Asn Ser Ile Pro Gly Ser Ala Val Cys Ala Phe
                320                 325                 330 agc atg gat gac att gaa aaa gta ttc aaa gga cgg ttt aag gaa cag    1480
Ser Met Asp Asp Ile Glu Lys Val Phe Lys Gly Arg Phe Lys Glu Gln
            335                 340                 345 aaa act cca gat tct gtt tgg aca gca gtt ccc gaa gac aaa gtg cca    1528
Lys Thr Pro Asp Ser Val Trp Thr Ala Val Pro Glu Asp Lys Val Pro
        350                 355                 360 aag cca agg cct ggc tgt tgt gca aaa cac ggc ctt gcc gaa gct tat    1576
Lys Pro Arg Pro Gly Cys Cys Ala Lys His Gly Leu Ala Glu Ala Tyr
    365                 370                 375 aaa acc tcc atc gat ttc ccg gat gaa act ctg tca ttc atc aaa tct    1624
Lys Thr Ser Ile Asp Phe Pro Asp Glu Thr Leu Ser Phe Ile Lys Ser
380                 385                 390                 395 cat ccc ctg atg gac tct gcc gtt cca ccc att gcc gat gag ccc tgg    1672
His Pro Leu Met Asp Ser Ala Val Pro Pro Ile Ala Asp Glu Pro Trp
                400                 405                 410 ttc aca aag act cgg gtc agg tac aga ctg acg gcc atc tca gtg gac    1720
Phe Thr Lys Thr Arg Val Arg Tyr Arg Leu Thr Ala Ile Ser Val Asp
                415                 420                 425 cat tca gcc gga ccc tac cag aac tac aca gtc atc ttt gtt ggc tct    1768
His Ser Ala Gly Pro Tyr Gln Asn Tyr Thr Val Ile Phe Val Gly Ser
            430                 435                 440 gaa gct ggc atg gta ctt aaa gtt ctg gca aag acc agt cct ttc tct    1816
Glu Ala Gly Met Val Leu Lys Val Leu Ala Lys Thr Ser Pro Phe Ser
        445                 450                 455 ttg aac gac agc gta tta ctg gaa gag att gaa gcc tac aac cat gca    1864
Leu Asn Asp Ser Val Leu Leu Glu Glu Ile Glu Ala Tyr Asn His Ala
    460                 465                 470                 475 aag tgc agt gct gag aat gag gaa gac aaa aag gtc atc tca tta cag    1912
Lys Cys Ser Ala Glu Asn Glu Glu Asp Lys Lys Val Ile Ser Leu Gln
                480                 485                 490 ttg gat aaa gat cac cac gct tta tat gtg gcg ttc tct agc tgc att    1960
Leu Asp Lys Asp His His Ala Leu Tyr Val Ala Phe Ser Ser Cys Ile
                495                 500                 505 atc cgc atc ccc ctc agt cgc tgt gag cgt tat gga tca tgt aaa aag    2008
Ile Arg Ile Pro Leu Ser Arg Cys Glu Arg Tyr Gly Ser Cys Lys Lys
            510                 515                 520 tct tgt att gca tct cgt gac ccg tat tgt ggc tgg tta agc cag gga    2056
Ser Cys Ile Ala Ser Arg Asp Pro Tyr Cys Gly Trp Leu Ser Gln Gly
525                 530                 535 tcc tgt ggt aga gtg acc cca ggg atg ctt gct gaa gga tat gaa caa    2104
Ser Cys Gly Arg Val Thr Pro Gly Met Leu Ala Glu Gly Tyr Glu Gln
540                 545                 550                 555 gac aca gaa ttc ggc aac aca gct cat cta ggg gac tgc cat gaa att    2152
Asp Thr Glu Phe Gly Asn Thr Ala His Leu Gly Asp Cys His Glu Ile
                560                 565                 570 ttg cct act tca act aca cca gat tac aaa ata ttt ggc ggt cca aca    2200
Leu Pro Thr Ser Thr Thr Pro Asp Tyr Lys Ile Phe Gly Gly Pro Thr
            575                 580                 585 tct ggt gta cga tgg gaa gtc cag tct gga gag tcc aac cag atg gtc    2248
Ser Gly Val Arg Trp Glu Val Gln Ser Gly Glu Ser Asn Gln Met Val
        590                 595                 600 cac atg aat gtc ctc atc acc tgt gtc ttt gct gct ttt gtt ttg ggg    2296
His Met Asn Val Leu Ile Thr Cys Val Phe Ala Ala Phe Val Leu Gly
    605                 610                 615
```

```
gca ttc att gca ggt gtg gca gta tac tgc tat cga gac atg ttt gtt      2344
Ala Phe Ile Ala Gly Val Ala Val Tyr Cys Tyr Arg Asp Met Phe Val
620             625                 630                 635 cgg aaa aac aga aag atc cat aaa gat gca gag tcc gcc cag tca tgc      2392
Arg Lys Asn Arg Lys Ile His Lys Asp Ala Glu Ser Ala Gln Ser Cys
            640                 645                 650 aca gac tcc agt gga agt ttt gcc aaa ctg aat ggt ctc ttt gac agc      2440
Thr Asp Ser Ser Gly Ser Phe Ala Lys Leu Asn Gly Leu Phe Asp Ser
                655                 660                 665 cct gtc aag gaa tac caa cag aat att gat tct cct aaa ctg tat agt      2488
Pro Val Lys Glu Tyr Gln Gln Asn Ile Asp Ser Pro Lys Leu Tyr Ser
            670                 675                 680 aac ctg cta acc agt cgg aaa gag cta cca ccc aat gga gat act aaa      2536
Asn Leu Leu Thr Ser Arg Lys Glu Leu Pro Pro Asn Gly Asp Thr Lys
685                 690                 695 tcc atg gta atg gac cat cga ggg caa cct cca gag ttg gct gct ctt      2584
Ser Met Val Met Asp His Arg Gly Gln Pro Pro Glu Leu Ala Ala Leu
700                 705                 710                 715 cct act cct gag tct aca ccc gtg ctt cac cag aag acc ctg cag gcc      2632
Pro Thr Pro Glu Ser Thr Pro Val Leu His Gln Lys Thr Leu Gln Ala
                720                 725                 730 atg aag agc cac tca gaa aag gcc cat ggc cat gga gct tca agg aaa      2680
Met Lys Ser His Ser Glu Lys Ala His Gly His Gly Ala Ser Arg Lys
            735                 740                 745 gaa acc cct cag ttt ttt ccg tct agt ccg cca cct cat tcc cca tta      2728
Glu Thr Pro Gln Phe Phe Pro Ser Ser Pro Pro Pro His Ser Pro Leu
                750                 755                 760 agt cat ggg cat atc ccc agt gcc att gtt ctt cca aat gct acc cat      2776
Ser His Gly His Ile Pro Ser Ala Ile Val Leu Pro Asn Ala Thr His
            765                 770                 775 gac tac aac acg tct ttc tca aac tcc aat gct cac aaa gct gaa aag      2824
Asp Tyr Asn Thr Ser Phe Ser Asn Ser Asn Ala His Lys Ala Glu Lys
780                 785                 790                 795 aag ctt caa aac att gat cac cct ctc aca aag tca tcc agt aag aga      2872
Lys Leu Gln Asn Ile Asp His Pro Leu Thr Lys Ser Ser Ser Lys Arg
                800                 805                 810 gat cac cgg cgt tct gtt gat tcc aga aat acc ctc aat gat ctc ctg      2920
Asp His Arg Arg Ser Val Asp Ser Arg Asn Thr Leu Asn Asp Leu Leu
            815                 820                 825 aag cat ctg aat gac cca aat agt aac ccc aaa gcc atc atg gga gac      2968
Lys His Leu Asn Asp Pro Asn Ser Asn Pro Lys Ala Ile Met Gly Asp
830                 835                 840 atc cag atg gca cac cag aac tta atg ctg gat ccc atg gga tcg atg      3016
Ile Gln Met Ala His Gln Asn Leu Met Leu Asp Pro Met Gly Ser Met
            845                 850                 855 tct gag gtc cca cct aaa gtc cct aac cgg gag gca tcg cta tac tcc      3064
Ser Glu Val Pro Pro Lys Val Pro Asn Arg Glu Ala Ser Leu Tyr Ser
860                 865                 870                 875 cct cct tca act ctc ccc aga aat agc cca acc aag cga gtg gat gtc      3112
Pro Pro Ser Thr Leu Pro Arg Asn Ser Pro Thr Lys Arg Val Asp Val
                880                 885                 890 ccc acc act cct gga gtc cca atg act tct ctg gaa aga caa aga ggt      3160
Pro Thr Thr Pro Gly Val Pro Met Thr Ser Leu Glu Arg Gln Arg Gly
            895                 900                 905 tat cac aaa aat tcc tcc cag agg cac tct ata tct gct atg cct aaa      3208
Tyr His Lys Asn Ser Ser Gln Arg His Ser Ile Ser Ala Met Pro Lys
                910                 915                 920 aac tta aac tca cca aat ggt gtt ttg tta tcc aga cag cct agt atg      3256
Asn Leu Asn Ser Pro Asn Gly Val Leu Leu Ser Arg Gln Pro Ser Met
```

```
                    925                 930                 935
aac cgt gga gga tat atg ccc acc ccc act ggg gcg aag gtg gac tat              3304
Asn Arg Gly Gly Tyr Met Pro Thr Pro Thr Gly Ala Lys Val Asp Tyr
940                 945                 950                 955 att cag gga aca cca gtg agt gtt cat ctg cag cct tcc ctc tcc aga              3352
Ile Gln Gly Thr Pro Val Ser Val His Leu Gln Pro Ser Leu Ser Arg
                960                 965                 970 cag agc agc tac acc agt aat ggc act ctt cct agg acg gga cta aag              3400
Gln Ser Ser Tyr Thr Ser Asn Gly Thr Leu Pro Arg Thr Gly Leu Lys
            975                 980                 985 agg acg ccg tcc tta aaa cct gac gtg cca cca aag cct tcc ttt gtt              3448
Arg Thr Pro Ser Leu Lys Pro Asp Val Pro Pro Lys Pro Ser Phe Val
        990                 995                 1000 cct caa acc cca tct gtc aga cca ctg aac aaa tac aca tac                      3490
Pro Gln Thr Pro Ser Val Arg Pro Leu Asn Lys Tyr Thr Tyr
    1005                1010                1015 taggcctcaa gtgtgctatt cccatgtggc tttatcctgt ccgtgttgtt gagaggatga            3550
tgttgtaagg gtaccttaaa acaagagact cgcttgtatt ttaagagaac caagtggcca            3610
aagaaactct ttctaacttt ggcaacatca gaacttgcca catgtagcta ctgcagcaag            3670
gcttctgtgt acttgcctga aaacaaagga aggtgctggt cattccattt cttttgtttg            3730
aagctaaaga gatgtgtagc tcacaggggc taccttacca gtataaagag ctgataacag            3790
tactcagaag aatctgtgaa caaatacttg aaaatgggtt caatgtagac tgccattatg            3850
tgtggtcttc ccattaaatg tgaacatttt aatatgtatg cattcacctt gcctcttgca            3910
caaatgtcaa aaaaagatg gtaatatctc aagaaatga acttgtagat taccaagcag             3970
tttgctaaaa attcaatctt tgacccaagc tgtagcattt tttttcatg tgtggcatct            4030 ttttcatgcc accaacaaac ttgttgtgtg tgtgcgtgtg tgtgtgtgtg tgtgtgtgtg            4090
tgtgtgtgtt ctgtacccac taggatttgt ttaggtgccc attgcatctt tttgtgctat           4150
ggagttgttt acattaagca tgaccgaacg agagacaata ctatttccca caggagtcca           4210
ttgggttcag cttttgaaaga ggaatagaat cgaggctcct ttgaccatca aaatgatgaa          4270
ctttacttat gtggtaccca atgccagaat gtaagagttg caagtgattt tgtgctgcta           4330
ttcattaaaa cttgtattcc agtcttgcca gcttaaggag atcaagatat taagaggtat          4390
ccttgattta ttttccagta ttcagtagta aaattttcct gtccactgtg aatcaaagcc          4450
tgagtcactc tatttaacct tggacacact aataaggttt tattttgatt gtgttcgttt          4510
cccccccccc aatagtaaaa tttctcctcc tttaactcct cctacccccc aaggtaagaa          4570
acaaaaaaca aacaaacaaa caaaatagaa agacaaaaga aagacatatg aaaggaattg          4630
taattggctt aacagaaaca gtctgtaaaa acctaacagt ggtgcaatca tgttgtctgt          4690
gttgtgttat gtgagaattt tctcctaagt catgcaggta atgacaatat actgtaaata          4750
ccacatgtga gttacctga atctgtgcat tttgtgcctt attcatgaga atgatagaag           4810
tactaaaatc tgtcaagtgt tttcagtata gcacattatt tactgagtgc cagttgtaaa          4870
tgtttttcaa ccagcaccta aaaagactct tttcaaaaaa tcacagaaac aacctaggac          4930
aattatttgt tacataatcc gacctcatag cagcattaca ttctttgccg tgataaacat           4990
tccactcctg ctttcctaag gatgaaacag tgataatgtg aactcaaatg aggtttcctg          5050
ggtaatgtga cacctgcaga aactatagag cgtcatttat acgtagtttg gcagaaacca          5110
cttacggcta atgatgcgca accctgctga ctgtttcagt taatatgctg cacaccacac          5170
acttgtttag tgaaccaaat ctagaaagta ccaaggcaga ggtatgctcc tgctgtaatc          5230
```

```
aggcaaatga gttcaactgg atttcttttg acaatactgt tggtacctat tacttggggg    5290
aggacatgtt gcagaagacc agatcatttt tatacagaat gtgaaatact gatacagtta    5350 ttctttttt taaagaacat tgttttataa agaacgtgat ttccagtgat ctctggaagc    5410
gctaaagcta aaatttctgt tcttgaaaca cttcagcttt gcaactaaaa tattacagat    5470
taataataaa ttaaaccaac caatgataaa cactactcag tccaccaaca acaaacgtgt    5530
ttgaattcac cttaccaata ttaatcccag cgtgtgtaaa acagaacagt aactctatgt    5590
gaccccagat aacatttgt aacattgtgc ttccttgtag tttgtaatgt gagttcaatc    5650
agtatttatg ttgaaatttc taacattaaa tctagtctct atcctgttaa tttaattttt    5710
aaatgcttta tccatttgtg caaggtaaa cgcagattgt atctttttta atggtacggc    5770
ataaaaagta accctcaagt gaagtgtctc tatactgttt tatagagtac tttaacatga    5830
atagatacct tgtaaacttg tattgtggat gtgtaaataa tatgtacttt gggtttttaa    5890
caccgcatgt aaagtcaaaa taaaatatac aaatcattat aaaaaaaaaa a            5941
```

<210> SEQ ID NO 26
<211> LENGTH: 1017
<212> TYPE: PRT
<213> ORGANISM: Homo sapiens

<400> SEQUENCE: 26

```
Met Arg Val Phe Leu Leu Cys Ala Tyr Ile Leu Leu Leu Met Val Ser
1               5                   10                  15

Gln Leu Arg Ala Val Ser Phe Pro Glu Asp Asp Glu Pro Leu Asn Thr
            20                  25                  30

Val Asp Tyr His Tyr Ser Arg Gln Tyr Pro Val Phe Arg Gly Arg Pro
        35                  40                  45

Ser Gly Asn Glu Ser Gln His Arg Leu Asp Phe Gln Leu Met Leu Lys
    50                  55                  60

Ile Arg Asp Thr Leu Tyr Ile Ala Gly Arg Asp Gln Val Tyr Thr Val
65                  70                  75                  80

Asn Leu Asn Glu Met Pro Lys Thr Glu Val Ile Pro Asn Lys Lys Leu
                85                  90                  95

Thr Trp Arg Ser Arg Gln Gln Asp Arg Glu Asn Cys Ala Met Lys Gly
            100                 105                 110

Lys His Lys Asp Glu Cys His Asn Phe Ile Lys Val Phe Val Pro Arg
        115                 120                 125

Asn Asp Glu Met Val Phe Val Cys Gly Thr Asn Ala Phe Asn Pro Met
    130                 135                 140

Cys Arg Tyr Tyr Arg Leu Ser Thr Leu Glu Tyr Asp Gly Glu Glu Ile
145                 150                 155                 160

Ser Gly Leu Ala Arg Cys Pro Phe Asp Ala Arg Gln Thr Asn Val Ala
                165                 170                 175

Leu Phe Ala Asp Gly Lys Leu Tyr Ser Ala Thr Val Ala Asp Phe Leu
            180                 185                 190

Ala Ser Asp Ala Val Ile Tyr Arg Ser Met Gly Asp Gly Ser Ala Leu
        195                 200                 205

Arg Thr Ile Lys Tyr Asp Ser Lys Trp Ile Lys Glu Pro His Phe Leu
    210                 215                 220

His Ala Ile Glu Tyr Gly Asn Tyr Val Tyr Phe Phe Arg Glu Ile
225                 230                 235                 240

Ala Val Glu His Asn Asn Leu Gly Lys Ala Val Tyr Ser Arg Val Ala
```

```
                245             250             255
Arg Ile Cys Lys Asn Asp Met Gly Gly Ser Gln Arg Val Leu Glu Lys
            260             265             270

His Trp Thr Ser Phe Leu Lys Ala Arg Leu Asn Cys Ser Val Pro Gly
            275             280             285

Asp Ser Phe Phe Tyr Phe Asp Val Leu Gln Ser Ile Thr Asp Ile Ile
            290             295             300

Gln Ile Asn Gly Ile Pro Thr Val Val Gly Val Phe Thr Thr Gln Leu
305             310             315             320

Asn Ser Ile Pro Gly Ser Ala Val Cys Ala Phe Ser Met Asp Asp Ile
            325             330             335

Glu Lys Val Phe Lys Gly Arg Phe Lys Glu Gln Lys Thr Pro Asp Ser
            340             345             350

Val Trp Thr Ala Val Pro Glu Asp Lys Val Pro Lys Pro Arg Pro Gly
            355             360             365

Cys Cys Ala Lys His Gly Leu Ala Glu Ala Tyr Lys Thr Ser Ile Asp
            370             375             380

Phe Pro Asp Glu Thr Leu Ser Phe Ile Lys Ser His Pro Leu Met Asp
385             390             395             400

Ser Ala Val Pro Pro Ile Ala Asp Glu Pro Trp Phe Thr Lys Thr Arg
            405             410             415

Val Arg Tyr Arg Leu Thr Ala Ile Ser Val Asp His Ser Ala Gly Pro
            420             425             430

Tyr Gln Asn Tyr Thr Val Ile Phe Val Gly Ser Glu Ala Gly Met Val
            435             440             445

Leu Lys Val Leu Ala Lys Thr Ser Pro Phe Ser Leu Asn Asp Ser Val
450             455             460

Leu Leu Glu Glu Ile Glu Ala Tyr Asn His Ala Lys Cys Ser Ala Glu
465             470             475             480

Asn Glu Glu Asp Lys Lys Val Ile Ser Leu Gln Leu Asp Lys Asp His
            485             490             495

His Ala Leu Tyr Val Ala Phe Ser Ser Cys Ile Ile Arg Ile Pro Leu
            500             505             510

Ser Arg Cys Glu Arg Tyr Gly Ser Cys Lys Lys Ser Cys Ile Ala Ser
            515             520             525

Arg Asp Pro Tyr Cys Gly Trp Leu Ser Gln Gly Ser Cys Gly Arg Val
            530             535             540

Thr Pro Gly Met Leu Ala Glu Gly Tyr Glu Gln Asp Thr Glu Phe Gly
545             550             555             560

Asn Thr Ala His Leu Gly Asp Cys His Glu Ile Leu Pro Thr Ser Thr
            565             570             575

Thr Pro Asp Tyr Lys Ile Phe Gly Gly Pro Thr Ser Gly Val Arg Trp
            580             585             590

Glu Val Gln Ser Gly Glu Ser Asn Gln Met Val His Met Asn Val Leu
            595             600             605

Ile Thr Cys Val Phe Ala Ala Phe Val Leu Gly Ala Phe Ile Ala Gly
            610             615             620

Val Ala Val Tyr Cys Tyr Arg Asp Met Phe Val Arg Lys Asn Arg Lys
625             630             635             640

Ile His Lys Asp Ala Glu Ser Ala Gln Ser Cys Thr Asp Ser Ser Gly
            645             650             655

Ser Phe Ala Lys Leu Asn Gly Leu Phe Asp Ser Pro Val Lys Glu Tyr
            660             665             670
```

```
Gln Gln Asn Ile Asp Ser Pro Lys Leu Tyr Ser Asn Leu Leu Thr Ser
            675                 680                 685

Arg Lys Glu Leu Pro Pro Asn Gly Asp Thr Lys Ser Met Val Met Asp
690                 695                 700

His Arg Gly Gln Pro Pro Glu Leu Ala Ala Leu Pro Thr Pro Glu Ser
705                 710                 715                 720

Thr Pro Val Leu His Gln Lys Thr Leu Gln Ala Met Lys Ser His Ser
                725                 730                 735

Glu Lys Ala His Gly His Gly Ala Ser Arg Lys Glu Thr Pro Gln Phe
            740                 745                 750

Phe Pro Ser Ser Pro Pro His Ser Pro Leu Ser His Gly His Ile
        755                 760                 765

Pro Ser Ala Ile Val Leu Pro Asn Ala Thr His Asp Tyr Asn Thr Ser
        770                 775                 780

Phe Ser Asn Ser Asn Ala His Lys Ala Glu Lys Leu Gln Asn Ile
785                 790                 795                 800

Asp His Pro Leu Thr Lys Ser Ser Lys Arg Asp His Arg Arg Ser
                805                 810                 815

Val Asp Ser Arg Asn Thr Leu Asn Asp Leu Leu Lys His Leu Asn Asp
            820                 825                 830

Pro Asn Ser Asn Pro Lys Ala Ile Met Gly Asp Ile Gln Met Ala His
            835                 840                 845

Gln Asn Leu Met Leu Asp Pro Met Gly Ser Met Ser Glu Val Pro Pro
850                 855                 860

Lys Val Pro Asn Arg Glu Ala Ser Leu Tyr Ser Pro Pro Ser Thr Leu
865                 870                 875                 880

Pro Arg Asn Ser Pro Thr Lys Arg Val Asp Val Pro Thr Thr Pro Gly
                885                 890                 895

Val Pro Met Thr Ser Leu Glu Arg Gln Arg Gly Tyr His Lys Asn Ser
            900                 905                 910

Ser Gln Arg His Ser Ile Ser Ala Met Pro Lys Asn Leu Asn Ser Pro
        915                 920                 925

Asn Gly Val Leu Leu Ser Arg Gln Pro Ser Met Asn Arg Gly Gly Tyr
        930                 935                 940

Met Pro Thr Pro Thr Gly Ala Lys Val Asp Tyr Ile Gln Gly Thr Pro
945                 950                 955                 960

Val Ser Val His Leu Gln Pro Ser Leu Ser Arg Gln Ser Ser Tyr Thr
                965                 970                 975

Ser Asn Gly Thr Leu Pro Arg Thr Gly Leu Lys Arg Thr Pro Ser Leu
            980                 985                 990

Lys Pro Asp Val Pro Lys Pro Ser Phe Val Pro Gln Thr Pro Ser
        995                 1000                 1005

Val Arg Pro Leu Asn Lys Tyr Thr Tyr
    1010                 1015

<210> SEQ ID NO 27
<211> LENGTH: 6109
<212> TYPE: DNA
<213> ORGANISM: Homo sapiens
<220> FEATURE:
<221> NAME/KEY: CDS
<222> LOCATION: (440)..(3658)

<400> SEQUENCE: 27
gcggccgctt cccaccgtcc ctctccccctt actggcagag cgcgctgcgg gcggactccc    60
```

```
gggcccggag cagcccaccg gccacccac cgcccaccg gctcccggtg tctcctcccg      120
gccgctctac ccagcaactt tccgtgcttt gttccccgac tggaaatgct ttacggaagc      180
gtcttggaca gggtctccgc caggcgacaa gagctcggtg ctgagatgtg ttacgttctc      240
atctccccat caattatgga tggaaacaaa taaggaagag tcaattttgc tgagcccctt      300
ctccggcaac gagaggcgtt ctgcagccgg gagggagccg ccgctcgcgc cggcagccgc      360 tgcaggggc atggtgagga ggaaggtagc tcagtggcat ttctgagcag gggccaccct      420
gacttcacct tggcccacc atg agg gtc ttc ctg ctt tgt gcc tac ata ctg      472
                     Met Arg Val Phe Leu Leu Cys Ala Tyr Ile Leu
                      1               5                      10 ctg ctg atg gtt tcc cag ttg agg gca gtc agc ttt cct gaa gat gat      520
Leu Leu Met Val Ser Gln Leu Arg Ala Val Ser Phe Pro Glu Asp Asp
         15                  20                  25 gaa ccc ctt aat act gtc gac tat cac tat tca agg caa tat ccg gtt      568
Glu Pro Leu Asn Thr Val Asp Tyr His Tyr Ser Arg Gln Tyr Pro Val
             30                  35                  40 ttt aga gga cgc cct tca ggc aat gaa tcg cag cac agg ctg gac ttt      616
Phe Arg Gly Arg Pro Ser Gly Asn Glu Ser Gln His Arg Leu Asp Phe
     45                  50                  55 cag ctg atg ttg aaa att cga gac aca ctt tat att gct ggc agg gat      664
Gln Leu Met Leu Lys Ile Arg Asp Thr Leu Tyr Ile Ala Gly Arg Asp
 60                  65                  70                  75 caa gtt tat aca gta aac tta aat gaa atg ccc aaa aca gaa gta ata      712
Gln Val Tyr Thr Val Asn Leu Asn Glu Met Pro Lys Thr Glu Val Ile
                 80                  85                  90 ccc aac aag aaa ctg aca tgg cga tca aga caa cag gat cga gaa aac      760
Pro Asn Lys Lys Leu Thr Trp Arg Ser Arg Gln Gln Asp Arg Glu Asn
             95                 100                 105 tgt gct atg aaa ggc aag cat aaa gat gaa tgc cac aac ttt atc aaa      808
Cys Ala Met Lys Gly Lys His Lys Asp Glu Cys His Asn Phe Ile Lys
         110                 115                 120 gta ttt gtt cca aga aac gat gag atg gtt ttt gtt tgt ggt acc aat      856
Val Phe Val Pro Arg Asn Asp Glu Met Val Phe Val Cys Gly Thr Asn
     125                 130                 135 gca ttc aat ccc atg tgt aga tac tac agg ttg agt acc tta gaa tat      904
Ala Phe Asn Pro Met Cys Arg Tyr Tyr Arg Leu Ser Thr Leu Glu Tyr
140                 145                 150                 155 gat ggg gaa gaa att agt ggc ctg gca aga tgc cca ttt gat gcc aga      952
Asp Gly Glu Glu Ile Ser Gly Leu Ala Arg Cys Pro Phe Asp Ala Arg
                 160                 165                 170 caa acc aat gtt gcc ctc ttt gct gat ggg aag ctg tat tct gcc aca     1000
Gln Thr Asn Val Ala Leu Phe Ala Asp Gly Lys Leu Tyr Ser Ala Thr
             175                 180                 185 gtg gct gac ttc ttg gcc agc gat gcc gtt att tat cga agc atg ggt     1048
Val Ala Asp Phe Leu Ala Ser Asp Ala Val Ile Tyr Arg Ser Met Gly
         190                 195                 200 gat gga tct gcc ctt cgc aca ata aaa tat gat tcc aaa tgg ata aaa     1096
Asp Gly Ser Ala Leu Arg Thr Ile Lys Tyr Asp Ser Lys Trp Ile Lys
     205                 210                 215 gag cca cac ttt ctt cat gcc ata gaa tat gga aac tat gtc tat ttc     1144
Glu Pro His Phe Leu His Ala Ile Glu Tyr Gly Asn Tyr Val Tyr Phe
220                 225                 230                 235 ttc ttt cga gaa atc gct gtc gaa cat aat aat tta ggc aag gct gtg     1192
Phe Phe Arg Glu Ile Ala Val Glu His Asn Asn Leu Gly Lys Ala Val
                 240                 245                 250 tat tcc cgc gtg gcc cgc ata tgt aaa aac gac atg ggt ggt tcc cag     1240
Tyr Ser Arg Val Ala Arg Ile Cys Lys Asn Asp Met Gly Gly Ser Gln
```

```
                      255                     260                     265
cgg gtc ctg gag aaa cac tgg act tca ttt cta aag gct cgg ctg aac        1288
Arg Val Leu Glu Lys His Trp Thr Ser Phe Leu Lys Ala Arg Leu Asn
                      270                     275                     280 tgt tct gtc cct gga gat tcg ttt ttc tac ttt gat gtt ctg cag tct        1336
Cys Ser Val Pro Gly Asp Ser Phe Phe Tyr Phe Asp Val Leu Gln Ser
        285                     290                     295 att aca gac ata ata caa atc aat ggc atc ccc act gtg gtc ggg gtg        1384
Ile Thr Asp Ile Ile Gln Ile Asn Gly Ile Pro Thr Val Val Gly Val
300                     305                     310                     315 ttt acc acg cag ctc aat agc atc cct ggt tct gct gtc tgt gca ttt        1432
Phe Thr Thr Gln Leu Asn Ser Ile Pro Gly Ser Ala Val Cys Ala Phe
                320                     325                     330 agc atg gat gac att gaa aaa gta ttc aaa gga cgg ttt aag gaa cag        1480
Ser Met Asp Asp Ile Glu Lys Val Phe Lys Gly Arg Phe Lys Glu Gln
        335                     340                     345 aaa act cca gat tct gtt tgg aca gca gtt ccc gaa gac aaa gtg cca        1528
Lys Thr Pro Asp Ser Val Trp Thr Ala Val Pro Glu Asp Lys Val Pro
350                     355                     360 aag cca agg cct ggc tgt tgt gca aaa cac ggc ctt gcc gaa gct tat        1576
Lys Pro Arg Pro Gly Cys Cys Ala Lys His Gly Leu Ala Glu Ala Tyr
                365                     370                     375 aaa acc tcc atc gat ttc ccg gat gaa act ctg tca ttc atc aaa tct        1624
Lys Thr Ser Ile Asp Phe Pro Asp Glu Thr Leu Ser Phe Ile Lys Ser
380                     385                     390                     395 cat ccc ctg atg gac tct gcc gtt cca ccc att gcc gat gag ccc tgg        1672
His Pro Leu Met Asp Ser Ala Val Pro Pro Ile Ala Asp Glu Pro Trp
                        400                     405                     410 ttc aca aag act cgg gtc agg tac aga ctg acg gcc atc tca gtg gac        1720
Phe Thr Lys Thr Arg Val Arg Tyr Arg Leu Thr Ala Ile Ser Val Asp
                415                     420                     425 cat tca gcc gga ccc tac cag aac tac aca gtc atc ttt gtt ggc tct        1768
His Ser Ala Gly Pro Tyr Gln Asn Tyr Thr Val Ile Phe Val Gly Ser
                430                     435                     440 gaa gct ggc atg gta ctt aaa gtt ctg gca aag acc agt cct ttc tct        1816
Glu Ala Gly Met Val Leu Lys Val Leu Ala Lys Thr Ser Pro Phe Ser
        445                     450                     455 ttg aac gac agc gta tta ctg gaa gag att gaa gcc tac aac cat gca        1864
Leu Asn Asp Ser Val Leu Leu Glu Glu Ile Glu Ala Tyr Asn His Ala
460                     465                     470                     475 aag tgc agt gct gag aat gag gaa gac aaa aag gtc atc tca tta cag        1912
Lys Cys Ser Ala Glu Asn Glu Glu Asp Lys Lys Val Ile Ser Leu Gln
                        480                     485                     490 ttg gat aaa gat cac cac gct tta tat gtg gcg ttc tct agc tgc att        1960
Leu Asp Lys Asp His His Ala Leu Tyr Val Ala Phe Ser Ser Cys Ile
                495                     500                     505 atc cgc atc ccc ctc agt cgc tgt gag cgt tat gga tca tgt aaa aag        2008
Ile Arg Ile Pro Leu Ser Arg Cys Glu Arg Tyr Gly Ser Cys Lys Lys
        510                     515                     520 tct tgt att gca tct cgt gac ccg tat tgt ggc tgg tta agc cag gga        2056
Ser Cys Ile Ala Ser Arg Asp Pro Tyr Cys Gly Trp Leu Ser Gln Gly
525                     530                     535 tcc tgt ggt aga gtg acc cca ggg atg ctt gct gaa gga tat gaa caa        2104
Ser Cys Gly Arg Val Thr Pro Gly Met Leu Ala Glu Gly Tyr Glu Gln
540                     545                     550                     555 gac aca gaa ttc ggc aac aca gct cat cta ggg gac tgc cat gaa att        2152
Asp Thr Glu Phe Gly Asn Thr Ala His Leu Gly Asp Cys His Glu Ile
                        560                     565                     570 ttg cct act tca act aca cca gat tac aaa ata ttt ggc ggt cca aca        2200
Leu Pro Thr Ser Thr Thr Pro Asp Tyr Lys Ile Phe Gly Gly Pro Thr
```

|  |  |  |  |  |  |  |  |  |  |  |  |  |  |
|---|---|---|---|---|---|---|---|---|---|---|---|---|---|
| Leu | Pro | Thr | Ser<br>575 | Thr | Thr | Pro | Asp<br>580 | Tyr | Lys | Ile | Phe | Gly<br>585 | Gly | Pro | Thr |

```
tct gac atg gag gta tct tca tct tct gtt acc aca atg gca agt atc      2248
Ser Asp Met Glu Val Ser Ser Ser Ser Val Thr Thr Met Ala Ser Ile
        590                 595                 600 cca gaa atc aca cct aaa gtg att gat acc tgg aga cct aaa ctg aca      2296
Pro Glu Ile Thr Pro Lys Val Ile Asp Thr Trp Arg Pro Lys Leu Thr
605                 610                 615 agc tct cgg aaa ttt gta gtt caa gat gat cca aac act tct gat ttt      2344
Ser Ser Arg Lys Phe Val Val Gln Asp Asp Pro Asn Thr Ser Asp Phe
620                 625                 630                 635 act gat cct tta tcg ggt atc cca aag ggt gta cga tgg gaa gtc cag      2392
Thr Asp Pro Leu Ser Gly Ile Pro Lys Gly Val Arg Trp Glu Val Gln
                640                 645                 650 tct gga gag tcc aac cag atg gtc cac atg aat gtc ctc atc acc tgt      2440
Ser Gly Glu Ser Asn Gln Met Val His Met Asn Val Leu Ile Thr Cys
        655                 660                 665 gtc ttt gct gct ttt gtt ttg ggg gca ttc att gca ggt gtg gca gta      2488
Val Phe Ala Ala Phe Val Leu Gly Ala Phe Ile Ala Gly Val Ala Val
670                 675                 680 tac tgc tat cga gac atg ttt gtt cgg aaa aac aga aag atc cat aaa      2536
Tyr Cys Tyr Arg Asp Met Phe Val Arg Lys Asn Arg Lys Ile His Lys
            685                 690                 695 gat gca gag tcc gcc cag tca tgc aca gac tcc agt gga agt ttt gcc      2584
Asp Ala Glu Ser Ala Gln Ser Cys Thr Asp Ser Ser Gly Ser Phe Ala
700                 705                 710                 715 aaa ctg aat ggt ctc ttt gac agc cct gtc aag gaa tac caa cag aat      2632
Lys Leu Asn Gly Leu Phe Asp Ser Pro Val Lys Glu Tyr Gln Gln Asn
                720                 725                 730 att gat tct cct aaa ctg tat agt aac ctg cta acc agt cgg aaa gag      2680
Ile Asp Ser Pro Lys Leu Tyr Ser Asn Leu Leu Thr Ser Arg Lys Glu
        735                 740                 745 cta cca ccc aat gga gat act aaa tcc atg gta atg gac cat cga ggg      2728
Leu Pro Pro Asn Gly Asp Thr Lys Ser Met Val Met Asp His Arg Gly
750                 755                 760 caa cct cca gag ttg gct gct ctt cct act cct gag tct aca ccc gtg      2776
Gln Pro Pro Glu Leu Ala Ala Leu Pro Thr Pro Glu Ser Thr Pro Val
            765                 770                 775 ctt cac cag aag acc ctg cag gcc atg aag agc cac tca gaa aag gcc      2824
Leu His Gln Lys Thr Leu Gln Ala Met Lys Ser His Ser Glu Lys Ala
780                 785                 790                 795 cat ggc cat gga gct tca agg aaa gaa acc cct cag ttt ttt ccg tct      2872
His Gly His Gly Ala Ser Arg Lys Glu Thr Pro Gln Phe Phe Pro Ser
                800                 805                 810 agt ccg cca cct cat tcc cca tta agt cat ggg cat atc ccc agt gcc      2920
Ser Pro Pro Pro His Ser Pro Leu Ser His Gly His Ile Pro Ser Ala
        815                 820                 825 att gtt ctt cca aat gct acc cat gac tac aac acg tct ttc tca aac      2968
Ile Val Leu Pro Asn Ala Thr His Asp Tyr Asn Thr Ser Phe Ser Asn
830                 835                 840 tcc aat gct cac aaa gct gaa aag aag ctt caa aac att gat cac cct      3016
Ser Asn Ala His Lys Ala Glu Lys Lys Leu Gln Asn Ile Asp His Pro
            845                 850                 855 ctc aca aag tca tcc agt aag aga gat cac cgg cgt tct gtt gat tcc      3064
Leu Thr Lys Ser Ser Ser Lys Arg Asp His Arg Arg Ser Val Asp Ser
860                 865                 870                 875 aga aat acc ctc aat gat ctc ctg aag cat ctg aat gac cca aat agt      3112
Arg Asn Thr Leu Asn Asp Leu Leu Lys His Leu Asn Asp Pro Asn Ser
                880                 885                 890
```

| | |
|---|---|
| aac ccc aaa gcc atc atg gga gac atc cag atg gca cac cag aac tta<br>Asn Pro Lys Ala Ile Met Gly Asp Ile Gln Met Ala His Gln Asn Leu<br>           895                 900                 905 | 3160 |
| atg ctg gat ccc atg gga tcg atg tct gag gtc cca cct aaa gtc cct<br>Met Leu Asp Pro Met Gly Ser Met Ser Glu Val Pro Pro Lys Val Pro<br>     910                915                 920 | 3208 |
| aac cgg gag gca tcg cta tac tcc cct cct tca act ctc ccc aga aat<br>Asn Arg Glu Ala Ser Leu Tyr Ser Pro Pro Ser Thr Leu Pro Arg Asn<br>925                 930                 935 | 3256 |
| agc cca acc aag cga gtg gat gtc ccc acc act cct gga gtc cca atg<br>Ser Pro Thr Lys Arg Val Asp Val Pro Thr Thr Pro Gly Val Pro Met<br>940                 945                 950                 955 | 3304 |
| act tct ctg gaa aga caa aga ggt tat cac aaa aat tcc tcc cag agg<br>Thr Ser Leu Glu Arg Gln Arg Gly Tyr His Lys Asn Ser Ser Gln Arg<br>                 960                 965                 970 | 3352 |
| cac tct ata tct gct atg cct aaa aac tta aac tca cca aat ggt gtt<br>His Ser Ile Ser Ala Met Pro Lys Asn Leu Asn Ser Pro Asn Gly Val<br>           975                 980                 985 | 3400 |
| ttg tta tcc aga cag cct agt atg aac cgt gga gga tat  atg ccc acc<br>Leu Leu Ser Arg Gln Pro Ser Met Asn Arg Gly Gly Tyr  Met Pro Thr<br>         990                   995                  1000 | 3448 |
| ccc act  ggg gcg aag gtg gac  tat att cag gga aca  cca gtg agt<br>Pro Thr  Gly Ala Lys Val Asp  Tyr Ile Gln Gly Thr  Pro Val Ser<br>    1005                    1010                 1015 | 3493 |
| gtt cat ctg cag cct tcc ctc tcc aga cag agc agc tac acc agt<br>Val His Leu Gln Pro Ser Leu Ser Arg Gln Ser Ser Tyr Thr Ser<br>1020                   1025                 1030 | 3538 |
| aat ggc act ctt cct agg acg  gga cta aag agg acg  ccg tcc tta<br>Asn Gly Thr Leu Pro Arg Thr  Gly Leu Lys Arg Thr  Pro Ser Leu<br>    1035                  1040                 1045 | 3583 |
| aaa cct gac gtg cca cca aag cct tcc ttt gtt cct  caa acc cca<br>Lys Pro Asp Val Pro Pro Lys Pro Ser Phe Val Pro  Gln Thr Pro<br>    1050                  1055                 1060 | 3628 |
| tct gtc aga cca ctg aac aaa  tac aca tac taggcctcaa gtgtgctatt<br>Ser Val Arg Pro Leu Asn Lys  Tyr Thr Tyr<br>    1065                  1070 | 3678 |
| cccatgtggc tttatcctgt ccgtgttgtt gagaggatga tgttgtaagg gtaccttaaa | 3738 |
| acaagagact cgcttgtatt ttaagagaac caagtggcca aagaaactct ttctaacttt | 3798 |
| ggcaacatca gaacttgcca catgtagcta ctgcagcaag gcttctgtgt acttgcctga | 3858 |
| aaacaaagga aggtgctggt cattccattt cttttgtttg aagctaaaga gatgtgtagc | 3918 |
| tcacaggggc taccttacca gtataaagag ctgataacag tactcagaag aatctgtgaa | 3978 |
| caaatacttg aaaatgggtt caatgtagac tgccattatg tgtggtcttc ccattaaatg | 4038 |
| tgaacatttt aatatgtatg cattcacctt gcctcttgca caaatgtcaa aaaaagatg | 4098 |
| gtaatatctc aaagaaatga acttgtagat taccaagcag tttgctaaaa attcaatctt | 4158 |
| tgacccaagc tgtagcattt tttttcatg tgtggcatct ttttcatgcc accaacaaac | 4218 |
| ttgttgtgtg tgtgcgtgtg tgtgtgtgtg tgtgtgtgtg tgtgtgtgtt ctgtacccac | 4278 |
| taggatttgt ttaggtgccc attgcatctt tttgtgctat ggagttgttt acattaagca | 4338 |
| tgaccgaacg agagacaata ctatttccca caggagtcca ttgggttcag ctttgaaaga | 4398 |
| ggaatagaat cgaggctcct tgaccatca aaatgatgaa ctttacttat gtggtaccca | 4458 |
| atgccagaat gtaagagttg caagtgattt tgtgctgcta ttcattaaaa cttgtattcc | 4518 |
| agtcttgcca gcttaaggag atcaagatat taagaggtat ccttgattta ttttccagta | 4578 |
| ttcagtagta aaattttcct gtccactgtg aatcaaagcc tgagtcactc tatttaacct | 4638 |

```
tggacacact aataaggttt tattttgatt gtgttcgttt ccccccccc aatagtaaaa    4698 tttctcctcc tttaactcct cctacccccc aaggtaagaa acaaaaaaca aacaaacaaa    4758
caaaaataga agacaaaaga aagacatatg aaaggaattg taattggctt aacagaaaca    4818
gtctgtaaaa acctaacagt ggtgcaatca tgttgtctgt gttgtgttat gtgagaattt    4878
tctcctaagt catgcaggta atgacaatat actgtaaata ccacatgtga gtttacctga    4938
atctgtgcat tttgtgcctt attcatgaga atgatagaag tactaaaatc tgtcaagtgt    4998
tttcagtata gcacattatt tactgagtgc cagttgtaaa tgttttttcaa ccagcaccta    5058 aaaagactct tttcaaaaaa tcacagaaac aacctaggac aattatttgt tacataatcc    5118
gacctcatag cagcattaca ttctttgccg tgataaacat tccactcctg ctttcctaag    5178
gatgaaacag tgataatgtg aactcaaatg aggtttcctg ggtaatgtga cacctgcaga    5238
aactatagag cgtcatttat acgtagtttg gcagaaacca cttacggctg atgatgcgca    5298
accctgctga ctgtttcagt taatatgctg cacaccacac acttgtttag tgaaccaaat    5358
ctagaaagta ccaaggcaga ggtatgctcc tgctgtaatc aggcaaatga gttcaactgg    5418
atttcttttg acaatactgt tggtacctat tacttggggg aggacatgtt gcagaagacc    5478
agatcatttt tatacagaat gtgaaatact gatacagtta ttcttttttt taaagaacat    5538 tgtttttataa agaacgtgat ttccagtgat ctctggaagc gctaaagcta aaatttctgt    5598
tcttgaaaca cttcagcttt gcaactaaaa tattacagat taataataaa ttaaaccaac    5658
caatgataaa cactactcag tccaccaaca acaaacgtgt ttgaattcac cttaccaata    5718
ttaatcccag cgtgtgtaaa acagaacagt aactctatgt gacccccagat aacatttttgt    5778 aacattgtgc ttccttgtag tttgtaatgt gagttcaatc agtatttatg ttgaaatttc    5838
taacattaaa tctagtctct atcctgttaa tttaattttt aaatgctttta tccatttgtg    5898 caaaggtaaa cgcagattgt atcttttttta atggtacggc ataaaaagta accctcaagt    5958
gaagtgtctc tatactgttt tatagagtac tttaacatga atagatacct tgtaaacttg    6018
tattgtggat gtgtaaataa tatgtacttt gggttttttaa caccgcatgt aaagtcaaaa    6078
taaaatatac aaatcattat aaaaaaaaaa a                                   6109
```

<210> SEQ ID NO 28
<211> LENGTH: 1073
<212> TYPE: PRT
<213> ORGANISM: Homo sapiens

<400> SEQUENCE: 28

```
Met Arg Val Phe Leu Leu Cys Ala Tyr Ile Leu Leu Met Val Ser
1               5                   10                  15

Gln Leu Arg Ala Val Ser Phe Pro Glu Asp Asp Glu Pro Leu Asn Thr
            20                  25                  30

Val Asp Tyr His Tyr Ser Arg Gln Tyr Pro Val Phe Arg Gly Arg Pro
        35                  40                  45

Ser Gly Asn Glu Ser Gln His Arg Leu Asp Phe Gln Leu Met Leu Lys
    50                  55                  60

Ile Arg Asp Thr Leu Tyr Ile Ala Gly Arg Asp Gln Val Tyr Thr Val
65                  70                  75                  80

Asn Leu Asn Glu Met Pro Lys Thr Glu Val Ile Pro Asn Lys Lys Leu
                85                  90                  95

Thr Trp Arg Ser Arg Gln Gln Asp Arg Glu Asn Cys Ala Met Lys Gly
            100                 105                 110
```

-continued

```
Lys His Lys Asp Glu Cys His Asn Phe Ile Lys Val Phe Val Pro Arg
    115                 120                 125
Asn Asp Glu Met Val Phe Val Cys Gly Thr Asn Ala Phe Asn Pro Met
130                 135                 140
Cys Arg Tyr Tyr Arg Leu Ser Thr Leu Glu Tyr Asp Gly Glu Ile
145                 150                 155                 160
Ser Gly Leu Ala Arg Cys Pro Phe Asp Ala Arg Gln Thr Asn Val Ala
                165                 170                 175
Leu Phe Ala Asp Gly Lys Leu Tyr Ser Ala Thr Val Ala Asp Phe Leu
            180                 185                 190
Ala Ser Asp Ala Val Ile Tyr Arg Ser Met Gly Asp Gly Ser Ala Leu
        195                 200                 205
Arg Thr Ile Lys Tyr Asp Ser Lys Trp Ile Lys Glu Pro His Phe Leu
    210                 215                 220
His Ala Ile Glu Tyr Gly Asn Tyr Val Tyr Phe Phe Phe Arg Glu Ile
225                 230                 235                 240
Ala Val Glu His Asn Asn Leu Gly Lys Ala Val Tyr Ser Arg Val Ala
                245                 250                 255
Arg Ile Cys Lys Asn Asp Met Gly Gly Ser Gln Arg Val Leu Glu Lys
            260                 265                 270
His Trp Thr Ser Phe Leu Lys Ala Arg Leu Asn Cys Ser Val Pro Gly
        275                 280                 285
Asp Ser Phe Phe Tyr Phe Asp Val Leu Gln Ser Ile Thr Asp Ile Ile
    290                 295                 300
Gln Ile Asn Gly Ile Pro Thr Val Val Gly Val Phe Thr Thr Gln Leu
305                 310                 315                 320
Asn Ser Ile Pro Gly Ser Ala Val Cys Ala Phe Ser Met Asp Asp Ile
                325                 330                 335
Glu Lys Val Phe Lys Gly Arg Phe Lys Glu Gln Lys Thr Pro Asp Ser
            340                 345                 350
Val Trp Thr Ala Val Pro Glu Asp Lys Val Pro Lys Pro Arg Pro Gly
        355                 360                 365
Cys Cys Ala Lys His Gly Leu Ala Glu Ala Tyr Lys Thr Ser Ile Asp
    370                 375                 380
Phe Pro Asp Glu Thr Leu Ser Phe Ile Lys Ser His Pro Leu Met Asp
385                 390                 395                 400
Ser Ala Val Pro Pro Ile Ala Asp Glu Pro Trp Phe Thr Lys Thr Arg
                405                 410                 415
Val Arg Tyr Arg Leu Thr Ala Ile Ser Val Asp His Ser Ala Gly Pro
            420                 425                 430
Tyr Gln Asn Tyr Thr Val Ile Phe Val Gly Ser Glu Ala Gly Met Val
        435                 440                 445
Leu Lys Val Leu Ala Lys Thr Ser Pro Phe Ser Leu Asn Asp Ser Val
    450                 455                 460
Leu Leu Glu Glu Ile Glu Ala Tyr Asn His Ala Lys Cys Ser Ala Glu
465                 470                 475                 480
Asn Glu Glu Asp Lys Lys Val Ile Ser Leu Gln Leu Asp Lys Asp His
                485                 490                 495
His Ala Leu Tyr Val Ala Phe Ser Ser Cys Ile Ile Arg Ile Pro Leu
            500                 505                 510
Ser Arg Cys Glu Arg Tyr Gly Ser Cys Lys Lys Ser Cys Ile Ala Ser
        515                 520                 525
```

-continued

Arg Asp Pro Tyr Cys Gly Trp Leu Ser Gln Gly Ser Cys Gly Arg Val
530                     535                 540

Thr Pro Gly Met Leu Ala Glu Gly Tyr Glu Gln Asp Thr Glu Phe Gly
545                 550                 555                 560

Asn Thr Ala His Leu Gly Asp Cys His Glu Ile Leu Pro Thr Ser Thr
            565                 570                 575

Thr Pro Asp Tyr Lys Ile Phe Gly Gly Pro Thr Ser Asp Met Glu Val
            580                 585                 590

Ser Ser Ser Ser Val Thr Thr Met Ala Ser Ile Pro Glu Ile Thr Pro
        595                 600                 605

Lys Val Ile Asp Thr Trp Arg Pro Lys Leu Thr Ser Ser Arg Lys Phe
610                 615                 620

Val Val Gln Asp Asp Pro Asn Thr Ser Asp Phe Thr Asp Pro Leu Ser
625                 630                 635                 640

Gly Ile Pro Lys Gly Val Arg Trp Glu Val Gln Ser Gly Glu Ser Asn
            645                 650                 655

Gln Met Val His Met Asn Val Leu Ile Thr Cys Val Phe Ala Ala Phe
            660                 665                 670

Val Leu Gly Ala Phe Ile Ala Gly Val Ala Val Tyr Cys Tyr Arg Asp
        675                 680                 685

Met Phe Val Arg Lys Asn Arg Lys Ile His Lys Asp Ala Glu Ser Ala
690                 695                 700

Gln Ser Cys Thr Asp Ser Ser Gly Ser Phe Ala Lys Leu Asn Gly Leu
705                 710                 715                 720

Phe Asp Ser Pro Val Lys Glu Tyr Gln Gln Asn Ile Asp Ser Pro Lys
            725                 730                 735

Leu Tyr Ser Asn Leu Leu Thr Ser Arg Lys Glu Leu Pro Pro Asn Gly
            740                 745                 750

Asp Thr Lys Ser Met Val Met Asp His Arg Gly Gln Pro Pro Glu Leu
        755                 760                 765

Ala Ala Leu Pro Thr Pro Glu Ser Thr Pro Val Leu His Gln Lys Thr
770                 775                 780

Leu Gln Ala Met Lys Ser His Ser Glu Lys Ala His Gly His Gly Ala
785                 790                 795                 800

Ser Arg Lys Glu Thr Pro Gln Phe Phe Pro Ser Ser Pro Pro His Ser
            805                 810                 815

Ser Pro Leu Ser His Gly His Ile Pro Ser Ala Ile Val Leu Pro Asn
        820                 825                 830

Ala Thr His Asp Tyr Asn Thr Ser Phe Ser Asn Ser Asn Ala His Lys
        835                 840                 845

Ala Glu Lys Lys Leu Gln Asn Ile Asp His Pro Leu Thr Lys Ser Ser
850                 855                 860

Ser Lys Arg Asp His Arg Arg Ser Val Asp Ser Arg Asn Thr Leu Asn
865                 870                 875                 880

Asp Leu Leu Lys His Leu Asn Asp Pro Asn Ser Asn Pro Lys Ala Ile
            885                 890                 895

Met Gly Asp Ile Gln Met Ala His Gln Asn Leu Met Leu Asp Pro Met
        900                 905                 910

Gly Ser Met Ser Glu Val Pro Lys Val Pro Asn Arg Glu Ala Ser
        915                 920                 925

Leu Tyr Ser Pro Pro Ser Thr Leu Pro Arg Asn Ser Pro Thr Lys Arg
930                 935                 940

Val Asp Val Pro Thr Thr Pro Gly Val Pro Met Thr Ser Leu Glu Arg

```
                       945                 950                 955                 960
           Gln Arg Gly Tyr His Lys Asn Ser Ser Gln Arg His Ser Ile Ser Ala
                           965                 970                 975

Met Pro Lys Asn Leu Asn Ser Pro Asn Gly Val Leu Leu Ser Arg Gln
                           980                 985                 990

Pro Ser Met Asn Arg Gly Gly Tyr  Met Pro Thr Pro Thr  Gly Ala Lys
                           995                1000                1005

Val Asp  Tyr Ile Gln Gly Thr  Pro Val Ser Val His  Leu Gln Pro
               1010                1015                1020

Ser Leu  Ser Arg Gln Ser Ser  Tyr Thr Ser Asn Gly  Thr Leu Pro
               1025                1030                1035

Arg Thr  Gly Leu Lys Arg Thr  Pro Ser Leu Lys Pro  Asp Val Pro
               1040                1045                1050

Pro Lys  Pro Ser Phe Val Pro  Gln Thr Pro Ser Val  Arg Pro Leu
               1055                1060                1065

Asn Lys  Tyr Thr Tyr
               1070

<210> SEQ ID NO 29
<211> LENGTH: 5919
<212> TYPE: DNA
<213> ORGANISM: Homo sapiens
<220> FEATURE:
<221> NAME/KEY: CDS
<222> LOCATION: (440)..(2230)

<400> SEQUENCE: 29
gcggccgctt cccaccgtcc ctctcccctt actggcagag cgcgctgcgg gcggactccc      60
gggcccggag cagcccaccg gccaccccac cgcccaccca gctcccggtg tctcctcccg     120
gccgctctac ccagcaactt tccgtgcttt gttccccgac tggaaatgct ttacggaagc     180
gtcttggaca gggtctccgc caggcgacaa gagctcggtg ctgagatgtg ttacgttctc     240
atctccccat caattatgga tggaaacaaa taaggaagag tcaattttgc tgagcccctt     300
ctccggcaac gagaggcgtt ctgcagccgg gagggagccg ccgctcgcgc cggcagccgc     360
tggcaggggc atggtgagga ggaaggtagc tcagtggcat ttctgagcag gggccaccct     420
gacttcacct tggcccacc atg agg gtc ttc ctg ctt tgt gcc tac ata ctg      472
                      Met Arg Val Phe Leu Leu Cys Ala Tyr Ile Leu
                       1               5                  10 ctg ctg atg gtt tcc cag ttg agg gca gtc agc ttt cct gaa gat gat      520
Leu Leu Met Val Ser Gln Leu Arg Ala Val Ser Phe Pro Glu Asp Asp
          15                  20                  25 gaa ccc ctt aat act gtc gac tat cac tat tca agg caa tat ccg gtt      568
Glu Pro Leu Asn Thr Val Asp Tyr His Tyr Ser Arg Gln Tyr Pro Val
      30                  35                  40 ttt aga gga cgc cct tca ggc aat gaa tcg cag cac agg ctg gac ttt      616
Phe Arg Gly Arg Pro Ser Gly Asn Glu Ser Gln His Arg Leu Asp Phe
  45                  50                  55 cag ctg atg ttg aaa att cga gac aca ctt tat att gct ggc agg gat      664
Gln Leu Met Leu Lys Ile Arg Asp Thr Leu Tyr Ile Ala Gly Arg Asp
60                  65                  70                  75 caa gtt tat aca gta aac tta aat gaa atg ccc aaa aca gaa gta ata      712
Gln Val Tyr Thr Val Asn Leu Asn Glu Met Pro Lys Thr Glu Val Ile
              80                  85                  90 ccc aac aag aaa ctg aca tgg cga tca aga caa cag gat cga gaa aac      760
Pro Asn Lys Lys Leu Thr Trp Arg Ser Arg Gln Gln Asp Arg Glu Asn
          95                 100                 105
```

| | | |
|---|---|---|
| tgt gct atg aaa ggc aag cat aaa gat gaa tgc cac aac ttt atc aaa<br>Cys Ala Met Lys Gly Lys His Lys Asp Glu Cys His Asn Phe Ile Lys<br>110                              115                            120 | | 808 |
| gta ttt gtt cca aga aac gat gag atg gtt ttt gtt tgt ggt acc aat<br>Val Phe Val Pro Arg Asn Asp Glu Met Val Phe Val Cys Gly Thr Asn<br>125                              130                            135 | | 856 |
| gca ttc aat ccc atg tgt aga tac tac agg ttg agt acc tta gaa tat<br>Ala Phe Asn Pro Met Cys Arg Tyr Tyr Arg Leu Ser Thr Leu Glu Tyr<br>140                              145                            150                            155 | | 904 |
| gat ggg gaa gaa att agt ggc ctg gca aga tgc cca ttt gat gcc aga<br>Asp Gly Glu Glu Ile Ser Gly Leu Ala Arg Cys Pro Phe Asp Ala Arg<br>                         160                            165                            170 | | 952 |
| caa acc aat gtt gcc ctc ttt gct gat ggg aag ctg tat tct gcc aca<br>Gln Thr Asn Val Ala Leu Phe Ala Asp Gly Lys Leu Tyr Ser Ala Thr<br>                         175                            180                            185 | | 1000 |
| gtg gct gac ttc ttg gcc agc gat gcc gtt att tat cga agc atg ggt<br>Val Ala Asp Phe Leu Ala Ser Asp Ala Val Ile Tyr Arg Ser Met Gly<br>                         190                            195                            200 | | 1048 |
| gat gga tct gcc ctt cgc aca ata aaa tat gat tcc aaa tgg ata aaa<br>Asp Gly Ser Ala Leu Arg Thr Ile Lys Tyr Asp Ser Lys Trp Ile Lys<br>205                              210                            215 | | 1096 |
| gag cca cac ttt ctt cat gcc ata gaa tat gga aac tat gtc tat ttc<br>Glu Pro His Phe Leu His Ala Ile Glu Tyr Gly Asn Tyr Val Tyr Phe<br>220                              225                            230                            235 | | 1144 |
| ttc ttt cga gaa atc gct gtc gaa cat aat aat tta ggc aag gct gtg<br>Phe Phe Arg Glu Ile Ala Val Glu His Asn Asn Leu Gly Lys Ala Val<br>                         240                            245                            250 | | 1192 |
| tat tcc cgc gtg gcc cgc ata tgt aaa aac gac atg ggt ggt tcc cag<br>Tyr Ser Arg Val Ala Arg Ile Cys Lys Asn Asp Met Gly Gly Ser Gln<br>                         255                            260                            265 | | 1240 |
| cgg gtc ctg gag aaa cac tgg act tca ttt cta aag gct cgg ctg aac<br>Arg Val Leu Glu Lys His Trp Thr Ser Phe Leu Lys Ala Arg Leu Asn<br>                         270                            275                            280 | | 1288 |
| tgt tct gtc cct gga gat tcg ttt ttc tac ttt gat gtt ctg cag tct<br>Cys Ser Val Pro Gly Asp Ser Phe Phe Tyr Phe Asp Val Leu Gln Ser<br>285                              290                            295 | | 1336 |
| att aca gac ata ata caa atc aat ggc atc ccc act gtg gtc ggg gtg<br>Ile Thr Asp Ile Ile Gln Ile Asn Gly Ile Pro Thr Val Val Gly Val<br>300                              305                            310                            315 | | 1384 |
| ttt acc acg cag ctc aat agc atc cct ggt tct gct gtc tgt gca ttt<br>Phe Thr Thr Gln Leu Asn Ser Ile Pro Gly Ser Ala Val Cys Ala Phe<br>                         320                            325                            330 | | 1432 |
| agc atg gat gac att gaa aaa gta ttc aaa gga cgg ttt aag gaa cag<br>Ser Met Asp Asp Ile Glu Lys Val Phe Lys Gly Arg Phe Lys Glu Gln<br>                         335                            340                            345 | | 1480 |
| aaa act cca gat tct gtt tgg aca gca gtt ccc gaa gac aaa gtg cca<br>Lys Thr Pro Asp Ser Val Trp Thr Ala Val Pro Glu Asp Lys Val Pro<br>                         350                            355                            360 | | 1528 |
| aag cca agg cct ggc tgt tgt gca aaa cac ggc ctt gcc gaa gct tat<br>Lys Pro Arg Pro Gly Cys Cys Ala Lys His Gly Leu Ala Glu Ala Tyr<br>365                              370                            375 | | 1576 |
| aaa acc tcc atc gat ttc ccg gat gaa act ctg tca ttc atc aaa tct<br>Lys Thr Ser Ile Asp Phe Pro Asp Glu Thr Leu Ser Phe Ile Lys Ser<br>380                              385                            390                            395 | | 1624 |
| cat ccc ctg atg gac tct gcc gtt cca ccc att gcc gat gag ccc tgg<br>His Pro Leu Met Asp Ser Ala Val Pro Pro Ile Ala Asp Glu Pro Trp<br>                         400                            405                            410 | | 1672 |
| ttc aca aag act cgg gtc agg tac aga ctg acg gcc atc tca gtg gac<br>Phe Thr Lys Thr Arg Val Arg Tyr Arg Leu Thr Ala Ile Ser Val Asp<br>                         415                            420                            425 | | 1720 |

```
cat tca gcc gga ccc tac cag aac tac aca gtc atc ttt gtt ggc tct      1768
His Ser Ala Gly Pro Tyr Gln Asn Tyr Thr Val Ile Phe Val Gly Ser
        430                 435                 440 gaa gct ggc atg gta ctt aaa gtt ctg gca aag acc agt cct ttc tct      1816
Glu Ala Gly Met Val Leu Lys Val Leu Ala Lys Thr Ser Pro Phe Ser
445                 450                 455 ttg aac gac agc gta tta ctg gaa gag att gaa gcc tac aac cat gca      1864
Leu Asn Asp Ser Val Leu Leu Glu Glu Ile Glu Ala Tyr Asn His Ala
460                 465                 470                 475 aag tgc agt gct gag aat gag gaa gac aaa aag gtc atc tca tta cag      1912
Lys Cys Ser Ala Glu Asn Glu Glu Asp Lys Lys Val Ile Ser Leu Gln
                480                 485                 490 ttg gat aaa gat cac cac gct tta tat gtg gcg ttc tct agc tgc att      1960
Leu Asp Lys Asp His His Ala Leu Tyr Val Ala Phe Ser Ser Cys Ile
            495                 500                 505 atc cgc atc ccc ctc agt cgc tgt gag cgt tat gga tca tgt aaa aag      2008
Ile Arg Ile Pro Leu Ser Arg Cys Glu Arg Tyr Gly Ser Cys Lys Lys
        510                 515                 520 tct tgt att gca tct cgt gac ccg tat tgt ggc tgg tta agc cag gga      2056
Ser Cys Ile Ala Ser Arg Asp Pro Tyr Cys Gly Trp Leu Ser Gln Gly
    525                 530                 535 tcc tgt ggt aga gtg acc cca ggg atg ctt gct gaa gga tat gaa caa      2104
Ser Cys Gly Arg Val Thr Pro Gly Met Leu Ala Glu Gly Tyr Glu Gln
540                 545                 550                 555 gac aca gaa ttc ggc aac aca gct cat cta ggg gac tgc cat gac atg      2152
Asp Thr Glu Phe Gly Asn Thr Ala His Leu Gly Asp Cys His Asp Met
                560                 565                 570 gag gta tct tca tct tct gtt acc aca atg gtg tac gat ggg aag tcc      2200
Glu Val Ser Ser Ser Ser Val Thr Thr Met Val Tyr Asp Gly Lys Ser
            575                 580                 585 agt ctg gag agt cca acc aga tgg tcc aca tgaatgtcct catcacctgt        2250
Ser Leu Glu Ser Pro Thr Arg Trp Ser Thr
        590                 595 gtctttgctg cttttgtttt gggggcattc attgcaggtg tggcagtata ctgctatcga   2310
gacatgtttg ttcggaaaaa cagaaagatc cataaagatg cagagtccgc ccagtcatgc   2370
acagactcca gtggaagttt tgccaaactg aatggtctct ttgacagccc tgtcaaggaa   2430
taccaacaga atattgattc tcctaaactg tatagtaacc tgctaaccag tcggaaagag   2490
ctaccaccca atggagatac taaatccatg gtaatggacc atcgagggca acctccagag   2550
ttggctgctc ttcctactcc tgagtctaca cccgtgcttc accagaagac cctgcaggcc   2610
atgaagagcc actcagaaaa ggcccatggc catggagctt caaggaaaga aacccctcag   2670 tttttttccgt ctagtccgcc acctcattcc ccattaagtc atgggcatat ccccagtgcc  2730
attgttcttc caaatgctac ccatgactac aacacgtctt tctcaaactc caatgctcac   2790
aaagctgaaa agaagcttca aaacattgat caccctctca caaagtcatc cagtaagaga   2850
gatcaccggc gttctgttga ttccagaaat accctcaatg atctcctgaa gcatctgaat   2910
gacccaaata gtaaccccaa agccatcatg ggagacatcc agatggcaca ccagaactta   2970
atgctggatc ccatgggatc gatgtctgag gtcccaccta agtccctaa ccggaggca    3030 tcgctatact cccctccttc aactctcccc agaaatagcc caaccaagcg agtggatgtc   3090
cccaccactc ctggagtccc aatgacttct ctggaaagac aaagaggtta tcacaaaaat   3150
tcctcccaga ggcactctat atctgctatg cctaaaaact taaactcacc aaatggtgtt   3210
ttgttatcca gacagcctag tatgaaccgt ggaggatata tgcccacccc cactggggcg   3270
```

```
aaggtggact atattcaggg aacaccagtg agtgttcatc tgcagccttc cctctccaga    3330
cagagcagct acaccagtaa tggcactctt cctaggacgg gactaaagag gacgccgtcc    3390
ttaaaacctg acgtgccacc aaagccttcc tttgttcctc aaaccccatc tgtcagacca    3450
ctgaacaaat acacatacta ggcctcaagt gtgctattcc catgtggctt tatcctgtcc    3510
gtgttgttga gaggatgatg ttgtaagggt accttaaaac aagagactcg cttgtatttt    3570
aagagaacca agtggccaaa gaaactctttt ctaactttgg caacatcaga acttgccaca    3630
tgtagctact gcagcaaggc ttctgtgtac ttgcctgaaa acaaaggaag gtgctggtca    3690
ttccatttct tttgtttgaa gctaaagaga tgtgtagctc acaggggcta ccttaccagt    3750
ataaagagct gataacagta ctcagaagaa tctgtgaaca aatacttgaa aatgggttca    3810
atgtagactg ccattatgtg tggtcttccc attaaatgtg aacattttaa tatgtatgca    3870
ttcaccttgc ctcttgcaca aatgtcaaaa aaagatggt aatatctcaa agaaatgaac    3930
ttgtagatta ccaagcagtt tgctaaaaat tcaatctttg acccaagctg tagcatttt     3990
ttttcatgtg tggcatcttt ttcatgccac caacaaactt gttgtgtgtg tgcgtgtgtg    4050
tgtgtgtgtg tgtgtgtgtg tgtgttct gtacccacta ggatttgttt aggtgcccat     4110
tgcatctttt tgtgctatgg agttgtttac attaagcatg accgaacgag agacaatact    4170
atttcccaca ggagtccatt gggttcagct ttgaaagagg aatagaatcg aggctccttt    4230
gaccatcaaa atgatgaact ttacttatgt ggtacccaat gccagaatgt aagagttgca    4290
agtgattttg tgctgctatt cattaaaact tgtattccag tcttgccagc ttaaggagat    4350
caagatatta agaggtatcc ttgatttatt ttccagtatt cagtagtaaa attttcctgt    4410
ccactgtgaa tcaaagcctg agtcactcta tttaaccttg gacacactaa taaggtttta    4470
ttttgattgt gttcgtttcc ccccccccaa tagtaaaatt tctcctcctt taactcctcc    4530
tacccccaa ggtaagaaac aaaaaacaaa caaacaaaca aaatagaag acaaaagaaa      4590
gacatatgaa aggaattgta attggcttaa cagaaacagt ctgtaaaaac ctaacagtgg    4650
tgcaatcatg ttgtctgtgt tgtgttatgt gagaattttc tcctaagtca tgcaggtaat    4710
gacaatatac tgtaaatacc acatgtgagt ttacctgaat ctgtgcattt tgtgccttat    4770
tcatgagaat gatagaagta ctaaaatctg tcaagtgttt tcagtatagc acattattta    4830
ctgagtgcca gttgtaaatg ttttcaacc agcacctaaa aagactctttt tcaaaaaatc    4890
acagaaacaa cctaggacaa ttatttgtta cataatccga cctcatagca gcattacatt    4950
cttgccgtg ataaacattc cactcctgct ttcctaagga tgaaacagtg ataatgtgaa     5010
ctcaaatgag gtttcctggg taatgtgaca cctgcagaaa ctatagagcg tcatttatac    5070
gtagttggc agaaaccact tacggctgat gatgcgcaac cctgctgact gtttcagtta     5130
atatgctgca caccacacac ttgtttagtg aaccaaatct agaaagtacc aaggcagagg    5190
tatgctcctg ctgtaatcag gcaaatgagt tcaactggat ttcttttgac aatactgttg    5250
gtacctatta cttgggggag gacatgttgc agaagaccag atcatttta tacagaatgt     5310
gaaatactga tacagttatt cttttttta aagaacattg ttttataaag aacgtgattt     5370
ccagtgatct ctggaagcgc taaagctaaa atttctgttc ttgaaacact tcagctttgc    5430
aactaaaata ttacagatta ataataaatt aaaccaacca atgataaaca ctactcagtc    5490
caccaacaac aaacgtgttt gaattcaccct taccaatatt aatcccagcg tgtgtaaaac   5550
agaacagtaa ctctatgtga ccccagataa cattttgtaa cattgtgctt ccttgtagtt    5610
tgtaatgtga gttcaatcag tatttatgtt gaaatttcta acattaaatc tagtctctat    5670
```

```
cctgttaatt taattttaa atgctttatc catttgtgca aaggtaaacg cagattgtat      5730
cttttttaat ggtacggcat aaaaagtaac cctcaagtga agtgtctcta tactgtttta      5790
tagagtactt taacatgaat agataccttg taaacttgta ttgtggatgt gtaaataata      5850
tgtactttgg gttttaaca ccgcatgtaa agtcaaaata aatatacaa atcattataa        5910 aaaaaaaaa                                                              5919
```

<210> SEQ ID NO 30
<211> LENGTH: 597
<212> TYPE: PRT
<213> ORGANISM: Homo sapiens

<400> SEQUENCE: 30

```
Met Arg Val Phe Leu Leu Cys Ala Tyr Ile Leu Leu Met Val Ser
1               5                   10                  15

Gln Leu Arg Ala Val Ser Phe Pro Glu Asp Glu Pro Leu Asn Thr
                20                  25                  30

Val Asp Tyr His Tyr Ser Arg Gln Tyr Pro Val Phe Arg Gly Arg Pro
            35                  40                  45

Ser Gly Asn Glu Ser Gln His Arg Leu Asp Phe Gln Leu Met Leu Lys
        50                  55                  60

Ile Arg Asp Thr Leu Tyr Ile Ala Gly Arg Asp Gln Val Tyr Thr Val
65                  70                  75                  80

Asn Leu Asn Glu Met Pro Lys Thr Glu Val Ile Pro Asn Lys Lys Leu
                85                  90                  95

Thr Trp Arg Ser Arg Gln Gln Asp Arg Glu Asn Cys Ala Met Lys Gly
                100                 105                 110

Lys His Lys Asp Glu Cys His Asn Phe Ile Lys Val Phe Val Pro Arg
        115                 120                 125

Asn Asp Glu Met Val Phe Val Cys Gly Thr Asn Ala Phe Asn Pro Met
    130                 135                 140

Cys Arg Tyr Tyr Arg Leu Ser Thr Leu Glu Tyr Asp Gly Glu Glu Ile
145                 150                 155                 160

Ser Gly Leu Ala Arg Cys Pro Phe Asp Ala Arg Gln Thr Asn Val Ala
                165                 170                 175

Leu Phe Ala Asp Gly Lys Leu Tyr Ser Ala Thr Val Ala Asp Phe Leu
            180                 185                 190

Ala Ser Asp Ala Val Ile Tyr Arg Ser Met Gly Asp Gly Ser Ala Leu
        195                 200                 205

Arg Thr Ile Lys Tyr Asp Ser Lys Trp Ile Lys Glu Pro His Phe Leu
    210                 215                 220

His Ala Ile Glu Tyr Gly Asn Tyr Val Tyr Phe Phe Arg Glu Ile
225                 230                 235                 240

Ala Val Glu His Asn Asn Leu Gly Lys Ala Val Tyr Ser Arg Val Ala
                245                 250                 255

Arg Ile Cys Lys Asn Asp Met Gly Gly Ser Gln Arg Val Leu Glu Lys
            260                 265                 270

His Trp Thr Ser Phe Leu Lys Ala Arg Leu Asn Cys Ser Val Pro Gly
        275                 280                 285

Asp Ser Phe Phe Tyr Phe Asp Val Leu Gln Ser Ile Thr Asp Ile Ile
    290                 295                 300

Gln Ile Asn Gly Ile Pro Thr Val Val Gly Val Phe Thr Thr Gln Leu
305                 310                 315                 320
```

| Asn | Ser | Ile | Pro | Gly | Ser | Ala | Val | Cys | Ala | Phe | Ser | Met | Asp | Asp | Ile |
| | | | | 325 | | | | | 330 | | | | | 335 | |

| Glu | Lys | Val | Phe | Lys | Gly | Arg | Phe | Lys | Glu | Gln | Lys | Thr | Pro | Asp | Ser |
| | | | 340 | | | | | 345 | | | | | 350 | | |

| Val | Trp | Thr | Ala | Val | Pro | Glu | Asp | Lys | Val | Pro | Lys | Pro | Arg | Pro | Gly |
| | | 355 | | | | | 360 | | | | | 365 | | | |

| Cys | Cys | Ala | Lys | His | Gly | Leu | Ala | Glu | Ala | Tyr | Lys | Thr | Ser | Ile | Asp |
| | 370 | | | | | 375 | | | | | 380 | | | | |

| Phe | Pro | Asp | Glu | Thr | Leu | Ser | Phe | Ile | Lys | Ser | His | Pro | Leu | Met | Asp |
| 385 | | | | | 390 | | | | | 395 | | | | | 400 |

| Ser | Ala | Val | Pro | Pro | Ile | Ala | Asp | Glu | Pro | Trp | Phe | Thr | Lys | Thr | Arg |
| | | | | 405 | | | | | 410 | | | | | 415 | |

| Val | Arg | Tyr | Arg | Leu | Thr | Ala | Ile | Ser | Val | Asp | His | Ser | Ala | Gly | Pro |
| | | | 420 | | | | | 425 | | | | | 430 | | |

| Tyr | Gln | Asn | Tyr | Thr | Val | Ile | Phe | Val | Gly | Ser | Glu | Ala | Gly | Met | Val |
| | | | 435 | | | | | 440 | | | | | 445 | | |

| Leu | Lys | Val | Leu | Ala | Lys | Thr | Ser | Pro | Phe | Ser | Leu | Asn | Asp | Ser | Val |
| | 450 | | | | | 455 | | | | | 460 | | | | |

| Leu | Leu | Glu | Glu | Ile | Glu | Ala | Tyr | Asn | His | Ala | Lys | Cys | Ser | Ala | Glu |
| 465 | | | | | 470 | | | | | 475 | | | | | 480 |

| Asn | Glu | Glu | Asp | Lys | Lys | Val | Ile | Ser | Leu | Gln | Leu | Asp | Lys | Asp | His |
| | | | | 485 | | | | | 490 | | | | | 495 | |

| His | Ala | Leu | Tyr | Val | Ala | Phe | Ser | Ser | Cys | Ile | Ile | Arg | Ile | Pro | Leu |
| | | | 500 | | | | | 505 | | | | | 510 | | |

| Ser | Arg | Cys | Glu | Arg | Tyr | Gly | Ser | Cys | Lys | Lys | Ser | Cys | Ile | Ala | Ser |
| | | 515 | | | | | 520 | | | | | 525 | | | |

| Arg | Asp | Pro | Tyr | Cys | Gly | Trp | Leu | Ser | Gln | Gly | Ser | Cys | Gly | Arg | Val |
| | 530 | | | | | 535 | | | | | 540 | | | | |

| Thr | Pro | Gly | Met | Leu | Ala | Glu | Gly | Tyr | Glu | Gln | Asp | Thr | Glu | Phe | Gly |
| 545 | | | | | 550 | | | | | 555 | | | | | 560 |

| Asn | Thr | Ala | His | Leu | Gly | Asp | Cys | His | Asp | Met | Glu | Val | Ser | Ser | Ser |
| | | | | 565 | | | | | 570 | | | | | 575 | |

| Ser | Val | Thr | Thr | Met | Val | Tyr | Asp | Gly | Lys | Ser | Ser | Leu | Glu | Ser | Pro |
| | | | 580 | | | | | 585 | | | | | 590 | | |

| Thr | Arg | Trp | Ser | Thr |
| | | | 595 | |

```
<210> SEQ ID NO 31
<211> LENGTH: 2290
<212> TYPE: DNA
<213> ORGANISM: Homo sapiens
<220> FEATURE:
<221> NAME/KEY: CDS
<222> LOCATION: (440)..(1867)

<400> SEQUENCE: 31
gcggccgctt cccaccgtcc ctctcccctt actggcagag cgcgctgcgg gcggactccc      60
gggcccggag cagcccaccg gccaccccac cgcccacccg gctcccggtg tctcctcccg     120
gccgctctac ccagcaactt tccgtgcttt gttccccgac tggaaatgct ttacggaagc     180
gtcttggaca gggtctccgc caggcgacaa gagctcggtg ctgagatgtg ttacgttctc     240
atctccccat caattatgga tggaaacaaa taaggaagag tcaattttgc tgagccccttt    300 ctccggcaac gagaggcgtt ctgcagccgg gaggagccg ccgctcgcgc cggcagccgc      360
tggcaggggc atggtgagga ggaaggtagc tcagtggcat ttctgagcag gggccaccct     420
```

```
gacttcacct tggcccacc atg agg gtc ttc ctg ctt tgt gcc tac ata ctg          472
                    Met Arg Val Phe Leu Leu Cys Ala Tyr Ile Leu
                     1               5                      10 ctg ctg atg gtt tcc cag ttg agg gca gtc agc ttt cct gaa gat gat           520
Leu Leu Met Val Ser Gln Leu Arg Ala Val Ser Phe Pro Glu Asp Asp
             15                  20                  25 gaa ccc ctt aat act gtc gac tat cac tat tca agg caa tat ccg gtt           568
Glu Pro Leu Asn Thr Val Asp Tyr His Tyr Ser Arg Gln Tyr Pro Val
         30                  35                  40 ttt aga gga cgc cct tca ggc aat gaa tcg cag cac agg ctg gac ttt           616
Phe Arg Gly Arg Pro Ser Gly Asn Glu Ser Gln His Arg Leu Asp Phe
     45                  50                  55 cag ctg atg ttg aaa att cga gac aca ctt tat att gct ggc agg gat           664
Gln Leu Met Leu Lys Ile Arg Asp Thr Leu Tyr Ile Ala Gly Arg Asp
 60              65                  70                  75 caa gtt tat aca gta aac tta aat gaa atg ccc aaa aca gaa gta ata           712
Gln Val Tyr Thr Val Asn Leu Asn Glu Met Pro Lys Thr Glu Val Ile
             80                  85                  90 ccc aac aag aaa ctg aca tgg cga tca aga caa cag gat cga gaa aac           760
Pro Asn Lys Lys Leu Thr Trp Arg Ser Arg Gln Gln Asp Arg Glu Asn
         95                  100                 105 tgt gct atg aaa ggc aag cat aaa gat gaa tgc cac aac ttt atc aaa           808
Cys Ala Met Lys Gly Lys His Lys Asp Glu Cys His Asn Phe Ile Lys
     110                 115                 120 gta ttt gtt cca aga aac gat gag atg gtt ttt gtt tgt ggt acc aat           856
Val Phe Val Pro Arg Asn Asp Glu Met Val Phe Val Cys Gly Thr Asn
125                 130                 135 gca ttc aat ccc atg tgt aga tac tac agg ttg agt acc tta gaa tat           904
Ala Phe Asn Pro Met Cys Arg Tyr Tyr Arg Leu Ser Thr Leu Glu Tyr
140                 145                 150                 155 gat ggg gaa gaa att agt ggc ctg gca aga tgc cca ttt gat gcc aga           952
Asp Gly Glu Glu Ile Ser Gly Leu Ala Arg Cys Pro Phe Asp Ala Arg
                 160                 165                 170 caa acc aat gtt gcc ctc ttt gct gat ggg aag ctg tat tct gcc aca          1000
Gln Thr Asn Val Ala Leu Phe Ala Asp Gly Lys Leu Tyr Ser Ala Thr
             175                 180                 185 gtg gct gac ttc ttg gcc agc gat gcc gtt att tat cga agc atg ggt          1048
Val Ala Asp Phe Leu Ala Ser Asp Ala Val Ile Tyr Arg Ser Met Gly
         190                 195                 200 gat gga tct gcc ctt cgc aca ata aaa tat gat tcc aaa tgg ata aaa          1096
Asp Gly Ser Ala Leu Arg Thr Ile Lys Tyr Asp Ser Lys Trp Ile Lys
     205                 210                 215 gag cca cac ttt ctt cat gcc ata gaa tat gga aac tat gtc tat ttc          1144
Glu Pro His Phe Leu His Ala Ile Glu Tyr Gly Asn Tyr Val Tyr Phe
220                 225                 230                 235 ttc ttt cga gaa atc gct gtc gaa cat aat aat tta ggc aag gct gtg          1192
Phe Phe Arg Glu Ile Ala Val Glu His Asn Asn Leu Gly Lys Ala Val
                 240                 245                 250 tat tcc cgc gtg gcc cgc ata tgt aaa aac gac atg ggt ggt tcc cag          1240
Tyr Ser Arg Val Ala Arg Ile Cys Lys Asn Asp Met Gly Gly Ser Gln
             255                 260                 265 cgg gtc ctg gag aaa cac tgg act tca ttt cta aag gct cgg ctg aac          1288
Arg Val Leu Glu Lys His Trp Thr Ser Phe Leu Lys Ala Arg Leu Asn
         270                 275                 280 tgt tct gtc cct gga gat tcg ttt ttc tac ttt gat gtt ctg cag tct          1336
Cys Ser Val Pro Gly Asp Ser Phe Phe Tyr Phe Asp Val Leu Gln Ser
     285                 290                 295 att aca gac ata ata caa atc aat ggc atc ccc act gtg gtc ggg gtg          1384
Ile Thr Asp Ile Ile Gln Ile Asn Gly Ile Pro Thr Val Val Gly Val
300                 305                 310                 315
```

```
ttt acc acg cag ctc aat agc atc cct ggt tct gct gtc tgt gca ttt    1432
Phe Thr Thr Gln Leu Asn Ser Ile Pro Gly Ser Ala Val Cys Ala Phe
            320                 325                 330 agc atg gat gac att gaa aaa gta ttc aaa gga cgg ttt aag gaa cag    1480
Ser Met Asp Asp Ile Glu Lys Val Phe Lys Gly Arg Phe Lys Glu Gln
        335                 340                 345 aaa act cca gat tct gtt tgg aca gca gtt ccc gaa gac aaa gtg cca    1528
Lys Thr Pro Asp Ser Val Trp Thr Ala Val Pro Glu Asp Lys Val Pro
    350                 355                 360 aag cca agg cct ggc tgt tgt gca aaa cac ggc ctt gcc gaa gct tat    1576
Lys Pro Arg Pro Gly Cys Cys Ala Lys His Gly Leu Ala Glu Ala Tyr
365                 370                 375 aaa acc tcc atc gat ttc ccg gat gaa act ctg tca ttc atc aaa tct    1624
Lys Thr Ser Ile Asp Phe Pro Asp Glu Thr Leu Ser Phe Ile Lys Ser
380                 385                 390                 395 cat ccc ctg atg gac tct gcc gtt cca ccc att gcc gat gag ccc tgg    1672
His Pro Leu Met Asp Ser Ala Val Pro Pro Ile Ala Asp Glu Pro Trp
            400                 405                 410 ttc aca aag act cgg gtc agg tac aga ctg acg gcc atc tca gtg gac    1720
Phe Thr Lys Thr Arg Val Arg Tyr Arg Leu Thr Ala Ile Ser Val Asp
        415                 420                 425 cat tca gcc gga ccc tac cag aac tac aca gtc atc ttt gtt ggc tct    1768
His Ser Ala Gly Pro Tyr Gln Asn Tyr Thr Val Ile Phe Val Gly Ser
    430                 435                 440 gaa gct ggc atg gta ctt aaa gtt ctg gca aag acc agt cct ttc tct    1816
Glu Ala Gly Met Val Leu Lys Val Leu Ala Lys Thr Ser Pro Phe Ser
445                 450                 455 ttg aac gac agc gta tta ctg gaa gag att gaa gcc tac aac cat gca    1864
Leu Asn Asp Ser Val Leu Leu Glu Glu Ile Glu Ala Tyr Asn His Ala
460                 465                 470                 475 aag                                                                1917
Lys   taggtatatg ttacgagaac gcccttcagc actgtcaaa aattttcggc atgtatttca tctagtcatg tccttttggt cctctaaatt agcagtggtt tggcataata   1977
gtgttttgtg ttttttttct cattgaaata aatcttgggt ttgtttttt cccgagcctg    2037 ctagggcgag gggggtgaat ggttgatgag tttaaaaata atgcagccct tgttttcac    2097 ctgtagaata tgagaacatt ttaacagcac ctctcttatc ttgcagatat attccaagat   2157
gctacatgca gcagacagct gtgagcttgc atacacacac acacaaatat acatgcacat   2217
acatacacag aatgcagtac tagttaagta tttccttcct atctttaata agtaagagaa   2277
tatttagacc att                                                     2290

<210> SEQ ID NO 32
<211> LENGTH: 476
<212> TYPE: PRT
<213> ORGANISM: Homo sapiens

<400> SEQUENCE: 32

Met Arg Val Phe Leu Leu Cys Ala Tyr Ile Leu Leu Met Val Ser
1               5                   10                  15

Gln Leu Arg Ala Val Ser Phe Pro Glu Asp Asp Glu Pro Leu Asn Thr
            20                  25                  30

Val Asp Tyr His Tyr Ser Arg Gln Tyr Pro Val Phe Arg Gly Arg Pro
        35                  40                  45

Ser Gly Asn Glu Ser Gln His Arg Leu Asp Phe Gln Leu Met Leu Lys
    50                  55                  60

Ile Arg Asp Thr Leu Tyr Ile Ala Gly Arg Asp Gln Val Tyr Thr Val
```

```
            65                  70                  75                  80
        Asn Leu Asn Glu Met Pro Lys Thr Glu Val Ile Pro Asn Lys Lys Leu
                            85                  90                  95

Thr Trp Arg Ser Arg Gln Gln Asp Arg Glu Asn Cys Ala Met Lys Gly
                        100                 105                 110

Lys His Lys Asp Glu Cys His Asn Phe Ile Lys Val Phe Val Pro Arg
                    115                 120                 125

Asn Asp Glu Met Val Phe Val Cys Gly Thr Asn Ala Phe Asn Pro Met
                130                 135                 140

Cys Arg Tyr Tyr Arg Leu Ser Thr Leu Glu Tyr Asp Gly Glu Glu Ile
        145                 150                 155                 160

Ser Gly Leu Ala Arg Cys Pro Phe Asp Ala Arg Gln Thr Asn Val Ala
                        165                 170                 175

Leu Phe Ala Asp Gly Lys Leu Tyr Ser Ala Thr Val Ala Asp Phe Leu
                    180                 185                 190

Ala Ser Asp Ala Val Ile Tyr Arg Ser Met Gly Asp Gly Ser Ala Leu
                195                 200                 205

Arg Thr Ile Lys Tyr Asp Ser Lys Trp Ile Lys Glu Pro His Phe Leu
        210                 215                 220

His Ala Ile Glu Tyr Gly Asn Tyr Val Tyr Phe Phe Arg Glu Ile
        225                 230                 235                 240

Ala Val Glu His Asn Asn Leu Gly Lys Ala Val Tyr Ser Arg Val Ala
                        245                 250                 255

Arg Ile Cys Lys Asn Asp Met Gly Gly Ser Gln Arg Val Leu Glu Lys
                    260                 265                 270

His Trp Thr Ser Phe Leu Lys Ala Arg Leu Asn Cys Ser Val Pro Gly
                275                 280                 285

Asp Ser Phe Phe Tyr Phe Asp Val Leu Gln Ser Ile Thr Asp Ile Ile
        290                 295                 300

Gln Ile Asn Gly Ile Pro Thr Val Val Gly Val Phe Thr Thr Gln Leu
        305                 310                 315                 320

Asn Ser Ile Pro Gly Ser Ala Val Cys Ala Phe Ser Met Asp Asp Ile
                        325                 330                 335

Glu Lys Val Phe Lys Gly Arg Phe Lys Glu Gln Lys Thr Pro Asp Ser
                    340                 345                 350

Val Trp Thr Ala Val Pro Glu Asp Lys Val Pro Lys Pro Arg Pro Gly
                355                 360                 365

Cys Cys Ala Lys His Gly Leu Ala Glu Ala Tyr Lys Thr Ser Ile Asp
        370                 375                 380

Phe Pro Asp Glu Thr Leu Ser Phe Ile Lys Ser His Pro Leu Met Asp
        385                 390                 395                 400

Ser Ala Val Pro Pro Ile Ala Asp Glu Pro Trp Phe Thr Lys Thr Arg
                        405                 410                 415

Val Arg Tyr Arg Leu Thr Ala Ile Ser Val Asp His Ser Ala Gly Pro
                    420                 425                 430

Tyr Gln Asn Tyr Thr Val Ile Phe Val Gly Ser Glu Ala Gly Met Val
                435                 440                 445

Leu Lys Val Leu Ala Lys Thr Ser Pro Phe Ser Leu Asn Asp Ser Val
                450                 455                 460

Leu Leu Glu Glu Ile Glu Ala Tyr Asn His Ala Lys
        465                 470                 475

<210> SEQ ID NO 33
```

<211> LENGTH: 6330
<212> TYPE: DNA
<213> ORGANISM: Mus musculus

<400> SEQUENCE: 33

```
ctccgctgac gctctgggtg cgtgatgggg gtgggacccc gagccgggag cccgcagcgc      60
agctgtgtgc ggacgcgtgt gtttgcgtgg gcgtagcgtc gtagctcccg ggagttcatt     120
gctctcccaa gccacacggt ctccagcggt gcccgaggcg ccaggggagg tctggctgac     180
cagtcccagc tggccggtgg gcggcctggg ggcggggcgg ggcagctcgg ccctcctcct     240
aggcgcaccc ctcctctgag gcgcacccct aagggaagaa aagacaccct gggctgcgag     300
gaaaagtttc ttcttggcag ggccggctcg gcgccgctcc gcaagccgtc agggtgagcc     360
cgccttcctc gctgcgggc ttggagcctc cagcccgccc gcagcgcagc ccggccgcc      420
gggccagctt cggccgggag aacgcaggga cagcctggga gtgcggagcc actgactgtc     480
cacgcgggga ccgtgagcac ccactcgcgg gtctcccagc cactctcccc cgcaactttg     540
cgtgctttgt tctctggctg aaaaaatgct ccacagaagc gccatagacc gggtctcctc     600
caggcggcaa gggctcggcc gggagacgtg ttacgctctc agctccccat caattatgga     660
tggaaacaaa taaggaaaag tcaattttgt atgagccgcg tctttcgcag ccagaggcgt     720
cttgtagcct ggagcagagg caggcaaacc gagcccaaca accaggtagc taagtgggac     780
ttctgaggag ggggagctca gatttcttct tggccaacca tggggttcct tctgctttgg     840
ttctgcgtgc tgttccttct ggtctccagg ttacgggcgg tcagcttccc agaagacgat     900
gagcccctca cacgggttga ctatcactat tcaaggcaat atccggtttt tagaggacgc     960
ccttcaggca acgaatcgca gcacaggctg gactttcagc tgatgttgaa aattcgagac    1020
acactttata ttgctggcag ggatcaagtc tatacagtga acttaaatga aatcccccaa    1080
acagaggtga taccaagcaa gaagctgacg tggaggtcca gacagcagga tcgagaaaat    1140
tgtgctatga aaggcaagca taagatgaa tgccacaact tcatcaaagt ctttgtccca    1200
agaaatgatg agatggtttt tgtctgtggt accaatgctt tcaacccgat gtgcagatac    1260
tataggttga aacgttaga gtatgatggg aagaaatta gtggcctggc acgatgcccg    1320
tttgatgccc gacaaaccaa tgtcgccctc tttgctgatg aaaactcta ttctgccaca    1380
gtggctgatt tcctggccag tgatgctgtc atttacagaa gcatgggaga tggatctgcc    1440
cttcgcacaa taaatacga ttccaagtgg atcaaagaac cacacttcct tcatgccata    1500
gaatatggaa actatgtcta tttcttcttc agagaaatcg ccgtggaaca taataactta    1560
ggcaaggctg tgtattcccg cgtggctcgc atttgtaaaa acgacatggg tggctcacag    1620
cgggtcctgg agaaacactg gacttccttc cttaaggctc ggctgaactg ctccgttcct    1680
ggagattcct ttttctactt cgacgtcctg cagtctataa cagacataat ccaaatcaat    1740
ggcatcccca ctgtggttgg ggtcttcacc acacagctca acagcattcc tggttctgca    1800
gtctgtgcct ttagcatgga cgacattgag aaagtgttca aagggcggtt caaagagcag    1860
aaaacccag actctgtttg acagcagtt cccgaagaca agtaccaaa accaaggcct    1920
ggctgttgtg ccaaacacgg cctcgcagaa gcttacaaga cctccatcga ctttccagat    1980
gacaccctgg ctttcatcaa gtcccacccg ctgatggact ctgccgtccc acccattgcc    2040
gatgagcccc ggttcacaaa gacacgggtc aggtacaggt tgacagccat cgaagtggac    2100
cgttcagcag ggccatacca aaactacaca gtcatctttg ttggctctga agctggcgtg    2160
gtacttaaag ttttggcaaa gaccagtcct ttctctctga atgacagtgt attactcgaa    2220
```

```
gagattgaag cttataaccc agccaagtgc agcgccgaga gtgaggagga cagaaaggtg    2280
gtctcattac agctggacaa ggatcaccat gctttatacg tggccttctc tagctgcgtg    2340
gtccgcatcc ccctcagccg ctgtgagcgc tacggatcgt gtaaaaagtc ttgcattgca    2400
tcacgtgacc cgtactgtgg ttggttaagc cagggagttt gtgagagagt gacccctaggg    2460 atgctgctgt taaccgaaga cttctttgct ttccataacc acagccctgg aggatatgag    2520
caggacacgg agtacggcaa cacagcccac ctaggggact gccacggtgt acggtgggaa    2580
gtccagtctg gagaatccaa tcagatggtc cacatgaatg tcctcatcac ctgcgtgttt    2640
gccgcttttg tcttgggcgc gttcatcgca ggagtggccg tgtactgcta ccgtgacatg    2700
ttcgttcgga agaacagaaa gatccataaa gacgcagaat ccgcccagtc gtgcacagac    2760
tccagcggaa gcttcgccaa gctgaacggc ctctttgaca gccccgtcaa ggaataccag    2820
cagaacattg attctcccaa actctacagc aacctgctga ccagtcggaa ggaactgcca    2880
ccaaacacgg atacaaagtc catggccgtg gaccacagag gccagcctcc cgagctggct    2940
gctctcccca cgccggaatc cacacctgtc ctccaccaga gaccctgca ggccatgaag    3000 agccactctg agaaggccca cagccacggt gcttcaagga aagaacaccc ccagttttt    3060 ccttctagtc ctccacccca ttccccattg agtcacgggc atatcccag tgccatcgtt    3120 cttccaaacg ccactcacga ctacaataca tccttctcca actcgaatgc ccacaaagcc    3180
gaaaagaagc ttcagagcat ggatcaccct cttacgaagt catccagtaa gcgggagcac    3240
cggcggtctg tggattccag gaatactctc aatgatctcc tgaagcatct aaatgaccca    3300
aacagtaacc ccaaagccat cctgggagag atccatatgg ctcatcaaac cctcatgctg    3360
gacccggtgg gaccaatggc tgaggtccca cccaaggtcc ctaaccggga ggcatctcta    3420
tactcccctc cctccacact ccccagaaat agtccaacca agagagtaga tgtccccacc    3480
actcctgggg tgccaatgac ttctctggaa agacaaaggg gttatacaa aaattcctcc    3540 cagaggcact ctatatctgc cgtgcctaaa aacttaaact caccaaatgg tgttttgtta    3600
tctagacagc cgagtatgaa ccgtggaggc tatatgccca ccccaacagg ggcgaaggtg    3660
gactatattc aggggacacc ggtgagtgtt catctgcagc cctccctctc cagacagagc    3720
agctatacca gtaatggcac cctccccagg acgggactaa agaggacacc atccttaaaa    3780
cctgatgtgc caccaaagcc ttcctttgtt ccgcaaacca catctgtcag accactgaac    3840
aagtacacgt actaggcctc aagtatgcta ttcccgtgtg gctttatcct gtccctgctg    3900
ttgcgaggaa gctgtgaggg taccttcaga tgagatacct gcttgtattt taagagaaac    3960
aagtagccaa agaaactctg tcactttggt aacaccagaa cttgccacat gtagctacta    4020
cagcaaggct tctgtgtact tgccggaaac gaagggaggg cctgctcact ccatttcttt    4080
cgtttgaagc agaagggatg tgtagccagg aaggctccc ttccaccagtg taaagagctg    4140 atacagtact cagaagactg aacaaatact tgaaaatggg ttcaatgtag actgccattc    4200
tgtgtggtct tcccattaaa tgtgaacatt ttaatatgta tgcattcacc ttgcctcttg    4260
cacaaatgtc aaaatggaaa gatgggaatg tctcaaaaca aaatgagctt ggagattacc    4320
aagcagtttg ctgaaaattc aatctttgac ccaaactgta gcaatttta ttttctgagt    4380 gtggcactgt tttgttttat ttttttgttt tgttttgttt ttcaatgcca ccaacaaact    4440
atgttaagag aggggcgagt gtgtgtgtgt gtgtgtgtgt gtgtgtgtgt gtgtgtgtga    4500
gagagagaga gagagagaga gagagagaga gagagatcta cccattagaa ttgatttagg    4560
```

-continued

```
tgcccattgc atcttttgta ctatggagtt gtttacagta agcatgactg aacaagcact    4620
aacatcctcc tacaccggtc catcgtgttc ggctctgatc aggaatagac aaggcttctt    4680
tgactgtcaa gtgattaaca tatggtaccc ggtgtcagaa catttaagcg ttctaaataa    4740
ttttgtgctg ctatccatca gaacgtctat tccagccttg ccagcttaag aacttagaga    4800
aattaagagg tatctttgat gtatctacca gtattcaata gtaacattta cctgtccact    4860
gtgaatcaaa gcctgggca cgctactcaa ccttagacac acttacaggc ttttattttg    4920
attgtgttat tttattttcc atacagtaaa aaatgtcctc tcttaactcc tctcacccc     4980 aactcccaag gcaaaagaga aaccaaaagt aggacaaaag aaagagacag acagacagac    5040
agacagaaca ggaattacag ttggcttagc agggaggatc tgtagagctc tcgatgatcc    5100
ttcctccatg tgtgtcctgt gaggattttg ctcatgagtc atgcaggcag tgacagtgaa    5160
ctgtaaatac cacatgtgag tttacctgga tctgtgcatt ttgtgcctta ttcactcgag    5220
tggtagaagt tccgcggtat gttgagtgtt tccactacag agcatcattt cccatgtgcc    5280
acttgtaaat gttttgcagc cagcacctga ggacttctta tacagtcata aagccaccta    5340
gagcgatttg ttgttgagca acgccgcccc ttccctccag gatcagaagc agcacccacc    5400
cttgccatga taaacattcc atcccctgct gttctgataa tgtgaagtca gatgagggtt    5460
cccaggttat gtggcacctg cggaaaccat gtctagagtc gtttctatgt agcttggcag    5520
agcccactga tggctgcagg tgtgtagcct actgacagct ttggttaacc cactgcacat    5580
cacccagtca tttacccaac ttactctaga aatgtccaca gctaaggaag gctcctgagc    5640
cagtcaggcg gagttcaagt gatatcttgg gacagtgacc atggtctgca ttacttgggg    5700
gaggatgggg tacaagacac cagatcattt ttatacagga tgtagagtac tgatgcggtt    5760
gatcttttcc ttcaagaaca ttcttttcta tagaaaatg attccctgtg atcttctgga    5820
agctccaaag ctgaaaccct tcagctttgc aactaaaaat attacagttt aataatcaat    5880
taaaccaacc aacaataagc actacacatc tgccaccaac aatgttgttt gcatttacct    5940
taccaatatt aatcccagcg tggtaactct gtgtgacccc gataacattt tgtaacattg    6000
tgctgcctta gagtttgtac tgtgagttct atcagtattt atgttgaaat ttctaacatg    6060
gattctagtc tctattctgt taatttaatt ttaaatgctt tatccatttg tgcaaaggta    6120
aacacagatt gtatctttt taatggtacg gcataaaaaa ataaccctaa agtgaagtgg    6180
ctctatactg ttttatagag tactttaacg tgtatagata tcttgtaaac ttgtattgtg    6240
gatgtgtaaa taatatgtac tttgggtttt taacaccgca tgtaaagtca aaataaaata    6300
tccaagtcat taaaaaaaaa aaaaaaaaaa                                    6330
```

<210> SEQ ID NO 34
<211> LENGTH: 3036
<212> TYPE: DNA
<213> ORGANISM: Mus musculus
<220> FEATURE:
<221> NAME/KEY: CDS
<222> LOCATION: (1)..(3033)

<400> SEQUENCE: 34

```
atg ggg ttc ctt ctg ctt tgg ttc tgc gtg ctg ttc ctt ctg gtc tcc    48
Met Gly Phe Leu Leu Leu Trp Phe Cys Val Leu Phe Leu Leu Val Ser
1               5                   10                  15 agg tta cgg gcg gtc agc ttc cca gaa gac gat gag ccc ctc aac acg    96
Arg Leu Arg Ala Val Ser Phe Pro Glu Asp Asp Glu Pro Leu Asn Thr
            20                  25                  30
```

-continued

| | |
|---|---|
| gtt gac tat cac tat tca agg caa tat ccg gtt ttt aga gga cgc cct<br>Val Asp Tyr His Tyr Ser Arg Gln Tyr Pro Val Phe Arg Gly Arg Pro<br>35                    40                    45 | 144 |
| tca ggc aac gaa tcg cag cac agg ctg gac ttt cag ctg atg ttg aaa<br>Ser Gly Asn Glu Ser Gln His Arg Leu Asp Phe Gln Leu Met Leu Lys<br>50                    55                    60 | 192 |
| att cga gac aca ctt tat att gct ggc agg gat caa gtc tat aca gtg<br>Ile Arg Asp Thr Leu Tyr Ile Ala Gly Arg Asp Gln Val Tyr Thr Val<br>65                    70                    75                    80 | 240 |
| aac tta aat gaa atc ccc caa aca gag gtg ata cca agc aag aag ctg<br>Asn Leu Asn Glu Ile Pro Gln Thr Glu Val Ile Pro Ser Lys Lys Leu<br>                  85                    90                    95 | 288 |
| acg tgg agg tcc aga cag cag gat cga gaa aat tgt gct atg aaa ggc<br>Thr Trp Arg Ser Arg Gln Gln Asp Arg Glu Asn Cys Ala Met Lys Gly<br>          100                    105                    110 | 336 |
| aag cat aaa gat gaa tgc cac aac ttc atc aaa gtc ttt gtc cca aga<br>Lys His Lys Asp Glu Cys His Asn Phe Ile Lys Val Phe Val Pro Arg<br>          115                    120                    125 | 384 |
| aat gat gag atg gtt ttt gtc tgt ggt acc aat gct ttc aac ccg atg<br>Asn Asp Glu Met Val Phe Val Cys Gly Thr Asn Ala Phe Asn Pro Met<br>130                    135                    140 | 432 |
| tgc aga tac tat agg ttg aga acg tta gag tat gat ggg gaa gaa att<br>Cys Arg Tyr Tyr Arg Leu Arg Thr Leu Glu Tyr Asp Gly Glu Glu Ile<br>145                    150                    155                    160 | 480 |
| agt ggc ctg gca cga tgc ccg ttt gat gcc cga caa acc aat gtc gcc<br>Ser Gly Leu Ala Arg Cys Pro Phe Asp Ala Arg Gln Thr Asn Val Ala<br>          165                    170                    175 | 528 |
| ctc ttt gct gat gga aaa ctc tat tct gcc aca gtg gct gat ttc ctg<br>Leu Phe Ala Asp Gly Lys Leu Tyr Ser Ala Thr Val Ala Asp Phe Leu<br>                180                    185                    190 | 576 |
| gcc agt gat gct gtc att tac aga agc atg gga gat gga tct gcc ctt<br>Ala Ser Asp Ala Val Ile Tyr Arg Ser Met Gly Asp Gly Ser Ala Leu<br>          195                    200                    205 | 624 |
| cgc aca ata aaa tac gat tcc aag tgg atc aaa gaa cca cac ttc ctt<br>Arg Thr Ile Lys Tyr Asp Ser Lys Trp Ile Lys Glu Pro His Phe Leu<br>210                    215                    220 | 672 |
| cat gcc ata gaa tat gga aac tat gtc tat ttc ttc aga gaa atc<br>His Ala Ile Glu Tyr Gly Asn Tyr Val Tyr Phe Phe Arg Glu Ile<br>225                    230                    235                    240 | 720 |
| gcc gtg gaa cat aat aac tta ggc aag gct gtg tat tcc cgc gtg gct<br>Ala Val Glu His Asn Asn Leu Gly Lys Ala Val Tyr Ser Arg Val Ala<br>                    245                    250                    255 | 768 |
| cgc att tgt aaa aac gac atg ggt ggc tca cag cgg gtc ctg gag aaa<br>Arg Ile Cys Lys Asn Asp Met Gly Gly Ser Gln Arg Val Leu Glu Lys<br>          260                    265                    270 | 816 |
| cac tgg act tcc ttc ctt aag gct cgg ctg aac tgc tcc gtt cct gga<br>His Trp Thr Ser Phe Leu Lys Ala Arg Leu Asn Cys Ser Val Pro Gly<br>          275                    280                    285 | 864 |
| gat tcc ttt ttc tac ttc gac gtc ctg cag tct ata aca gac ata atc<br>Asp Ser Phe Phe Tyr Phe Asp Val Leu Gln Ser Ile Thr Asp Ile Ile<br>290                      295                    300 | 912 |
| caa atc aat ggc atc ccc act gtg gtt ggg gtc ttc acc aca cag ctc<br>Gln Ile Asn Gly Ile Pro Thr Val Val Gly Val Phe Thr Thr Gln Leu<br>305                    310                    315                    320 | 960 |
| aac agc att cct ggt tct gca gtc tgt gcc ttt agc atg gac gac att<br>Asn Ser Ile Pro Gly Ser Ala Val Cys Ala Phe Ser Met Asp Asp Ile<br>                    325                    330                    335 | 1008 |
| gag aaa gtg ttc aaa ggg cgg ttc aaa gag cag aaa acc cca gac tct<br>Glu Lys Val Phe Lys Gly Arg Phe Lys Glu Gln Lys Thr Pro Asp Ser<br>          340                    345                    350 | 1056 |

-continued

```
gtt tgg aca gca gtt ccc gaa gac aaa gta cca aaa cca agg cct ggc      1104
Val Trp Thr Ala Val Pro Glu Asp Lys Val Pro Lys Pro Arg Pro Gly
        355                 360                 365 tgt tgt gcc aaa cac ggc ctc gca gaa gct tac aag acc tcc atc gac      1152
Cys Cys Ala Lys His Gly Leu Ala Glu Ala Tyr Lys Thr Ser Ile Asp
    370                 375                 380 ttt cca gat gac acc ctg gct ttc atc aag tcc cac ccg ctg atg gac      1200
Phe Pro Asp Asp Thr Leu Ala Phe Ile Lys Ser His Pro Leu Met Asp
385                 390                 395                 400 tct gcc gtc cca ccc att gcc gat gag ccc tgg ttc aca aag aca cgg      1248
Ser Ala Val Pro Pro Ile Ala Asp Glu Pro Trp Phe Thr Lys Thr Arg
                405                 410                 415 gtc agg tac agg ttg aca gcc atc gaa gtg gac cgt tca gca ggg cca      1296
Val Arg Tyr Arg Leu Thr Ala Ile Glu Val Asp Arg Ser Ala Gly Pro
            420                 425                 430 tac caa aac tac aca gtc atc ttt gtt ggc tct gaa gct ggc gtg gta      1344
Tyr Gln Asn Tyr Thr Val Ile Phe Val Gly Ser Glu Ala Gly Val Val
        435                 440                 445 ctt aaa gtt ttg gca aag acc agt cct ttc tct ctg aat gac agt gta      1392
Leu Lys Val Leu Ala Lys Thr Ser Pro Phe Ser Leu Asn Asp Ser Val
    450                 455                 460 tta ctc gaa gag att gaa gct tat aac cca gcc aag tgc agc gcc gag      1440
Leu Leu Glu Glu Ile Glu Ala Tyr Asn Pro Ala Lys Cys Ser Ala Glu
465                 470                 475                 480 agt gag gag gac aga aag gtg gtc tca tta cag ctg gac aag gat cac      1488
Ser Glu Glu Asp Arg Lys Val Val Ser Leu Gln Leu Asp Lys Asp His
                485                 490                 495 cat gct tta tac gtg gcc ttc tct agc tgc gtg gtc cgc atc ccc ctc      1536
His Ala Leu Tyr Val Ala Phe Ser Ser Cys Val Val Arg Ile Pro Leu
            500                 505                 510 agc cgc tgt gag cgc tac gga tcg tgt aaa aag tct tgc att gca tca      1584
Ser Arg Cys Glu Arg Tyr Gly Ser Cys Lys Lys Ser Cys Ile Ala Ser
        515                 520                 525 cgt gac ccg tac tgt ggt tgg tta agc cag gga gtt tgt gag aga gtg      1632
Arg Asp Pro Tyr Cys Gly Trp Leu Ser Gln Gly Val Cys Glu Arg Val
    530                 535                 540 acc cta ggg atg ctg ctg tta acc gaa gac ttc ttt gct ttc cat aac      1680
Thr Leu Gly Met Leu Leu Leu Thr Glu Asp Phe Phe Ala Phe His Asn
545                 550                 555                 560 cac agc cct gga gga tat gag cag gac acg gag tac ggc aac aca gcc      1728
His Ser Pro Gly Gly Tyr Glu Gln Asp Thr Glu Tyr Gly Asn Thr Ala
                565                 570                 575 cac cta ggg gac tgc cac ggt gta cgg tgg gaa gtc cag tct gga gaa      1776
His Leu Gly Asp Cys His Gly Val Arg Trp Glu Val Gln Ser Gly Glu
            580                 585                 590 tcc aat cag atg gtc cac atg aat gtc ctc atc acc tgc gtg ttt gcc      1824
Ser Asn Gln Met Val His Met Asn Val Leu Ile Thr Cys Val Phe Ala
        595                 600                 605 gct ttt gtc ttg ggc gcg ttc atc gca gga gtg gcc gtg tac tgc tac      1872
Ala Phe Val Leu Gly Ala Phe Ile Ala Gly Val Ala Val Tyr Cys Tyr
    610                 615                 620 cgt gac atg ttc gtt cgg aag aac aga aag atc cat aaa gac gca gaa      1920
Arg Asp Met Phe Val Arg Lys Asn Arg Lys Ile His Lys Asp Ala Glu
625                 630                 635                 640 tcc gcc cag tcg tgc aca gac tcc agc gga agc ttc gcc aag ctg aac      1968
Ser Ala Gln Ser Cys Thr Asp Ser Ser Gly Ser Phe Ala Lys Leu Asn
                645                 650                 655 ggc ctc ttt gac agc ccc gtc aag gaa tac cag cag aac att gat tct      2016
Gly Leu Phe Asp Ser Pro Val Lys Glu Tyr Gln Gln Asn Ile Asp Ser
```

```
                660                 665                 670
ccc aaa ctc tac agc aac ctg ctg acc agt cgg aag gaa ctg cca cca      2064
Pro Lys Leu Tyr Ser Asn Leu Leu Thr Ser Arg Lys Glu Leu Pro Pro
        675                 680                 685 aac acg gat aca aag tcc atg gcc gtg gac cac aga ggc cag cct ccc      2112
Asn Thr Asp Thr Lys Ser Met Ala Val Asp His Arg Gly Gln Pro Pro
690                 695                 700 gag ctg gct gct ctc ccc acg ccg gaa tcc aca cct gtc ctc cac cag      2160
Glu Leu Ala Ala Leu Pro Thr Pro Glu Ser Thr Pro Val Leu His Gln
705                 710                 715                 720 aag acc ctg cag gcc atg aag agc cac tct gag aag gcc cac agc cac      2208
Lys Thr Leu Gln Ala Met Lys Ser His Ser Glu Lys Ala His Ser His
                725                 730                 735 ggt gct tca agg aaa gaa cac ccc cag ttt ttt cct tct agt cct cca      2256
Gly Ala Ser Arg Lys Glu His Pro Gln Phe Phe Pro Ser Ser Pro Pro
        740                 745                 750 ccc cat tcc cca ttg agt cac ggg cat atc ccc agt gcc atc gtt ctt      2304
Pro His Ser Pro Leu Ser His Gly His Ile Pro Ser Ala Ile Val Leu
755                 760                 765 cca aac gcc act cac gac tac aat aca tcc ttc tcc aac tcg aat gcc      2352
Pro Asn Ala Thr His Asp Tyr Asn Thr Ser Phe Ser Asn Ser Asn Ala
770                 775                 780 cac aaa gcc gaa aag aag ctt cag agc atg gat cac cct ctt acg aag      2400
His Lys Ala Glu Lys Lys Leu Gln Ser Met Asp His Pro Leu Thr Lys
785                 790                 795                 800 tca tcc agt aag cgg gag cac cgg cgg tct gtg gat tcc agg aat act      2448
Ser Ser Ser Lys Arg Glu His Arg Arg Ser Val Asp Ser Arg Asn Thr
                805                 810                 815 ctc aat gat ctc ctg aag cat cta aat gac cca aac agt aac ccc aaa      2496
Leu Asn Asp Leu Leu Lys His Leu Asn Asp Pro Asn Ser Asn Pro Lys
        820                 825                 830 gcc atc ctg gga gag atc cat atg gct cat caa acc ctc atg ctg gac      2544
Ala Ile Leu Gly Glu Ile His Met Ala His Gln Thr Leu Met Leu Asp
835                 840                 845 ccg gtg gga cca atg gct gag gtc cca ccc aag gtc cct aac cgg gag      2592
Pro Val Gly Pro Met Ala Glu Val Pro Pro Lys Val Pro Asn Arg Glu
850                 855                 860 gca tct cta tac tcc cct ccc tcc aca ctc ccc aga aat agt cca acc      2640
Ala Ser Leu Tyr Ser Pro Pro Ser Thr Leu Pro Arg Asn Ser Pro Thr
865                 870                 875                 880 aag aga gta gat gtc ccc acc act cct ggg gtg cca atg act tct ctg      2688
Lys Arg Val Asp Val Pro Thr Thr Pro Gly Val Pro Met Thr Ser Leu
                885                 890                 895 gaa aga caa agg ggt tat cac aaa aat tcc tcc cag agg cac tct ata      2736
Glu Arg Gln Arg Gly Tyr His Lys Asn Ser Ser Gln Arg His Ser Ile
        900                 905                 910 tct gcc gtg cct aaa aac tta aac tca cca aat ggt gtt ttg tta tct      2784
Ser Ala Val Pro Lys Asn Leu Asn Ser Pro Asn Gly Val Leu Leu Ser
915                 920                 925 aga cag ccg agt atg aac cgt gga ggc tat atg ccc acc cca aca ggg      2832
Arg Gln Pro Ser Met Asn Arg Gly Gly Tyr Met Pro Thr Pro Thr Gly
930                 935                 940 gcg aag gtg gac tat att cag ggg aca ccg gtg agt gtt cat ctg cag      2880
Ala Lys Val Asp Tyr Ile Gln Gly Thr Pro Val Ser Val His Leu Gln
945                 950                 955                 960 ccc tcc ctc tcc aga cag agc agc tat acc agt aat ggc acc ctc ccc      2928
Pro Ser Leu Ser Arg Gln Ser Ser Tyr Thr Ser Asn Gly Thr Leu Pro
                965                 970                 975 agg acg gga cta aag agg aca cca tcc tta aaa cct gat gtg cca cca      2976
```

```
                Arg Thr Gly Leu Lys Arg Thr Pro Ser Leu Lys Pro Asp Val Pro Pro
                            980                 985                 990 aag cct tcc ttt gtt ccg caa acc  aca tct gtc aga cca  ctg aac aag      3024
Lys Pro Ser Phe Val Pro Gln Thr  Thr Ser Val Arg Pro  Leu Asn Lys
            995                 1000                 1005 tac acg tac tag                                                        3036
Tyr Thr Tyr
    1010

<210> SEQ ID NO 35
<211> LENGTH: 1011
<212> TYPE: PRT
<213> ORGANISM: Mus musculus

<400> SEQUENCE: 35

Met Gly Phe Leu Leu Trp Phe Cys Val Leu Phe Leu Val Ser
1               5                   10                  15

Arg Leu Arg Ala Val Ser Phe Pro Glu Asp Glu Pro Leu Asn Thr
            20                  25                  30

Val Asp Tyr His Tyr Ser Arg Gln Tyr Pro Val Phe Arg Gly Arg Pro
            35                  40                  45

Ser Gly Asn Glu Ser Gln His Arg Leu Asp Phe Gln Leu Met Leu Lys
            50                  55                  60

Ile Arg Asp Thr Leu Tyr Ile Ala Gly Arg Asp Gln Val Tyr Thr Val
65                  70                  75                  80

Asn Leu Asn Glu Ile Pro Gln Thr Glu Val Ile Pro Ser Lys Lys Leu
                85                  90                  95

Thr Trp Arg Ser Arg Gln Gln Asp Arg Glu Asn Cys Ala Met Lys Gly
            100                 105                 110

Lys His Lys Asp Glu Cys His Asn Phe Ile Lys Val Phe Val Pro Arg
            115                 120                 125

Asn Asp Glu Met Val Phe Val Cys Gly Thr Asn Ala Phe Asn Pro Met
            130                 135                 140

Cys Arg Tyr Tyr Arg Leu Arg Thr Leu Glu Tyr Asp Gly Glu Glu Ile
145                 150                 155                 160

Ser Gly Leu Ala Arg Cys Pro Phe Asp Ala Arg Gln Thr Asn Val Ala
                165                 170                 175

Leu Phe Ala Asp Gly Lys Leu Tyr Ser Ala Thr Val Ala Asp Phe Leu
            180                 185                 190

Ala Ser Asp Ala Val Ile Tyr Arg Ser Met Gly Asp Gly Ser Ala Leu
            195                 200                 205

Arg Thr Ile Lys Tyr Asp Ser Lys Trp Ile Lys Glu Pro His Phe Leu
            210                 215                 220

His Ala Ile Glu Tyr Gly Asn Tyr Val Tyr Phe Phe Arg Glu Ile
225                 230                 235                 240

Ala Val Glu His Asn Asn Leu Gly Lys Ala Val Tyr Ser Arg Val Ala
                245                 250                 255

Arg Ile Cys Lys Asn Asp Met Gly Gly Ser Gln Arg Val Leu Glu Lys
            260                 265                 270

His Trp Thr Ser Phe Leu Lys Ala Arg Leu Asn Cys Ser Val Pro Gly
            275                 280                 285

Asp Ser Phe Phe Tyr Phe Asp Val Leu Gln Ser Ile Thr Asp Ile Ile
            290                 295                 300

Gln Ile Asn Gly Ile Pro Thr Val Gly Val Phe Thr Thr Gln Leu
305                 310                 315                 320
```

```
Asn Ser Ile Pro Gly Ser Ala Val Cys Ala Phe Ser Met Asp Asp Ile
            325                 330                 335
Glu Lys Val Phe Lys Gly Arg Phe Lys Glu Gln Lys Thr Pro Asp Ser
        340                 345                 350
Val Trp Thr Ala Val Pro Glu Asp Lys Val Pro Lys Pro Arg Pro Gly
        355                 360                 365
Cys Cys Ala Lys His Gly Leu Ala Glu Ala Tyr Lys Thr Ser Ile Asp
    370                 375                 380
Phe Pro Asp Asp Thr Leu Ala Phe Ile Lys Ser His Pro Leu Met Asp
385                 390                 395                 400
Ser Ala Val Pro Pro Ile Ala Asp Glu Pro Trp Phe Thr Lys Thr Arg
                405                 410                 415
Val Arg Tyr Arg Leu Thr Ala Ile Glu Val Asp Arg Ser Ala Gly Pro
            420                 425                 430
Tyr Gln Asn Tyr Thr Val Ile Phe Val Gly Ser Glu Ala Gly Val Val
        435                 440                 445
Leu Lys Val Leu Ala Lys Thr Ser Pro Phe Ser Leu Asn Asp Ser Val
    450                 455                 460
Leu Leu Glu Glu Ile Glu Ala Tyr Asn Pro Ala Lys Cys Ser Ala Glu
465                 470                 475                 480
Ser Glu Glu Asp Arg Lys Val Val Ser Leu Gln Leu Asp Lys Asp His
                485                 490                 495
His Ala Leu Tyr Val Ala Phe Ser Ser Cys Val Val Arg Ile Pro Leu
            500                 505                 510
Ser Arg Cys Glu Arg Tyr Gly Ser Cys Lys Lys Ser Cys Ile Ala Ser
        515                 520                 525
Arg Asp Pro Tyr Cys Gly Trp Leu Ser Gln Gly Val Cys Glu Arg Val
    530                 535                 540
Thr Leu Gly Met Leu Leu Leu Thr Glu Asp Phe Phe Ala Phe His Asn
545                 550                 555                 560
His Ser Pro Gly Gly Tyr Glu Gln Asp Thr Gly Tyr Gly Asn Thr Ala
                565                 570                 575
His Leu Gly Asp Cys His Gly Val Arg Trp Glu Val Gln Ser Gly Glu
            580                 585                 590
Ser Asn Gln Met Val His Met Asn Val Leu Ile Thr Cys Val Phe Ala
        595                 600                 605
Ala Phe Val Leu Gly Ala Phe Ile Ala Gly Val Ala Val Tyr Cys Tyr
    610                 615                 620
Arg Asp Met Phe Val Arg Lys Asn Arg Lys Ile His Lys Asp Ala Glu
625                 630                 635                 640
Ser Ala Gln Ser Cys Thr Asp Ser Ser Gly Ser Phe Ala Lys Leu Asn
                645                 650                 655
Gly Leu Phe Asp Ser Pro Val Lys Glu Tyr Gln Gln Asn Ile Asp Ser
            660                 665                 670
Pro Lys Leu Tyr Ser Asn Leu Leu Thr Ser Arg Lys Glu Leu Pro Pro
        675                 680                 685
Asn Thr Asp Thr Lys Ser Met Ala Val Asp His Arg Gly Gln Pro Pro
    690                 695                 700
Glu Leu Ala Ala Leu Pro Thr Pro Glu Ser Thr Pro Val Leu His Gln
705                 710                 715                 720
Lys Thr Leu Gln Ala Met Lys Ser His Ser Glu Lys Ala His Ser His
                725                 730                 735
Gly Ala Ser Arg Lys Glu His Pro Gln Phe Phe Pro Ser Ser Pro Pro
```

-continued

```
                  740                 745                 750
Pro His Ser Pro Leu Ser His Gly His Ile Pro Ser Ala Ile Val Leu
            755                 760                 765

Pro Asn Ala Thr His Asp Tyr Asn Thr Ser Phe Ser Asn Ser Asn Ala
770                 775                 780

His Lys Ala Glu Lys Lys Leu Gln Ser Met Asp His Pro Leu Thr Lys
785                 790                 795                 800

Ser Ser Ser Lys Arg Glu His Arg Arg Ser Val Asp Ser Arg Asn Thr
                805                 810                 815

Leu Asn Asp Leu Leu Lys His Leu Asn Asp Pro Asn Ser Asn Pro Lys
            820                 825                 830

Ala Ile Leu Gly Glu Ile His Met Ala His Gln Thr Leu Met Leu Asp
        835                 840                 845

Pro Val Gly Pro Met Ala Glu Val Pro Pro Lys Val Pro Asn Arg Glu
    850                 855                 860

Ala Ser Leu Tyr Ser Pro Pro Ser Thr Leu Pro Arg Asn Ser Pro Thr
865                 870                 875                 880

Lys Arg Val Asp Val Pro Thr Thr Pro Gly Val Pro Met Thr Ser Leu
                885                 890                 895

Glu Arg Gln Arg Gly Tyr His Lys Asn Ser Ser Gln Arg His Ser Ile
            900                 905                 910

Ser Ala Val Pro Lys Asn Leu Asn Ser Pro Asn Gly Val Leu Leu Ser
        915                 920                 925

Arg Gln Pro Ser Met Asn Arg Gly Gly Tyr Met Pro Thr Pro Thr Gly
    930                 935                 940

Ala Lys Val Asp Tyr Ile Gln Gly Thr Pro Val Ser Val His Leu Gln
945                 950                 955                 960

Pro Ser Leu Ser Arg Gln Ser Ser Tyr Thr Ser Asn Gly Thr Leu Pro
                965                 970                 975

Arg Thr Gly Leu Lys Arg Thr Pro Ser Leu Lys Pro Asp Val Pro Pro
            980                 985                 990

Lys Pro Ser Phe Val Pro Gln Thr  Thr Ser Val Arg Pro  Leu Asn Lys
        995                 1000                 1005

Tyr Thr Tyr
    1010

<210> SEQ ID NO 36
<211> LENGTH: 2997
<212> TYPE: DNA
<213> ORGANISM: Mus musculus
<220> FEATURE:
<221> NAME/KEY: CDS
<222> LOCATION: (1)..(2994)

<400> SEQUENCE: 36 atg ggg ttc ctt ctg ctt tgg ttc tgc gtg ctg ttc ctt ctg gtc tcc      48
Met Gly Phe Leu Leu Leu Trp Phe Cys Val Leu Phe Leu Leu Val Ser
1               5                   10                  15 agg tta cgg gcg gtc agc ttc cca gaa gac gat gag ccc ctc aac acg      96
Arg Leu Arg Ala Val Ser Phe Pro Glu Asp Asp Glu Pro Leu Asn Thr
            20                  25                  30 gtt gac tat cac tat tca agg caa tat ccg gtt ttt aga gga cgc cct     144
Val Asp Tyr His Tyr Ser Arg Gln Tyr Pro Val Phe Arg Gly Arg Pro
        35                  40                  45 tca ggc aac gaa tcg cag cac agg ctg gac ttt cag ctg atg ttg aaa     192
Ser Gly Asn Glu Ser Gln His Arg Leu Asp Phe Gln Leu Met Leu Lys
    50                  55                  60
```

```
att cga gac aca ctt tat att gct ggc agg gat caa gtc tat aca gtg      240
Ile Arg Asp Thr Leu Tyr Ile Ala Gly Arg Asp Gln Val Tyr Thr Val
 65                  70                  75                  80 aac tta aat gaa atc ccc caa aca gag gtg ata cca agc aag aag ctg      288
Asn Leu Asn Glu Ile Pro Gln Thr Glu Val Ile Pro Ser Lys Lys Leu
                 85                  90                  95 acg tgg agg tcc aga cag cag gat cga gaa aat tgt gct atg aaa ggc      336
Thr Trp Arg Ser Arg Gln Gln Asp Arg Glu Asn Cys Ala Met Lys Gly
            100                 105                 110 aag cat aaa gat gaa tgc cac aac ttc atc aaa gtc ttt gtc cca aga      384
Lys His Lys Asp Glu Cys His Asn Phe Ile Lys Val Phe Val Pro Arg
        115                 120                 125 aat gat gag atg gtt ttt gtc tgt ggt acc aat gct ttc aac ccg atg      432
Asn Asp Glu Met Val Phe Val Cys Gly Thr Asn Ala Phe Asn Pro Met
    130                 135                 140 tgc aga tac tat agg ttg aga acg tta gag tat gat ggg gaa gaa att      480
Cys Arg Tyr Tyr Arg Leu Arg Thr Leu Glu Tyr Asp Gly Glu Glu Ile
145                 150                 155                 160 agt ggc ctg gca cga tgc ccg ttt gat gcc cga caa acc aat gtc gcc      528
Ser Gly Leu Ala Arg Cys Pro Phe Asp Ala Arg Gln Thr Asn Val Ala
                165                 170                 175 ctc ttt gct gat gga aaa ctc tat tct gcc aca gtg gct gat ttc ctg      576
Leu Phe Ala Asp Gly Lys Leu Tyr Ser Ala Thr Val Ala Asp Phe Leu
            180                 185                 190 gcc agt gat gct gtc att tac aga agc atg gga gat gga tct gcc ctt      624
Ala Ser Asp Ala Val Ile Tyr Arg Ser Met Gly Asp Gly Ser Ala Leu
        195                 200                 205 cgc aca ata aaa tac gat tcc aag tgg atc aaa gaa cca cac ttc ctt      672
Arg Thr Ile Lys Tyr Asp Ser Lys Trp Ile Lys Glu Pro His Phe Leu
    210                 215                 220 cat gcc ata gaa tat gga aac tat gtc tat ttc ttc aga gaa atc      720
His Ala Ile Glu Tyr Gly Asn Tyr Val Tyr Phe Phe Arg Glu Ile
225                 230                 235                 240 gcc gtg gaa cat aat aac tta ggc aag gct gtg tat tcc cgc gtg gct      768
Ala Val Glu His Asn Asn Leu Gly Lys Ala Val Tyr Ser Arg Val Ala
                245                 250                 255 cgc att tgt aaa aac gac atg ggt ggc tca cag cgg gtc ctg gag aaa      816
Arg Ile Cys Lys Asn Asp Met Gly Gly Ser Gln Arg Val Leu Glu Lys
            260                 265                 270 cac tgg act tcc ttc ctt aag gct cgg ctg aac tgc tcc gtt cct gga      864
His Trp Thr Ser Phe Leu Lys Ala Arg Leu Asn Cys Ser Val Pro Gly
        275                 280                 285 gat tcc ttt ttc tac ttc gac gtc ctg cag tct ata aca gac ata atc      912
Asp Ser Phe Phe Tyr Phe Asp Val Leu Gln Ser Ile Thr Asp Ile Ile
    290                 295                 300 caa atc aat ggc atc ccc act gtg gtt ggg gtc ttc acc aca cag ctc      960
Gln Ile Asn Gly Ile Pro Thr Val Val Gly Val Phe Thr Thr Gln Leu
305                 310                 315                 320 aac agc att cct ggt tct gca gtc tgt gcc ttt agc atg gac gac att     1008
Asn Ser Ile Pro Gly Ser Ala Val Cys Ala Phe Ser Met Asp Asp Ile
                325                 330                 335 gag aaa gtg ttc aaa ggg cgg ttc aaa gag cag aaa acc cca gac tct     1056
Glu Lys Val Phe Lys Gly Arg Phe Lys Glu Gln Lys Thr Pro Asp Ser
            340                 345                 350 gtt tgg aca gca gtt ccc gaa gac aaa gta cca aaa cca agg cct ggc     1104
Val Trp Thr Ala Val Pro Glu Asp Lys Val Pro Lys Pro Arg Pro Gly
        355                 360                 365 tgt tgt gcc aaa cac ggc ctc gca gaa gct tac aag acc tcc atc gac     1152
Cys Cys Ala Lys His Gly Leu Ala Glu Ala Tyr Lys Thr Ser Ile Asp
```

```
                370                 375                 380
ttt cca gat gac acc ctg gct ttc atc aag tcc cac ccg ctg atg gac       1200
Phe Pro Asp Asp Thr Leu Ala Phe Ile Lys Ser His Pro Leu Met Asp
385                 390                 395                 400 tct gcc gtc cca ccc att gcc gat gag ccc tgg ttc aca aag aca cgg       1248
Ser Ala Val Pro Pro Ile Ala Asp Glu Pro Trp Phe Thr Lys Thr Arg
                405                 410                 415 gtc agg tac agg ttg aca gcc atc gaa gtg gac cgt tca gca ggg cca       1296
Val Arg Tyr Arg Leu Thr Ala Ile Glu Val Asp Arg Ser Ala Gly Pro
                420                 425                 430 tac caa aac tac aca gtc atc ttt gtt ggc tct gaa gct ggc gtg gta       1344
Tyr Gln Asn Tyr Thr Val Ile Phe Val Gly Ser Glu Ala Gly Val Val
                435                 440                 445 ctt aaa gtt ttg gca aag acc agt cct ttc tct ctg aat gac agt gta       1392
Leu Lys Val Leu Ala Lys Thr Ser Pro Phe Ser Leu Asn Asp Ser Val
450                 455                 460 tta ctc gaa gag att gaa gct tat aac cca gcc aag tgc agc gcc gag       1440
Leu Leu Glu Glu Ile Glu Ala Tyr Asn Pro Ala Lys Cys Ser Ala Glu
465                 470                 475                 480 agt gag gag gac aga aag gtg gtc tca tta cag ctg gac aag gat cac       1488
Ser Glu Glu Asp Arg Lys Val Val Ser Leu Gln Leu Asp Lys Asp His
                485                 490                 495 cat gct tta tac gtg gcc ttc tct agc tgc gtg gtc cgc atc ccc ctc       1536
His Ala Leu Tyr Val Ala Phe Ser Ser Cys Val Val Arg Ile Pro Leu
                500                 505                 510 agc cgc tgt gag cgc tac gga tcg tgt aaa aag tct tgc att gca tca       1584
Ser Arg Cys Glu Arg Tyr Gly Ser Cys Lys Lys Ser Cys Ile Ala Ser
                515                 520                 525 cgt gac ccg tac tgt ggt tgg tta agc cag gga gtt tgt gag aga gtg       1632
Arg Asp Pro Tyr Cys Gly Trp Leu Ser Gln Gly Val Cys Glu Arg Val
530                 535                 540 acc cta ggg atg ctc cct gga gga tat gag cag gac acg gag tac ggc       1680
Thr Leu Gly Met Leu Pro Gly Gly Tyr Glu Gln Asp Thr Glu Tyr Gly
545                 550                 555                 560 aac aca gcc cac cta ggg gac tgc cac ggt gta cgg tgg gaa gtc cag       1728
Asn Thr Ala His Leu Gly Asp Cys His Gly Val Arg Trp Glu Val Gln
                565                 570                 575 tct gga gaa tcc aat cag atg gtc cac atg aat gtc ctc atc acc tgc       1776
Ser Gly Glu Ser Asn Gln Met Val His Met Asn Val Leu Ile Thr Cys
                580                 585                 590 gtg ttt gcc gct ttt gtc ttg ggc gcg ttc atc gca gga gtg gcc gtg       1824
Val Phe Ala Ala Phe Val Leu Gly Ala Phe Ile Ala Gly Val Ala Val
                595                 600                 605 tac tgc tac cgt gac atg ttc gtt cgg aag aac aga aag atc cat aaa       1872
Tyr Cys Tyr Arg Asp Met Phe Val Arg Lys Asn Arg Lys Ile His Lys
                610                 615                 620 gac gca gaa tcc gcc cag tcg tgc aca gac tcc agc gga agc ttc gcc       1920
Asp Ala Glu Ser Ala Gln Ser Cys Thr Asp Ser Ser Gly Ser Phe Ala
625                 630                 635                 640 aag ctg aac ggc ctc ttt gac agc ccc gtc aag gaa tac cag cag aac       1968
Lys Leu Asn Gly Leu Phe Asp Ser Pro Val Lys Glu Tyr Gln Gln Asn
                645                 650                 655 att gat tct ccc aaa ctc tac agc aac ctg ctg acc agt cgg aag gaa       2016
Ile Asp Ser Pro Lys Leu Tyr Ser Asn Leu Leu Thr Ser Arg Lys Glu
                660                 665                 670 ctg cca cca aac acg gat aca aag tcc atg gcc gtg gac cac aga ggc       2064
Leu Pro Pro Asn Thr Asp Thr Lys Ser Met Ala Val Asp His Arg Gly
                675                 680                 685 cag cct ccc gag ctg gct gct ctc ccc acg ccg gaa tcc aca cct gtc       2112
```

-continued

| | | |
|---|---|---|
| Gln Pro Pro Glu Leu Ala Ala Leu Pro Thr Pro Glu Ser Thr Pro Val<br>690                        695                        700 | | ctc cac cag aag acc ctg cag gcc atg aag agc cac tct gag aag gcc    2160
Leu His Gln Lys Thr Leu Gln Ala Met Lys Ser His Ser Glu Lys Ala
705                  710                  715                  720 cac agc cac ggt gct tca agg aaa gaa cac ccc cag ttt ttt cct tct    2208
His Ser His Gly Ala Ser Arg Lys Glu His Pro Gln Phe Phe Pro Ser
                  725                  730                  735 agt cct cca ccc cat tcc cca ttg agt cac ggg cat atc ccc agt gcc    2256
Ser Pro Pro Pro His Ser Pro Leu Ser His Gly His Ile Pro Ser Ala
            740                  745                  750 atc gtt ctt cca aac gcc act cac gac tac aat aca tcc ttc tcc aac    2304
Ile Val Leu Pro Asn Ala Thr His Asp Tyr Asn Thr Ser Phe Ser Asn
                  755                  760                  765 tcg aat gcc cac aaa gcc gaa aag aag ctt cag agc atg gat cac cct    2352
Ser Asn Ala His Lys Ala Glu Lys Lys Leu Gln Ser Met Asp His Pro
770                  775                  780 ctt acg aag tca tcc agt aag cgg gag cac cgg cgg tct gtg gat tcc    2400
Leu Thr Lys Ser Ser Ser Lys Arg Glu His Arg Arg Ser Val Asp Ser
785                  790                  795                  800 agg aat act ctc aat gat ctc ctg aag cat cta aat gac cca aac agt    2448
Arg Asn Thr Leu Asn Asp Leu Leu Lys His Leu Asn Asp Pro Asn Ser
                  805                  810                  815 aac ccc aaa gcc atc ctg gga gag atc cat atg gct cat caa acc ctc    2496
Asn Pro Lys Ala Ile Leu Gly Glu Ile His Met Ala His Gln Thr Leu
            820                  825                  830 atg ctg gac ccg gtg gga cca atg gct gag gtc cca ccc aag gtc cct    2544
Met Leu Asp Pro Val Gly Pro Met Ala Glu Val Pro Pro Lys Val Pro
835                  840                  845 aac cgg gag gca tct cta tac tcc cct ccc tcc aca ctc ccc aga aat    2592
Asn Arg Glu Ala Ser Leu Tyr Ser Pro Pro Ser Thr Leu Pro Arg Asn
850                  855                  860 agt cca acc aag aga gta gat gtc ccc acc act cct ggg gtg cca atg    2640
Ser Pro Thr Lys Arg Val Asp Val Pro Thr Thr Pro Gly Val Pro Met
865                  870                  875                  880 act tct ctg gaa aga caa agg ggt tat cac aaa aat tcc tcc cag agg    2688
Thr Ser Leu Glu Arg Gln Arg Gly Tyr His Lys Asn Ser Ser Gln Arg
                  885                  890                  895 cac tct ata tct gcc gtg cct aaa aac tta aac tca cca aat ggt gtt    2736
His Ser Ile Ser Ala Val Pro Lys Asn Leu Asn Ser Pro Asn Gly Val
            900                  905                  910 ttg tta tct aga cag ccg agt atg aac cgt gga ggc tat atg ccc acc    2784
Leu Leu Ser Arg Gln Pro Ser Met Asn Arg Gly Gly Tyr Met Pro Thr
                  915                  920                  925 cca aca ggg gcg aag gtg gac tat att cag ggg aca ccg gtg agt gtt    2832
Pro Thr Gly Ala Lys Val Asp Tyr Ile Gln Gly Thr Pro Val Ser Val
930                  935                  940 cat ctg cag ccc tcc ctc tcc aga cag agc agc tat acc agt aat ggc    2880
His Leu Gln Pro Ser Leu Ser Arg Gln Ser Ser Tyr Thr Ser Asn Gly
945                  950                  955                  960 acc ctc ccc agg acg gga cta aag agg aca cca tcc tta aaa cct gat    2928
Thr Leu Pro Arg Thr Gly Leu Lys Arg Thr Pro Ser Leu Lys Pro Asp
                  965                  970                  975 gtg cca cca aag cct tcc ttt gtt ccg caa acc aca tct gtc aga cca    2976
Val Pro Pro Lys Pro Ser Phe Val Pro Gln Thr Thr Ser Val Arg Pro
            980                  985                  990 ctg aac aag tac acg tac tag    2997
Leu Asn Lys Tyr Thr Tyr
            995

<210> SEQ ID NO 37
<211> LENGTH: 998
<212> TYPE: PRT
<213> ORGANISM: Mus musculus

<400> SEQUENCE: 37

```
Met Gly Phe Leu Leu Trp Phe Cys Val Leu Phe Leu Leu Val Ser
1               5                   10                  15

Arg Leu Arg Ala Val Ser Phe Pro Glu Asp Glu Pro Leu Asn Thr
            20                  25                  30

Val Asp Tyr His Tyr Ser Arg Gln Tyr Pro Val Phe Arg Gly Arg Pro
            35                  40                  45

Ser Gly Asn Glu Ser Gln His Arg Leu Asp Phe Gln Leu Met Leu Lys
        50                  55                  60

Ile Arg Asp Thr Leu Tyr Ile Ala Gly Arg Asp Gln Val Tyr Thr Val
65                  70                  75                  80

Asn Leu Asn Glu Ile Pro Gln Thr Glu Val Ile Pro Ser Lys Lys Leu
            85                  90                  95

Thr Trp Arg Ser Arg Gln Gln Asp Arg Glu Asn Cys Ala Met Lys Gly
            100                 105                 110

Lys His Lys Asp Glu Cys His Asn Phe Ile Lys Val Phe Val Pro Arg
        115                 120                 125

Asn Asp Glu Met Val Phe Val Cys Gly Thr Asn Ala Phe Asn Pro Met
130                 135                 140

Cys Arg Tyr Tyr Arg Leu Arg Thr Leu Glu Tyr Asp Gly Glu Glu Ile
145                 150                 155                 160

Ser Gly Leu Ala Arg Cys Pro Phe Asp Ala Arg Gln Thr Asn Val Ala
            165                 170                 175

Leu Phe Ala Asp Gly Lys Leu Tyr Ser Ala Thr Val Ala Asp Phe Leu
        180                 185                 190

Ala Ser Asp Ala Val Ile Tyr Arg Ser Met Gly Asp Gly Ser Ala Leu
        195                 200                 205

Arg Thr Ile Lys Tyr Asp Ser Lys Trp Ile Lys Glu Pro His Phe Leu
    210                 215                 220

His Ala Ile Glu Tyr Gly Asn Tyr Val Tyr Phe Phe Arg Glu Ile
225                 230                 235             240

Ala Val Glu His Asn Asn Leu Gly Lys Ala Val Tyr Ser Arg Val Ala
            245                 250                 255

Arg Ile Cys Lys Asn Asp Met Gly Gly Ser Gln Arg Val Leu Glu Lys
            260                 265                 270

His Trp Thr Ser Phe Leu Lys Ala Arg Leu Asn Cys Ser Val Pro Gly
        275                 280                 285

Asp Ser Phe Phe Tyr Phe Asp Val Leu Gln Ser Ile Thr Asp Ile Ile
    290                 295                 300

Gln Ile Asn Gly Ile Pro Thr Val Val Gly Val Phe Thr Thr Gln Leu
305                 310                 315                 320

Asn Ser Ile Pro Gly Ser Ala Val Cys Ala Phe Ser Met Asp Asp Ile
            325                 330                 335

Glu Lys Val Phe Lys Gly Arg Phe Lys Glu Gln Lys Thr Pro Asp Ser
            340                 345                 350

Val Trp Thr Ala Val Pro Glu Asp Lys Val Pro Lys Pro Arg Pro Gly
        355                 360                 365

Cys Cys Ala Lys His Gly Leu Ala Glu Ala Tyr Lys Thr Ser Ile Asp
    370                 375                 380
```

-continued

```
Phe Pro Asp Asp Thr Leu Ala Phe Ile Lys Ser His Pro Leu Met Asp
385                 390                 395                 400

Ser Ala Val Pro Pro Ile Ala Asp Glu Pro Trp Phe Thr Lys Thr Arg
                405                 410                 415

Val Arg Tyr Arg Leu Thr Ala Ile Glu Val Asp Arg Ser Ala Gly Pro
            420                 425                 430

Tyr Gln Asn Tyr Thr Val Ile Phe Val Gly Ser Glu Ala Gly Val Val
        435                 440                 445

Leu Lys Val Leu Ala Lys Thr Ser Pro Phe Ser Leu Asn Asp Ser Val
    450                 455                 460

Leu Leu Glu Glu Ile Glu Ala Tyr Asn Pro Ala Lys Cys Ser Ala Glu
465                 470                 475                 480

Ser Glu Glu Asp Arg Lys Val Val Ser Leu Gln Leu Asp Lys Asp His
                485                 490                 495

His Ala Leu Tyr Val Ala Phe Ser Ser Cys Val Val Arg Ile Pro Leu
            500                 505                 510

Ser Arg Cys Glu Arg Tyr Gly Ser Cys Lys Lys Ser Cys Ile Ala Ser
        515                 520                 525

Arg Asp Pro Tyr Cys Gly Trp Leu Ser Gln Gly Val Cys Glu Arg Val
    530                 535                 540

Thr Leu Gly Met Leu Pro Gly Gly Tyr Glu Gln Asp Thr Glu Tyr Gly
545                 550                 555                 560

Asn Thr Ala His Leu Gly Asp Cys His Gly Val Arg Trp Glu Val Gln
                565                 570                 575

Ser Gly Glu Ser Asn Gln Met Val His Met Asn Val Leu Ile Thr Cys
            580                 585                 590

Val Phe Ala Ala Phe Val Leu Gly Ala Phe Ile Ala Gly Val Ala Val
        595                 600                 605

Tyr Cys Tyr Arg Asp Met Phe Val Arg Lys Asn Arg Lys Ile His Lys
    610                 615                 620

Asp Ala Glu Ser Ala Gln Ser Cys Thr Asp Ser Ser Gly Ser Phe Ala
625                 630                 635                 640

Lys Leu Asn Gly Leu Phe Asp Ser Pro Val Lys Glu Tyr Gln Gln Asn
                645                 650                 655

Ile Asp Ser Pro Lys Leu Tyr Ser Asn Leu Leu Thr Ser Arg Lys Glu
            660                 665                 670

Leu Pro Pro Asn Thr Asp Thr Lys Ser Met Ala Val Asp His Arg Gly
        675                 680                 685

Gln Pro Pro Glu Leu Ala Ala Leu Pro Thr Pro Glu Ser Thr Pro Val
    690                 695                 700

Leu His Gln Lys Thr Leu Gln Ala Met Lys Ser His Ser Glu Lys Ala
705                 710                 715                 720

His Ser His Gly Ala Ser Arg Lys Glu His Pro Gln Phe Phe Pro Ser
                725                 730                 735

Ser Pro Pro Pro His Ser Pro Leu Ser His Gly His Ile Pro Ser Ala
            740                 745                 750

Ile Val Leu Pro Asn Ala Thr His Asp Tyr Asn Thr Ser Phe Ser Asn
        755                 760                 765

Ser Asn Ala His Lys Ala Glu Lys Leu Gln Ser Met Asp His Pro
    770                 775                 780

Leu Thr Lys Ser Ser Lys Arg Glu His Arg Arg Ser Val Asp Ser
785                 790                 795                 800
```

```
Arg Asn Thr Leu Asn Asp Leu Leu Lys His Leu Asn Asp Pro Asn Ser
                805                 810                 815

Asn Pro Lys Ala Ile Leu Gly Glu Ile His Met Ala His Gln Thr Leu
            820                 825                 830

Met Leu Asp Pro Val Gly Pro Met Ala Glu Val Pro Pro Lys Val Pro
        835                 840                 845

Asn Arg Glu Ala Ser Leu Tyr Ser Pro Pro Ser Thr Leu Pro Arg Asn
    850                 855                 860

Ser Pro Thr Lys Arg Val Asp Val Pro Thr Thr Pro Gly Val Pro Met
865                 870                 875                 880

Thr Ser Leu Glu Arg Gln Arg Gly Tyr His Lys Asn Ser Ser Gln Arg
                885                 890                 895

His Ser Ile Ser Ala Val Pro Lys Asn Leu Asn Ser Pro Asn Gly Val
            900                 905                 910

Leu Leu Ser Arg Gln Pro Ser Met Asn Arg Gly Gly Tyr Met Pro Thr
        915                 920                 925

Pro Thr Gly Ala Lys Val Asp Tyr Ile Gln Gly Thr Pro Val Ser Val
    930                 935                 940

His Leu Gln Pro Ser Leu Ser Arg Gln Ser Ser Tyr Thr Ser Asn Gly
945                 950                 955                 960

Thr Leu Pro Arg Thr Gly Leu Lys Arg Thr Pro Ser Leu Lys Pro Asp
                965                 970                 975

Val Pro Pro Lys Pro Ser Phe Val Pro Gln Thr Thr Ser Val Arg Pro
            980                 985                 990

Leu Asn Lys Tyr Thr Tyr
        995

<210> SEQ ID NO 38
<211> LENGTH: 3222
<212> TYPE: DNA
<213> ORGANISM: Mus musculus
<220> FEATURE:
<221> NAME/KEY: CDS
<222> LOCATION: (1)..(3219)

<400> SEQUENCE: 38 atg ggg ttc ctt ctg ctt tgg ttc tgc gtg ctg ttc ctt ctg gtc tcc      48
Met Gly Phe Leu Leu Leu Trp Phe Cys Val Leu Phe Leu Leu Val Ser
1               5                   10                  15 agg tta cgg gcg gtc agc ttc cca gaa gac gat gag ccc ctc aac acg      96
Arg Leu Arg Ala Val Ser Phe Pro Glu Asp Asp Glu Pro Leu Asn Thr
            20                  25                  30 gtt gac tat cac tat tca agg caa tat ccg gtt ttt aga gga cgc cct     144
Val Asp Tyr His Tyr Ser Arg Gln Tyr Pro Val Phe Arg Gly Arg Pro
        35                  40                  45 tca ggc aac gaa tcg cag cac agg ctg gac ttt cag ctg atg ttg aaa     192
Ser Gly Asn Glu Ser Gln His Arg Leu Asp Phe Gln Leu Met Leu Lys
    50                  55                  60 att cga gac aca ctt tat att gct ggc agg gat caa gtc tat aca gtg     240
Ile Arg Asp Thr Leu Tyr Ile Ala Gly Arg Asp Gln Val Tyr Thr Val
65                  70                  75                  80 aac tta aat gaa atc ccc caa aca gag gtg ata cca agc aag aag ctg     288
Asn Leu Asn Glu Ile Pro Gln Thr Glu Val Ile Pro Ser Lys Lys Leu
                85                  90                  95 acg tgg agg tcc aga cag cag gat cga gaa aat tgt gct atg aaa ggc     336
Thr Trp Arg Ser Arg Gln Gln Asp Arg Glu Asn Cys Ala Met Lys Gly
            100                 105                 110 aag cat aaa gat gaa tgc cac aac ttc atc aaa gtc ttt gtc cca aga     384
```

```
                Lys His Lys Asp Glu Cys His Asn Phe Ile Lys Val Phe Val Pro Arg
                    115                 120                 125 aat gat gag atg gtt ttt gtc tgt ggt acc aat gct ttc aac ccg atg           432
Asn Asp Glu Met Val Phe Val Cys Gly Thr Asn Ala Phe Asn Pro Met
130                 135                 140 tgc aga tac tat agg ttg aga acg tta gag tat gat ggg gaa gaa att           480
Cys Arg Tyr Tyr Arg Leu Arg Thr Leu Glu Tyr Asp Gly Glu Glu Ile
145                 150                 155                 160 agt ggc ctg gca cga tgc ccg ttt gat gcc cga caa acc aat gtc gcc           528
Ser Gly Leu Ala Arg Cys Pro Phe Asp Ala Arg Gln Thr Asn Val Ala
                165                 170                 175 ctc ttt gct gat gga aaa ctc tat tct gcc aca gtg gct gat ttc ctg           576
Leu Phe Ala Asp Gly Lys Leu Tyr Ser Ala Thr Val Ala Asp Phe Leu
                180                 185                 190 gcc agt gat gct gtc att tac aga agc atg gga gat gga tct gcc ctt           624
Ala Ser Asp Ala Val Ile Tyr Arg Ser Met Gly Asp Gly Ser Ala Leu
                195                 200                 205 cgc aca ata aaa tac gat tcc aag tgg atc aaa gaa cca cac ttc ctt           672
Arg Thr Ile Lys Tyr Asp Ser Lys Trp Ile Lys Glu Pro His Phe Leu
210                 215                 220 cat gcc ata gaa tat gga aac tat gtc tat ttc ttc aga gaa atc               720
His Ala Ile Glu Tyr Gly Asn Tyr Val Tyr Phe Phe Arg Glu Ile
225                 230                 235                 240 gcc gtg gaa cat aat aac tta ggc aag gct gtg tat tcc cgc gtg gct           768
Ala Val Glu His Asn Asn Leu Gly Lys Ala Val Tyr Ser Arg Val Ala
                245                 250                 255 cgc att tgt aaa aac gac atg ggt ggc tca cag cgg gtc ctg gag aaa           816
Arg Ile Cys Lys Asn Asp Met Gly Gly Ser Gln Arg Val Leu Glu Lys
                260                 265                 270 cac tgg act tcc ttc ctt aag gct cgg ctg aac tgc tcc gtt cct gga           864
His Trp Thr Ser Phe Leu Lys Ala Arg Leu Asn Cys Ser Val Pro Gly
                275                 280                 285 gat tcc ttt ttc tac ttc gac gtc ctg cag tct ata aca gac ata atc           912
Asp Ser Phe Phe Tyr Phe Asp Val Leu Gln Ser Ile Thr Asp Ile Ile
                290                 295                 300 caa atc aat ggc atc ccc act gtg gtt ggg gtc ttc acc aca cag ctc           960
Gln Ile Asn Gly Ile Pro Thr Val Val Gly Val Phe Thr Thr Gln Leu
305                 310                 315                 320 aac agc att cct ggt tct gca gtc tgt gcc ttt agc atg gac gac att          1008
Asn Ser Ile Pro Gly Ser Ala Val Cys Ala Phe Ser Met Asp Asp Ile
                325                 330                 335 gag aaa gtg ttc aaa ggg cgg ttc aaa gag cag aaa acc cca gac tct          1056
Glu Lys Val Phe Lys Gly Arg Phe Lys Glu Gln Lys Thr Pro Asp Ser
                340                 345                 350 gtt tgg aca gca gtt ccc gaa gac aaa gta cca aaa cca agg cct ggc          1104
Val Trp Thr Ala Val Pro Glu Asp Lys Val Pro Lys Pro Arg Pro Gly
                355                 360                 365 tgt tgt gcc aaa cac ggc ctc gca gaa gct tac aag acc tcc atc gac          1152
Cys Cys Ala Lys His Gly Leu Ala Glu Ala Tyr Lys Thr Ser Ile Asp
370                 375                 380 ttt cca gat gac acc ctg gct ttc atc aag tcc cac ccg ctg atg gac          1200
Phe Pro Asp Asp Thr Leu Ala Phe Ile Lys Ser His Pro Leu Met Asp
385                 390                 395                 400 tct gcc gtc cca ccc att gcc gat gag ccc tgg ttc aca aag aca cgg          1248
Ser Ala Val Pro Pro Ile Ala Asp Glu Pro Trp Phe Thr Lys Thr Arg
                405                 410                 415 gtc agg tac agg ttg aca gcc atc gaa gtg gac cgt tca gca ggg cca          1296
Val Arg Tyr Arg Leu Thr Ala Ile Glu Val Asp Arg Ser Ala Gly Pro
                420                 425                 430
```

```
tac caa aac tac aca gtc atc ttt gtt ggc tct gaa gct ggc gtg gta    1344
Tyr Gln Asn Tyr Thr Val Ile Phe Val Gly Ser Glu Ala Gly Val Val
        435                 440                 445 ctt aaa gtt ttg gca aag acc agt cct ttc tct ctg aat gac agt gta    1392
Leu Lys Val Leu Ala Lys Thr Ser Pro Phe Ser Leu Asn Asp Ser Val
450                 455                 460 tta ctc gaa gag att gaa gct tat aac cca gcc aag tgc agc gcc gag    1440
Leu Leu Glu Glu Ile Glu Ala Tyr Asn Pro Ala Lys Cys Ser Ala Glu
465                 470                 475                 480 agt gag gag gac aga aag gtg gtc tca tta cag ctg gac aag gat cac    1488
Ser Glu Glu Asp Arg Lys Val Val Ser Leu Gln Leu Asp Lys Asp His
                485                 490                 495 cat gct tta tac gtg gcc ttc tct agc tgc gtg gtc cgc atc ccc ctc    1536
His Ala Leu Tyr Val Ala Phe Ser Ser Cys Val Val Arg Ile Pro Leu
            500                 505                 510 agc cgc tgt gag cgc tac gga tcg tgt aaa aag tct tgc att gca tca    1584
Ser Arg Cys Glu Arg Tyr Gly Ser Cys Lys Lys Ser Cys Ile Ala Ser
        515                 520                 525 cgt gac ccg tac tgt ggt tgg tta agc cag gga gtt tgt gag aga gtg    1632
Arg Asp Pro Tyr Cys Gly Trp Leu Ser Gln Gly Val Cys Glu Arg Val
530                 535                 540 acc cta ggg atg ctc cct gga gga tat gag cag gac acg gag tac ggc    1680
Thr Leu Gly Met Leu Pro Gly Gly Tyr Glu Gln Asp Thr Glu Tyr Gly
545                 550                 555                 560 aac aca gcc cac cta ggg gac tgc cac gaa agt ttg cct cct tca act    1728
Asn Thr Ala His Leu Gly Asp Cys His Glu Ser Leu Pro Pro Ser Thr
                565                 570                 575 aca cca gat tac aaa ata ttt ggc ggt cca aca tct gac atg gag gta    1776
Thr Pro Asp Tyr Lys Ile Phe Gly Gly Pro Thr Ser Asp Met Glu Val
            580                 585                 590 tcc tca tct tct gtt acc act gtg gca agt agc cca gaa att aca tct    1824
Ser Ser Ser Ser Val Thr Thr Val Ala Ser Ser Pro Glu Ile Thr Ser
        595                 600                 605 aaa gtg att gat acc tgg aga cct aaa ctg acg agc tcc cgg aaa ttt    1872
Lys Val Ile Asp Thr Trp Arg Pro Lys Leu Thr Ser Ser Arg Lys Phe
610                 615                 620 gta gtt caa gat gac cca aat act tct gat ttt act gat act ata tca    1920
Val Val Gln Asp Asp Pro Asn Thr Ser Asp Phe Thr Asp Thr Ile Ser
625                 630                 635                 640 ggt atc cca aag ggt gta cgg tgg gaa gtc cag tct gga gaa tcc aat    1968
Gly Ile Pro Lys Gly Val Arg Trp Glu Val Gln Ser Gly Glu Ser Asn
                645                 650                 655 cag atg gtc cac atg aat gtc ctc atc acc tgc gtg ttt gcc gct ttt    2016
Gln Met Val His Met Asn Val Leu Ile Thr Cys Val Phe Ala Ala Phe
            660                 665                 670 gtc ttg ggc gcg ttc atc gca gga gtg gcc gtg tac tgc tac cgt gac    2064
Val Leu Gly Ala Phe Ile Ala Gly Val Ala Val Tyr Cys Tyr Arg Asp
        675                 680                 685 atg ttc gtt cgg aag aac aga aag atc cat aaa gac gca gaa tcc gcc    2112
Met Phe Val Arg Lys Asn Arg Lys Ile His Lys Asp Ala Glu Ser Ala
690                 695                 700 cag tcg tgc aca gac tcc agc gga agc ttc gcc aag ctg aac ggc ctc    2160
Gln Ser Cys Thr Asp Ser Ser Gly Ser Phe Ala Lys Leu Asn Gly Leu
705                 710                 715                 720 ttt gac agc ccc gtc aag gaa tac cag cag aac att gat tct ccc aaa    2208
Phe Asp Ser Pro Val Lys Glu Tyr Gln Gln Asn Ile Asp Ser Pro Lys
                725                 730                 735 ctc tac agc aac ctg ctg acc agt cgg aag gaa ctg cca cca aac acg    2256
Leu Tyr Ser Asn Leu Leu Thr Ser Arg Lys Glu Leu Pro Pro Asn Thr
            740                 745                 750
```

-continued

```
gat aca aag tcc atg gcc gtg gac cac aga ggc cag cct ccc gag ctg       2304
Asp Thr Lys Ser Met Ala Val Asp His Arg Gly Gln Pro Pro Glu Leu
        755                 760                 765 gct gct ctc ccc acg ccg gaa tcc aca cct gtc ctc cac cag aag acc       2352
Ala Ala Leu Pro Thr Pro Glu Ser Thr Pro Val Leu His Gln Lys Thr
770                 775                 780 ctg cag gcc atg aag agc cac tct gag aag gcc cac agc cac ggt gct       2400
Leu Gln Ala Met Lys Ser His Ser Glu Lys Ala His Ser His Gly Ala
785                 790                 795                 800 tca agg aaa gaa cac ccc cag ttt ttt cct tct agt cct cca ccc cat       2448
Ser Arg Lys Glu His Pro Gln Phe Phe Pro Ser Ser Pro Pro Pro His
                805                 810                 815 tcc cca ttg agt cac ggg cat atc ccc agt gcc atc gtt ctt cca aac       2496
Ser Pro Leu Ser His Gly His Ile Pro Ser Ala Ile Val Leu Pro Asn
            820                 825                 830 gcc act cac gac tac aat aca tcc ttc tcc aac tcg aat gcc cac aaa       2544
Ala Thr His Asp Tyr Asn Thr Ser Phe Ser Asn Ser Asn Ala His Lys
        835                 840                 845 gcc gaa aag aag ctt cag agc atg gat cac cct ctt acg aag tca tcc       2592
Ala Glu Lys Lys Leu Gln Ser Met Asp His Pro Leu Thr Lys Ser Ser
850                 855                 860 agt aag cgg gag cac cgg cgg tct gtg gat tcc agg aat act ctc aat       2640
Ser Lys Arg Glu His Arg Arg Ser Val Asp Ser Arg Asn Thr Leu Asn
865                 870                 875                 880 gat ctc ctg aag cat cta aat gac cca aac agt aac ccc aaa gcc atc       2688
Asp Leu Leu Lys His Leu Asn Asp Pro Asn Ser Asn Pro Lys Ala Ile
                885                 890                 895 ctg gga gag atc cat atg gct cat caa acc ctc atg ctg gac ccg gtg       2736
Leu Gly Glu Ile His Met Ala His Gln Thr Leu Met Leu Asp Pro Val
            900                 905                 910 gga cca atg gct gag gtc cca ccc aag gtc cct aac cgg gag gca tct       2784
Gly Pro Met Ala Glu Val Pro Pro Lys Val Pro Asn Arg Glu Ala Ser
        915                 920                 925 cta tac tcc cct ccc tcc aca ctc ccc aga aat agt cca acc aag aga       2832
Leu Tyr Ser Pro Pro Ser Thr Leu Pro Arg Asn Ser Pro Thr Lys Arg
930                 935                 940 gta gat gtc ccc acc act cct ggg gtg cca atg act tct ctg gaa aga       2880
Val Asp Val Pro Thr Thr Pro Gly Val Pro Met Thr Ser Leu Glu Arg
945                 950                 955                 960 caa agg ggt tat cac aaa aat tcc tcc cag agg cac tct ata tct gcc       2928
Gln Arg Gly Tyr His Lys Asn Ser Ser Gln Arg His Ser Ile Ser Ala
                965                 970                 975 gtg cct aaa aac tta aac tca cca aat ggt gtt tgt tta tct aga cag       2976
Val Pro Lys Asn Leu Asn Ser Pro Asn Gly Val Leu Leu Ser Arg Gln
            980                 985                 990 ccg agt atg aac cgt gga ggc tat atg ccc acc cca aca ggg gcg aag       3024
Pro Ser Met Asn Arg Gly Gly Tyr Met Pro Thr Pro Thr Gly Ala Lys
        995                 1000                1005 gtg gac tat att cag ggg aca ccg gtg agt gtt cat ctg cag ccc          3069
Val Asp Tyr Ile Gln Gly Thr Pro Val Ser Val His Leu Gln Pro
    1010                1015                1020 tcc ctc tcc aga cag agc agc tat acc agt aat ggc acc ctc ccc          3114
Ser Leu Ser Arg Gln Ser Ser Tyr Thr Ser Asn Gly Thr Leu Pro
    1025                1030                1035 agg acg gga cta aag agg aca cca tcc tta aaa cct gat gtg cca          3159
Arg Thr Gly Leu Lys Arg Thr Pro Ser Leu Lys Pro Asp Val Pro
    1040                1045                1050 cca aag cct tcc ttt gtt ccg caa acc aca tct gtc aga cca ctg          3204
Pro Lys Pro Ser Phe Val Pro Gln Thr Thr Ser Val Arg Pro Leu
```

```
                    1055              1060              1065
       aac aag tac acg tac tag                                            3222
       Asn Lys Tyr Thr Tyr
           1070
```

<210> SEQ ID NO 39
<211> LENGTH: 1073
<212> TYPE: PRT
<213> ORGANISM: Mus musculus

<400> SEQUENCE: 39

```
Met Gly Phe Leu Leu Leu Trp Phe Cys Val Leu Phe Leu Leu Val Ser
1               5                  10                  15

Arg Leu Arg Ala Val Ser Phe Pro Glu Asp Glu Pro Leu Asn Thr
            20                  25                  30

Val Asp Tyr His Tyr Ser Arg Gln Tyr Pro Val Phe Arg Gly Arg Pro
        35                  40                  45

Ser Gly Asn Glu Ser Gln His Arg Leu Asp Phe Gln Leu Met Leu Lys
    50                  55                  60

Ile Arg Asp Thr Leu Tyr Ile Ala Gly Arg Asp Gln Val Tyr Thr Val
65                  70                  75                  80

Asn Leu Asn Glu Ile Pro Gln Thr Glu Val Ile Pro Ser Lys Lys Leu
                85                  90                  95

Thr Trp Arg Ser Arg Gln Gln Asp Arg Glu Asn Cys Ala Met Lys Gly
            100                 105                 110

Lys His Lys Asp Glu Cys His Asn Phe Ile Lys Val Phe Val Pro Arg
        115                 120                 125

Asn Asp Glu Met Val Phe Val Cys Gly Thr Asn Ala Phe Asn Pro Met
    130                 135                 140

Cys Arg Tyr Tyr Arg Leu Arg Thr Leu Glu Tyr Asp Gly Glu Glu Ile
145                 150                 155                 160

Ser Gly Leu Ala Arg Cys Pro Phe Asp Ala Arg Gln Thr Asn Val Ala
                165                 170                 175

Leu Phe Ala Asp Gly Lys Leu Tyr Ser Ala Thr Val Ala Asp Phe Leu
            180                 185                 190

Ala Ser Asp Ala Val Ile Tyr Arg Ser Met Gly Asp Gly Ser Ala Leu
        195                 200                 205

Arg Thr Ile Lys Tyr Asp Ser Lys Trp Ile Lys Glu Pro His Phe Leu
    210                 215                 220

His Ala Ile Glu Tyr Gly Asn Tyr Val Tyr Phe Phe Arg Glu Ile
225                 230                 235                 240

Ala Val Glu His Asn Asn Leu Gly Lys Ala Val Tyr Ser Arg Val Ala
                245                 250                 255

Arg Ile Cys Lys Asn Asp Met Gly Gly Ser Gln Arg Val Leu Glu Lys
            260                 265                 270

His Trp Thr Ser Phe Leu Lys Ala Arg Leu Asn Cys Ser Val Pro Gly
        275                 280                 285

Asp Ser Phe Phe Tyr Phe Asp Val Leu Gln Ser Ile Thr Asp Ile Ile
    290                 295                 300

Gln Ile Asn Gly Ile Pro Thr Val Gly Val Phe Thr Gln Leu
305                 310                 315                 320

Asn Ser Ile Pro Gly Ser Ala Val Cys Ala Phe Ser Met Asp Asp Ile
                325                 330                 335

Glu Lys Val Phe Lys Gly Arg Phe Lys Glu Gln Lys Thr Pro Asp Ser
            340                 345                 350
```

```
Val Trp Thr Ala Val Pro Glu Asp Lys Val Pro Lys Pro Arg Pro Gly
        355                 360                 365

Cys Cys Ala Lys His Gly Leu Ala Glu Ala Tyr Lys Thr Ser Ile Asp
    370                 375                 380

Phe Pro Asp Asp Thr Leu Ala Phe Ile Lys Ser His Pro Leu Met Asp
385                 390                 395                 400

Ser Ala Val Pro Pro Ile Ala Asp Glu Pro Trp Phe Thr Lys Thr Arg
                405                 410                 415

Val Arg Tyr Arg Leu Thr Ala Ile Glu Val Asp Arg Ser Ala Gly Pro
            420                 425                 430

Tyr Gln Asn Tyr Thr Val Ile Phe Val Gly Ser Glu Ala Gly Val Val
        435                 440                 445

Leu Lys Val Leu Ala Lys Thr Ser Pro Phe Ser Leu Asn Asp Ser Val
    450                 455                 460

Leu Leu Glu Glu Ile Glu Ala Tyr Asn Pro Ala Lys Cys Ser Ala Glu
465                 470                 475                 480

Ser Glu Glu Asp Arg Lys Val Val Ser Leu Gln Leu Asp Lys Asp His
                485                 490                 495

His Ala Leu Tyr Val Ala Phe Ser Ser Cys Val Val Arg Ile Pro Leu
            500                 505                 510

Ser Arg Cys Glu Arg Tyr Gly Ser Cys Lys Lys Ser Cys Ile Ala Ser
        515                 520                 525

Arg Asp Pro Tyr Cys Gly Trp Leu Ser Gln Gly Val Cys Glu Arg Val
    530                 535                 540

Thr Leu Gly Met Leu Pro Gly Gly Tyr Glu Gln Asp Thr Glu Tyr Gly
545                 550                 555                 560

Asn Thr Ala His Leu Gly Asp Cys His Glu Ser Leu Pro Pro Ser Thr
                565                 570                 575

Thr Pro Asp Tyr Lys Ile Phe Gly Gly Pro Thr Ser Asp Met Glu Val
            580                 585                 590

Ser Ser Ser Ser Val Thr Thr Val Ala Ser Ser Pro Glu Ile Thr Ser
        595                 600                 605

Lys Val Ile Asp Thr Trp Arg Pro Lys Leu Thr Ser Arg Lys Phe
    610                 615                 620

Val Val Gln Asp Pro Asn Thr Ser Asp Phe Thr Asp Thr Ile Ser
625                 630                 635                 640

Gly Ile Pro Lys Gly Val Arg Trp Glu Val Gln Ser Gly Glu Ser Asn
                645                 650                 655

Gln Met Val His Met Asn Val Leu Ile Thr Cys Val Phe Ala Ala Phe
            660                 665                 670

Val Leu Gly Ala Phe Ile Ala Gly Val Ala Val Tyr Cys Tyr Arg Asp
        675                 680                 685

Met Phe Val Arg Lys Asn Arg Lys Ile His Lys Asp Ala Glu Ser Ala
    690                 695                 700

Gln Ser Cys Thr Asp Ser Ser Gly Ser Phe Ala Lys Leu Asn Gly Leu
705                 710                 715                 720

Phe Asp Ser Pro Val Lys Glu Tyr Gln Gln Asn Ile Asp Ser Pro Lys
                725                 730                 735

Leu Tyr Ser Asn Leu Leu Thr Ser Arg Lys Glu Leu Pro Pro Asn Thr
            740                 745                 750

Asp Thr Lys Ser Met Ala Val Asp His Arg Gly Gln Pro Pro Glu Leu
        755                 760                 765
```

-continued

Ala Ala Leu Pro Thr Pro Glu Ser Thr Pro Val Leu His Gln Lys Thr
770                 775                 780

Leu Gln Ala Met Lys Ser His Ser Glu Lys Ala His Ser His Gly Ala
785                 790                 795                 800

Ser Arg Lys Glu His Pro Gln Phe Phe Pro Ser Ser Pro Pro His
            805                 810                 815

Ser Pro Leu Ser His Gly His Ile Pro Ser Ala Ile Val Leu Pro Asn
            820                 825                 830

Ala Thr His Asp Tyr Asn Thr Ser Phe Ser Asn Ser Asn Ala His Lys
            835                 840                 845

Ala Glu Lys Lys Leu Gln Ser Met Asp His Pro Leu Thr Lys Ser Ser
850                 855                 860

Ser Lys Arg Glu His Arg Arg Ser Val Asp Ser Arg Asn Thr Leu Asn
865                 870                 875                 880

Asp Leu Leu Lys His Leu Asn Asp Pro Asn Ser Asn Pro Lys Ala Ile
                885                 890                 895

Leu Gly Glu Ile His Met Ala His Gln Thr Leu Met Leu Asp Pro Val
                900                 905                 910

Gly Pro Met Ala Glu Val Pro Pro Lys Val Pro Asn Arg Glu Ala Ser
            915                 920                 925

Leu Tyr Ser Pro Pro Ser Thr Leu Pro Arg Asn Ser Pro Thr Lys Arg
            930                 935                 940

Val Asp Val Pro Thr Thr Pro Gly Val Pro Met Thr Ser Leu Glu Arg
945                 950                 955                 960

Gln Arg Gly Tyr His Lys Asn Ser Ser Gln Arg His Ser Ile Ser Ala
            965                 970                 975

Val Pro Lys Asn Leu Asn Ser Pro Asn Gly Val Leu Leu Ser Arg Gln
            980                 985                 990

Pro Ser Met Asn Arg Gly Gly Tyr Met Pro Thr Pro Thr Gly Ala Lys
        995                 1000                1005

Val Asp Tyr Ile Gln Gly Thr Pro Val Ser Val His Leu Gln Pro
    1010                1015                1020

Ser Leu Ser Arg Gln Ser Ser Tyr Thr Ser Asn Gly Thr Leu Pro
    1025                1030                1035

Arg Thr Gly Leu Lys Arg Thr Pro Ser Leu Lys Pro Asp Val Pro
    1040                1045                1050

Pro Lys Pro Ser Phe Val Pro Gln Thr Thr Ser Val Arg Pro Leu
    1055                1060                1065

Asn Lys Tyr Thr Tyr
    1070

<210> SEQ ID NO 40
<211> LENGTH: 23
<212> TYPE: DNA
<213> ORGANISM: Artificial
<220> FEATURE:
<223> OTHER INFORMATION: Sequencing primer

<400> SEQUENCE: 40
aaagcagaag gaaccccatg gtt                                          23

<210> SEQ ID NO 41
<211> LENGTH: 25
<212> TYPE: DNA
<213> ORGANISM: Artificial
<220> FEATURE:
<223> OTHER INFORMATION: Sequencing primer

<400> SEQUENCE: 41
accaggtagc taagtgggac ttctg                                              25

<210> SEQ ID NO 42
<211> LENGTH: 23
<212> TYPE: DNA
<213> ORGANISM: Artificial
<220> FEATURE:
<223> OTHER INFORMATION: Sequencing primer

<400> SEQUENCE: 42
tgacaccctg gctttcatca agt                                                23

<210> SEQ ID NO 43
<211> LENGTH: 25
<212> TYPE: DNA
<213> ORGANISM: Artificial
<220> FEATURE:
<223> OTHER INFORMATION: Sequencing primer

<400> SEQUENCE: 43
aaagtcttgc attgcatcac gtgac                                              25

<210> SEQ ID NO 44
<211> LENGTH: 22
<212> TYPE: DNA
<213> ORGANISM: Artificial
<220> FEATURE:
<223> OTHER INFORMATION: Sequencing primer

<400> SEQUENCE: 44
ccaatcagat ggtccacatg aa                                                 22

<210> SEQ ID NO 45
<211> LENGTH: 23
<212> TYPE: DNA
<213> ORGANISM: Artificial
<220> FEATURE:
<223> OTHER INFORMATION: Sequencing primer

<400> SEQUENCE: 45
atgaagagcc actctgagaa ggc                                                23

<210> SEQ ID NO 46
<211> LENGTH: 22
<212> TYPE: DNA
<213> ORGANISM: Artificial
<220> FEATURE:
<223> OTHER INFORMATION: Sequencing primer

<400> SEQUENCE: 46
taaccgggag gcatctctat ac                                                 22

<210> SEQ ID NO 47
<211> LENGTH: 3093
<212> TYPE: DNA
<213> ORGANISM: Mus musculus
<220> FEATURE:
<221> NAME/KEY: CDS
<222> LOCATION: (1)..(3090)

<400> SEQUENCE: 47 atg ggg ttc ctt ctg ctt tgg ttc tgc gtg ctg ttc ctt ctg gtc tcc         48
Met Gly Phe Leu Leu Leu Trp Phe Cys Val Leu Phe Leu Leu Val Ser
1               5                   10                  15

-continued

| | |
|---|---|
| agg tta cgg gcg gtc agc ttc cca gaa gac gat gag ccc ctc aac acg<br>Arg Leu Arg Ala Val Ser Phe Pro Glu Asp Asp Glu Pro Leu Asn Thr<br>     20                          25                      30 | 96 |
| gtt gac tat cac tat tca agg caa tat ccg gtt ttt aga gga cgc cct<br>Val Asp Tyr His Tyr Ser Arg Gln Tyr Pro Val Phe Arg Gly Arg Pro<br>         35                    40                    45 | 144 |
| tca ggc aac gaa tcg cag cac agg ctg gac ttt cag ctg atg ttg aaa<br>Ser Gly Asn Glu Ser Gln His Arg Leu Asp Phe Gln Leu Met Leu Lys<br>50                       55                    60 | 192 |
| att cga gac aca ctt tat att gct ggc agg gat caa gtc tat aca gtg<br>Ile Arg Asp Thr Leu Tyr Ile Ala Gly Arg Asp Gln Val Tyr Thr Val<br>65                       70                    75                   80 | 240 |
| aac tta aat gaa atc ccc caa aca gag gtg ata cca agc aag aag ctg<br>Asn Leu Asn Glu Ile Pro Gln Thr Glu Val Ile Pro Ser Lys Lys Leu<br>                   85                    90                    95 | 288 |
| acg tgg agg tcc aga cag cag gat cga gaa aat tgt gct atg aaa ggc<br>Thr Trp Arg Ser Arg Gln Gln Asp Arg Glu Asn Cys Ala Met Lys Gly<br>               100                    105                  110 | 336 |
| aag cat aaa gat gaa tgc cac aac ttc atc aaa gtc ttt gtc cca aga<br>Lys His Lys Asp Glu Cys His Asn Phe Ile Lys Val Phe Val Pro Arg<br>           115                    120                  125 | 384 |
| aat gat gag atg gtt ttt gtc tgt ggt acc aat gct ttc aac ccg atg<br>Asn Asp Glu Met Val Phe Val Cys Gly Thr Asn Ala Phe Asn Pro Met<br>130                    135                    140 | 432 |
| tgc aga tac tat agg ttg aga acg tta gag tat gat ggg gaa gaa att<br>Cys Arg Tyr Tyr Arg Leu Arg Thr Leu Glu Tyr Asp Gly Glu Glu Ile<br>145                    150                    155                  160 | 480 |
| agt ggc ctg gca cga tgc ccg ttt gat gcc cga caa acc aat gtc gcc<br>Ser Gly Leu Ala Arg Cys Pro Phe Asp Ala Arg Gln Thr Asn Val Ala<br>                   165                    170                  175 | 528 |
| ctc ttt gct gat gga aaa ctc tat tct gcc aca gtg gct gat ttc ctg<br>Leu Phe Ala Asp Gly Lys Leu Tyr Ser Ala Thr Val Ala Asp Phe Leu<br>         180                    185                  190 | 576 |
| gcc agt gat gct gtc att tac aga agc atg gga gat gga tct gcc ctt<br>Ala Ser Asp Ala Val Ile Tyr Arg Ser Met Gly Asp Gly Ser Ala Leu<br>           195                    200                  205 | 624 |
| cgc aca ata aaa tac gat tcc aag tgg atc aaa gaa cca cac ttc ctt<br>Arg Thr Ile Lys Tyr Asp Ser Lys Trp Ile Lys Glu Pro His Phe Leu<br>210                    215                    220 | 672 |
| cat gcc ata gaa tat gga aac tat gtc tat ttc ttc aga gaa atc<br>His Ala Ile Glu Tyr Gly Asn Tyr Val Tyr Phe Phe Phe Arg Glu Ile<br>225                    230                    235                  240 | 720 |
| gcc gtg gaa cat aat aac tta ggc aag gct gtg tat tcc cgc gtg gct<br>Ala Val Glu His Asn Asn Leu Gly Lys Ala Val Tyr Ser Arg Val Ala<br>                   245                    250                  255 | 768 |
| cgc att tgt aaa aac gac atg ggt ggc tca cag cgg gtc ctg gag aaa<br>Arg Ile Cys Lys Asn Asp Met Gly Gly Ser Gln Arg Val Leu Glu Lys<br>                   260                    265                  270 | 816 |
| cac tgg act tcc ttc ctt aag gct cgg ctg aac tgc tcc gtt cct gga<br>His Trp Thr Ser Phe Leu Lys Ala Arg Leu Asn Cys Ser Val Pro Gly<br>           275                    280                  285 | 864 |
| gat tcc ttt ttc tac ttc gac gtc ctg cag tct ata aca gac ata atc<br>Asp Ser Phe Phe Tyr Phe Asp Val Leu Gln Ser Ile Thr Asp Ile Ile<br>290                    295                    300 | 912 |
| caa atc aat ggc atc ccc act gtg gtt ggg gtc ttc acc aca cag ctc<br>Gln Ile Asn Gly Ile Pro Thr Val Val Gly Val Phe Thr Thr Gln Leu<br>305                    310                    315                  320 | 960 |
| aac agc att cct ggt tct gca gtc tgt gcc ttt agc atg gac gac att<br>Asn Ser Ile Pro Gly Ser Ala Val Cys Ala Phe Ser Met Asp Asp Ile | 1008 |

```
                325                 330                 335
gag aaa gtg ttc aaa ggg cgg ttc aaa gag cag aaa acc cca gac tct   1056
Glu Lys Val Phe Lys Gly Arg Phe Lys Glu Gln Lys Thr Pro Asp Ser
            340                 345                 350 gtt tgg aca gca gtt ccc gaa gac aaa gta cca aaa cca agg cct ggc   1104
Val Trp Thr Ala Val Pro Glu Asp Lys Val Pro Lys Pro Arg Pro Gly
        355                 360                 365 tgt tgt gcc aaa cac ggc ctc gca gaa gct tac aag acc tcc atc gac   1152
Cys Cys Ala Lys His Gly Leu Ala Glu Ala Tyr Lys Thr Ser Ile Asp
    370                 375                 380 ttt cca gat gac acc ctg gct ttc atc aag tcc cac ccg ctg atg gac   1200
Phe Pro Asp Asp Thr Leu Ala Phe Ile Lys Ser His Pro Leu Met Asp
385                 390                 395                 400 tct gcc gtc cca ccc att gcc gat gag ccc tgg ttc aca aag aca cgg   1248
Ser Ala Val Pro Pro Ile Ala Asp Glu Pro Trp Phe Thr Lys Thr Arg
                405                 410                 415 gtc agg tac agg ttg aca gcc atc gaa gtg gac cgt tca gca ggg cca   1296
Val Arg Tyr Arg Leu Thr Ala Ile Glu Val Asp Arg Ser Ala Gly Pro
            420                 425                 430 tac caa aac tac aca gtc atc ttt gtt ggc tct gaa gct ggc gtg gta   1344
Tyr Gln Asn Tyr Thr Val Ile Phe Val Gly Ser Glu Ala Gly Val Val
        435                 440                 445 ctt aaa gtt ttg gca aag acc agt cct ttc tct ctg aat gac agt gta   1392
Leu Lys Val Leu Ala Lys Thr Ser Pro Phe Ser Leu Asn Asp Ser Val
    450                 455                 460 tta ctc gaa gag att gaa gct tat aac cca gcc aag tgc agc gcc gag   1440
Leu Leu Glu Glu Ile Glu Ala Tyr Asn Pro Ala Lys Cys Ser Ala Glu
465                 470                 475                 480 agt gag gag gac aga aag gtg gtc tca tta cag ctg gac aag gat cac   1488
Ser Glu Glu Asp Arg Lys Val Val Ser Leu Gln Leu Asp Lys Asp His
                485                 490                 495 cat gct tta tac gtg gcc ttc tct agc tgc gtg gtc cgc atc ccc ctc   1536
His Ala Leu Tyr Val Ala Phe Ser Ser Cys Val Val Arg Ile Pro Leu
            500                 505                 510 agc cgc tgt gag cgc tac gga tcg tgt aaa aag tct tgc att gca tca   1584
Ser Arg Cys Glu Arg Tyr Gly Ser Cys Lys Lys Ser Cys Ile Ala Ser
        515                 520                 525 cgt gac ccg tac tgt ggt tgg tta agc cag gga gtt tgt gag aga gtg   1632
Arg Asp Pro Tyr Cys Gly Trp Leu Ser Gln Gly Val Cys Glu Arg Val
    530                 535                 540 acc cta ggg atg ctg ctg tta acc gaa gac ttc ttt gct ttc cat aac   1680
Thr Leu Gly Met Leu Leu Leu Thr Glu Asp Phe Phe Ala Phe His Asn
545                 550                 555                 560 cac agc cct gga gga tat gag cag gac acg gag tac ggc aac aca gcc   1728
His Ser Pro Gly Gly Tyr Glu Gln Asp Thr Glu Tyr Gly Asn Thr Ala
                565                 570                 575 cac cta ggg gac tgc cac gaa agt ttg cct cct tca act aca cca gat   1776
His Leu Gly Asp Cys His Glu Ser Leu Pro Pro Ser Thr Thr Pro Asp
            580                 585                 590 tac aaa ata ttt ggc ggt cca aca tct ggt gta cgg tgg gaa gtc cag   1824
Tyr Lys Ile Phe Gly Gly Pro Thr Ser Gly Val Arg Trp Glu Val Gln
        595                 600                 605 tct gga gaa tcc aat cag atg gtc cac atg aat gtc ctc atc acc tgc   1872
Ser Gly Glu Ser Asn Gln Met Val His Met Asn Val Leu Ile Thr Cys
    610                 615                 620 gtg ttt gcc gct ttt gtc ttg ggc gcg ttc atc gca gga gtg gcc gtg   1920
Val Phe Ala Ala Phe Val Leu Gly Ala Phe Ile Ala Gly Val Ala Val
625                 630                 635                 640 tac tgc tac cgt gac atg ttc gtt cgg aag aac aga aag atc cat aaa   1968
```

```
              Tyr Cys Tyr Arg Asp Met Phe Val Arg Lys Asn Arg Lys Ile His Lys
                              645             650             655 gac gca gaa tcc gcc cag tcg tgc aca gac tcc agc gga agc ttc gcc        2016
Asp Ala Glu Ser Ala Gln Ser Cys Thr Asp Ser Ser Gly Ser Phe Ala
            660             665             670 aag ctg aac ggc ctc ttt gac agc ccc gtc aag gaa tac cag cag aac        2064
Lys Leu Asn Gly Leu Phe Asp Ser Pro Val Lys Glu Tyr Gln Gln Asn
            675             680             685 att gat tct ccc aaa ctc tac agc aac ctg ctg acc agt cgg aag gaa        2112
Ile Asp Ser Pro Lys Leu Tyr Ser Asn Leu Leu Thr Ser Arg Lys Glu
        690             695             700 ctg cca cca aac acg gat aca aag tcc atg gcc gtg gac cac aga ggc        2160
Leu Pro Pro Asn Thr Asp Thr Lys Ser Met Ala Val Asp His Arg Gly
705             710             715             720 cag cct ccc gag ctg gct gct ctc ccc acg ccg gaa tcc aca cct gtc        2208
Gln Pro Pro Glu Leu Ala Ala Leu Pro Thr Pro Glu Ser Thr Pro Val
            725             730             735 ctc cac cag aag acc ctg cag gcc atg aag agc cac tct gag aag gcc        2256
Leu His Gln Lys Thr Leu Gln Ala Met Lys Ser His Ser Glu Lys Ala
            740             745             750 cac agc cac ggt gct tca agg aaa gaa cac ccc cag ttt ttt cct tct        2304
His Ser His Gly Ala Ser Arg Lys Glu His Pro Gln Phe Phe Pro Ser
            755             760             765 agt cct cca ccc cat tcc cca ttg agt cac ggg cat atc ccc agt gcc        2352
Ser Pro Pro Pro His Ser Pro Leu Ser His Gly His Ile Pro Ser Ala
770             775             780 atc gtt ctt cca aac gcc act cac gac tac aat aca tcc ttc tcc aac        2400
Ile Val Leu Pro Asn Ala Thr His Asp Tyr Asn Thr Ser Phe Ser Asn
785             790             795             800 tcg aat gcc cac aaa gcc gaa aag aag ctt cag agc atg gat cac cct        2448
Ser Asn Ala His Lys Ala Glu Lys Lys Leu Gln Ser Met Asp His Pro
            805             810             815 ctt acg aag tca tcc agt aag cgg gag cac cgg cgg tct gtg gat tcc        2496
Leu Thr Lys Ser Ser Ser Lys Arg Glu His Arg Arg Ser Val Asp Ser
            820             825             830 agg aat act ctc aat gat ctc ctg aag cat cta aat gac cca aac agt        2544
Arg Asn Thr Leu Asn Asp Leu Leu Lys His Leu Asn Asp Pro Asn Ser
            835             840             845 aac ccc aaa gcc atc ctg gga gag atc cat atg gct cat caa acc ctc        2592
Asn Pro Lys Ala Ile Leu Gly Glu Ile His Met Ala His Gln Thr Leu
850             855             860 atg ctg gac ccg gtg gga cca atg gct gag gtc cca ccc aag gtc cct        2640
Met Leu Asp Pro Val Gly Pro Met Ala Glu Val Pro Pro Lys Val Pro
865             870             875             880 aac cgg gag gca tct cta tac tcc cct ccc tca aca ctc ccc aga aat        2688
Asn Arg Glu Ala Ser Leu Tyr Ser Pro Pro Ser Thr Leu Pro Arg Asn
            885             890             895 agt cca acc aag aga gta gat gtc ccc acc act cct ggg gtg cca atg        2736
Ser Pro Thr Lys Arg Val Asp Val Pro Thr Thr Pro Gly Val Pro Met
            900             905             910 act tct ctg gaa aga caa agg ggt tat cac aaa aat tcc tcc cag agg        2784
Thr Ser Leu Glu Arg Gln Arg Gly Tyr His Lys Asn Ser Ser Gln Arg
            915             920             925 cac tct ata tct gcc gtg cct aaa aac tta aac tca cca aat ggt gtt        2832
His Ser Ile Ser Ala Val Pro Lys Asn Leu Asn Ser Pro Asn Gly Val
            930             935             940 ttg tta tct aga cag ccg agt atg aac cgt gga ggc tat atg ccc acc        2880
Leu Leu Ser Arg Gln Pro Ser Met Asn Arg Gly Gly Tyr Met Pro Thr
945             950             955             960
```

| | | | | | | | | | | | | | | | | |
|---|---|---|---|---|---|---|---|---|---|---|---|---|---|---|---|---|
| cca | aca | ggg | gcg | aag | gtg | gac | tat | att | cag | ggg | aca | ccg | gtg | agt | gtt | 2928 |
| Pro | Thr | Gly | Ala | Lys | Val | Asp | Tyr | Ile | Gln | Gly | Thr | Pro | Val | Ser | Val | |
| | | | | 965 | | | | 970 | | | | | 975 | | | |
| cat | ctg | cag | ccc | tcc | ctc | tcc | aga | cag | agc | agc | tat | acc | agt | aat | ggc | 2976 |
| His | Leu | Gln | Pro | Ser | Leu | Ser | Arg | Gln | Ser | Ser | Tyr | Thr | Ser | Asn | Gly | |
| | | | 980 | | | | | 985 | | | | | 990 | | | |
| acc | ctc | ccc | agg | acg | gga | cta | aag | agg | aca | cca | tcc | tta | aaa | cct | gat | 3024 |
| Thr | Leu | Pro | Arg | Thr | Gly | Leu | Lys | Arg | Thr | Pro | Ser | Leu | Lys | Pro | Asp | |
| | | 995 | | | | | 1000 | | | | | 1005 | | | | |
| gtg | cca | cca | aag | cct | tcc | ttt | gtt | ccg | caa | acc | aca | tct | gtc | aga | | 3069 |
| Val | Pro | Pro | Lys | Pro | Ser | Phe | Val | Pro | Gln | Thr | Thr | Ser | Val | Arg | | |
| | 1010 | | | | 1015 | | | | | 1020 | | | | | | |
| cca | ctg | aac | aag | tac | acg | tac | tag | | | | | | | | | 3093 |
| Pro | Leu | Asn | Lys | Tyr | Thr | Tyr | | | | | | | | | | |
| | 1025 | | | | 1030 | | | | | | | | | | | |

<210> SEQ ID NO 48
<211> LENGTH: 1030
<212> TYPE: PRT
<213> ORGANISM: Mus musculus

<400> SEQUENCE: 48

```
Met Gly Phe Leu Leu Leu Trp Phe Cys Val Leu Phe Leu Leu Val Ser
1               5                   10                  15

Arg Leu Arg Ala Val Ser Phe Pro Glu Asp Asp Glu Pro Leu Asn Thr
            20                  25                  30

Val Asp Tyr His Tyr Ser Arg Gln Tyr Pro Val Phe Arg Gly Arg Pro
        35                  40                  45

Ser Gly Asn Glu Ser Gln His Arg Leu Asp Phe Gln Leu Met Leu Lys
    50                  55                  60

Ile Arg Asp Thr Leu Tyr Ile Ala Gly Arg Asp Gln Val Tyr Thr Val
65                  70                  75                  80

Asn Leu Asn Glu Ile Pro Gln Thr Glu Val Ile Pro Ser Lys Lys Leu
                85                  90                  95

Thr Trp Arg Ser Arg Gln Gln Asp Arg Glu Asn Cys Ala Met Lys Gly
            100                 105                 110

Lys His Lys Asp Glu Cys His Asn Phe Ile Lys Val Phe Val Pro Arg
        115                 120                 125

Asn Asp Glu Met Val Phe Val Cys Gly Thr Asn Ala Phe Asn Pro Met
    130                 135                 140

Cys Arg Tyr Tyr Arg Leu Arg Thr Leu Glu Tyr Asp Gly Glu Glu Ile
145                 150                 155                 160

Ser Gly Leu Ala Arg Cys Pro Phe Asp Ala Arg Gln Thr Asn Val Ala
                165                 170                 175

Leu Phe Ala Asp Gly Lys Leu Tyr Ser Ala Thr Val Ala Asp Phe Leu
            180                 185                 190

Ala Ser Asp Ala Val Ile Tyr Arg Ser Met Gly Asp Gly Ser Ala Leu
        195                 200                 205

Arg Thr Ile Lys Tyr Asp Ser Lys Trp Ile Lys Glu Pro His Phe Leu
    210                 215                 220

His Ala Ile Glu Tyr Gly Asn Tyr Val Tyr Phe Phe Phe Arg Glu Ile
225                 230                 235                 240

Ala Val Glu His Asn Asn Leu Gly Lys Ala Val Tyr Ser Arg Val Ala
                245                 250                 255

Arg Ile Cys Lys Asn Asp Met Gly Gly Ser Gln Arg Val Leu Glu Lys
            260                 265                 270
```

```
His Trp Thr Ser Phe Leu Lys Ala Arg Leu Asn Cys Ser Val Pro Gly
            275                 280                 285

Asp Ser Phe Phe Tyr Phe Asp Val Leu Gln Ser Ile Thr Asp Ile Ile
290                 295                 300

Gln Ile Asn Gly Ile Pro Thr Val Val Gly Val Phe Thr Thr Gln Leu
305                 310                 315                 320

Asn Ser Ile Pro Gly Ser Ala Val Cys Ala Phe Ser Met Asp Asp Ile
                325                 330                 335

Glu Lys Val Phe Lys Gly Arg Phe Lys Glu Gln Lys Thr Pro Asp Ser
            340                 345                 350

Val Trp Thr Ala Val Pro Glu Asp Lys Val Pro Lys Pro Arg Pro Gly
            355                 360                 365

Cys Cys Ala Lys His Gly Leu Ala Glu Ala Tyr Lys Thr Ser Ile Asp
            370                 375                 380

Phe Pro Asp Asp Thr Leu Ala Phe Ile Lys Ser His Pro Leu Met Asp
385                 390                 395                 400

Ser Ala Val Pro Pro Ile Ala Asp Glu Pro Trp Phe Thr Lys Thr Arg
                405                 410                 415

Val Arg Tyr Arg Leu Thr Ala Ile Glu Val Asp Arg Ser Ala Gly Pro
            420                 425                 430

Tyr Gln Asn Tyr Thr Val Ile Phe Val Gly Ser Glu Ala Gly Val Val
            435                 440                 445

Leu Lys Val Leu Ala Lys Thr Ser Pro Phe Ser Leu Asn Asp Ser Val
450                 455                 460

Leu Leu Glu Glu Ile Glu Ala Tyr Asn Pro Ala Lys Cys Ser Ala Glu
465                 470                 475                 480

Ser Glu Glu Asp Arg Lys Val Val Ser Leu Gln Leu Asp Lys Asp His
                485                 490                 495

His Ala Leu Tyr Val Ala Phe Ser Ser Cys Val Val Arg Ile Pro Leu
            500                 505                 510

Ser Arg Cys Glu Arg Tyr Gly Ser Cys Lys Lys Ser Cys Ile Ala Ser
            515                 520                 525

Arg Asp Pro Tyr Cys Gly Trp Leu Ser Gln Gly Val Cys Glu Arg Val
530                 535                 540

Thr Leu Gly Met Leu Leu Thr Glu Asp Phe Phe Ala Phe His Asn
545                 550                 555                 560

His Ser Pro Gly Gly Tyr Glu Gln Asp Thr Glu Tyr Gly Asn Thr Ala
                565                 570                 575

His Leu Gly Asp Cys His Glu Ser Leu Pro Pro Ser Thr Thr Pro Asp
            580                 585                 590

Tyr Lys Ile Phe Gly Gly Pro Thr Ser Gly Val Arg Trp Glu Val Gln
            595                 600                 605

Ser Gly Glu Ser Asn Gln Met Val His Met Asn Val Leu Ile Thr Cys
610                 615                 620

Val Phe Ala Ala Phe Val Leu Gly Ala Phe Ile Ala Gly Val Ala Val
625                 630                 635                 640

Tyr Cys Tyr Arg Asp Met Phe Val Arg Lys Asn Arg Lys Ile His Lys
                645                 650                 655

Asp Ala Glu Ser Ala Gln Ser Cys Thr Asp Ser Ser Gly Ser Phe Ala
            660                 665                 670

Lys Leu Asn Gly Leu Phe Asp Ser Pro Val Lys Glu Tyr Gln Gln Asn
            675                 680                 685

Ile Asp Ser Pro Lys Leu Tyr Ser Asn Leu Leu Thr Ser Arg Lys Glu
```

```
                    690                 695                 700
Leu Pro Pro Asn Thr Asp Thr Lys Ser Met Ala Val Asp His Arg Gly
705                 710                 715                 720

Gln Pro Pro Glu Leu Ala Ala Leu Pro Thr Pro Glu Ser Thr Pro Val
                725                 730                 735

Leu His Gln Lys Thr Leu Gln Ala Met Lys Ser His Ser Glu Lys Ala
            740                 745                 750

His Ser His Gly Ala Ser Arg Lys Glu His Pro Gln Phe Phe Pro Ser
        755                 760                 765

Ser Pro Pro His Ser Pro Leu Ser His Gly His Ile Pro Ser Ala
    770                 775                 780

Ile Val Leu Pro Asn Ala Thr His Asp Tyr Asn Thr Ser Phe Ser Asn
785                 790                 795                 800

Ser Asn Ala His Lys Ala Glu Lys Lys Leu Gln Ser Met Asp His Pro
                805                 810                 815

Leu Thr Lys Ser Ser Ser Lys Arg Glu His Arg Arg Ser Val Asp Ser
            820                 825                 830

Arg Asn Thr Leu Asn Asp Leu Leu Lys His Leu Asn Asp Pro Asn Ser
        835                 840                 845

Asn Pro Lys Ala Ile Leu Gly Glu Ile His Met Ala His Gln Thr Leu
    850                 855                 860

Met Leu Asp Pro Val Gly Pro Met Ala Glu Val Pro Pro Lys Val Pro
865                 870                 875                 880

Asn Arg Glu Ala Ser Leu Tyr Ser Pro Pro Ser Thr Leu Pro Arg Asn
                885                 890                 895

Ser Pro Thr Lys Arg Val Asp Val Pro Thr Thr Pro Gly Val Pro Met
            900                 905                 910

Thr Ser Leu Glu Arg Gln Arg Gly Tyr His Lys Asn Ser Ser Gln Arg
        915                 920                 925

His Ser Ile Ser Ala Val Pro Lys Asn Leu Asn Ser Pro Asn Gly Val
    930                 935                 940

Leu Leu Ser Arg Gln Pro Ser Met Asn Arg Gly Gly Tyr Met Pro Thr
945                 950                 955                 960

Pro Thr Gly Ala Lys Val Asp Tyr Ile Gln Gly Thr Pro Val Ser Val
                965                 970                 975

His Leu Gln Pro Ser Leu Ser Arg Gln Ser Ser Tyr Thr Ser Asn Gly
            980                 985                 990

Thr Leu Pro Arg Thr Gly Leu Lys Arg Thr Pro Ser Leu Lys Pro Asp
        995                 1000                1005

Val Pro  Pro Lys Pro Ser Phe  Val Pro Gln Thr Thr  Ser Val Arg
    1010                1015                1020

Pro Leu  Asn Lys Tyr Thr Tyr
    1025                1030

<210> SEQ ID NO 49
<211> LENGTH: 3165
<212> TYPE: DNA
<213> ORGANISM: Mus musculus
<220> FEATURE:
<221> NAME/KEY: CDS
<222> LOCATION: (1)..(3162)

<400> SEQUENCE: 49 atg ggg ttc ctt ctg ctt tgg ttc tgc gtg ctg ttc ctt ctg gtc tcc         48
Met Gly Phe Leu Leu Leu Trp Phe Cys Val Leu Phe Leu Leu Val Ser
1               5                   10                  15
```

```
agg tta cgg gcg gtc agc ttc cca gaa gac gat gag ccc ctc aac acg      96
Arg Leu Arg Ala Val Ser Phe Pro Glu Asp Asp Glu Pro Leu Asn Thr
         20                  25                  30 gtt gac tat cac tat tca agg caa tat ccg gtt ttt aga gga cgc cct     144
Val Asp Tyr His Tyr Ser Arg Gln Tyr Pro Val Phe Arg Gly Arg Pro
             35                  40                  45 tca ggc aac gaa tcg cag cac agg ctg gac ttt cag ctg atg ttg aaa     192
Ser Gly Asn Glu Ser Gln His Arg Leu Asp Phe Gln Leu Met Leu Lys
 50                  55                  60 att cga gac aca ctt tat att gct ggc agg gat caa gtc tat aca gtg     240
Ile Arg Asp Thr Leu Tyr Ile Ala Gly Arg Asp Gln Val Tyr Thr Val
 65                  70                  75                  80 aac tta aat gaa atc ccc caa aca gag gtg ata cca agc aag aag ctg     288
Asn Leu Asn Glu Ile Pro Gln Thr Glu Val Ile Pro Ser Lys Lys Leu
                     85                  90                  95 acg tgg agg tcc aga cag cag gat cga gaa aat tgt gct atg aaa ggc     336
Thr Trp Arg Ser Arg Gln Gln Asp Arg Glu Asn Cys Ala Met Lys Gly
                 100                 105                 110 aag cat aaa gat gaa tgc cac aac ttc atc aaa gtc ttt gtc cca aga     384
Lys His Lys Asp Glu Cys His Asn Phe Ile Lys Val Phe Val Pro Arg
             115                 120                 125 aat gat gag atg gtt ttt gtc tgt ggt acc aat gct ttc aac ccg atg     432
Asn Asp Glu Met Val Phe Val Cys Gly Thr Asn Ala Phe Asn Pro Met
130                 135                 140 tgc aga tac tat agg ttg aga acg tta gag tat gat ggg gaa gaa att     480
Cys Arg Tyr Tyr Arg Leu Arg Thr Leu Glu Tyr Asp Gly Glu Glu Ile
145                 150                 155                 160 agt ggc ctg gca cga tgc ccg ttt gat gcc cga caa acc aat gtc gcc     528
Ser Gly Leu Ala Arg Cys Pro Phe Asp Ala Arg Gln Thr Asn Val Ala
                 165                 170                 175 ctc ttt gct gat gga aaa ctc tat tct gcc aca gtg gct gat ttc ctg     576
Leu Phe Ala Asp Gly Lys Leu Tyr Ser Ala Thr Val Ala Asp Phe Leu
             180                 185                 190 gcc agt gat gct gtc att tac aga agc atg gga gat gga tct gcc ctt     624
Ala Ser Asp Ala Val Ile Tyr Arg Ser Met Gly Asp Gly Ser Ala Leu
         195                 200                 205 cgc aca ata aaa tac gat tcc aag tgg atc aaa gaa cca cac ttc ctt     672
Arg Thr Ile Lys Tyr Asp Ser Lys Trp Ile Lys Glu Pro His Phe Leu
 210                 215                 220 cat gcc ata gaa tat gga aac tat gtc tat ttc ttc aga gaa atc       720
His Ala Ile Glu Tyr Gly Asn Tyr Val Tyr Phe Phe Phe Arg Glu Ile
225                 230                 235                 240 gcc gtg gaa cat aat aac tta ggc aag gct gtg tat tcc cgc gtg gct     768
Ala Val Glu His Asn Asn Leu Gly Lys Ala Val Tyr Ser Arg Val Ala
                 245                 250                 255 cgc att tgt aaa aac gac atg ggt ggc tca cag cgg gtc ctg gag aaa     816
Arg Ile Cys Lys Asn Asp Met Gly Gly Ser Gln Arg Val Leu Glu Lys
             260                 265                 270 cac tgg act tcc ttc ctt aag gct cgg ctg aac tgc tcc gtt cct gga     864
His Trp Thr Ser Phe Leu Lys Ala Arg Leu Asn Cys Ser Val Pro Gly
         275                 280                 285 gat tcc ttt ttc tac ttc gac gtc ctg cag tct ata aca gac ata atc     912
Asp Ser Phe Phe Tyr Phe Asp Val Leu Gln Ser Ile Thr Asp Ile Ile
 290                 295                 300 caa atc aat ggc atc ccc act gtg gtt ggg gtc ttc acc aca cag ctc     960
Gln Ile Asn Gly Ile Pro Thr Val Val Gly Val Phe Thr Thr Gln Leu
305                 310                 315                 320 aac agc att cct ggt tct gca gtc tgt gcc ttt agc atg gac gac att    1008
Asn Ser Ile Pro Gly Ser Ala Val Cys Ala Phe Ser Met Asp Asp Ile
```

-continued

```
                   325                 330                 335
gag aaa gtg ttc aaa ggg cgg ttc aaa gag cag aaa acc cca gac tct   1056
Glu Lys Val Phe Lys Gly Arg Phe Lys Glu Gln Lys Thr Pro Asp Ser
            340                 345                 350 gtt tgg aca gca gtt ccc gaa gac aaa gta cca aaa cca agg cct ggc   1104
Val Trp Thr Ala Val Pro Glu Asp Lys Val Pro Lys Pro Arg Pro Gly
                355                 360                 365 tgt tgt gcc aaa cac ggc ctc gca gaa gct tac aag acc tcc atc gac   1152
Cys Cys Ala Lys His Gly Leu Ala Glu Ala Tyr Lys Thr Ser Ile Asp
        370                 375                 380 ttt cca gat gac acc ctg gct ttc atc aag tcc cac ccg ctg atg gac   1200
Phe Pro Asp Asp Thr Leu Ala Phe Ile Lys Ser His Pro Leu Met Asp
385                 390                 395                 400 tct gcc gtc cca ccc att gcc gat gag ccc tgg ttc aca aag aca cgg   1248
Ser Ala Val Pro Pro Ile Ala Asp Glu Pro Trp Phe Thr Lys Thr Arg
                405                 410                 415 gtc agg tac agg ttg aca gcc atc gaa gtg gac cgt tca gca ggg cca   1296
Val Arg Tyr Arg Leu Thr Ala Ile Glu Val Asp Arg Ser Ala Gly Pro
            420                 425                 430 tac caa aac tac aca gtc atc ttt gtt ggc tct gaa gct ggc gtg gta   1344
Tyr Gln Asn Tyr Thr Val Ile Phe Val Gly Ser Glu Ala Gly Val Val
        435                 440                 445 ctt aaa gtt ttg gca aag acc agt cct ttc tct ctg aat gac agt gta   1392
Leu Lys Val Leu Ala Lys Thr Ser Pro Phe Ser Leu Asn Asp Ser Val
450                 455                 460 tta ctc gaa gag att gaa gct tat aac cca gcc aag tgc agc gcc gag   1440
Leu Leu Glu Glu Ile Glu Ala Tyr Asn Pro Ala Lys Cys Ser Ala Glu
465                 470                 475                 480 agt gag gag gac aga aag gtg gtc tca tta cag ctg gac aag gat cac   1488
Ser Glu Glu Asp Arg Lys Val Val Ser Leu Gln Leu Asp Lys Asp His
                485                 490                 495 cat gct tta tac gtg gcc ttc tct agc tgc gtg gtc cgc atc ccc ctc   1536
His Ala Leu Tyr Val Ala Phe Ser Ser Cys Val Val Arg Ile Pro Leu
            500                 505                 510 agc cgc tgt gag cgc tac gga tcg tgt aaa aag tct tgc att gca tca   1584
Ser Arg Cys Glu Arg Tyr Gly Ser Cys Lys Lys Ser Cys Ile Ala Ser
        515                 520                 525 cgt gac ccg tac tgt ggt tgg tta agc cag gga gtt tgt gag aga gtg   1632
Arg Asp Pro Tyr Cys Gly Trp Leu Ser Gln Gly Val Cys Glu Arg Val
    530                 535                 540 acc cta ggg atg ctc cct gga gga tat gag cag gac acg gag tac ggc   1680
Thr Leu Gly Met Leu Pro Gly Gly Tyr Glu Gln Asp Thr Glu Tyr Gly
545                 550                 555                 560 aac aca gcc cac cta ggg gac tgc cac gac atg gag gta tcc tca tct   1728
Asn Thr Ala His Leu Gly Asp Cys His Asp Met Glu Val Ser Ser Ser
                565                 570                 575 tct gtt acc act gtg gca agt agc cca gaa att aca tct aaa gtg att   1776
Ser Val Thr Thr Val Ala Ser Ser Pro Glu Ile Thr Ser Lys Val Ile
            580                 585                 590 gat acc tgg aga cct aaa ctg acg agc tcc cgg aaa ttt gta gtt caa   1824
Asp Thr Trp Arg Pro Lys Leu Thr Ser Ser Arg Lys Phe Val Val Gln
        595                 600                 605 gat gac cca aat act tct gat ttt act gat act ata tca ggt atc cca   1872
Asp Asp Pro Asn Thr Ser Asp Phe Thr Asp Thr Ile Ser Gly Ile Pro
    610                 615                 620 aag ggt gta cgg tgg gaa gtc cag tct gga gaa tcc aat cag atg gtc   1920
Lys Gly Val Arg Trp Glu Val Gln Ser Gly Glu Ser Asn Gln Met Val
625                 630                 635                 640 cac atg aat gtc ctc atc acc tgc gtg ttt gcc gct ttt gtc ttg ggc   1968
His Met Asn Val Leu Ile Thr Cys Val Phe Ala Ala Phe Val Leu Gly
```

```
            His Met Asn Val Leu Ile Thr Cys Val Phe Ala Ala Phe Val Leu Gly
                            645                 650                 655 gcg ttc atc gca gga gtg gcc gtg tac tgc tac cgt gac atg ttc gtt        2016
Ala Phe Ile Ala Gly Val Ala Val Tyr Cys Tyr Arg Asp Met Phe Val
                660                 665                 670 cgg aag aac aga aag atc cat aaa gac gca gaa tcc gcc cag tcg tgc        2064
Arg Lys Asn Arg Lys Ile His Lys Asp Ala Glu Ser Ala Gln Ser Cys
            675                 680                 685 aca gac tcc agc gga agc ttc gcc aag ctg aac ggc ctc ttt gac agc        2112
Thr Asp Ser Ser Gly Ser Phe Ala Lys Leu Asn Gly Leu Phe Asp Ser
        690                 695                 700 ccc gtc aag gaa tac cag cag aac att gat tct ccc aaa ctc tac agc        2160
Pro Val Lys Glu Tyr Gln Gln Asn Ile Asp Ser Pro Lys Leu Tyr Ser
705                 710                 715                 720 aac ctg ctg acc agt cgg aag gaa ctg cca cca aac acg gat aca aag        2208
Asn Leu Leu Thr Ser Arg Lys Glu Leu Pro Pro Asn Thr Asp Thr Lys
                725                 730                 735 tcc atg gcc gtg gac cac aga ggc cag cct ccc gag ctg gct gct ctc        2256
Ser Met Ala Val Asp His Arg Gly Gln Pro Pro Glu Leu Ala Ala Leu
            740                 745                 750 ccc acg ccg gaa tcc aca cct gtc ctc cac cag aag acc ctg cag gcc        2304
Pro Thr Pro Glu Ser Thr Pro Val Leu His Gln Lys Thr Leu Gln Ala
        755                 760                 765 atg aag agc cac tct gag aag gcc cac agc cac ggt gct tca agg aaa        2352
Met Lys Ser His Ser Glu Lys Ala His Ser His Gly Ala Ser Arg Lys
770                 775                 780 gaa cac ccc cag ttt ttt cct tct agt cct cca ccc cat tcc cca ttg        2400
Glu His Pro Gln Phe Phe Pro Ser Ser Pro Pro Pro His Ser Pro Leu
785                 790                 795                 800 agt cac ggg cat atc ccc agt gcc atc gtt ctt cca aac gcc act cac        2448
Ser His Gly His Ile Pro Ser Ala Ile Val Leu Pro Asn Ala Thr His
                805                 810                 815 gac tac aat aca tcc ttc tcc aac tcg aat gcc cac aaa gcc gaa aag        2496
Asp Tyr Asn Thr Ser Phe Ser Asn Ser Asn Ala His Lys Ala Glu Lys
            820                 825                 830 aag ctt cag agc atg gat cac cct ctt acg aag tca tcc agt aag cgg        2544
Lys Leu Gln Ser Met Asp His Pro Leu Thr Lys Ser Ser Ser Lys Arg
        835                 840                 845 gag cac cgg cgg tct gtg gat tcc agg aat act ctc aat gat ctc ctg        2592
Glu His Arg Arg Ser Val Asp Ser Arg Asn Thr Leu Asn Asp Leu Leu
850                 855                 860 aag cat cta aat gac cca aac agt aac ccc aaa gcc atc ctg gga gag        2640
Lys His Leu Asn Asp Pro Asn Ser Asn Pro Lys Ala Ile Leu Gly Glu
865                 870                 875                 880 atc cat atg gct cat caa acc ctc atg ctg gac ccg gtg gga cca atg        2688
Ile His Met Ala His Gln Thr Leu Met Leu Asp Pro Val Gly Pro Met
                885                 890                 895 gct gag gtc cca ccc aag gtc cct aac cgg gag gca tct cta tac tcc        2736
Ala Glu Val Pro Pro Lys Val Pro Asn Arg Glu Ala Ser Leu Tyr Ser
            900                 905                 910 cct ccc tcc aca ctc ccc aga aat agt cca acc aag aga gta gat gtc        2784
Pro Pro Ser Thr Leu Pro Arg Asn Ser Pro Thr Lys Arg Val Asp Val
        915                 920                 925 ccc acc act cct ggg gtg cca atg act tct ctg gaa aga caa agg ggt        2832
Pro Thr Thr Pro Gly Val Pro Met Thr Ser Leu Glu Arg Gln Arg Gly
    930                 935                 940 tat cac aaa aat tcc tcc cag agg cac tct ata tct gcc gtg cct aaa        2880
Tyr His Lys Asn Ser Ser Gln Arg His Ser Ile Ser Ala Val Pro Lys
945                 950                 955                 960
```

| | | | | | | | | | | | | | | | |
|---|---|---|---|---|---|---|---|---|---|---|---|---|---|---|---|
| aac | tta | aac | tca | cca | aat | ggt | gtt | ttg | tta | tct | aga | cag | ccg | agt | atg | 2928 |
| Asn | Leu | Asn | Ser | Pro | Asn | Gly | Val | Leu | Leu | Ser | Arg | Gln | Pro | Ser | Met | |
| | | | | 965 | | | | 970 | | | | | 975 | | | |
| aac | cgt | gga | ggc | tat | atg | ccc | acc | cca | aca | ggg | gcg | aag | gtg | gac | tat | 2976 |
| Asn | Arg | Gly | Gly | Tyr | Met | Pro | Thr | Pro | Thr | Gly | Ala | Lys | Val | Asp | Tyr | |
| | | 980 | | | | | 985 | | | | | 990 | | | | |
| att | cag | ggg | aca | ccg | gtg | agt | gtt | cat | ctg | cag | ccc | tcc | ctc | tcc | aga | 3024 |
| Ile | Gln | Gly | Thr | Pro | Val | Ser | Val | His | Leu | Gln | Pro | Ser | Leu | Ser | Arg | |
| | | 995 | | | | | 1000 | | | | | 1005 | | | | |
| cag | agc | agc | tat | acc | agt | aat | ggc | acc | ctc | ccc | agg | acg | gga | cta | | 3069 |
| Gln | Ser | Ser | Tyr | Thr | Ser | Asn | Gly | Thr | Leu | Pro | Arg | Thr | Gly | Leu | | |
| | 1010 | | | | 1015 | | | | | 1020 | | | | | | |
| aag | agg | aca | cca | tcc | tta | aaa | cct | gat | gtg | cca | cca | aag | cct | tcc | | 3114 |
| Lys | Arg | Thr | Pro | Ser | Leu | Lys | Pro | Asp | Val | Pro | Pro | Lys | Pro | Ser | | |
| | 1025 | | | | 1030 | | | | | 1035 | | | | | | |
| ttt | gtt | ccg | caa | acc | aca | tct | gtc | aga | cca | ctg | aac | aag | tac | acg | | 3159 |
| Phe | Val | Pro | Gln | Thr | Thr | Ser | Val | Arg | Pro | Leu | Asn | Lys | Tyr | Thr | | |
| | 1040 | | | | 1045 | | | | | 1050 | | | | | | |
| tac | tag | | | | | | | | | | | | | | | 3165 |
| Tyr | | | | | | | | | | | | | | | | |

<210> SEQ ID NO 50
<211> LENGTH: 1054
<212> TYPE: PRT
<213> ORGANISM: Mus musculus

<400> SEQUENCE: 50

Met Gly Phe Leu Leu Leu Trp Phe Cys Val Leu Phe Leu Leu Val Ser
1               5                   10                  15

Arg Leu Arg Ala Val Ser Phe Pro Glu Asp Asp Glu Pro Leu Asn Thr
            20                  25                  30

Val Asp Tyr His Tyr Ser Arg Gln Tyr Pro Val Phe Arg Gly Arg Pro
        35                  40                  45

Ser Gly Asn Glu Ser Gln His Arg Leu Asp Phe Gln Leu Met Leu Lys
    50                  55                  60

Ile Arg Asp Thr Leu Tyr Ile Ala Gly Arg Asp Gln Val Tyr Thr Val
65                  70                  75                  80

Asn Leu Asn Glu Ile Pro Gln Thr Glu Val Ile Pro Ser Lys Lys Leu
                85                  90                  95

Thr Trp Arg Ser Arg Gln Gln Asp Arg Glu Asn Cys Ala Met Lys Gly
            100                 105                 110

Lys His Lys Asp Glu Cys His Asn Phe Ile Lys Val Phe Val Pro Arg
        115                 120                 125

Asn Asp Glu Met Val Phe Val Cys Gly Thr Asn Ala Phe Asn Pro Met
    130                 135                 140

Cys Arg Tyr Tyr Arg Leu Arg Thr Leu Glu Tyr Asp Gly Glu Glu Ile
145                 150                 155                 160

Ser Gly Leu Ala Arg Cys Pro Phe Asp Ala Arg Gln Thr Asn Val Ala
                165                 170                 175

Leu Phe Ala Asp Gly Lys Leu Tyr Ser Ala Thr Val Ala Asp Phe Leu
            180                 185                 190

Ala Ser Asp Ala Val Ile Tyr Arg Ser Met Gly Asp Gly Ser Ala Leu
        195                 200                 205

Arg Thr Ile Lys Tyr Asp Ser Lys Trp Ile Lys Glu Pro His Phe Leu
    210                 215                 220

His Ala Ile Glu Tyr Gly Asn Tyr Val Tyr Phe Phe Arg Glu Ile
225                 230                 235                 240

```
Ala Val Glu His Asn Asn Leu Gly Lys Ala Val Tyr Ser Arg Val Ala
            245                 250                 255

Arg Ile Cys Lys Asn Asp Met Gly Gly Ser Gln Arg Val Leu Glu Lys
        260                 265                 270

His Trp Thr Ser Phe Leu Lys Ala Arg Leu Asn Cys Ser Val Pro Gly
    275                 280                 285

Asp Ser Phe Phe Tyr Phe Asp Val Leu Gln Ser Ile Thr Asp Ile Ile
290                 295                 300

Gln Ile Asn Gly Ile Pro Thr Val Val Gly Val Phe Thr Thr Gln Leu
305                 310                 315                 320

Asn Ser Ile Pro Gly Ser Ala Val Cys Ala Phe Ser Met Asp Asp Ile
                325                 330                 335

Glu Lys Val Phe Lys Gly Arg Phe Lys Glu Gln Lys Thr Pro Asp Ser
                340                 345                 350

Val Trp Thr Ala Val Pro Glu Asp Lys Val Pro Lys Pro Arg Pro Gly
            355                 360                 365

Cys Cys Ala Lys His Gly Leu Ala Glu Ala Tyr Lys Thr Ser Ile Asp
        370                 375                 380

Phe Pro Asp Asp Thr Leu Ala Phe Ile Lys Ser His Pro Leu Met Asp
385                 390                 395                 400

Ser Ala Val Pro Pro Ile Ala Asp Glu Pro Trp Phe Thr Lys Thr Arg
                405                 410                 415

Val Arg Tyr Arg Leu Thr Ala Ile Glu Val Asp Arg Ser Ala Gly Pro
            420                 425                 430

Tyr Gln Asn Tyr Thr Val Ile Phe Val Gly Ser Glu Ala Gly Val Val
        435                 440                 445

Leu Lys Val Leu Ala Lys Thr Ser Pro Phe Ser Leu Asn Asp Ser Val
450                 455                 460

Leu Leu Glu Glu Ile Glu Ala Tyr Asn Pro Ala Lys Cys Ser Ala Glu
465                 470                 475                 480

Ser Glu Glu Asp Arg Lys Val Val Ser Leu Gln Leu Asp Lys Asp His
                485                 490                 495

His Ala Leu Tyr Val Ala Phe Ser Ser Cys Val Val Arg Ile Pro Leu
            500                 505                 510

Ser Arg Cys Glu Arg Tyr Gly Ser Cys Lys Lys Ser Cys Ile Ala Ser
        515                 520                 525

Arg Asp Pro Tyr Cys Gly Trp Leu Ser Gln Gly Val Cys Glu Arg Val
530                 535                 540

Thr Leu Gly Met Leu Pro Gly Gly Tyr Glu Gln Asp Thr Glu Tyr Gly
545                 550                 555                 560

Asn Thr Ala His Leu Gly Asp Cys His Asp Met Glu Val Ser Ser Ser
                565                 570                 575

Ser Val Thr Thr Val Ala Ser Ser Pro Glu Ile Thr Ser Lys Val Ile
            580                 585                 590

Asp Thr Trp Arg Pro Lys Leu Thr Ser Ser Arg Lys Phe Val Val Gln
        595                 600                 605

Asp Asp Pro Asn Thr Ser Asp Phe Thr Asp Thr Ile Ser Gly Ile Pro
610                 615                 620

Lys Gly Val Arg Trp Glu Val Gln Ser Gly Glu Ser Asn Gln Met Val
625                 630                 635                 640

His Met Asn Val Leu Ile Thr Cys Val Phe Ala Ala Phe Val Leu Gly
                645                 650                 655
```

```
Ala Phe Ile Ala Gly Val Ala Val Tyr Cys Tyr Arg Asp Met Phe Val
            660                 665                 670

Arg Lys Asn Arg Lys Ile His Lys Asp Ala Glu Ser Ala Gln Ser Cys
        675                 680                 685

Thr Asp Ser Ser Gly Ser Phe Ala Lys Leu Asn Gly Leu Phe Asp Ser
    690                 695                 700

Pro Val Lys Glu Tyr Gln Gln Asn Ile Asp Ser Pro Lys Leu Tyr Ser
705                 710                 715                 720

Asn Leu Leu Thr Ser Arg Lys Glu Leu Pro Asn Thr Asp Thr Lys
                725                 730                 735

Ser Met Ala Val Asp His Arg Gly Gln Pro Glu Leu Ala Ala Leu
            740                 745                 750

Pro Thr Pro Glu Ser Thr Pro Val Leu His Gln Lys Thr Leu Gln Ala
            755                 760                 765

Met Lys Ser His Ser Glu Lys Ala His Ser His Gly Ala Ser Arg Lys
    770                 775                 780

Glu His Pro Gln Phe Phe Pro Ser Ser Pro Pro His Ser Pro Leu
785                 790                 795                 800

Ser His Gly His Ile Pro Ser Ala Ile Val Leu Pro Asn Ala Thr His
                805                 810                 815

Asp Tyr Asn Thr Ser Phe Ser Asn Ser Asn Ala His Lys Ala Glu Lys
            820                 825                 830

Lys Leu Gln Ser Met Asp His Pro Leu Thr Lys Ser Ser Lys Arg
        835                 840                 845

Glu His Arg Arg Ser Val Asp Ser Arg Asn Thr Leu Asn Asp Leu Leu
    850                 855                 860

Lys His Leu Asn Asp Pro Asn Ser Asn Pro Lys Ala Ile Leu Gly Glu
865                 870                 875                 880

Ile His Met Ala His Gln Thr Leu Met Leu Asp Pro Val Gly Pro Met
                885                 890                 895

Ala Glu Val Pro Pro Lys Val Pro Asn Arg Glu Ala Ser Leu Tyr Ser
            900                 905                 910

Pro Pro Ser Thr Leu Pro Arg Asn Ser Pro Thr Lys Arg Val Asp Val
            915                 920                 925

Pro Thr Thr Pro Gly Val Pro Met Thr Ser Leu Glu Arg Gln Arg Gly
    930                 935                 940

Tyr His Lys Asn Ser Ser Gln Arg His Ser Ile Ser Ala Val Pro Lys
945                 950                 955                 960

Asn Leu Asn Ser Pro Asn Gly Val Leu Leu Ser Arg Gln Pro Ser Met
                965                 970                 975

Asn Arg Gly Gly Tyr Met Pro Thr Pro Thr Gly Ala Lys Val Asp Tyr
            980                 985                 990

Ile Gln Gly Thr Pro Val Ser Val His Leu Gln Pro Ser Leu Ser Arg
        995                 1000                1005

Gln Ser Ser Tyr Thr Ser Asn Gly Thr Leu Pro Arg Thr Gly Leu
        1010                1015                1020

Lys Arg Thr Pro Ser Leu Lys Pro Asp Val Pro Pro Lys Pro Ser
        1025                1030                1035

Phe Val Pro Gln Thr Thr Ser Val Arg Pro Leu Asn Lys Tyr Thr
        1040                1045                1050

Tyr

<210> SEQ ID NO 51
```

<211> LENGTH: 3165
<212> TYPE: DNA
<213> ORGANISM: Mus musculus

<400> SEQUENCE: 51

| | | | | | |
|---|---|---|---|---|---|
| atggggttcc | ttctgctttg | gttctgcgtg | ctgttccttc | tggtctccag | gttacgggcg | 60 |
| gtcagcttcc | cagaagacga | tgagcccctc | aacacggttg | actatcacta | ttcaaggcaa | 120 |
| tatccggttt | ttagaggacg | cccttcaggc | aacgaatcgc | agcacaggct | ggactttcag | 180 |
| ctgatgttga | aaattcgaga | cacactttat | attgctggca | gggatcaagt | ctatacagtg | 240 |
| aacttaaatg | aaatccccca | aacagaggtg | ataccaagca | agaagctgac | gtggaggtcc | 300 |
| agacagcagg | atcgagaaaa | ttgtgctatg | aaaggcaagc | ataaagatga | atgccacaac | 360 |
| ttcatcaaag | tctttgtccc | aagaaatgat | gagatggttt | ttgtctgtgg | taccaatgct | 420 |
| ttcaacccga | tgtgcagata | ctataggttg | agaacgttag | agtatgatgg | ggaagaaatt | 480 |
| agtggcctgg | cacgatgccc | gtttgatgcc | cgacaaacca | atgtcgccct | ctttgctgat | 540 |
| ggaaaactct | attctgccac | agtggctgat | ttcctggcca | gtgatgctgt | catttacaga | 600 |
| agcatgggag | atggatctgc | ccttcgcaca | ataaaatacg | attccaagtg | atcaaagaa | 660 |
| ccacacttcc | ttcatgccat | agaatatgga | aactatgtct | atttcttctt | cagagaaatc | 720 |
| gccgtggaac | ataataactt | aggcaaggct | gtgtattccc | gcgtggctcg | catttgtaaa | 780 |
| aacgacatgg | gtggctcaca | gcgggtcctg | agaaacact | ggacttcctt | ccttaaggct | 840 |
| cggctgaact | gctccgttcc | tggagattcc | tttttctact | tcgacgtcct | gcagtctata | 900 |
| acagacataa | tccaaatcaa | tggcatcccc | actgtggttg | gggtcttcac | cacacagctc | 960 |
| aacagcattc | ctggttctgc | agtctgtgcc | tttagcatgg | acgacattga | aaagtgttc | 1020 |
| aaagggcggt | tcaaagagca | gaaaacccca | gactctgttt | ggacagcagt | tcccgaagac | 1080 |
| aaagtaccaa | aaccaaggcc | tggctgttgt | gccaaacacg | gcctcgcaga | agcttacaag | 1140 |
| acctccatcg | actttccaga | tgacaccctg | gctttcatca | gtcccaccc | gctgatggac | 1200 |
| tctgccgtcc | cacccattgc | cgatgagccc | tggttcacaa | agacacgggt | caggtacagg | 1260 |
| ttgacagcca | tcgaagtgga | ccgttcagca | gggccatacc | aaaactacac | agtcatcttt | 1320 |
| gttggctctg | aagctggcgt | ggtacttaaa | gttttggcaa | agaccagtcc | tttctctctg | 1380 |
| aatgacagtg | tattactcga | agagattgaa | gcttataacc | cagccaagtg | cagcgccgag | 1440 |
| agtgaggagg | acagaaaggt | ggtctcatta | cagctggaca | aggatcacca | tgctttatac | 1500 |
| gtggccttct | ctagctgcgt | ggtccgcatc | cccctcagcc | gctgtgagcg | ctacggatcg | 1560 |
| tgtaaaaagt | cttgcattgc | atcacgtgac | ccgtactgtg | gttggttaag | ccagggagtt | 1620 |
| tgtgagagag | tgaccctagg | gatgctccct | ggaggatatg | agcaggacac | ggagtacggc | 1680 |
| aacacagccc | acctagggga | ctgccacgac | atggaggtat | cctcatcttc | tgttaccact | 1740 |
| gtggcaagta | gccagaaaat | tacatctaaa | gtgattgata | cctggagacc | taaactgacg | 1800 |
| agctcccgga | aatttgtagt | tcaagatgac | ccaaatactt | ctgattttac | tgatactata | 1860 |
| tcaggtatcc | caagggtgt | acggtgggaa | gtccagtctg | agaatccaa | tcagatggtc | 1920 |
| cacatgaatg | tcctcatcac | ctgcgtgttt | gccgcttttg | tcttgggcgc | gttcatcgca | 1980 |
| ggagtggccg | tgtactgcta | ccgtgacatg | ttcgttcgga | agaacagaaa | gatccataaa | 2040 |
| gacgcagaat | ccgcccagtc | gtgcacagac | tccagcggaa | gcttcgccaa | gctgaacggc | 2100 |
| ctctttgaca | gccccgtcaa | ggaataccag | cagaacattg | attctcccaa | actctacagc | 2160 |
| aacctgctga | ccagtcggaa | ggaactgcca | ccaaacacgg | atacaaagtc | catggccgtg | 2220 |

-continued

```
gaccacagag gccagcctcc cgagctggct gctctcccca cgccggaatc cacacctgtc   2280
ctccaccaga agaccctgca ggccatgaag agccactctg agaaggccca cagccacggt   2340
gcttcaagga agaacaccc ccagttttt ccttctagtc ctccacccca ttccccattg    2400
agtcacgggc atatcccag tgccatcgtt cttccaaacg ccactcacga ctacaataca    2460
tccttctcca actcgaatgc ccacaaagcc gaaagaagc ttcagagcat ggatcaccct    2520
cttacgaagt catccagtaa gcgggagcac cggcggtctg tggattccag gaatactctc   2580
aatgatctcc tgaagcatct aaatgaccca acagtaacc ccaaagccat cctgggagag    2640
atccatatgg ctcatcaaac cctcatgctg gacccgtgg gaccaatggc tgaggtccca    2700
cccaaggtcc ctaaccggga ggcatctcta tactcccctc cctccacact cccagaaat    2760 agtccaacca agagtaga tgtccccacc actcctgggg tgccaatgac ttctctggaa    2820
agacaaaggg gttatcacaa aaattcctcc cagaggcact ctatatctgc cgtgcctaaa   2880
aacttaaact caccaaatgg tgttttgtta tctagacagc cgagtatgaa ccgtggaggc    2940
tatatgccca ccccaacagg ggcgaaggtg gactatattc aggggacacc ggtgagtgtt    3000
catctgcagc cctccctctc cagacagagc agctatacca gtaatggcac cctccccagg    3060
acgggactaa agaggacacc atccttaaaa cctgatgtgc caccaaagcc ttcctttgtt    3120
ccgcaaacca catctgtcag accactgaac aagtacacgt actag                    3165
```

<210> SEQ ID NO 52
<211> LENGTH: 3410
<212> TYPE: DNA
<213> ORGANISM: Danio rerio
<220> FEATURE:
<221> NAME/KEY: CDS
<222> LOCATION: (122)..(2761)

<400> SEQUENCE: 52

```
gactgaatgt acagctctgc tcttctgacg ctcagattta agaaaacac gggaaatatg     60 gaataagatg gtgttcgaag ccaaacggtt gacggaaaga acatggtgtt gctctgtcat    120 c atg gcg atg gtc tta tta gcc tgg ctc ctc cca ctc att act tct gcc    169
  Met Ala Met Val Leu Leu Ala Trp Leu Leu Pro Leu Ile Thr Ser Ala
  1               5                  10                  15 acg cct ttt cct aga gat ctg cag cca att agt gtg gtg gga ttg gac    217
Thr Pro Phe Pro Arg Asp Leu Gln Pro Ile Ser Val Val Gly Leu Asp
            20                  25                  30 gac tcg tac ctg tac ccc agt ttt cag ggt ctg gtg tcc agc aat gag    265
Asp Ser Tyr Leu Tyr Pro Ser Phe Gln Gly Leu Val Ser Ser Asn Glu
        35                  40                  45 acg gag cgt ctg ggt ctg gac tat cag cgc atg atg agg atc cag cac    313
Thr Glu Arg Leu Gly Leu Asp Tyr Gln Arg Met Met Arg Ile Gln His
    50                  55                  60 atg ctg tac atc gcc gcc aga gac cat gtg ttt gtt gta aat ctc aca    361
Met Leu Tyr Ile Ala Ala Arg Asp His Val Phe Val Val Asn Leu Thr
65                  70                  75                  80 acg gca gta gat gaa att att cca cag cag atc ctg acg tgg aga tcc    409
Thr Ala Val Asp Glu Ile Ile Pro Gln Gln Ile Leu Thr Trp Arg Ser
                85                  90                  95 aca gac gtg tcc aag tgc acc gtc aga gga aga aac agt gat gaa tgt    457
Thr Asp Val Ser Lys Cys Thr Val Arg Gly Arg Asn Ser Asp Glu Cys
            100                 105                 110 tac aat tat atc aag gtt ctt gtt cct cgt aat gac gag act ctg ttt    505
Tyr Asn Tyr Ile Lys Val Leu Val Pro Arg Asn Asp Glu Thr Leu Phe
        115                 120                 125
```

```
gcc tgt gga aca aac gcg ttg aat cct gcc tgc cgc aac tac aga ttg      553
Ala Cys Gly Thr Asn Ala Leu Asn Pro Ala Cys Arg Asn Tyr Arg Leu
    130                 135                 140 agt tca ctg gag cag gtc gga cag gag ctc ttg ggt cag gca aga tgt      601
Ser Ser Leu Glu Gln Val Gly Gln Glu Leu Leu Gly Gln Ala Arg Cys
145                 150                 155                 160 cca ttt gag tct cga cag tcc aat gta gga gtg ttt gca ggt ggt cat      649
Pro Phe Glu Ser Arg Gln Ser Asn Val Gly Val Phe Ala Gly Gly His
                165                 170                 175 ttc tat tca gcc aca gtg acg gac ttc cag gcg agt gat gct gtg atc      697
Phe Tyr Ser Ala Thr Val Thr Asp Phe Gln Ala Ser Asp Ala Val Ile
            180                 185                 190 tac agg agt tta gga gga gag ggc cga cct gtt ctg cgc act gtc aaa      745
Tyr Arg Ser Leu Gly Gly Glu Gly Arg Pro Val Leu Arg Thr Val Lys
        195                 200                 205 tac gac tcc aaa tgg ctc aga gag cct cat ttc ctg cac gct gtc gaa      793
Tyr Asp Ser Lys Trp Leu Arg Glu Pro His Phe Leu His Ala Val Glu
    210                 215                 220 tac ggg aac tat gtg tat ttc ttc ttc agt gag att gct gtg gag cac      841
Tyr Gly Asn Tyr Val Tyr Phe Phe Phe Ser Glu Ile Ala Val Glu His
225                 230                 235                 240 act gct gct ggg aag gtt gtg tat tct cgt gtg gcg cga gtg tgt aag      889
Thr Ala Ala Gly Lys Val Val Tyr Ser Arg Val Ala Arg Val Cys Lys
                245                 250                 255 aat gat aac ggc ggc tcc acg cga gtg ttg gac cga cac tgg aca tca      937
Asn Asp Asn Gly Gly Ser Thr Arg Val Leu Asp Arg His Trp Thr Ser
            260                 265                 270 ttt ctg aag gct cgg ctg aac tgc tcc gtt cct gga gac act ttc ttc      985
Phe Leu Lys Ala Arg Leu Asn Cys Ser Val Pro Gly Asp Thr Phe Phe
        275                 280                 285 tac ttc gat gtg ctt cag tct ctg acc aat gtg ctg cag atc aac cag     1033
Tyr Phe Asp Val Leu Gln Ser Leu Thr Asn Val Leu Gln Ile Asn Gln
    290                 295                 300 aga ccc gct gta gtc gga gtg ttc acc aca cag acc aac agt att ccc     1081
Arg Pro Ala Val Val Gly Val Phe Thr Thr Gln Thr Asn Ser Ile Pro
305                 310                 315                 320 gga tcc gct gtt tgc ggt ttc tat ctg gat gac att gag cga gtg ttt     1129
Gly Ser Ala Val Cys Gly Phe Tyr Leu Asp Asp Ile Glu Arg Val Phe
                325                 330                 335 aat ggg agg ttt aaa gag cag aag aac agt gac tcc atg tgg acg gca     1177
Asn Gly Arg Phe Lys Glu Gln Lys Asn Ser Asp Ser Met Trp Thr Ala
            340                 345                 350 gta ccg gag gaa cag gtg ccc aaa cca cgt cca ggt tcg tgt gca ggt     1225
Val Pro Glu Glu Gln Val Pro Lys Pro Arg Pro Gly Ser Cys Ala Gly
        355                 360                 365 gag ggt tcg gcc tcc tcc tat tcc tct tct gtt cag ttt cca gac tct     1273
Glu Gly Ser Ala Ser Ser Tyr Ser Ser Ser Val Gln Phe Pro Asp Ser
    370                 375                 380 gtg ctg tcg ttc atc aaa aca cac ccg ctg atg gag gag agc gtg ccg     1321
Val Leu Ser Phe Ile Lys Thr His Pro Leu Met Glu Glu Ser Val Pro
385                 390                 395                 400 tca gtc aac agc caa ccg ctg atc acc aac acc gcc agc agg tat aag     1369
Ser Val Asn Ser Gln Pro Leu Ile Thr Asn Thr Ala Ser Arg Tyr Lys
                405                 410                 415 ctg act cag att gtg gtg gac act gct gct ggg cct cat aag aac cgc     1417
Leu Thr Gln Ile Val Val Asp Thr Ala Ala Gly Pro His Lys Asn Arg
            420                 425                 430 acc gta gtg ttt ctg ggc tct gaa gac gga cgc gtg ctg aag atc ctg     1465
Thr Val Val Phe Leu Gly Ser Glu Asp Gly Arg Val Leu Lys Ile Leu
```

-continued

|  | 435 |  |  |  | 440 |  |  |  | 445 |  |  |  |  |
|---|---|---|---|---|---|---|---|---|---|---|---|---|---|
| acc | aac | aca | cac | tcc | aac | agc | tca | cac | aca | tcc | cag | ctg | ctg | gag | gac | 1513 |
| Thr | Asn | Thr | His | Ser | Asn | Ser | Ser | His | Thr | Ser | Gln | Leu | Leu | Glu | Asp |  |
|  | 450 |  |  |  |  | 455 |  |  |  |  | 460 |  |  |  |  |  |

| atc | gac | gtg | ttt | aat | ccc | aca | cgg | tgt | gtt | ggt | gag | cgt | gca | gtg | ttg | 1561 |
| Ile | Asp | Val | Phe | Asn | Pro | Thr | Arg | Cys | Val | Gly | Glu | Arg | Ala | Val | Leu |  |
| 465 |  |  |  |  | 470 |  |  |  |  | 475 |  |  |  |  | 480 |  |

| ggt | ctg | gag | ctg | gat | aag | gag | cat | cac | gct | ctg | ttt | gtg | gcc | ttc | tcc | 1609 |
| Gly | Leu | Glu | Leu | Asp | Lys | Glu | His | His | Ala | Leu | Phe | Val | Ala | Phe | Ser |  |
|  |  |  |  | 485 |  |  |  |  | 490 |  |  |  |  | 495 |  |  |

| agc | tgt | gtg | atc | aga | gtt | cct | ctc | agc | cgc | tgc | gct | cag | cac | gcc | acc | 1657 |
| Ser | Cys | Val | Ile | Arg | Val | Pro | Leu | Ser | Arg | Cys | Ala | Gln | His | Ala | Thr |  |
|  |  |  | 500 |  |  |  |  | 505 |  |  |  |  | 510 |  |  |  |

| tgc | agg | aga | cgc | tgc | ctc | tac | aca | cat | gac | cca | tac | tgc | atc | tgg | ctg | 1705 |
| Cys | Arg | Arg | Arg | Cys | Leu | Tyr | Thr | His | Asp | Pro | Tyr | Cys | Ile | Trp | Leu |  |
|  | 515 |  |  |  |  | 520 |  |  |  |  | 525 |  |  |  |  |  |

| cgg | acg | gga | cgc | tgt | gct | gac | atg | gcc | cca | ggg | ttc | aag | gcg | gga | ttt | 1753 |
| Arg | Thr | Gly | Arg | Cys | Ala | Asp | Met | Ala | Pro | Gly | Phe | Lys | Ala | Gly | Phe |  |
|  | 530 |  |  |  |  | 535 |  |  |  |  | 540 |  |  |  |  |  |

| gaa | cag | gac | att | gat | ggt | gaa | caa | aca | cat | tta | ttt | gac | aca | tgc | act | 1801 |
| Glu | Gln | Asp | Ile | Asp | Gly | Glu | Gln | Thr | His | Leu | Phe | Asp | Thr | Cys | Thr |  |
| 545 |  |  |  |  | 550 |  |  |  |  | 555 |  |  |  |  | 560 |  |

| gat | gtg | atg | tca | tca | gca | gga | agt | gat | gtc | aaa | tca | gct | gtg | gat | tcg | 1849 |
| Asp | Val | Met | Ser | Ser | Ala | Gly | Ser | Asp | Val | Lys | Ser | Ala | Val | Asp | Ser |  |
|  |  |  |  | 565 |  |  |  |  | 570 |  |  |  |  | 575 |  |  |

| gcc | tct | gga | gta | aag | cag | ctt | ccc | gac | gcc | gac | agt | ctg | agc | gac | ggc | 1897 |
| Ala | Ser | Gly | Val | Lys | Gln | Leu | Pro | Asp | Ala | Asp | Ser | Leu | Ser | Asp | Gly |  |
|  |  |  | 580 |  |  |  |  | 585 |  |  |  |  | 590 |  |  |  |

| tat | cac | ttc | act | ctt | ctg | ggc | gcg | tgt | gtg | ttg | cta | gcg | ttt | gtg | ttg | 1945 |
| Tyr | His | Phe | Thr | Leu | Leu | Gly | Ala | Cys | Val | Leu | Leu | Ala | Phe | Val | Leu |  |
|  |  | 595 |  |  |  |  | 600 |  |  |  |  | 605 |  |  |  |  |

| ggg | gcg | atc | gcg | tca | ggt | ttg | ctg | gtg | tcg | tgt | tac | tgc | aga | cag | agc | 1993 |
| Gly | Ala | Ile | Ala | Ser | Gly | Leu | Leu | Val | Ser | Cys | Tyr | Cys | Arg | Gln | Ser |  |
|  | 610 |  |  |  |  | 615 |  |  |  |  | 620 |  |  |  |  |  |

| tct | ccg | cca | acg | cca | gag | cct | gaa | gca | aca | ctc | gca | cac | aca | cat | gca | 2041 |
| Ser | Pro | Pro | Thr | Pro | Glu | Pro | Glu | Ala | Thr | Leu | Ala | His | Thr | His | Ala |  |
| 625 |  |  |  |  | 630 |  |  |  |  | 635 |  |  |  |  | 640 |  |

| cac | aca | ctc | tcg | ctc | agc | agc | ctc | gct | aag | atc | aac | ctg | ctg | atg | gac | 2089 |
| His | Thr | Leu | Ser | Leu | Ser | Ser | Leu | Ala | Lys | Ile | Asn | Leu | Leu | Met | Asp |  |
|  |  |  |  | 645 |  |  |  |  | 650 |  |  |  |  | 655 |  |  |

| aac | aaa | cca | gag | aaa | aag | agc | gag | tct | cca | tcc | gca | cac | atc | tac | tcg | 2137 |
| Asn | Lys | Pro | Glu | Lys | Lys | Ser | Glu | Ser | Pro | Ser | Ala | His | Ile | Tyr | Ser |  |
|  |  |  | 660 |  |  |  |  | 665 |  |  |  |  | 670 |  |  |  |

| ccc | gct | aaa | cct | cca | gaa | gag | ctg | cca | ccc | acg | ccc | gac | tcg | acc | cca | 2185 |
| Pro | Ala | Lys | Pro | Pro | Glu | Glu | Leu | Pro | Pro | Thr | Pro | Asp | Ser | Thr | Pro |  |
|  |  | 675 |  |  |  |  | 680 |  |  |  |  | 685 |  |  |  |  |

| gaa | ctg | cca | atc | aaa | aac | atc | aaa | gcc | atc | agc | agc | caa | tgg | gag | aga | 2233 |
| Glu | Leu | Pro | Ile | Lys | Asn | Ile | Lys | Ala | Ile | Ser | Ser | Gln | Trp | Glu | Arg |  |
|  |  | 690 |  |  |  |  | 695 |  |  |  |  | 700 |  |  |  |  |

| agc | cac | acc | cac | aac | tcc | acc | ctc | cag | ctc | att | ccg | acc | aat | cag | agt | 2281 |
| Ser | His | Thr | His | Asn | Ser | Thr | Leu | Gln | Leu | Ile | Pro | Thr | Asn | Gln | Ser |  |
| 705 |  |  |  |  | 710 |  |  |  |  | 715 |  |  |  |  | 720 |  |

| cat | cca | atg | ctt | tca | gaa | aat | ccc | agt | gat | gat | ata | agc | agt | agc | agt | 2329 |
| His | Pro | Met | Leu | Ser | Glu | Asn | Pro | Ser | Asp | Asp | Ile | Ser | Ser | Ser | Ser |  |
|  |  |  |  | 725 |  |  |  |  | 730 |  |  |  |  | 735 |  |  |

| caa | cgt | tct | gat | gcc | acc | ctt | atg | tca | cct | gct | gga | tta | aag | tca | tac | 2377 |
| Gln | Arg | Ser | Asp | Ala | Thr | Leu | Met | Ser | Pro | Ala | Gly | Leu | Lys | Ser | Tyr |  |
|  |  |  | 740 |  |  |  |  | 745 |  |  |  |  | 750 |  |  |  |

| aat | cgg | act | tta | tta | ccg | aag | tcg | tat | tac | agc | tgt | ctg | aaa | gag | ccg | 2425 |

| | | | | | | | | | | | | | |
|---|---|---|---|---|---|---|---|---|---|---|---|---|---|
| Asn | Arg | Thr | Leu | Leu | Pro | Lys | Ser | Tyr | Tyr | Ser | Cys | Leu | Lys | Glu | Pro |
| | | 755 | | | | | 760 | | | | | 765 | | | |

```
tca gaa tgt tcc acg ctt cag cag att ccc gaa cag ccc tcc gca cag    2473
Ser Glu Cys Ser Thr Leu Gln Gln Ile Pro Glu Gln Pro Ser Ala Gln
    770                 775                 780 cgc cac gtc ctc att aaa atg ggt aac ggg atc acc agc gcg cgc cag    2521
Arg His Val Leu Ile Lys Met Gly Asn Gly Ile Thr Ser Ala Arg Gln
785                 790                 795                 800 cac acc ttc aac ccc aag atg aac tcc aat acg ggg aat att tac gag    2569
His Thr Phe Asn Pro Lys Met Asn Ser Asn Thr Gly Asn Ile Tyr Glu
                805                 810                 815 atc cag cgg ccg ctc gtc gcc ggc ggc tcg tgt ttg acg cgg cag cac    2617
Ile Gln Arg Pro Leu Val Ala Gly Gly Ser Cys Leu Thr Arg Gln His
            820                 825                 830 agt tac agc gag ccg cca cag ctc cag cgc agc gct atc gtc aga cgc    2665
Ser Tyr Ser Glu Pro Pro Gln Leu Gln Arg Ser Ala Ile Val Arg Arg
        835                 840                 845 acc gca tcg cta aaa cca cag ata ccg ccc aaa cca ctg aac ata cct    2713
Thr Ala Ser Leu Lys Pro Gln Ile Pro Pro Lys Pro Leu Asn Ile Pro
    850                 855                 860 gct aaa aca ctg ccc tct gct ggc aca cac aac cac aca cac aac tac    2761
Ala Lys Thr Leu Pro Ser Ala Gly Thr His Asn His Thr His Asn Tyr
865                 870                 875                 880 tgacacacac acacacacac acacacacac actgacccca aggtcacatg            2821
acacacacaa ctactgacac acacacacat acacaaatac tgaccccgta gtcacgtcac   2881
acacacaatt acctaccagc acacacatac acaactattg actccacggt cacaagacgc   2941
gcacaactac tgactctctc acacacacac acacacacac acacacacac acacaaaaat   3001
actgacctcg cgctcacatt acacacacaa ctattgacta cacagtcaca tggcatacac   3061
acacaactat tgaccctgtg ggacaacact ggtcacacaa cacacacatg caattactaa   3121
ccccgcgatc acgacacaca actactgacc ccgcgatcac atgacacaaa cacaactact   3181
gaccatgtgt tcacatgaca cacaaacgac acacaactga gcccacacac tcaggggtca   3241
gaataccagc acattgatga ctgcagtgtg taaatatagt gtgtatatag tgtaaatata   3301
agagatggga tgttattatg gtgcacactg aatgattatg cagtggtgga gggttatttt   3361
tgtcaataaa tctggtttct tgcatttgtt aaaaaaaaaa aaaaaaaaa              3410
```

<210> SEQ ID NO 53
<211> LENGTH: 880
<212> TYPE: PRT
<213> ORGANISM: Danio rerio

<400> SEQUENCE: 53

| | | | | | | | | | | | | | | |
|---|---|---|---|---|---|---|---|---|---|---|---|---|---|---|
| Met | Ala | Met | Val | Leu | Leu | Ala | Trp | Leu | Leu | Pro | Leu | Ile | Thr | Ser | Ala |
| 1 | | | | 5 | | | | | 10 | | | | | 15 | |

| | | | | | | | | | | | | | | |
|---|---|---|---|---|---|---|---|---|---|---|---|---|---|---|
| Thr | Pro | Phe | Pro | Arg | Asp | Leu | Gln | Pro | Ile | Ser | Val | Val | Gly | Leu | Asp |
| | | | 20 | | | | | 25 | | | | | 30 | | |

| | | | | | | | | | | | | | | |
|---|---|---|---|---|---|---|---|---|---|---|---|---|---|---|
| Asp | Ser | Tyr | Leu | Tyr | Pro | Ser | Phe | Gln | Gly | Leu | Val | Ser | Ser | Asn | Glu |
| | | | 35 | | | | | 40 | | | | | 45 | | |

| | | | | | | | | | | | | | | |
|---|---|---|---|---|---|---|---|---|---|---|---|---|---|---|
| Thr | Glu | Arg | Leu | Gly | Leu | Asp | Tyr | Gln | Arg | Met | Met | Arg | Ile | Gln | His |
| | 50 | | | | | 55 | | | | | 60 | | | | |

| | | | | | | | | | | | | | | |
|---|---|---|---|---|---|---|---|---|---|---|---|---|---|---|
| Met | Leu | Tyr | Ile | Ala | Ala | Arg | Asp | His | Val | Phe | Val | Val | Asn | Leu | Thr |
| 65 | | | | 70 | | | | | 75 | | | | | 80 | |

| | | | | | | | | | | | | | | |
|---|---|---|---|---|---|---|---|---|---|---|---|---|---|---|
| Thr | Ala | Val | Asp | Glu | Ile | Ile | Pro | Gln | Gln | Ile | Leu | Thr | Trp | Arg | Ser |
| | | | 85 | | | | | 90 | | | | | 95 | | |

```
Thr Asp Val Ser Lys Cys Thr Val Arg Gly Arg Asn Ser Asp Glu Cys
            100                 105                 110

Tyr Asn Tyr Ile Lys Val Leu Val Pro Arg Asn Asp Glu Thr Leu Phe
            115                 120                 125

Ala Cys Gly Thr Asn Ala Leu Asn Pro Ala Cys Arg Asn Tyr Arg Leu
            130                 135                 140

Ser Ser Leu Glu Gln Val Gly Gln Glu Leu Leu Gly Gln Ala Arg Cys
145                 150                 155                 160

Pro Phe Glu Ser Arg Gln Ser Asn Val Gly Val Phe Ala Gly Gly His
                165                 170                 175

Phe Tyr Ser Ala Thr Val Thr Asp Phe Gln Ala Ser Asp Ala Val Ile
            180                 185                 190

Tyr Arg Ser Leu Gly Gly Glu Gly Arg Pro Val Leu Arg Thr Val Lys
            195                 200                 205

Tyr Asp Ser Lys Trp Leu Arg Glu Pro His Phe Leu His Ala Val Glu
            210                 215                 220

Tyr Gly Asn Tyr Val Tyr Phe Phe Ser Glu Ile Ala Val Glu His
225                 230                 235                 240

Thr Ala Ala Gly Lys Val Val Tyr Ser Arg Val Ala Arg Val Cys Lys
                245                 250                 255

Asn Asp Asn Gly Gly Ser Thr Arg Val Leu Asp Arg His Trp Thr Ser
            260                 265                 270

Phe Leu Lys Ala Arg Leu Asn Cys Ser Val Pro Gly Asp Thr Phe Phe
            275                 280                 285

Tyr Phe Asp Val Leu Gln Ser Leu Thr Asn Val Leu Gln Ile Asn Gln
290                 295                 300

Arg Pro Ala Val Val Gly Val Phe Thr Gln Thr Asn Ser Ile Pro
305                 310                 315                 320

Gly Ser Ala Val Cys Gly Phe Tyr Leu Asp Asp Ile Glu Arg Val Phe
                325                 330                 335

Asn Gly Arg Phe Lys Glu Gln Lys Asn Ser Asp Ser Met Trp Thr Ala
            340                 345                 350

Val Pro Glu Glu Gln Val Pro Lys Pro Arg Pro Gly Ser Cys Ala Gly
            355                 360                 365

Glu Gly Ser Ala Ser Ser Tyr Ser Ser Ser Val Gln Phe Pro Asp Ser
    370                 375                 380

Val Leu Ser Phe Ile Lys Thr His Pro Leu Met Glu Glu Ser Val Pro
385                 390                 395                 400

Ser Val Asn Ser Gln Pro Leu Ile Thr Asn Thr Ala Ser Arg Tyr Lys
                405                 410                 415

Leu Thr Gln Ile Val Val Asp Thr Ala Ala Gly Pro His Lys Asn Arg
            420                 425                 430

Thr Val Val Phe Leu Gly Ser Glu Asp Gly Arg Val Leu Lys Ile Leu
            435                 440                 445

Thr Asn Thr His Ser Asn Ser His Thr Ser Gln Leu Leu Glu Asp
            450                 455                 460

Ile Asp Val Phe Asn Pro Thr Arg Cys Val Gly Glu Arg Ala Val Leu
465                 470                 475                 480

Gly Leu Glu Leu Asp Lys Glu His His Ala Leu Phe Val Ala Phe Ser
                485                 490                 495

Ser Cys Val Ile Arg Val Pro Leu Ser Arg Cys Ala Gln His Ala Thr
            500                 505                 510

Cys Arg Arg Arg Cys Leu Tyr Thr His Asp Pro Tyr Cys Ile Trp Leu
```

```
                      515                 520                 525
Arg Thr Gly Arg Cys Ala Asp Met Ala Pro Gly Phe Lys Ala Gly Phe
530                 535                 540

Glu Gln Asp Ile Asp Gly Glu Gln Thr His Leu Phe Asp Thr Cys Thr
545                 550                 555                 560

Asp Val Met Ser Ser Ala Gly Ser Asp Val Lys Ser Ala Val Asp Ser
                565                 570                 575

Ala Ser Gly Val Lys Gln Leu Pro Asp Ala Asp Ser Leu Ser Asp Gly
            580                 585                 590

Tyr His Phe Thr Leu Leu Gly Ala Cys Val Leu Leu Ala Phe Val Leu
                595                 600                 605

Gly Ala Ile Ala Ser Gly Leu Leu Val Ser Cys Tyr Cys Arg Gln Ser
610                 615                 620

Ser Pro Pro Thr Pro Glu Pro Glu Ala Thr Leu Ala His Thr His Ala
625                 630                 635                 640

His Thr Leu Ser Leu Ser Ser Leu Ala Lys Ile Asn Leu Leu Met Asp
                645                 650                 655

Asn Lys Pro Glu Lys Ser Glu Ser Pro Ser Ala His Ile Tyr Ser
                660                 665                 670

Pro Ala Lys Pro Pro Glu Glu Leu Pro Pro Thr Pro Asp Ser Thr Pro
            675                 680                 685

Glu Leu Pro Ile Lys Asn Ile Lys Ala Ile Ser Ser Gln Trp Glu Arg
690                 695                 700

Ser His Thr His Asn Ser Thr Leu Gln Leu Ile Pro Thr Asn Gln Ser
705                 710                 715                 720

His Pro Met Leu Ser Glu Asn Pro Ser Asp Asp Ile Ser Ser Ser Ser
                725                 730                 735

Gln Arg Ser Asp Ala Thr Leu Met Ser Pro Ala Gly Leu Lys Ser Tyr
            740                 745                 750

Asn Arg Thr Leu Leu Pro Lys Ser Tyr Ser Cys Leu Lys Glu Pro
                755                 760                 765

Ser Glu Cys Ser Thr Leu Gln Gln Ile Pro Glu Gln Pro Ser Ala Gln
770                 775                 780

Arg His Val Leu Ile Lys Met Gly Asn Gly Ile Thr Ser Ala Arg Gln
785                 790                 795                 800

His Thr Phe Asn Pro Lys Met Asn Ser Asn Thr Gly Asn Ile Tyr Glu
                805                 810                 815

Ile Gln Arg Pro Leu Val Ala Gly Gly Ser Cys Leu Thr Arg Gln His
            820                 825                 830

Ser Tyr Ser Glu Pro Pro Gln Leu Gln Arg Ser Ala Ile Val Arg Arg
            835                 840                 845

Thr Ala Ser Leu Lys Pro Gln Ile Pro Pro Lys Pro Leu Asn Ile Pro
                850                 855                 860

Ala Lys Thr Leu Pro Ser Ala Gly Thr His Asn His Thr His Asn Tyr
865                 870                 875                 880
```

<210> SEQ ID NO 54
<211> LENGTH: 4317
<212> TYPE: DNA
<213> ORGANISM: Rattus norvegicus
<220> FEATURE:
<221> NAME/KEY: CDS
<222> LOCATION: (1)..(4314)

<400> SEQUENCE: 54

| | | |
|---|---|---|
| atg aag gcg agg agc cag agt gaa cta ggg ata aag tat cca ctc ttc<br>Met Lys Ala Arg Ser Gln Ser Glu Leu Gly Ile Lys Tyr Pro Leu Phe<br>1               5                  10                 15 | | 48 |
| agt aga cta gga aat aag gac act ctg cta tgt gga caa ccg agg gag<br>Ser Arg Leu Gly Asn Lys Asp Thr Leu Leu Cys Gly Gln Pro Arg Glu<br>        20                 25                 30 | | 96 |
| tgt aaa aat aac tgc tac ttc tcc ttg aga gct tgc act gtg cca aac<br>Cys Lys Asn Asn Cys Tyr Phe Ser Leu Arg Ala Cys Thr Val Pro Asn<br>    35                 40                 45 | | 144 |
| agc gta atg ata gtc ata cta gca ggc aac tgc gtc atg agg acc ctg<br>Ser Val Met Ile Val Ile Leu Ala Gly Asn Cys Val Met Arg Thr Leu<br>50                 55                 60 | | 192 |
| agc caa acg ctg ctt gaa aca gta cca gtg tgg ata cat aga aga tgc<br>Ser Gln Thr Leu Leu Glu Thr Val Pro Val Trp Ile His Arg Arg Cys<br>65                 70                 75                 80 | | 240 |
| cta aca ccc tct ggt gat gtc aca cat gag tct ccc agc cgc cct gca<br>Leu Thr Pro Ser Gly Asp Val Thr His Glu Ser Pro Ser Arg Pro Ala<br>            85                 90                 95 | | 288 |
| gca tgc acg tgc aca gac aat gca cat ctc cat agc agt aag ggg tct<br>Ala Cys Thr Cys Thr Asp Asn Ala His Leu His Ser Ser Lys Gly Ser<br>        100                105                110 | | 336 |
| ccc ttc tgc agg agg aga ctg gca gaa agg ctg gct aca ctg tca tcc<br>Pro Phe Cys Arg Arg Arg Leu Ala Glu Arg Leu Ala Thr Leu Ser Ser<br>    115                120                125 | | 384 |
| atg tgg att act gca gcc ctg gct agt ggc aag tct cag cag ttc tgc<br>Met Trp Ile Thr Ala Ala Leu Ala Ser Gly Lys Ser Gln Gln Phe Cys<br>130                135                140 | | 432 |
| cag gct ggc agc tgt acc agg gca gct ccc aag gtt gac gac tta caa<br>Gln Ala Gly Ser Cys Thr Arg Ala Ala Pro Lys Val Asp Asp Leu Gln<br>145                150                155                160 | | 480 |
| atg aga cct ctg gaa ccg tct tta gaa aat ata cgt tct gag tca aca<br>Met Arg Pro Leu Glu Pro Ser Leu Glu Asn Ile Arg Ser Glu Ser Thr<br>            165                170                175 | | 528 |
| tgg tta ata gtg tgc ctt ggt gtg aaa act aag aca aaa ctt cgg ggt<br>Trp Leu Ile Val Cys Leu Gly Val Lys Thr Lys Thr Lys Leu Arg Gly<br>        180                185                190 | | 576 |
| aca act gcg ccc acc gca cca ctg ggc tgc agc cat ttg tcc tcc gat<br>Thr Thr Ala Pro Thr Ala Pro Leu Gly Cys Ser His Leu Ser Ser Asp<br>    195                200                205 | | 624 |
| cgt cta ggg tgg ctg gct ggg aga gta gtg agg gcg cct gga gga agg<br>Arg Leu Gly Trp Leu Ala Gly Arg Val Val Arg Ala Pro Gly Gly Arg<br>210                215                220 | | 672 |
| gag agg cgg ctt tgc agg cta cag agg cgg cgc cag ctg ggc gac ccg<br>Glu Arg Arg Leu Cys Arg Leu Gln Arg Arg Arg Gln Leu Gly Asp Pro<br>225                230                235                240 | | 720 |
| gct cgg aga ggc gcg gga gga gcg gct ccg cta agg tgg gag agc ctg<br>Ala Arg Arg Gly Ala Gly Gly Ala Ala Pro Leu Arg Trp Glu Ser Leu<br>            245                250                255 | | 768 |
| ggc gcg cgg ccg agc gcg atc agg gac gcg gcg gcc act ggg gtc gag<br>Gly Ala Arg Pro Ser Ala Ile Arg Asp Ala Ala Ala Thr Gly Val Glu<br>        260                265                270 | | 816 |
| gcc gcg gcg cgc gta gga ctc tgg gcg gcg ctg gcc gcg gtg gga gct<br>Ala Ala Ala Arg Val Gly Leu Trp Ala Ala Leu Ala Ala Val Gly Ala<br>    275                280                285 | | 864 |
| gca gag cgg cga ggg agc cgg gat ctc agg gag cga ctc gga gat gga<br>Ala Glu Arg Arg Gly Ser Arg Asp Leu Arg Glu Arg Leu Gly Asp Gly<br>290                295                300 | | 912 |
| tcg aat tac acc att tgc cga gca gcg gac ctc gtt cag act ctt gag<br>Ser Asn Tyr Thr Ile Cys Arg Ala Ala Asp Leu Val Gln Thr Leu Glu<br>305                310                315                320 | | 960 |

```
gtc aac ctg gca gtc cac agc gct aac ttt gct cag aat cca cgg aag    1008
Val Asn Leu Ala Val His Ser Ala Asn Phe Ala Gln Asn Pro Arg Lys
            325                 330                 335 cta agt ggg act tct gag gag gga gct cag ata cct tct cgg cca acc    1056
Leu Ser Gly Thr Ser Glu Glu Gly Ala Gln Ile Pro Ser Arg Pro Thr
        340                 345                 350 atg agg ttc ttt ctg ctg tgg ttc tgt gtg ctg ttc ctt ctg gtc tcc    1104
Met Arg Phe Phe Leu Leu Trp Phe Cys Val Leu Phe Leu Leu Val Ser
    355                 360                 365 agg tta cgg gcc gtc agc ttc cct gag gac gat gag ccc ctt aac acg    1152
Arg Leu Arg Ala Val Ser Phe Pro Glu Asp Asp Glu Pro Leu Asn Thr
370                 375                 380 gtt gac tac cac tat tca agg caa tat ccg gtt ttt aga gga cgc cct    1200
Val Asp Tyr His Tyr Ser Arg Gln Tyr Pro Val Phe Arg Gly Arg Pro
385                 390                 395                 400 tca ggc aac gaa tcg cag cat agg ctg gac ttt cag ctg atg ttg aaa    1248
Ser Gly Asn Glu Ser Gln His Arg Leu Asp Phe Gln Leu Met Leu Lys
                405                 410                 415 att cga gac aca ctt tat att gct ggc agg gat caa gtc tat aca gtg    1296
Ile Arg Asp Thr Leu Tyr Ile Ala Gly Arg Asp Gln Val Tyr Thr Val
            420                 425                 430 aac tta aat gac atc ccc caa aca gag gtg atc ccg agc aag aag ctg    1344
Asn Leu Asn Asp Ile Pro Gln Thr Glu Val Ile Pro Ser Lys Lys Leu
        435                 440                 445 aca tgg agg tcc aga cag cag gat cga gaa aat tgt gct atg aaa ggc    1392
Thr Trp Arg Ser Arg Gln Gln Asp Arg Glu Asn Cys Ala Met Lys Gly
    450                 455                 460 aag cat aaa gat gaa tgt cac aac ttc atc aaa gtc ttt gtc cca aga    1440
Lys His Lys Asp Glu Cys His Asn Phe Ile Lys Val Phe Val Pro Arg
465                 470                 475                 480 aat gat gag atg gtt ttt gtc tgt ggc acc aac gct ttc aac ccg atg    1488
Asn Asp Glu Met Val Phe Val Cys Gly Thr Asn Ala Phe Asn Pro Met
                485                 490                 495 tgc aga tac tat agg ttg agt acc tta gag tat gat ggg gaa gaa att    1536
Cys Arg Tyr Tyr Arg Leu Ser Thr Leu Glu Tyr Asp Gly Glu Glu Ile
            500                 505                 510 agt ggc ctg gca cgg tgc ccg ttt gat gcc cga caa acc aat gtt gcc    1584
Ser Gly Leu Ala Arg Cys Pro Phe Asp Ala Arg Gln Thr Asn Val Ala
        515                 520                 525 ctc ttt gct gat ggg aaa ctg tat tct gcc aca gtg gct gat ttc ctg    1632
Leu Phe Ala Asp Gly Lys Leu Tyr Ser Ala Thr Val Ala Asp Phe Leu
    530                 535                 540 gcc agt gat gct gtc att tac aga agc atg ggt gat gga tcg gcc ctc    1680
Ala Ser Asp Ala Val Ile Tyr Arg Ser Met Gly Asp Gly Ser Ala Leu
545                 550                 555                 560 cgc aca ata aaa tac gac tcc aaa tgg atc aaa gaa cca cac ttt ctt    1728
Arg Thr Ile Lys Tyr Asp Ser Lys Trp Ile Lys Glu Pro His Phe Leu
                565                 570                 575 cac gcc ata gaa tat gga aac tat gtc tat ttc ttc aga gaa atc    1776
His Ala Ile Glu Tyr Gly Asn Tyr Val Tyr Phe Phe Arg Glu Ile
            580                 585                 590 gcc gtg gaa cat aat aac tta ggc aag gct gtg tac tcc cga gtg gcc    1824
Ala Val Glu His Asn Asn Leu Gly Lys Ala Val Tyr Ser Arg Val Ala
        595                 600                 605 cgc att tgt aaa aac gac atg ggt ggc tca cag cgg gtc ctg gag aaa    1872
Arg Ile Cys Lys Asn Asp Met Gly Gly Ser Gln Arg Val Leu Glu Lys
    610                 615                 620 cac tgg act tcc ttc ctg aag gct cgg ctt aac tgc tca gtc cct gga    1920
His Trp Thr Ser Phe Leu Lys Ala Arg Leu Asn Cys Ser Val Pro Gly
```

```
                    -continued 625                 630                 635                 640 gat tcc ttt ttc tac ttc gat gtt ctg cag tcc atc aca gac atc atc    1968
Asp Ser Phe Phe Tyr Phe Asp Val Leu Gln Ser Ile Thr Asp Ile Ile
            645                 650                 655 caa atc aat ggc atc ccc acc gtg atc ggg gtc ttc acc acg cag ctc    2016
Gln Ile Asn Gly Ile Pro Thr Val Ile Gly Val Phe Thr Thr Gln Leu
            660                 665                 670 aac agc att cct ggc tct gca gtc tgt gcc ttt agc atg gac gac att    2064
Asn Ser Ile Pro Gly Ser Ala Val Cys Ala Phe Ser Met Asp Asp Ile
            675                 680                 685 gag aaa gtg ttc aaa ggg cgg ttc aaa gag cag aaa acc cca gac tct    2112
Glu Lys Val Phe Lys Gly Arg Phe Lys Glu Gln Lys Thr Pro Asp Ser
            690                 695                 700 gtt tgg aca gcg gtt cct gaa gac aaa gta cca aaa cca agg cct ggc    2160
Val Trp Thr Ala Val Pro Glu Asp Lys Val Pro Lys Pro Arg Pro Gly
705                 710                 715                 720 tgt tgt gcc aaa cat ggc ctc gcg gaa gct tac aaa acc tcc atc gac    2208
Cys Cys Ala Lys His Gly Leu Ala Glu Ala Tyr Lys Thr Ser Ile Asp
            725                 730                 735 ttt cca gat gat acc ctg tct ttc atc aag tcc cac ccg ctg atg gac    2256
Phe Pro Asp Asp Thr Leu Ser Phe Ile Lys Ser His Pro Leu Met Asp
            740                 745                 750 tcc gct gtc cca ccc att gct gat gag ccc tgg ttc aca aag act cgg    2304
Ser Ala Val Pro Pro Ile Ala Asp Glu Pro Trp Phe Thr Lys Thr Arg
            755                 760                 765 gtc cgg tac agg ctg aca gcc atc gaa gtg gac cgt tcg gca ggg ccg    2352
Val Arg Tyr Arg Leu Thr Ala Ile Glu Val Asp Arg Ser Ala Gly Pro
            770                 775                 780 tac caa aac tac aca gtc atc ttt gtt ggc tct gag gcc ggc gtg gtg    2400
Tyr Gln Asn Tyr Thr Val Ile Phe Val Gly Ser Glu Ala Gly Val Val
785                 790                 795                 800 ctt aaa gtt ttg gca aag acc agt cct ttc tct ttg aac gac agt gta    2448
Leu Lys Val Leu Ala Lys Thr Ser Pro Phe Ser Leu Asn Asp Ser Val
            805                 810                 815 tta ctc gaa gag atc gaa gct tat aac cca gcc aag tgc agc gcc gag    2496
Leu Leu Glu Glu Ile Glu Ala Tyr Asn Pro Ala Lys Cys Ser Ala Glu
            820                 825                 830 agt gag gag gac agg aag gtc gtc tcg tta cag ctg gac agg gat cac    2544
Ser Glu Glu Asp Arg Lys Val Val Ser Leu Gln Leu Asp Arg Asp His
            835                 840                 845 cat gct tta tac gtg gcc ttc tcc agc tgc gtg gtc cgc atc ccc ctc    2592
His Ala Leu Tyr Val Ala Phe Ser Ser Cys Val Val Arg Ile Pro Leu
850                 855                 860 agc cgc tgt gag cgc tat ggc tcc tgt aaa aag tct tgc att gca tca    2640
Ser Arg Cys Glu Arg Tyr Gly Ser Cys Lys Lys Ser Cys Ile Ala Ser
865                 870                 875                 880 cga gac ccg tac tgt ggt tgg tta agc cag gga gtg tgt gag aga gtg    2688
Arg Asp Pro Tyr Cys Gly Trp Leu Ser Gln Gly Val Cys Glu Arg Val
            885                 890                 895 acc tta ggg atg ctg ctg tta acc gaa gac ttc ttt gct ttc cat aac    2736
Thr Leu Gly Met Leu Leu Leu Thr Glu Asp Phe Phe Ala Phe His Asn
            900                 905                 910 cac agt gct gga gga tat gag cag gac acc gag tat ggc aac acg gcc    2784
His Ser Ala Gly Gly Tyr Glu Gln Asp Thr Glu Tyr Gly Asn Thr Ala
            915                 920                 925 cac cta ggg gac tgc cac gaa agt ttg cct act tca act aca cca gat    2832
His Leu Gly Asp Cys His Glu Ser Leu Pro Thr Ser Thr Thr Pro Asp
            930                 935                 940 tac aaa ata ttt ggc ggt cca aca tct gac atg gag gta ccc tca tct    2880
```

-continued

```
                Tyr Lys Ile Phe Gly Gly Pro Thr Ser Asp Met Glu Val Pro Ser Ser
                945                 950                 955                 960 tct gtt acc act gtg gca agt agc cca gaa att aca tct aaa gtg att            2928
Ser Val Thr Thr Val Ala Ser Ser Pro Glu Ile Thr Ser Lys Val Ile
                    965                 970                 975 gat acc tgg aga cct aaa ctg acg agc tcc cgg aaa ttt gta gtt caa            2976
Asp Thr Trp Arg Pro Lys Leu Thr Ser Ser Arg Lys Phe Val Val Gln
                980                 985                 990 gat gac cca aac act tcc gat ttt  act gat act ata tca  ggt atc cca          3024
Asp Asp Pro Asn Thr Ser Asp Phe Thr Asp Thr Ile Ser  Gly Ile Pro
                995                 1000                1005 aag ggt gta cgg tgg gaa gtc cag tct gga gat tcc  aac cag atg               3069
Lys Gly Val Arg Trp Glu Val Gln Ser Gly Asp Ser  Asn Gln Met
        1010                1015                1020 gtc cac atg aat gtc ctc atc acc tgc gtg ttt gca  gct ttt gtc               3114
Val His Met Asn Val Leu Ile Thr Cys Val Phe Ala  Ala Phe Val
        1025                1030                1035 ttg ggc gcg ttc atc gca gga gtg gct gtg tac tgc  tat cgt gac               3159
Leu Gly Ala Phe Ile Ala Gly Val Ala Val Tyr Cys  Tyr Arg Asp
        1040                1045                1050 atg ttt gtt cgg aag aac aga aag atc cat aaa gat gca gaa tcg                3204
Met Phe Val Arg Lys Asn Arg Lys Ile His Lys Asp Ala Glu Ser
        1055                1060                1065 gcc cag tca tgc aca gat tcc agt gga agc ttt gcc aag ctg aat                3249
Ala Gln Ser Cys Thr Asp Ser Ser Gly Ser Phe Ala Lys Leu Asn
        1070                1075                1080 ggt ctc ttt gac agc ccc gtc aag gag tac cag cag aac atc gat                3294
Gly Leu Phe Asp Ser Pro Val Lys Glu Tyr Gln Gln Asn Ile Asp
        1085                1090                1095 tca ccc aaa ctg tac agc aac ctg ctg acc agt cgg aag gag ctg                3339
Ser Pro Lys Leu Tyr Ser Asn Leu Leu Thr Ser Arg Lys Glu Leu
        1100                1105                1110 cct ccc aac acg gat cca aag tcc atg gcc atg gac cat cga ggc                3384
Pro Pro Asn Thr Asp Pro Lys Ser Met Ala Met Asp His Arg Gly
        1115                1120                1125 cag cct cca gag ctg gct gct ctc ccc acg cca gag tct aca cct                3429
Gln Pro Pro Glu Leu Ala Ala Leu Pro Thr Pro Glu Ser Thr Pro
        1130                1135                1140 gta ctc cac cag aag acc ctg cag gcc atg aag agc cac tcc gat                3474
Val Leu His Gln Lys Thr Leu Gln Ala Met Lys Ser His Ser Asp
        1145                1150                1155 aag gcc cat ggc cat ggt gct tca agg aag gaa cac ccc cag ttt                3519
Lys Ala His Gly His Gly Ala Ser Arg Lys Glu His Pro Gln Phe
        1160                1165                1170 ttt cct tct agt cct cca ccc cat tcc ccg tta agt cac ggg cat                3564
Phe Pro Ser Ser Pro Pro Pro His Ser Pro Leu Ser His Gly His
        1175                1180                1185 att ccc agt gcc atc gtt ctt cca aac gcc act cat gac tac aac                3609
Ile Pro Ser Ala Ile Val Leu Pro Asn Ala Thr His Asp Tyr Asn
        1190                1195                1200 aca tcc ttc tca aac tct aac gct cac aaa gcc gaa aag aag ctt                3654
Thr Ser Phe Ser Asn Ser Asn Ala His Lys Ala Glu Lys Lys Leu
        1205                1210                1215 cag aac gtt gat cac cct ctc aca aag tca tcc agt aag agg gaa                3699
Gln Asn Val Asp His Pro Leu Thr Lys Ser Ser Ser Lys Arg Glu
        1220                1225                1230 cac cgg cgc tct gtg gac tcc aga aac acc ctc aat gat ctc ttg                3744
His Arg Arg Ser Val Asp Ser Arg Asn Thr Leu Asn Asp Leu Leu
        1235                1240                1245
```

| | | | | | | | | | | | | |
|---|---|---|---|---|---|---|---|---|---|---|---|---|
| aag | cat | ctc | aat | gac | cca | aac | agt | aac | gcc | aaa | gcc | atc | atg | gga | 3789 |
| Lys | His | Leu | Asn | Asp | Pro | Asn | Ser | Asn | Ala | Lys | Ala | Ile | Met | Gly | |
| | 1250 | | | | 1255 | | | | 1260 | | | | | | |
| gaa | atc | cac | atg | gcc | cat | cag | acc | ctc | atg | ctg | gac | cca | gtg | gga | 3834 |
| Glu | Ile | His | Met | Ala | His | Gln | Thr | Leu | Met | Leu | Asp | Pro | Val | Gly | |
| 1265 | | | | | 1270 | | | | | 1275 | | | | | |
| cca | atg | tct | gag | gtc | cca | ccc | aag | gtt | cct | aac | cgg | gag | gca | tcc | 3879 |
| Pro | Met | Ser | Glu | Val | Pro | Pro | Lys | Val | Pro | Asn | Arg | Glu | Ala | Ser | |
| 1280 | | | | | 1285 | | | | | 1290 | | | | | |
| cta | tac | tcc | ccc | ccc | tca | aca | ctc | ccc | aga | aat | agt | cca | acc | aag | 3924 |
| Leu | Tyr | Ser | Pro | Pro | Ser | Thr | Leu | Pro | Arg | Asn | Ser | Pro | Thr | Lys | |
| 1295 | | | | | 1300 | | | | | 1305 | | | | | |
| aga | gta | gat | gtc | ccc | acc | act | cct | ggg | gtc | cca | atg | act | tct | ctg | 3969 |
| Arg | Val | Asp | Val | Pro | Thr | Thr | Pro | Gly | Val | Pro | Met | Thr | Ser | Leu | |
| 1310 | | | | | 1315 | | | | | 1320 | | | | | |
| gaa | aga | caa | agg | ggt | tat | cac | aaa | aac | tcc | tcc | cag | agg | cac | tct | 4014 |
| Glu | Arg | Gln | Arg | Gly | Tyr | His | Lys | Asn | Ser | Ser | Gln | Arg | His | Ser | |
| 1325 | | | | | 1330 | | | | | 1335 | | | | | |
| ata | tct | gcc | gtg | cct | aaa | aac | tta | aac | tca | cca | aac | ggt | gtt | ttg | 4059 |
| Ile | Ser | Ala | Val | Pro | Lys | Asn | Leu | Asn | Ser | Pro | Asn | Gly | Val | Leu | |
| | 1340 | | | | 1345 | | | | | 1350 | | | | | |
| tta | tct | aga | cag | ccg | agt | atg | aac | cgt | gga | gga | tat | atg | ccc | acc | 4104 |
| Leu | Ser | Arg | Gln | Pro | Ser | Met | Asn | Arg | Gly | Gly | Tyr | Met | Pro | Thr | |
| 1355 | | | | | 1360 | | | | | 1365 | | | | | |
| cca | aca | ggg | gcg | aag | gtg | gac | tat | att | cag | ggg | aca | ccg | gtg | agt | 4149 |
| Pro | Thr | Gly | Ala | Lys | Val | Asp | Tyr | Ile | Gln | Gly | Thr | Pro | Val | Ser | |
| 1370 | | | | | 1375 | | | | | 1380 | | | | | |
| gtc | cat | ctg | cag | ccc | tcc | ctc | tcc | aga | cag | agc | agc | tac | acc | agt | 4194 |
| Val | His | Leu | Gln | Pro | Ser | Leu | Ser | Arg | Gln | Ser | Ser | Tyr | Thr | Ser | |
| 1385 | | | | | 1390 | | | | | 1395 | | | | | |
| aat | ggt | acc | cta | ccc | agg | acg | gga | cta | aag | agg | aca | cca | tcc | tta | 4239 |
| Asn | Gly | Thr | Leu | Pro | Arg | Thr | Gly | Leu | Lys | Arg | Thr | Pro | Ser | Leu | |
| | 1400 | | | | 1405 | | | | | 1410 | | | | | |
| aaa | cct | gat | gtg | cca | cca | aag | cct | tcc | ttt | gtt | cct | caa | acc | aca | 4284 |
| Lys | Pro | Asp | Val | Pro | Pro | Lys | Pro | Ser | Phe | Val | Pro | Gln | Thr | Thr | |
| 1415 | | | | | 1420 | | | | | 1425 | | | | | |
| tct | gtc | aga | cca | ctg | aac | aaa | tac | act | tac | tag | | | | | 4317 |
| Ser | Val | Arg | Pro | Leu | Asn | Lys | Tyr | Thr | Tyr | | | | | | |
| | 1430 | | | | 1435 | | | | | | | | | | |

<210> SEQ ID NO 55
<211> LENGTH: 1438
<212> TYPE: PRT
<213> ORGANISM: Rattus norvegicus

<400> SEQUENCE: 55

Met Lys Ala Arg Ser Gln Ser Glu Leu Gly Ile Lys Tyr Pro Leu Phe
1               5                   10                  15

Ser Arg Leu Gly Asn Lys Asp Thr Leu Leu Cys Gly Gln Pro Arg Glu
            20                  25                  30

Cys Lys Asn Asn Cys Tyr Phe Ser Leu Arg Ala Cys Thr Val Pro Asn
        35                  40                  45

Ser Val Met Ile Val Ile Leu Ala Gly Asn Cys Val Met Arg Thr Leu
    50                  55                  60

Ser Gln Thr Leu Leu Glu Thr Val Pro Val Trp Ile His Arg Arg Cys
65                  70                  75                  80

Leu Thr Pro Ser Gly Asp Val Thr His Glu Ser Pro Ser Arg Pro Ala
                85                  90                  95

Ala Cys Thr Cys Thr Asp Asn Ala His Leu His Ser Ser Lys Gly Ser

```
            100                 105                 110
Pro Phe Cys Arg Arg Leu Ala Glu Arg Leu Ala Thr Leu Ser Ser
            115                 120                 125
Met Trp Ile Thr Ala Ala Leu Ala Ser Gly Lys Ser Gln Gln Phe Cys
            130                 135             140
Gln Ala Gly Ser Cys Thr Arg Ala Ala Pro Lys Val Asp Asp Leu Gln
145             150                 155                 160
Met Arg Pro Leu Glu Pro Ser Leu Glu Asn Ile Arg Ser Glu Ser Thr
                165                 170                 175
Trp Leu Ile Val Cys Leu Gly Val Lys Thr Lys Thr Lys Leu Arg Gly
                180                 185                 190
Thr Thr Ala Pro Thr Ala Pro Leu Gly Cys Ser His Leu Ser Ser Asp
            195                 200                 205
Arg Leu Gly Trp Leu Ala Gly Arg Val Val Arg Ala Pro Gly Gly Arg
210                 215                 220
Glu Arg Arg Leu Cys Arg Leu Gln Arg Arg Gln Leu Gly Asp Pro
225                 230                 235                 240
Ala Arg Arg Gly Ala Gly Gly Ala Ala Pro Leu Arg Trp Glu Ser Leu
                245                 250                 255
Gly Ala Arg Pro Ser Ala Ile Arg Asp Ala Ala Thr Gly Val Glu
                260                 265                 270
Ala Ala Ala Arg Val Gly Leu Trp Ala Ala Leu Ala Ala Val Gly Ala
            275                 280                 285
Ala Glu Arg Arg Gly Ser Arg Asp Leu Arg Glu Arg Leu Gly Asp Gly
            290                 295                 300
Ser Asn Tyr Thr Ile Cys Arg Ala Ala Asp Leu Val Gln Thr Leu Glu
305                 310                 315                 320
Val Asn Leu Ala Val His Ser Ala Asn Phe Ala Gln Asn Pro Arg Lys
                325                 330                 335
Leu Ser Gly Thr Ser Glu Glu Gly Ala Gln Ile Pro Ser Arg Pro Thr
                340                 345                 350
Met Arg Phe Phe Leu Leu Trp Phe Cys Val Leu Phe Leu Leu Val Ser
            355                 360                 365
Arg Leu Arg Ala Val Ser Phe Pro Glu Asp Asp Glu Pro Leu Asn Thr
370                 375                 380
Val Asp Tyr His Tyr Ser Arg Gln Tyr Pro Val Phe Arg Gly Arg Pro
385                 390                 395                 400
Ser Gly Asn Glu Ser Gln His Arg Leu Asp Phe Gln Leu Met Leu Lys
            405                 410                 415
Ile Arg Asp Thr Leu Tyr Ile Ala Gly Arg Asp Gln Val Tyr Thr Val
            420                 425                 430
Asn Leu Asn Asp Ile Pro Gln Thr Glu Val Ile Pro Ser Lys Lys Leu
            435                 440                 445
Thr Trp Arg Ser Arg Gln Gln Asp Arg Glu Asn Cys Ala Met Lys Gly
            450                 455                 460
Lys His Lys Asp Glu Cys His Asn Phe Ile Lys Val Phe Val Pro Arg
465                 470                 475                 480
Asn Asp Glu Met Val Phe Val Cys Gly Thr Asn Ala Phe Asn Pro Met
                485                 490                 495
Cys Arg Tyr Tyr Arg Leu Ser Thr Leu Glu Tyr Asp Gly Glu Glu Ile
                500                 505                 510
Ser Gly Leu Ala Arg Cys Pro Phe Asp Ala Arg Gln Thr Asn Val Ala
            515                 520                 525
```

```
Leu Phe Ala Asp Gly Lys Leu Tyr Ser Ala Thr Val Ala Asp Phe Leu
    530                 535                 540

Ala Ser Asp Ala Val Ile Tyr Arg Ser Met Gly Asp Gly Ser Ala Leu
545                 550                 555                 560

Arg Thr Ile Lys Tyr Asp Ser Lys Trp Ile Lys Glu Pro His Phe Leu
                565                 570                 575

His Ala Ile Glu Tyr Gly Asn Tyr Val Tyr Phe Phe Arg Glu Ile
            580                 585                 590

Ala Val Glu His Asn Asn Leu Gly Lys Ala Val Tyr Ser Arg Val Ala
        595                 600                 605

Arg Ile Cys Lys Asn Asp Met Gly Gly Ser Gln Arg Val Leu Glu Lys
    610                 615                 620

His Trp Thr Ser Phe Leu Lys Ala Arg Leu Asn Cys Ser Val Pro Gly
625                 630                 635                 640

Asp Ser Phe Phe Tyr Phe Asp Val Leu Gln Ser Ile Thr Asp Ile Ile
                645                 650                 655

Gln Ile Asn Gly Ile Pro Thr Val Ile Gly Val Phe Thr Thr Gln Leu
            660                 665                 670

Asn Ser Ile Pro Gly Ser Ala Val Cys Ala Phe Ser Met Asp Asp Ile
        675                 680                 685

Glu Lys Val Phe Lys Gly Arg Phe Lys Glu Gln Lys Thr Pro Asp Ser
    690                 695                 700

Val Trp Thr Ala Val Pro Glu Asp Lys Val Pro Lys Pro Arg Pro Gly
705                 710                 715                 720

Cys Cys Ala Lys His Gly Leu Ala Glu Ala Tyr Lys Thr Ser Ile Asp
                725                 730                 735

Phe Pro Asp Asp Thr Leu Ser Phe Ile Lys Ser His Pro Leu Met Asp
            740                 745                 750

Ser Ala Val Pro Pro Ile Ala Asp Glu Pro Trp Phe Thr Lys Thr Arg
        755                 760                 765

Val Arg Tyr Arg Leu Thr Ala Ile Glu Val Asp Arg Ser Ala Gly Pro
    770                 775                 780

Tyr Gln Asn Tyr Thr Val Ile Phe Val Gly Ser Glu Ala Gly Val Val
785                 790                 795                 800

Leu Lys Val Leu Ala Lys Thr Ser Pro Phe Ser Leu Asn Asp Ser Val
                805                 810                 815

Leu Leu Glu Glu Ile Glu Ala Tyr Asn Pro Ala Lys Cys Ser Ala Glu
            820                 825                 830

Ser Glu Glu Asp Arg Lys Val Val Ser Leu Gln Leu Asp Arg Asp His
        835                 840                 845

His Ala Leu Tyr Val Ala Phe Ser Ser Cys Val Val Arg Ile Pro Leu
    850                 855                 860

Ser Arg Cys Glu Arg Tyr Gly Ser Cys Lys Lys Ser Cys Ile Ala Ser
865                 870                 875                 880

Arg Asp Pro Tyr Cys Gly Trp Leu Ser Gln Gly Val Cys Glu Arg Val
                885                 890                 895

Thr Leu Gly Met Leu Leu Leu Thr Glu Asp Phe Phe Ala Phe His Asn
            900                 905                 910

His Ser Ala Gly Gly Tyr Glu Gln Asp Thr Glu Tyr Gly Asn Thr Ala
        915                 920                 925

His Leu Gly Asp Cys His Glu Ser Leu Pro Thr Ser Thr Pro Asp
    930                 935                 940
```

```
Tyr Lys Ile Phe Gly Gly Pro Thr Ser Asp Met Glu Val Pro Ser Ser
945                 950                 955                 960

Ser Val Thr Thr Val Ala Ser Ser Pro Glu Ile Thr Ser Lys Val Ile
            965                 970                 975

Asp Thr Trp Arg Pro Lys Leu Thr Ser Ser Arg Lys Phe Val Val Gln
        980                 985                 990

Asp Asp Pro Asn Thr Ser Asp Phe Thr Asp Thr Ile Ser Gly Ile Pro
    995                 1000                1005

Lys Gly Val Arg Trp Glu Val Gln Ser Gly Asp Ser Asn Gln Met
1010                1015                1020

Val His Met Asn Val Leu Ile Thr Cys Val Phe Ala Ala Phe Val
1025                1030                1035

Leu Gly Ala Phe Ile Ala Gly Val Ala Val Tyr Cys Tyr Arg Asp
1040                1045                1050

Met Phe Val Arg Lys Asn Arg Lys Ile His Lys Asp Ala Glu Ser
1055                1060                1065

Ala Gln Ser Cys Thr Asp Ser Ser Gly Ser Phe Ala Lys Leu Asn
1070                1075                1080

Gly Leu Phe Asp Ser Pro Val Lys Glu Tyr Gln Gln Asn Ile Asp
1085                1090                1095

Ser Pro Lys Leu Tyr Ser Asn Leu Leu Thr Ser Arg Lys Glu Leu
1100                1105                1110

Pro Pro Asn Thr Asp Pro Lys Ser Met Ala Met Asp His Arg Gly
1115                1120                1125

Gln Pro Pro Glu Leu Ala Ala Leu Pro Thr Pro Glu Ser Thr Pro
1130                1135                1140

Val Leu His Gln Lys Thr Leu Gln Ala Met Lys Ser His Ser Asp
1145                1150                1155

Lys Ala His Gly His Gly Ala Ser Arg Lys Glu His Pro Gln Phe
1160                1165                1170

Phe Pro Ser Ser Pro Pro Pro His Ser Pro Leu Ser His Gly His
1175                1180                1185

Ile Pro Ser Ala Ile Val Leu Pro Asn Ala Thr His Asp Tyr Asn
1190                1195                1200

Thr Ser Phe Ser Asn Ser Asn Ala His Lys Ala Glu Lys Lys Leu
1205                1210                1215

Gln Asn Val Asp His Pro Leu Thr Lys Ser Ser Ser Lys Arg Glu
1220                1225                1230

His Arg Arg Ser Val Asp Ser Arg Asn Thr Leu Asn Asp Leu Leu
1235                1240                1245

Lys His Leu Asn Asp Pro Asn Ser Asn Ala Lys Ala Ile Met Gly
1250                1255                1260

Glu Ile His Met Ala His Gln Thr Leu Met Leu Asp Pro Val Gly
1265                1270                1275

Pro Met Ser Glu Val Pro Pro Lys Val Pro Asn Arg Glu Ala Ser
1280                1285                1290

Leu Tyr Ser Pro Pro Ser Thr Leu Pro Arg Asn Ser Pro Thr Lys
1295                1300                1305

Arg Val Asp Val Pro Thr Thr Pro Gly Val Pro Met Thr Ser Leu
1310                1315                1320

Glu Arg Gln Arg Gly Tyr His Lys Asn Ser Ser Gln Arg His Ser
1325                1330                1335

Ile Ser Ala Val Pro Lys Asn Leu Asn Ser Pro Asn Gly Val Leu
```

```
              1340                1345                1350
Leu Ser Arg Gln Pro Ser Met Asn Arg Gly Gly Tyr Met Pro Thr
        1355                1360                1365

Pro Thr Gly Ala Lys Val Asp Tyr Ile Gln Gly Thr Pro Val Ser
    1370                1375                1380

Val His Leu Gln Pro Ser Leu Ser Arg Gln Ser Ser Tyr Thr Ser
    1385                1390                1395

Asn Gly Thr Leu Pro Arg Thr Gly Leu Lys Arg Thr Pro Ser Leu
    1400                1405                1410

Lys Pro Asp Val Pro Pro Lys Pro Ser Phe Val Pro Gln Thr Thr
    1415                1420                1425

Ser Val Arg Pro Leu Asn Lys Tyr Thr Tyr
    1430                1435

<210> SEQ ID NO 56
<211> LENGTH: 5634
<212> TYPE: DNA
<213> ORGANISM: Bos taurus
<220> FEATURE:
<221> NAME/KEY: CDS
<222> LOCATION: (344)..(3202)

<400> SEQUENCE: 56
cggcgcccgg gtttctcttc ccagccactc tcccccgcaa ctttccgtgc tttgttctcc     60
cgctggaaat gatttacgga agcgtcttgg acagggtctc cgccaggcgg caagagccca    120
gcgctgagat gtgttacgtt tcatctacc catcaattat ggatgaaaac aaataaggaa     180
gagtcaattt tgcatgagcc ccttctccgg cggctagagg catccgcagc cgggagggag    240
ccgccgcgcg cgtcggcagc tgctggcaag ggggatggtg aggagaaggt agctaagtgg    300
actctctgag gaggggctgc tctgccttca cgttggccca acc atg agg ttc ttc      355
                                               Met Arg Phe Phe
                                                 1 ctg ctc tgt gcc tac atg ctg ctg cta ctg att tcc cag ttg agg gca      403
Leu Leu Cys Ala Tyr Met Leu Leu Leu Leu Ile Ser Gln Leu Arg Ala
  5                  10                  15                  20 gtc agc ttt cct gaa gat gat gaa ccc ctt aat act gtt gac tat cac      451
Val Ser Phe Pro Glu Asp Asp Glu Pro Leu Asn Thr Val Asp Tyr His
                 25                  30                  35 tat tca agg caa tat ccg gtt ttt aga gga cgt cct tca ggc aat gaa      499
Tyr Ser Arg Gln Tyr Pro Val Phe Arg Gly Arg Pro Ser Gly Asn Glu
             40                  45                  50 tca cag cac agg ctg gac ttt cag ctg atg ttg aaa att cga gac aca      547
Ser Gln His Arg Leu Asp Phe Gln Leu Met Leu Lys Ile Arg Asp Thr
         55                  60                  65 ctt tat att gct ggc agg gat caa gtt tat aca gta aac tta aat gaa      595
Leu Tyr Ile Ala Gly Arg Asp Gln Val Tyr Thr Val Asn Leu Asn Glu
     70                  75                  80 atc ccc aaa aca gaa gta ata cca aac aag aaa ctg aca tgg cgg tca      643
Ile Pro Lys Thr Glu Val Ile Pro Asn Lys Lys Leu Thr Trp Arg Ser
 85                  90                  95                 100 aga caa cag gat cga gaa aac tgt gct atg aaa ggc aag cat aaa gat      691
Arg Gln Gln Asp Arg Glu Asn Cys Ala Met Lys Gly Lys His Lys Asp
                105                 110                 115 gaa tgc cac aac ttt att aaa gta ttt gtt cca aga aac gat gag atg      739
Glu Cys His Asn Phe Ile Lys Val Phe Val Pro Arg Asn Asp Glu Met
            120                 125                 130 gtt ttt gtt tgt ggc acc aat gcg ttt aat ccc atg tgt aga tac tat      787
Val Phe Val Cys Gly Thr Asn Ala Phe Asn Pro Met Cys Arg Tyr Tyr
```

-continued

```
                135                 140                 145
aag ttg aat acc tta gag tat gat gga gaa gaa att agt ggc ctg gca      835
Lys Leu Asn Thr Leu Glu Tyr Asp Gly Glu Glu Ile Ser Gly Leu Ala
    150                 155                 160 aga tgc cca ttt gat gcc aga caa act aat gtt gcc ctt ttt gct ggt      883
Arg Cys Pro Phe Asp Ala Arg Gln Thr Asn Val Ala Leu Phe Ala Gly
165                 170                 175                 180 ggc gct gct gta tct gcc aca gtg gct gac ttc ttg gcc agt gat gct      931
Gly Ala Ala Val Ser Ala Thr Val Ala Asp Phe Leu Ala Ser Asp Ala
                185                 190                 195 gtt att tat cga agc atg ggt gat gga tct gct ctt cgt aca ata aaa      979
Val Ile Tyr Arg Ser Met Gly Asp Gly Ser Ala Leu Arg Thr Ile Lys
    200                 205                 210 tat gat tcc aaa tgg atc aaa gag cca cac ttt ctg cat gct ata gaa     1027
Tyr Asp Ser Lys Trp Ile Lys Glu Pro His Phe Leu His Ala Ile Glu
215                 220                 225 tac gga aac tac gtc tat ttc ttc ttt cga gaa att gct gta gaa cat     1075
Tyr Gly Asn Tyr Val Tyr Phe Phe Phe Arg Glu Ile Ala Val Glu His
        230                 235                 240 aac aac tta ggc aag gca aaa cag gtc cgc cgt ccc ctg atg ctg ttc     1123
Asn Asn Leu Gly Lys Ala Lys Gln Val Arg Arg Pro Leu Met Leu Phe
245                 250                 255                 260 ctc ttt ttc agc att cct ggt tcc gca gtc tgt gcg ttt agc atg gat     1171
Leu Phe Phe Ser Ile Pro Gly Ser Ala Val Cys Ala Phe Ser Met Asp
                265                 270                 275 gac att gaa aaa gta ttc aaa gga cgg ttt aaa gaa cag aaa act cca     1219
Asp Ile Glu Lys Val Phe Lys Gly Arg Phe Lys Glu Gln Lys Thr Pro
    280                 285                 290 gat tct gtt tgg aca gcg gtc cct gaa gac aaa gta cca aag cca agg     1267
Asp Ser Val Trp Thr Ala Val Pro Glu Asp Lys Val Pro Lys Pro Arg
295                 300                 305 cct ggg tgt tgt gca aag cac ggt ctt gcg gaa gca tat aaa acc tcc     1315
Pro Gly Cys Cys Ala Lys His Gly Leu Ala Glu Ala Tyr Lys Thr Ser
        310                 315                 320 atc gat ttc ccg gat gaa acc ctg tca ttc atc aaa tcc cac ccc ctg     1363
Ile Asp Phe Pro Asp Glu Thr Leu Ser Phe Ile Lys Ser His Pro Leu
325                 330                 335                 340 atg gac tcg gcc gtc cca ccc att gcc gac gaa ccc tgg ttc aca aag     1411
Met Asp Ser Ala Val Pro Pro Ile Ala Asp Glu Pro Trp Phe Thr Lys
                345                 350                 355 act cgg atc agg tac aga ctg acg gcc atc gcc gtc gac cat tct gcc     1459
Thr Arg Ile Arg Tyr Arg Leu Thr Ala Ile Ala Val Asp His Ser Ala
    360                 365                 370 gga ccc cac cag aac tac aca gtc atc ttt gtt ggc tca gaa gct ggc     1507
Gly Pro His Gln Asn Tyr Thr Val Ile Phe Val Gly Ser Glu Ala Gly
375                 380                 385 gtg gtg ctt aaa gtt ttg gcg aag acc agc cct ttc tct ttg aat gac     1555
Val Val Leu Lys Val Leu Ala Lys Thr Ser Pro Phe Ser Leu Asn Asp
        390                 395                 400 agc gta tta ctg gaa gag att gaa gca tac aac cat gca aag tgc agt     1603
Ser Val Leu Leu Glu Glu Ile Glu Ala Tyr Asn His Ala Lys Cys Ser
405                 410                 415                 420 gct gaa aat gag gag gac aga aag gtc atc tca tta cag ttg gat aaa     1651
Ala Glu Asn Glu Glu Asp Arg Lys Val Ile Ser Leu Gln Leu Asp Lys
                425                 430                 435 gac cat cat gct tta tat gtg gcg ttc tct agc tgc gtt atc cgc atc     1699
Asp His His Ala Leu Tyr Val Ala Phe Ser Ser Cys Val Ile Arg Ile
    440                 445                 450 ccc ctc agt cgc tgt gag cgt tat gga tca tgt aaa aag tct tgt att     1747
```

```
                Pro Leu Ser Arg Cys Glu Arg Tyr Gly Ser Cys Lys Ser Cys Ile
                            455                 460                 465 gca tct cga gac cca tac tgt ggc tgg tta agc caa ggg gcc tgt ggt      1795
Ala Ser Arg Asp Pro Tyr Cys Gly Trp Leu Ser Gln Gly Ala Cys Gly
        470                 475                 480 cga gtg agc cca gcg atg ctg ctg tta act gaa gac ttg ttt gct ttc      1843
Arg Val Ser Pro Ala Met Leu Leu Leu Thr Glu Asp Leu Phe Ala Phe
485                 490                 495                 500 cat aac cac agc gct gga gga ttt gaa caa gac aca gaa tat ggc aac      1891
His Asn His Ser Ala Gly Gly Phe Glu Gln Asp Thr Glu Tyr Gly Asn
                505                 510                 515 acg gcc cat cta ggg gac tgc cac ggt gta cgg tgg gaa gtc cag tct      1939
Thr Ala His Leu Gly Asp Cys His Gly Val Arg Trp Glu Val Gln Ser
            520                 525                 530 gga gag gcc aac cag atg gtc cac atg aat gtc ctc atc acc tgt gtc      1987
Gly Glu Ala Asn Gln Met Val His Met Asn Val Leu Ile Thr Cys Val
        535                 540                 545 ttt gca gct ttt gtc ttg ggt gcg ttc att gca ggt gtg gca gtc tac      2035
Phe Ala Ala Phe Val Leu Gly Ala Phe Ile Ala Gly Val Ala Val Tyr
    550                 555                 560 tgt tac cgt gac atg ttt gtt cgg aaa aac aga aag atc cat aaa gat      2083
Cys Tyr Arg Asp Met Phe Val Arg Lys Asn Arg Lys Ile His Lys Asp
565                 570                 575                 580 gca gaa tct gcc cag tca tgc aca gac tcc agt gga agt ttt gcc aag      2131
Ala Glu Ser Ala Gln Ser Cys Thr Asp Ser Ser Gly Ser Phe Ala Lys
                585                 590                 595 ctg aat ggt ctc ttt gac agc ccc gtc aag gaa tac caa cag aat att      2179
Leu Asn Gly Leu Phe Asp Ser Pro Val Lys Glu Tyr Gln Gln Asn Ile
            600                 605                 610 gat tct ccc aaa tta tat agt aac ctg ctg acc agt cgg aaa gag ctg      2227
Asp Ser Pro Lys Leu Tyr Ser Asn Leu Leu Thr Ser Arg Lys Glu Leu
        615                 620                 625 cca ccc aat gga gat aca aaa tcc atg gtc atg gac cat cga ggc caa      2275
Pro Pro Asn Gly Asp Thr Lys Ser Met Val Met Asp His Arg Gly Gln
    630                 635                 640 cct cct gag ttg gct gct ctc ccc act cct gag tct acg cct gtg ctt      2323
Pro Pro Glu Leu Ala Ala Leu Pro Thr Pro Glu Ser Thr Pro Val Leu
645                 650                 655                 660 cac cag aag acc ctg cag gcc atg aag agc cac tca gaa aag gcc cat      2371
His Gln Lys Thr Leu Gln Ala Met Lys Ser His Ser Glu Lys Ala His
                665                 670                 675 ggc cat gga gct tca agg aaa gaa acc ccc cag ttt ttt cct tct agt      2419
Gly His Gly Ala Ser Arg Lys Glu Thr Pro Gln Phe Phe Pro Ser Ser
            680                 685                 690 cct cca cca cat tcc cca cta agt cac ggg cat atc ccc agc gcc att      2467
Pro Pro Pro His Ser Pro Leu Ser His Gly His Ile Pro Ser Ala Ile
        695                 700                 705 gtt ctt cct aat gct acc cat gac tac aac act tct ttc tca aac tcc      2515
Val Leu Pro Asn Ala Thr His Asp Tyr Asn Thr Ser Phe Ser Asn Ser
    710                 715                 720 aat gct cac aaa gct gaa aag aag ctt caa aac att gac cat cct ctt      2563
Asn Ala His Lys Ala Glu Lys Lys Leu Gln Asn Ile Asp His Pro Leu
725                 730                 735                 740 aca aag tca tcc agt aaa aga gat cac cgg cgt tct gtg gat tcc aga      2611
Thr Lys Ser Ser Ser Lys Arg Asp His Arg Arg Ser Val Asp Ser Arg
                745                 750                 755 aat acc ctc aat gat ctc ctg aag cat cta aat gac cca aac agt aac      2659
Asn Thr Leu Asn Asp Leu Leu Lys His Leu Asn Asp Pro Asn Ser Asn
            760                 765                 770
```

| | |
|---|---|
| ccc aaa gcc atc atg gga gac atc cag atg gcc cac cag acc cta atg<br>Pro Lys Ala Ile Met Gly Asp Ile Gln Met Ala His Gln Thr Leu Met<br>775 780 785 | 2707 |
| ctg gat ccc gtg gga cct atg tct gaa gtc ccg ccc aag gtc cct aac<br>Leu Asp Pro Val Gly Pro Met Ser Glu Val Pro Pro Lys Val Pro Asn<br>790 795 800 | 2755 |
| cgc gag gca tct ctc tac tct cct ccc tcg act ctt ccc aga aat agc<br>Arg Glu Ala Ser Leu Tyr Ser Pro Pro Ser Thr Leu Pro Arg Asn Ser<br>805 810 815 820 | 2803 |
| cca acc aag cga gtg gat gtt ccc acc act cct gga gtt ccg atg act<br>Pro Thr Lys Arg Val Asp Val Pro Thr Thr Pro Gly Val Pro Met Thr<br>825 830 835 | 2851 |
| tct ttg gaa aga cag agg ggt tac cat aaa aat tcc tcc cag agg cac<br>Ser Leu Glu Arg Gln Arg Gly Tyr His Lys Asn Ser Ser Gln Arg His<br>840 845 850 | 2899 |
| tct ata tcg gct atg cct aaa aac tta agt tca cca aat ggt gtt ttg<br>Ser Ile Ser Ala Met Pro Lys Asn Leu Ser Ser Pro Asn Gly Val Leu<br>855 860 865 | 2947 |
| tta tct aga cag cct agt atg aac cgt gga ggg tac gtg ccc acc cct<br>Leu Ser Arg Gln Pro Ser Met Asn Arg Gly Gly Tyr Val Pro Thr Pro<br>870 875 880 | 2995 |
| gca ggg cca aag gtg gac tat att cag gga gca cca gtg agt gct cac<br>Ala Gly Pro Lys Val Asp Tyr Ile Gln Gly Ala Pro Val Ser Ala His<br>885 890 895 900 | 3043 |
| cta cag cct tcc ctc tcc aga cag agc agc tac acc agt aat ggc acc<br>Leu Gln Pro Ser Leu Ser Arg Gln Ser Ser Tyr Thr Ser Asn Gly Thr<br>905 910 915 | 3091 |
| ctt ccc cgg acg gga cta aag agg aca ccg tcc tta aaa cct gac gtg<br>Leu Pro Arg Thr Gly Leu Lys Arg Thr Pro Ser Leu Lys Pro Asp Val<br>920 925 930 | 3139 |
| ccg cca aag cct tca ttt gtt cct caa acc acc tcc gtc aga cca ctg<br>Pro Pro Lys Pro Ser Phe Val Pro Gln Thr Thr Ser Val Arg Pro Leu<br>935 940 945 | 3187 |
| aac aaa tac act tac taggcctcaa gtgtgccctt ccttgtgtgg ctttatcctg<br>Asn Lys Tyr Thr Tyr<br>950 | 3242 |
| tctatgttgt tgagaggatg atatggtaag ggtaccttaa gaaaagagac tcgcttgtat | 3302 |
| ttcaagagaa gcaagtggcc aaagaaactc ttcctaactt tggcaacatc agaacttgcc | 3362 |
| atatgtagct actgcagcaa ggcttctgtg tacttgcctg aaaacaaagg aaggtgctgg | 3422 |
| tcattccatt tcttttgttt gaagctaaag agatgtgtgg ctctgagggg ctacctgtaa | 3482 |
| ccagtataaa gagctgatcc agtgctcaga gaatctgtc tgtgagcaaa tacttgaaaa | 3542 |
| tgggttcaac ttagactgcc atttttgtgtg gtcttcccat taaatgtgaa cattttaata | 3602 |
| tgtatgcatt caccttgcct cttgcacaaa tgtcaaaaaa aaaaaaaatg gtaatgtctc | 3662 |
| aaagaaacga acttgtagat taccaaacaa tttgctaaaa attcagtctt tgacccaaac | 3722 |
| tgtagcatct ttttcatgtg tggcattttt ttccgtgcca ccaaggaact gtgttgtgtg | 3782 |
| tgcatgtgtg tgtgagtgtg tgtgagtgtg tgtgagtgtg tgtgttct gtccccacta | 3842 |
| gcatttgttt cggtgcccat tgcatctttt tgtgctatgg agttgtttac atcgcgcatg | 3902 |
| actgaacaag agacaataat ttcttcccac agcagtccat tgggttcagc tttgagaaag | 3962 |
| aaaaccaagg ctgattttga cagtcaaaat gattaactcg acttccatgt tacccagtgc | 4022 |
| cagaatgtaa gagtactaag taattttgtg ctgctattca ctgaaacttc aattacagtc | 4082 |
| ttgccagctt aaggagatag agacgttaag aggtatcctt aatttatcca ccagtttcag | 4142 |
| tagtaaaatt caccagtcca ctgtgaatcc aagccccagt gactctgtta accttggaca | 4202 |

-continued

```
cactaacaag gttttatttt tactgtgttt ggtttctccc ctgtagtaaa attcctcttg    4262
ttttaattcc cctctaaccc caagatggaa aaaaaaaga accacacaca catacaaaac    4322
agaagacaaa agaagggaat gtgagaggct catagttggc ttaacaggaa cagtctatgg    4382
gaacctaaca gtggtgcaat catgttgtct gtgttgtgtg atgtgagaac tttctcctaa    4442
gtcatgcagg taacgacagt atactgtaaa tattacatgt gagtttacct gaatctgtgc    4502
attttgtgcc ttattcatga gaatgataga agtactcaaa tacgtcaagt gttttcagta    4562
tagcacatca tttactgagt gccagttgta catgtttttc aaccagcacc tgaaaagact    4622
tttcaaaaaa atcataacaa cgacctagaa caattaactg taaagcaatc catccagata    4682
gccgcattac atcctttgcc atgataaaca ttccactcct gctttcacta aggatgaatc    4742
agtgataatg tgaagtcaaa tgaggtttcc cgggtaatgt gacacctgca gaaaccatat    4802
agagtcattt attcgtagtt ttgcagaagc cacttacagt tgatgatgtg caaccctgac    4862
gactgtttca gttaatatgc tgcacaccac ggtttattga acctcatcta gaaagtatca    4922
aggcagagga atgctcctga cttagtcaga caaataagtt caactgattt cctgtgatga    4982
tatcttatta cttgggggag gatgggttgc aaaagaccag agcatttttta tacagaatat    5042
agaatacgga tgcagttatt cttttctttt gagaatattg ttttataaag aacatgattc    5102
cctgaggtct ctggaagctc aaaagctaaa acttctgttt ttgcaacact tcagctttga    5162
aactaaaata atacagattg ataataaatt aaaccaacca acgataaaca ctactcagtc    5222
cactgccgac aaacctgttt gaattcaccc tgccaatatt aatcctggcg tgcggaaaat    5282
ggaacagtaa ctgtatgtga acccggataa cattttgtga cattgtgctg ccttgtagtt    5342
tgtaatgtga gttctatcag tatttatgtt gagatttcta acacaaaatc tagtctctat    5402
cctgttaatt taatctttaa atgctttatt catttgtgca aaggtaaaca cagattgtat    5462
ctttttttaat ggtacggcat aaaaagtaac cctaaagtga agtggctcta tactgtttta    5522
tagagtactt taacatgtat agatatcttg taaacttgta ttgtggatgt gtaaataata    5582
tgtactttgg gttttttaaca ccgcatgtaa agtcaaaata aaatatacaa at           5634
```

<210> SEQ ID NO 57
<211> LENGTH: 953
<212> TYPE: PRT
<213> ORGANISM: Bos taurus

<400> SEQUENCE: 57

Met Arg Phe Phe Leu Leu Cys Ala Tyr Met Leu Leu Leu Ile Ser
1               5                   10                  15

Gln Leu Arg Ala Val Ser Phe Pro Glu Asp Asp Glu Pro Leu Asn Thr
            20                  25                  30

Val Asp Tyr His Tyr Ser Arg Gln Tyr Pro Val Phe Arg Gly Arg Pro
        35                  40                  45

Ser Gly Asn Glu Ser Gln His Arg Leu Asp Phe Gln Leu Met Leu Lys
    50                  55                  60

Ile Arg Asp Thr Leu Tyr Ile Ala Gly Arg Asp Gln Val Tyr Thr Val
65                  70                  75                  80

Asn Leu Asn Glu Ile Pro Lys Thr Glu Val Ile Pro Asn Lys Lys Leu
                85                  90                  95

Thr Trp Arg Ser Arg Gln Gln Asp Arg Glu Asn Cys Ala Met Lys Gly
            100                 105                 110

Lys His Lys Asp Glu Cys His Asn Phe Ile Lys Val Phe Val Pro Arg

-continued

```
            115                 120                 125
Asn Asp Glu Met Val Phe Val Cys Gly Thr Asn Ala Phe Asn Pro Met
130                 135                 140

Cys Arg Tyr Tyr Lys Leu Asn Thr Leu Glu Tyr Asp Gly Glu Glu Ile
145                 150                 155                 160

Ser Gly Leu Ala Arg Cys Pro Phe Asp Ala Arg Gln Thr Asn Val Ala
                165                 170                 175

Leu Phe Ala Gly Gly Ala Ala Val Ser Ala Thr Val Ala Asp Phe Leu
                180                 185                 190

Ala Ser Asp Ala Val Ile Tyr Arg Ser Met Gly Asp Gly Ser Ala Leu
                195                 200                 205

Arg Thr Ile Lys Tyr Asp Ser Lys Trp Ile Lys Glu Pro His Phe Leu
                210                 215                 220

His Ala Ile Glu Tyr Gly Asn Tyr Val Tyr Phe Phe Arg Glu Ile
225                 230                 235                 240

Ala Val Glu His Asn Asn Leu Gly Lys Ala Lys Gln Val Arg Arg Pro
                245                 250                 255

Leu Met Leu Phe Leu Phe Phe Ser Ile Pro Gly Ser Ala Val Cys Ala
                260                 265                 270

Phe Ser Met Asp Asp Ile Glu Lys Val Phe Lys Gly Arg Phe Lys Glu
                275                 280                 285

Gln Lys Thr Pro Asp Ser Val Trp Thr Ala Val Pro Glu Asp Lys Val
290                 295                 300

Pro Lys Pro Arg Pro Gly Cys Cys Ala Lys His Gly Leu Ala Glu Ala
305                 310                 315                 320

Tyr Lys Thr Ser Ile Asp Phe Pro Asp Glu Thr Leu Ser Phe Ile Lys
                325                 330                 335

Ser His Pro Leu Met Asp Ser Ala Val Pro Ile Ala Asp Glu Pro
                340                 345                 350

Trp Phe Thr Lys Thr Arg Ile Arg Tyr Arg Leu Thr Ala Ile Ala Val
                355                 360                 365

Asp His Ser Ala Gly Pro His Gln Asn Tyr Thr Val Ile Phe Val Gly
                370                 375                 380

Ser Glu Ala Gly Val Val Leu Lys Val Leu Ala Lys Thr Ser Pro Phe
385                 390                 395                 400

Ser Leu Asn Asp Ser Val Leu Leu Glu Glu Ile Glu Ala Tyr Asn His
                405                 410                 415

Ala Lys Cys Ser Ala Glu Asn Glu Glu Asp Arg Lys Val Ile Ser Leu
                420                 425                 430

Gln Leu Asp Lys Asp His His Ala Leu Tyr Val Ala Phe Ser Ser Cys
                435                 440                 445

Val Ile Arg Ile Pro Leu Ser Arg Cys Glu Arg Tyr Gly Ser Cys Lys
                450                 455                 460

Lys Ser Cys Ile Ala Ser Arg Asp Pro Tyr Cys Gly Trp Leu Ser Gln
465                 470                 475                 480

Gly Ala Cys Gly Arg Val Ser Pro Ala Met Leu Leu Leu Thr Glu Asp
                485                 490                 495

Leu Phe Ala Phe His Asn His Ser Ala Gly Phe Glu Gln Asp Thr
                500                 505                 510

Glu Tyr Gly Asn Thr Ala His Leu Gly Asp Cys His Gly Val Arg Trp
                515                 520                 525

Glu Val Gln Ser Gly Glu Ala Asn Gln Met Val His Met Asn Val Leu
530                 535                 540
```

```
Ile Thr Cys Val Phe Ala Ala Phe Val Leu Gly Ala Phe Ile Ala Gly
545                 550                 555                 560

Val Ala Val Tyr Cys Tyr Arg Asp Met Phe Val Arg Lys Asn Arg Lys
            565                 570                 575

Ile His Lys Asp Ala Glu Ser Ala Gln Ser Cys Thr Asp Ser Ser Gly
        580                 585                 590

Ser Phe Ala Lys Leu Asn Gly Leu Phe Asp Ser Pro Val Lys Glu Tyr
        595                 600                 605

Gln Gln Asn Ile Asp Ser Pro Lys Leu Tyr Ser Asn Leu Leu Thr Ser
        610                 615                 620

Arg Lys Glu Leu Pro Pro Asn Gly Asp Thr Lys Ser Met Val Met Asp
625                 630                 635                 640

His Arg Gly Gln Pro Pro Glu Leu Ala Ala Leu Pro Thr Pro Glu Ser
                645                 650                 655

Thr Pro Val Leu His Gln Lys Thr Leu Gln Ala Met Lys Ser His Ser
                660                 665                 670

Glu Lys Ala His Gly His Gly Ala Ser Arg Lys Glu Thr Pro Gln Phe
        675                 680                 685

Phe Pro Ser Ser Pro Pro His Ser Pro Leu Ser His Gly His Ile
690                 695                 700

Pro Ser Ala Ile Val Leu Pro Asn Ala Thr His Asp Tyr Asn Thr Ser
705                 710                 715                 720

Phe Ser Asn Ser Asn Ala His Lys Ala Glu Lys Lys Leu Gln Asn Ile
                725                 730                 735

Asp His Pro Leu Thr Lys Ser Ser Ser Lys Arg Asp His Arg Arg Ser
                740                 745                 750

Val Asp Ser Arg Asn Thr Leu Asn Asp Leu Leu Lys His Leu Asn Asp
            755                 760                 765

Pro Asn Ser Asn Pro Lys Ala Ile Met Gly Asp Ile Gln Met Ala His
        770                 775                 780

Gln Thr Leu Met Leu Asp Pro Val Gly Pro Met Ser Glu Val Pro Pro
785                 790                 795                 800

Lys Val Pro Asn Arg Glu Ala Ser Leu Tyr Ser Pro Pro Ser Thr Leu
                805                 810                 815

Pro Arg Asn Ser Pro Thr Lys Arg Val Asp Val Pro Thr Thr Pro Gly
                820                 825                 830

Val Pro Met Thr Ser Leu Glu Arg Gln Arg Gly Tyr His Lys Asn Ser
            835                 840                 845

Ser Gln Arg His Ser Ile Ser Ala Met Pro Lys Asn Leu Ser Ser Pro
        850                 855                 860

Asn Gly Val Leu Leu Ser Arg Gln Pro Ser Met Asn Arg Gly Gly Tyr
865                 870                 875                 880

Val Pro Thr Pro Ala Gly Pro Lys Val Asp Tyr Ile Gln Gly Ala Pro
                885                 890                 895

Val Ser Ala His Leu Gln Pro Ser Leu Ser Arg Gln Ser Ser Tyr Thr
                900                 905                 910

Ser Asn Gly Thr Leu Pro Arg Thr Gly Leu Lys Arg Thr Pro Ser Leu
            915                 920                 925

Lys Pro Asp Val Pro Lys Pro Ser Phe Val Pro Gln Thr Thr Ser
            930                 935                 940

Val Arg Pro Leu Asn Lys Tyr Thr Tyr
945                 950
```

<210> SEQ ID NO 58
<211> LENGTH: 2633
<212> TYPE: DNA
<213> ORGANISM: Artificial
<220> FEATURE:
<223> OTHER INFORMATION: Murine Sema6D-Ig fusion protein CDS

<400> SEQUENCE: 58

```
atggggttcc ttctgctttg gttctgcgtg ctgttccttc tggtctccag gttacgggcg      60
gtcagcttcc cagaagacga tgagcccctc aacacggttg actatcacta ttcaaggcaa     120
tatccggttt ttagaggacg cccttcaggc aacgaatcgc agcacaggct ggactttcag     180
ctgatgttga aaattcgaga cacactttat attgctggca gggatcaagt ctatacagtg     240
aacttaaatg aaatccccca aacagaggtg ataccaagca agaagctgac gtggaggtcc     300
agacagcagg atcgagaaaa ttgtgctatg aaaggcaagc ataaagatga atgccacaac     360
ttcatcaaag tctttgtccc aagaaatgat gagatggttt ttgtctgtgg taccaatgct     420
ttcaacccga tgtgcagata ctataggttg agaacgttag agtatgatgg ggaagaaatt     480
agtggcctgg cacgatgccc gtttgatgcc cgacaaacca atgtcgccct ctttgctgat     540
ggaaaactct attctgccac agtggctgat ttcctggcca gtgatgctgt catttacaga     600
agcatgggag atggatctgc ccttcgcaca ataaaatacg attccaagtg atcaaagaa     660
ccacacttcc ttcatgccat agaatatgga actatgtct atttcttctt cagagaaatc     720
gccgtggaac ataataactt aggcaaggct gtgtattccc gcgtggctcg catttgtaaa     780
aacgacatgg gtggctcaca gcgggtcctg agaaacact ggacttcctt ccttaaggct     840
cggctgaact gctccgttcc tggagattcc ttttctact tcgacgtcct gcagtctata     900
acagacataa tccaaatcaa tggcatcccc actgtggttg gggtcttcac cacacagctc     960
aacagcattc ctggttctgc agtctgtgcc tttagcatgg acgacattga aaagtgttc    1020
aaagggcggt tcaaagagca gaaaaccccca gactctgttt ggacagcagt tcccgaagac    1080
aaagtaccaa aaccaaggcc tggctgttgt gccaaacacg gcctcgcaga agcttacaag    1140
acctccatcg acttttccaga tgacaccctg gctttcatca gtccacccc gctgatggac    1200
tctgccgtcc cacccattgc cgatgagccc tggttcacaa agacacgggt caggtacagg    1260
ttgacagcca tcgaagtgga ccgttcagca gggccatacc aaaactacac agtcatcttt    1320
gttggctctg aagctggcgt ggtacttaaa gttttggcaa agaccagtcc tttctctctg    1380
aatgacagtg tattactcga agagattgaa gcttataacc cagccaagtg cagcgccgag    1440
agtgaggagg acagaaaggt ggtctcatta cagctggaca aggatcacca tgctttatac    1500
gtggccttct ctagctgcgt ggtccgcatc cccctcagcc gctgtgagcg ctacggatcg    1560
tgtaaaaagt cttgcattgc atcacgtgac ccgtactgtg gttggttaag ccagggagtt    1620
tgtgagagag tgaccctagg gatgctccct ggaggatatg agcaggacac ggagtacggc    1680
aacacagccc acctagggga ctgccacgac atggaggtat cctcatcttc tgttaccact    1740
gtggcaagta gcccagaaat tacatctaaa gtgattgata cctggagacc taaactgacg    1800
agctcccgga aatttgtagt tcaagatgac caaatacttc tgattttac tgatactata    1860
tcaggtatcc caagggtgt acggtgggaa gtccagtctg agaatccaa tcagatggtc    1920
cacatgaatg tcctcatcac ctgcgtgttt gccgctggat ccgagcccaa atcttgtgac    1980
aaaactcaca catgcccacc gtgcccagca cctgaactcc tggggggacc gtcagtcttc    2040
ctcttccccc caaaacccaa ggacaccctc atgatctccc ggacccctga ggtcacatgc    2100
```

```
gtggtggtgg acgtgagcca cgaagaccct gaggtcaagt tcaactggta cgtggacggc    2160
gtggaggtgc ataatgccaa gacaaagccg cgggaggagc agtacaacag cacgtaccgt    2220
gtggtcagcg tcctcaccgt cctgcaccag gactggctga atggcaagga gtacaagtgc    2280
aaggtctcca acaaagccct cccagccccc atcgagaaaa ccatctccaa agccaaaggg    2340
cagccccgag aaccacaggt gtacaccctg cccccatccc gggatgagct gaccaagaac    2400
caggtcagcc tgacctgcct ggtcaaaggc ttctatccca gcgacatcgc cgtggagtgg    2460
gagagcaatg ggcagccgga gaacaactac aagaccacgc ctcccgtgct ggactccgac    2520
ggctccttct tcctctacag caagctcacc gtggacaaga gcaggtggca gcagggaac    2580 gtcttctcat gctccgtgat gcatgaggct ctgcacaacc actacacgca gaa           2633
```

METHODS AND COMPOSITIONS FOR MODULATING T CELL AND/OR B CELL ACTIVATION

STATEMENT OF PRIORITY

This application is a continuation application of, and claims priority to, U.S. application Ser. No. 13/284,341, filed Oct. 28, 2011 issued as U.S. Pat. No. 8,501,677, which is a continuation application of, and claims priority to, U.S. application Ser. No. 12/293,913, filed Mar. 10, 2009, which is a 35 U.S.C. §371 National Phase Application of International Application No. PCT/US2007/007331, filed Mar. 23, 2007, which claims the benefit, under 35 U.S.C. §119(e), of U.S. Provisional Application No. 60/785,310, filed Mar. 23, 2006, the entire contents of each of which are incorporated by reference herein.

STATEMENT REGARDING ELECTRONIC FILING OF A SEQUENCE LISTING

A Sequence Listing in ASCII text format, submitted under 37 C.F.R. §1.821, entitled 5470-447TSCT2_ST25.txt, 384, 829 bytes in size, generated on Sep. 6, 2013 and filed via EFS-Web, is provided in lieu of a paper copy. This Sequence Listing is hereby incorporated by reference into the specification for its disclosures.

STATEMENT OF GOVERNMENT SUPPORT

This invention was made with government support under Grant No. RO1-AI-29564 awarded by the National Institutes of Health. The government has certain rights in this invention.

FIELD OF THE INVENTION

The present invention relates to regulating immune responses by modulating T cell activation and/or B cell activation.

BACKGROUND ART

The immune system is comprised of a complex network of autonomous cells working together to manage a chaotic situation. The regulation of the immune network is equally complex, characterized by hubs of activation control. The dendritic cell (DC) represents one hub of immune control via its unique abilities to regulate activation of CD4$^+$ T cells. In turn, CD4$^+$ T cells are able to affect the activity of a wide variety of immune cells of both the adaptive and innate categories. During an initial interaction, DCs present antigen (Ag) in the context of MHC class II molecules for recognition by CD4$^+$ T cells via their T cell receptor (TCR). Binding of Ag by the TCR represents signal one, but further stimulation derived from costimulatory signals is required for full activation of T cells via DCs. Many co-stimulatory receptor-ligand pairs have been identified between T cells and DCs. The prototypical costimulation interacting pairs on T cells and DCs are CD154-CD40 and CD28-B7 (T-DC respectively). Since their identification, experimental manipulation of these receptors and ligands has proven to be a powerful tool in modulating a wide variety of immune responses ranging from transplant tolerance and autoimmunity to tumor rejection (1-7).

The present invention overcomes previous shortcomings in the art by demonstrating that PlexA1 expressed on DCs and Sema6D expressed on T cells (e.g., CD4$^+$ T cells) and on B cells, represent a novel receptor-ligand costimulation pair, capable of regulating immune system activity.

SUMMARY OF THE INVENTION

The present invention provides a method of reducing T cell activation in a subject, comprising administering to the subject an effective amount of an inhibitor of Semaphorin 6D (Sema6D) activity on T cells.

Further provided herein is a method of increasing T cell activation in a subject, comprising administering to the subject an effective amount of an enhancer of Semaphorin 6D (Sema6D) activity on T cells.

In addition, the present invention provides a method of identifying an activated T cell, comprising detecting Sema6D on the surface of the T cell.

The present invention also provides a method of monitoring T cell activation over time, comprising detecting Sema6D on the surface of a T cell over time and measuring changes in the amount of Sema6D on the surface of a T cell over time.

In further embodiments, the present invention provides a method of identifying a substance having the ability to inhibit Sema6D activity, comprising contacting the substance with T cells under conditions wherein Sema6D activity can occur and measuring the amount of Sema6D activity in the presence and in the absence of the substance; whereby a decrease in Sema6D activity in the presence of the substance as compared to the amount of Sema6D activity in the absence of the substance identifies a substance having the ability to inhibit Sema6D activity.

Additionally provided is a method of identifying a substance having the ability to enhance Sema6D activity, comprising contacting the substance with T cells under conditions whereby Sema6D activity can occur and measuring the amount of Sema6D activity in the presence and in the absence of the substance; whereby an increase in Sema6D activity in the presence of the substance as compared to the amount of Sema6D activity in the absence of the substance identifies a substance having the ability to enhance Sema6D activity.

Further provided herein is a method of reducing B cell activation in a subject, comprising administering to a subject in need of reduced B cell activation an effective amount of an inhibitor of Semaphorin 6D (Sema6D) activity on B cells.

In further embodiments, the present invention provides a method of increasing B cell activation in a subject, comprising administering to a subject in need of increased B cell activation an effective amount of an enhancer of Semaphorin 6D (Sema6D) activity on B cells.

Also provided herein is a method of identifying an activated B cell, comprising detecting Sema6D on the surface of the B cell and a method of identifying an activated B cell, comprising detecting messenger RNA encoding Sema6D in the B cell.

Additional embodiments include a method of monitoring B cell activation over time, comprising detecting Sema6D on the surface of a B cell over time and measuring changes in the amount of Sema6D on the surface of a B cell over time, as well as a method of monitoring B cell activation over time, comprising detecting messenger RNA encoding Sema6D in a B cell over time and measuring changes in the amount of messenger RNA encoding Sema6D in the B cell over time.

Additionally provided herein is a method of identifying a substance having an inhibitory effect on Sema6D activity and/or having an inhibitory effect on B cell activation, comprising contacting the substance with B cells under conditions whereby Sema6D activity and/or B cell activation can occur and measuring the amount of Sema6D activity and/or B cell activation in the presence and in the absence of the substance; whereby a decrease in Sema6D activity and/or B cell activation in the presence of the substance as compared to the amount of Sema6D activity and or/B cell activation in the absence of the substance identifies a substance having the ability to inhibit Sema6D activity and/or B cell activation.

Furthermore, the present invention provides a method of identifying a substance having an enhancing effect on Sema6D activity and/or B cell activation, comprising contacting the substance with B cells under conditions whereby Sema6D activity and/or B cell activation can occur and measuring the amount of Sema6D activity and/or B cell activation in the presence and in the absence of the substance; whereby an increase in Sema6D activity and/or B cell activation in the presence of the substance as compared to the amount of Sema6D activity and/or B cell activation in the absence of the substance identifies a substance having the ability to enhance Sema6D activity and/or B cell activation.

It is further contemplated herein that the present invention provides a method of treating a B cell-related disorder and/or a T cell related disorder and/or other white blood cell-related disorder in a subject, comprising administering to the subject a therapeutic amount of an inhibitor of Semaphorin 6D (Sema6D) activity on B cells, T cells and/or other white blood cells.

Various other objectives and advantages of the present invention will become apparent from the following detailed description.

BRIEF DESCRIPTION OF THE DRAWINGS

FIG. 1 shows expression of Sema6D mRNA in the immune system. (a) SymAtlas gene array mouse cell and tissue expression of Sema6D mRNA. (b) SymAtlas gene array human cell and tissue expression of Sema6D mRNA. (c) SymAtlas gene array human cancer cell expression of Sema6D mRNA.

DETAILED DESCRIPTION OF THE INVENTION

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

Except as otherwise indicated, standard methods can be used for the production of viral and non-viral vectors, manipulation of nucleic acid sequences, production of transformed cells, and the like according to the present invention. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

The present invention is based on the unexpected discovery that the semaphorin 6D protein on a T cell (e.g., $CD4^+$ T cell) surface is a ligand for the Plexin-A1 (PlexA1) receptor protein on antigen-presenting cells, thereby providing the first identification of a ligand for a Plexin-A1 receptor on an immune system cell. Thus, in one embodiment, the present invention provides a method of reducing or inhibiting T cell activation in a subject, comprising administering to the subject (e.g., a subject in need of reduced T cell activation) an effective amount of an inhibitor of Semaphorin 6D (Sema6D) activity on $CD4^+$ T cells.

The present invention additionally provides a method of reducing or inhibiting B cell activation in a subject, comprising administering to a subject in need of reduced B cell activation an effective amount of an inhibitor of Semaphorin 6D (Sema6D) activity on B cells.

In the methods of this invention whereby T cell activation and/or B cell activation is reduced or inhibited, a subject of these methods can include a subject having, or at risk of having, an autoimmune disorder or disease, a transplant recipient, a subject having an inflammatory response or at risk of having an inflammatory response, a subject having an allergic response or at risk of having an allergic response and any subject in whom it is desirable to suppress an immune response associated with T cell activation and/or B cell activation, as known in the art.

According to the methods of this invention, an inhibitor of Sema6D activity can be, but is not limited to an antibody or antibody fragment that specifically binds Sema6D, a fusion protein comprising the extracellular domain of the Sema6D protein and an immunoglobulin fragment, an antibody or antibody fragment that specifically binds PlexA1, small molecule mimetics that block the binding of Sema6D to PlexA1 and any substance that inhibits binding of Sema6D to PlexA1 as now known or later identified.

Also included in the methods described herein is a substance that reduces or inhibits Sema6D activity and/or PlexA1 activity at the transcriptional, post-transcriptional, translational and/or post-translational level. For example, —the transcription factor class II transactivator (CIITA) can activate the PlexA1 gene expression in immune dendritic cells (*Nature Immunol.* 4(9):891-8 2003) and this method of activation is not likely to occur in other tissues with PlexA1 such as neurons and heart cells, since CIITA is not expressed in these other cells. It would be possible to alter CIITA to induce a change in PlexA1 expression predominantly in immune dendritic cells.

In further embodiments of this invention, the inhibitor of Sema6D activity and/or inhibitor of PlexA1 activity is administered in combination (either before, after and/or simultaneously) with another anti-T cell therapeutic and/or anti-B cell therapeutic, either simultaneously, before and/or after administration of the inhibitor of Sema6D activity and/or inhibitor of PlexA1 activity. Nonlimiting examples of an anti-T cell therapeutic include an antibody or fragment thereof or other ligand or fragment thereof that specifically binds and/or inhibits activity of CD3 protein, CD40 protein, B7 family proteins, and/or CD28 family proteins; cyclosporine; FK504; steroids; and/or substances that target MHC-I and/or MHC-II molecules, immunosuppressive drugs, interferons, corticosteroids, azathioprine, cyclophosphamide, etc. Also included are anti-T cell therapeutics that reduce or inhibit CD3 (e.g., OKT®3 monoclonal antibody), CD40, B7 and/or CD28 activity in T cells at the transcriptional, post-transcriptional, translational and/or post-translational level (e.g., an antisense nucleic acid that binds a coding sequence of the Sema6D protein, an interfering RNA that inhibits or suppresses transcription and/or translation of the Sema6D protein, a ribozyme, etc.), therapies that target T cell activation transcription factors, such as inhibitors of IκB kinase (IKK), which would also inhibit the transcription factor, Nuclear Factor kappa light chain enhancer in B cells (NF-κb), or cyclosporine, which inhibits the calcineurin pathway important for the activation of the transcription factor, Nuclear Factor of Activated T cells). Also included are Basiliximab (anti-CD25), Alefacept (LFA3-Ig fusion; blocks CD2), Daclizumab (Anti-CD25), Tysabri (anti-VLA4) and anti-CLA4 Ab. Other inhibitors that can be used in the methods of this invention include but are not limited to Omalizumab (Anti-IgE mab; targets mast cells and basophils) and Lumiliximab (Anti-CD23; targets mast cells and basophils).

Nonlimiting examples of an anti-B cell therapeutic include an antibody or fragment thereof or other ligand or fragment thereof that specifically binds and/or inhibits activity of CD20 protein (e.g., Rituximab® monoclonal antibody), immunosuppressive drugs, interferons, corticosteroids, azathioprine, cyclophosphamide, CTLA4-IG (targets CD80/86 on DCs and B cells), Belimumab (targets Blys (BAFF) interactions with receptors on B cells), and Natalizumab or Tysabri (Anti-VLA4; targets T cells and B cells), Further provided is a method of increasing T cell and/or B cell activation in a subject, comprising administering to the subject (e.g., a subject in need of increased T cell activation and/or increased B cell activation) an effective amount of an enhancer of Semaphorin 6D (Sema6D) activity on T cells and/or B cells.

In the methods provided herein for enhancing T cell activation and/or B cell activation, a subject can be a subject having an infection or at risk of having an infection, a subject having a suppressed immune system or suppressed immune response or at risk of having a suppressed immune system or suppressed immune response, as known in the art. Examples of infections that cause immunosuppression include but are not limited to human immunodeficiency virus infection, cytomegalovirus infection, vaccinia virus infection, and *F. tularenesis* bacterial infection. Conditions under which immune suppression occurs include severe immunodeficiencies, advanced age, chemotherapy, radiation therapy, irradiation and upon severe burn. In additional embodiments, the enhancer of T cell activation and/or B cell activation can be administered in combination (either before, after and/or simultaneously) with a T cell activation therapeutic and/or a B cell activation therapeutic. Nonlimiting examples of a T cell activation and/or a B cell activation therapeutic of this invention include vaccines such as peptides, DNA and glycoproteins and adjuvants such as toll-like receptor agonists, and the *Bacillus* Calmette-Guerin.

It is further contemplated herein that T cell activation and/or B cell activation can be reduced, inhibited or enhanced in methods employing ex vivo T cells and/or B cells and/or antigen presenting cells that have been removed from a subject and are subsequently administered to the same subject or a different subject of the same species. Thus, the present invention provides a method of enhancing T cell activation and/or B cell activation, comprising contacting a T cell and/or a B cell with an enhancer of Sema6D activity and/or an enhancer of PlexA1 activity in the presence of an antigen presenting cell having PlexA1 on the surface, under conditions whereby T cell activation and/or B cell activation can occur and then administering the activated T cell and/or activated B cell and/or antigen presenting cell to a subject. Further provided is a method of reducing T cell activation and/or B cell activation, comprising contacting a T cell and/or B cell with an inhibitor of Sema6D activity and/or an inhibitor of PlexA1 activity in the presence of an antigen presenting cell having PlexA1 on the surface, under conditions whereby inhibition of T cell activation and/or inhibition of B cell activation can occur and then administering the T cell and/or B cell and/or antigen presenting cell to a subject.

In other embodiments, the present invention provides a method of identifying an activated T cell or activated B cell, comprising detecting Sema6D on the surface of the T cell or B cell. Further provided herein is a method of identifying an activated T cell or activated B cell, comprising detecting messenger RNA encoding Sema6D in the T cell or B cell.

In methods of this invention wherein Sema6D is detected on the surface of a T cell or a B cell, such detection can be carried out according to methods standard in the art for detecting a protein on the surface of a cell and such methods can be qualitative and/or quantitative. Furthermore, in methods of this invention wherein an amount of messenger RNA encoding Sema6D is detected, such detection can be carried out according to standard methods for detecting nucleic acid in a cell (e.g., polymerase chain reaction (PCR) and other nucleic acid amplification protocols, real-time PCR, RNase protection, in situ hybridization, Northern blots, etc.) and such methods can be qualitative and/or quantitative.

Thus, in some embodiments, the identification of an activated T cell or activated B cell can be carried out by identifying an increase in the amount of Sema6D on the surface of a cell relative to a cell that is not activated. An amount of Sema6D on a T cell or B cell that is not activated can be determined by identifying T cells or B cells that are not activated (as determined by features other than the absence of Sema6D, such as the absence of CD69, CD25, HLA-DR, CD62L, CD154 and/or CD44CD25, IL-2 production, ZAP70, LAT and Lck phosphorylation in T cells) and measuring the amount of Sema6D on the surface of said nonactivated cells to establish a baseline amount of Sema6D. Thus, an activated T cell or activated B cell would be identified as having an amount of Sema6D on the surface that is increased relative to the baseline amount.

Thus, in some embodiments, the increase in Sema6D protein can be an increase of at least about 1%, 2%, 3%, 4%, 5%, 6%, 7%. 8%, 9%, 10%, 12%, 15%, 18%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 300%, etc., relative to the amount of Sema6D protein on the surface of a nonactivated T cell or nonactivated B cell.

In addition, the increase in Sema6D protein can be at least about 0.1 fold, 0.2 fold, 0.5 fold, 1.0 fold, 1.5 fold, 2.0 fold, 2.5 fold, 3.0 fold, 3.5 fold, 4.0 fold, 4.5 fold, 5.0 fold, 5.5 fold, 6.0 fold, 6.5 fold, 7.0 fold, 7.5 fold, 8.0 fold, 8.5 fold, 9.0 fold, 9.5 fold, 10 fold, 20 fold, 30 fold, 40 fold, 50 fold, 60 fold, 70 fold, 80 fold, 90 fold, 100 fold, etc., relative to the amount of Sema6D protein on the surface of a nonactivated T cell or nonactivated B cell.

In other embodiments, the increase in Sema6D activity can be an increase of at least about 1%, 2%, 3%, 4%, 5%, 6%, 7%. 8%, 9%, 10%, 12%, 15%, 18%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 300%, etc., relative to the amount of Sema6D protein on the surface of a nonactivated T cell or nonactivated B cell.

In addition, the increase in Sema6D activity can be at least about 0.1 fold, 0.2 fold, 0.5 fold, 1.0 fold, 1.5 fold, 2.0 fold, 2.5 fold, 3.0 fold, 3.5 fold, 4.0 fold, 4.5 fold, 5.0 fold, 5.5 fold, 6.0 fold, 6.5 fold, 7.0 fold, 7.5 fold, 8.0 fold, 8.5 fold, 9.0 fold, 9.5 fold, 10 fold, 20 fold, 30 fold, 40 fold, 50 fold, 60 fold, 70 fold, 80 fold, 90 fold, 100 fold, etc., relative to the amount of Sema6D protein on the surface of a nonactivated T cell or nonactivated B cell.

Furthermore, in methods wherein the amount of mRNA encoding Sema6D is measured to identify an activated T cell or activated B cell, a baseline amount of mRNA in a nonactivated T cell or nonactivated B cell can be determined and an activated T cell or activated B cell can be identified by measuring the amount of mRNA relative to the baseline amount.

Thus, the increase in Sema6D mRNA can be of at least about 1%, 2%, 3%, 4%, 5%, 6%, 7%, 8%, 9%, 10%, 12%, 15%, 18%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 300%, etc., relative to the amount of Sema6D mRNA in a nonactivated T cell or nonactivated B cell.

In addition, the increase in Sema6D mRNA can be at least about 0.1 fold, 0.2 fold, 0.5 fold, 1.0 fold, 1.5 fold, 2.0 fold, 2.5 fold, 3.0 fold, 3.5 fold, 4.0 fold, 4.5 fold, 5.0 fold, 5.5 fold, 6.0 fold, 6.5 fold, 7.0 fold, 7.5 fold, 8.0 fold, 8.5 fold, 9.0 fold, 9.5 fold, 10 fold, 20 fold, 30 fold, 40 fold, 50 fold, 60 fold, 70 fold, 80 fold, 90 fold, 100 fold, etc., relative to the amount of Sema6D mRNA in a nonactivated T cell or nonactivated B cell.

Additionally, in methods of this invention wherein T cell activation and/or B cell activation is inhibited, such inhibition can be detected by identifying a decrease in Sema6D protein on the surface of a T cell and/or B cell and/or by identifying a decrease in mRNA encoding Sema6D protein in a T cell and/or B cell. Such inhibition can be detected by identifying a decrease in Sema6D protein and/or mRNA relative to the amount of Sema6D protein and/or mRNA present in a T cell identified as an activated T cell and/or in a B cell identified as an activate B cell. Typical surface and biochemical activation markers on T cells include but are not limited to CD69, CD25, HLA-DR, CD62L, CD154 and/or the production of IL-2, calcium mobilization, ZAP-70 phosphorylation, LAT phosphorylation, Lck phosphorylation and c-abl kinase activation. Immunologic assays measuring T cell and/or B cell proliferation and cytotoxicity (defined as the ability to kill target cells) can also be used.

Thus, in some embodiments, the inhibition or reduction of T cell activation or B cell activation can be a decrease in Sema6D protein and/or mRNA of at least about 1%, 2%, 3%, 4%, 5%, 6%, 7%. 8%, 9%, 10%, 12%, 15%, 18%, 20%, 25%, 30%, 35%, 40%, 45%, 50%, 55%, 60%, 65%, 70%, 75%, 80%, 85%, 90%, 95%, 100%, etc., relative to the amount of Sema6D protein and/or mRNA in an activated T cell or activated B cell.

In addition, the inhibition or reduction of T cell activation or B cell activation can be a decrease of Sema6D protein and/or mRNA of at least about 0.1 fold, 0.2 fold, 0.5 fold, 1.0 fold, 1.5 fold, 2.0 fold, 2.5 fold, 3.0 fold, 3.5 fold, 4.0 fold, 4.5 fold, 5.0 fold, 5.5 fold, 6.0 fold, 6.5 fold, 7.0 fold, 7.5 fold, 8.0 fold, 8.5 fold, 9.0 fold, 9.5 fold, 10 fold, 20 fold, 30 fold, 40 fold, 50 fold, 60 fold, 70 fold, 80 fold, 90 fold, 100 fold, etc., relative to the amount of Sema6D protein and/or mRNA in an activated T cell or activated B cell.

The present invention also provides a method of monitoring T cell activation and/or B cell activation over time, comprising detecting Sema6D on the surface of a T cell and/or B cell over time and measuring changes in the amount of Sema6D on the surface of a T cell and/or B cell over time. Additionally provided is a method of monitoring T cell activation and/or B cell activation over time, comprising detecting mRNA encoding Sema6D in a T cell and/or B cell over time and measuring changes in the amount of mRNA encoding Sema6D in the cell over time. Thus a baseline measurement of Sema6D protein and/or mRNA can be performed according to methods known in the art and as described herein and measurements of Sema6D protein and/or mRNA can be carried out at any time interval (e.g., minutes, hours, days, etc.) and under conditions whereby T cell activation and/or B cell activation can be modulated. Changes in the amount of Sema6D protein and/or mRNA can be detected, whereby an increase or decrease in the amount of Sema6D protein and/or mRNA can identify an increase or decrease, respectively in the activation of a T cell and/or B cell over time.

The present invention further provides screening methods, including a method of identifying a substance having the ability to inhibit Sema6D activity, comprising contacting the substance with T cells and/or B cells expressing Sema6D under conditions whereby Sema6D activity can occur and measuring the amount of Sema6D activity in the presence and in the absence of the substance; whereby a decrease in Sema6D activity in the presence of the substance as compared to the amount of Sema6D activity in the absence of the substance identifies a substance having the ability to inhibit Sema6D activity.

Further provided herein is a method of identifying a substance having the ability to enhance Sema6D activity, comprising contacting the substance with T cells and/or B cells expressing Sema6D under conditions whereby Sema6D activity can occur and measuring the amount of Sema6D activity in the presence and in the absence of the substance; whereby an increase in Sema6D activity in the presence of the substance as compared to the amount of Sema6D activity in the absence of the substance identifies a substance having the ability to enhance Sema6D activity.

In the screening methods of this invention, Sema6D activity indicates activation of T cells, as determined by measurement of T cell activation markers such as CD25, CD69, CD62L, CD154, CD44, HLA-DR, IL-2 production, calcium mobilization, phosphorylation of LAT, ZAP70, lck, c-Abl etc., in response to a substance that can bind and activate through the Sema6D molecule. An example would be a fusion protein consisting of the extramembrane domain of PlexA1 coupled with the Fc portion of immunoglobulin as described herein.

Sema6D activity can be measured by, for example, identifying the T cell and/or B cell activation status of a T cell and/or B cell in the absence of a test substance and measuring the T cell and/or B cell activation status of the T cell and/or B cell in the presence of the substance, whereby an increase in T cell and/or B cell activation in the presence of the substance identifies the substance as having the ability to enhance Sema6D activity and whereby a decrease in T cell and/or B cell activation in the presence of the substance identifies a substance having the ability to inhibit Sema6D activity. The activation status of a T cell can be measured by methods standard in the art, including but not limited to, measuring an increase in the production and/or expression of CD69, CD25, HLA-DR, CD62L, CD154 and/or CD44, either singly or in any combination, in the T cell, according to art-known methods. T cell activation status can also be determined by employing art-known methods for detecting cytotoxic T cell responses, T helper responses and/or IL-2 production. The activation status of a B cell can be measured by methods standard in the art.

In some embodiments, the screening methods of this invention can include the step of contacting the T cells and/or B cells with a known inhibitor of Sema6D activity, such as an antibody that specifically binds a Sema6D protein or a fusion protein of this invention comprising the extracellular domain of a Sema6D protein and an immunoglobulin fragment and establishing a baseline amount of T cell and/or B cell activation and then contacting the T cell and/or B cell with the substance to be screened and identifying a change in the T cell and/or B cell activation status to identify a substance that either inhibits or enhances Sema6D activity. Typical surface and biochemical activation markers on T cells include but are not limited to CD69, CD25, HLA-DR, CD62L, CD154 and/or the production of IL-2, calcium mobilization, ZAP-70 phosphorylation, LAT phosphorylation, and Lck phosphorylation. T cell proliferation and cytotoxicity (defined as the ability to kill target cells) can also be measured. Sema6D activity can be measured by the methods described herein.

In some embodiments of this invention, substances can be screened for the ability to inhibit or enhance Sema6D activity by affecting the ability of Sema6D to bind PlexA1. This inhibition or enhancement of binding activity can be detected by any of a variety of art-recognized methods for evaluating binding activity. As one example, the substance to be tested and a PlexA1 protein or an active fragment thereof can be contacted in the presence of T cells and/or B cells having Sema6D on the surface. The amount of binding of PlexA1 to the cells in the presence of the substance and the amount of binding of PlexA1 to the cells in the absence of the substance can be determined and a decrease or increase in the amount of binding in the presence of the substance identifies the substance as having the ability to inhibit or enhance binding, respectively and thus inhibit or enhance Sema6D activity, respectively.

In some embodiments, binding of the PlexA1 protein to a T cell or B cell can be measured by attaching a detectable moiety to the PlexA1 polypeptide or fragment (e.g., a fluorescence moiety, histochemically detectable moiety, radioactive moiety, etc.). The amount of detectable moiety can be measured in the presence and absence of the substance to be tested and the amounts can be compared to determine inhibition or enhancement. T cell activation can be measured by methods not limited to the following: detection and/or quantitation of cell surface markers such as CD69, CD25, HLA-DR, CD62L, CD154 and/or the production of IL-2, calcium mobilization, ZAP-70 phosphorylation, LAT phosphorylation, Lck phosphorylation; NF-κB activation, MEK activation, NFAT activation, Ap-1 activation; T cell proliferation and cytotoxicity (defined as the ability to kill target cells).

Substances suitable for screening according to the above methods include small molecules, natural products, peptides, nucleic acids, etc. Sources for compounds include natural product extracts, collections of synthetic compounds, and compound libraries generated by combinatorial chemistry. Libraries of compounds are well known in the art. Small molecule libraries can be obtained from various commercial entities, for example, SPECS and BioSPEC B.V. (Rijswijk, the Netherlands), Chembridge Corporation (San Diego, Calif.), Comgenex USA Inc., (Princeton, N.J.), Maybridge Chemical Ltd. (Cornwall, UK), and Asinex (Moscow, Russia). One representative example is known as DIVERSet™, available from ChemBridge Corporation, 16981 Via Tazon, Suite G, San Diego, Calif. 92127. DIVERSet™ contains between 10,000 and 50,000 drug-like, hand-synthesized small molecules. The compounds are pre-selected to form a "universal" library that covers the maximum pharmacophore diversity with the minimum number of compounds and is suitable for either high throughput or lower throughput screening. For descriptions of additional libraries, see, for example, Tan et al. "Stereoselective Synthesis of Over Two Million Compounds Having Structural Features Both Reminiscent of Natural Products and Compatible with Miniaturized Cell-Based Assays" *Am. Chem Soc.* 120, 8565-8566, 1998; Floyd et al. *Prog Med Chem* 36:91-168, 1999. Numerous libraries are commercially available, e.g., from Analyti-Con USA Inc., P.O. Box 5926, Kingwood, Tex. 77325; 3-Dimensional Pharmaceuticals, Inc., 665 Stockton Drive, Suite 104, Exton, Pa. 19341-1151; Tripos, Inc., 1699 Hanley Rd., St. Louis, Mo., 63144-2913, etc. In certain embodiments of the invention the methods are performed in a high-throughput format using techniques that are well known in the art, e.g., in multiwell plates, using robotics for sample preparation and dispensing, etc. Representative examples of various screening methods may be found, for example, in U.S. Pat. Nos. 5,985,829, 5,726,025, 5,972,621, and 6,015,692. The skilled practitioner will readily be able to modify and adapt these methods as appropriate.

The present invention further provides compositions, such as a fusion protein comprising the extracellular domain of a Sema6D protein or an active portion or fragment thereof and any active or functional fragment of an immunoglobulin molecule, as would be well known in the art. Also provided is a fusion protein comprising a transmembrane domain or an active portion or fragment thereof of a Sema6D protein and/or an intracellular domain or an active portion or fragment thereof of a Sema6D protein and an active or functional fragment of an immunoglobulin molecule. The present invention further provides a composition comprising a fusion protein of this invention in a pharmaceutically acceptable carrier. Additionally provided is a composition comprising an antibody or other ligand that specifically binds a Sema6D protein in a pharmaceutically acceptable carrier. Further provided herein is a nucleotide sequence encoding a fusion protein of this invention, which nucleotide sequence can be present in a composition comprising a pharmaceutically acceptable carrier. These compositions can be delivered to a subject of this invention in methods as described herein and in methods of treating disorders and diseases as described herein associated with increased or decreased T cell and/or B cell activation.

Thus, in further embodiments, the present invention provides a method of treating a T-cell-related disorder, B cell-related disorder and/or other white blood cell related disease or disorder in a subject, comprising administering to the subject a therapeutic amount of an inhibitor of Semaphorin 6D (Sema6D) activity on T cells, B cells and/or other white blood cells.

Nonlimiting examples of the diseases and disorders that can be treated according to the methods of this invention include but are not limited to leukemia (e.g., lymphoblastic leukemia, chronic myelogenous leukemia; promyelocytic leukemia, etc.; FIG. 1), lymphoma (e.g., B cell lymphomas, T cell lymphomas, Burkitts lymphoma, etc.), autoimmune diseases and disorders, inflammatory disorders and diseases, transplant rejection, psoriasis, asthmatic and allergic disorders and any combination thereof.

Nonlimiting examples of autoimmune disorders and diseases that can be treated and/or prevented by the methods of this invention include arthritis (e.g., rheumatoid arthritis or RA), multiple sclerosis (MS), diabetes (e.g., insulin dependent diabetes mellitus or IDDM), systemic lupus erythematosus (SLE), allergic reactions, asthmatic reaction, myasthenia gravis, Crohns' disease, regional enteritis, vasculitis, ulcerative colitis, Sjogren's syndrome, ankylosing spondylitis, polymyositis and any other autoimmune disorder now known or later identified.

An inflammatory disease or disorder of this invention can include but is not limited to inflammation of any organ, e.g., skin, heart, gastrointestinal tract, central nervous system, liver, pancreas, ovary, lung, eye, ear, throat, etc., such as, e.g., in psoriasis and general tissue fibrosis.

Additionally provided is a method of reducing the likelihood of transplant rejection (or increasing the likelihood of successful transplantation) in a transplant recipient, comprising administering to the transplant recipient an effective amount of an inhibitor of T cell and/or B cell activation of this invention. The reduction in the likelihood of transplant rejection or increase in the likelihood of successful transplantation is in comparison to the likelihood of transplant rejection or likelihood of successful transplantation in a transplant recipient that did not receive an inhibitor of T cell and/or B cell activation, as such likelihood would be known and/or determined according to art-known standards. Furthermore, the inhibitor of these methods can be administered to the transplant recipient at any time relative to the transplantation (i.e., before, after and/or simultaneously, in any combination).

In further embodiments, the present invention provides nucleic acids that inhibit T cell and/or B cell activation and nucleic acids that enhance T cell and/or B cell activation. These nucleic acids can be present in a composition comprising a pharmaceutically acceptable carrier. These nucleic acids can be present in vectors, plasmids, and/or other vehicles for delivery of nucleic acids to cells to carry out the methods of this invention, as described herein. These nucleic acids can encode inhibitors and enhancers of T cell and/or B cell activation and/or these nucleic acids can act directly to inhibit or enhance T cell and/or B cell activation, for example, by inhibiting or enhancing Sema6D activity at the nucleic acid level.

Also provided herein is a method of treating a disorder or disease associated with decreased T cell and/or B cell activation, comprising administering to the subject an effective amount of an enhancer of T cell and/or B cell activation as described herein.

In the methods provided herein for enhancing T cell and/or B cell activation in a subject, such an enhancement can be identified by comparison with T cell and/or B cell activation in a subject that did not receive the enhancer of this invention. Such comparative studies can be carried out according to well known protocols in the art for detecting and/or measuring T cell and/or B cell activation, and as described herein.

Thus, the present invention further provides a method of initiating, inducing and/or enhancing a T cell-mediated immune response and/or a B cell-mediated immune response in a subject, comprising administering to the subject an effective amount of an enhancer of Semaphorin 6D (Sema6D) activity on T cells and/or B cells.

The subject of this invention can be any subject in need of the immunomodulating effects of the methods of this invention. Such a subject can be any type of animal that is susceptible to diseases and disorders associated with increased T cell and/or B cell activation or decreased T cell and/or B cell activation and/or that can be treated by increasing or decreasing T cell and/or B cell activation according to the methods of this invention, as well as any animal to whom the compositions of this invention can be administered according to the methods of this invention. For example, an animal of this invention can be a mammal, a bird or a reptile. In certain embodiments, the subject of this invention is a human.

As noted above, the compositions of this invention can be administered to a cell of a subject or to a subject either in vivo or ex vivo. For administration to a cell of the subject in vivo, as well as for administration to the subject, the compositions of this invention can be administered orally, parenterally (e.g., intravenously), by intramuscular injection, by intraperitoneal injection, subcutaneous injection, transdermally, extracorporeally, topically, by transdermal patch, or the like.

The exact amount of the composition required will vary from subject to subject, depending on the species, age, weight and general condition of the subject, the particular composition used, its mode of administration, the condition being treated and the like. Thus, it is not possible to specify an exact amount for every composition of this invention. However, an effective amount can be determined by one of ordinary skill in the art using only routine experimentation given the teachings herein.

As an example, one or more doses of between about 0.1 µg/kg and about 1000 mg/kg of an inhibitor and/or biologically active fragment of this invention can be administered orally and/or parenterally to a subject in whom it is desirable to decrease T cell activation, at hourly, daily and/or weekly intervals until an evaluation of the subject's clinical parameters indicate that the subject's condition has improved and/or the subject demonstrates the desired response.

If ex vivo methods are employed, cells or tissues can be removed and maintained outside the subject's body according to standard protocols well known in the art. The compositions of this invention can be introduced into the cells via known mechanisms for uptake of materials into cells (e.g., phagocytosis, pulsing onto class I MHC-expressing cells, liposomes, etc.). The cells can then be infused (e.g., in a pharmaceutically acceptable carrier) or transplanted back into the same subject or a different subject per standard methods for the cell or tissue type. Standard methods are known for transplantation or infusion of various cells into a subject.

The pharmaceutical compositions of this invention include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration, although the most suitable route in any given case will depend, as is well known in the art, on such factors as the species, age, gender and overall condition of the subject, the nature and severity of the condition being treated and/or on the nature of the particular composition (i.e., dosage, formulation) that is being administered.

Pharmaceutical compositions suitable for oral administration can be presented in discrete units, such as capsules, cachets, lozenges, or tables, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a composition of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sub-lingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions of this invention suitable for parenteral administration can comprise sterile aqueous and non-aqueous injection solutions of the composition of this invention, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit\dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 0.1 µg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration are preferably presented as unit dose suppositories. These can be prepared by admixing the composition with one or more conventional solid carriers, such as for example, cocoa butter and then shaping the resulting mixture.

Pharmaceutical compositions of this invention suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharmaceutical Research* 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

Furthermore, the compositions of this invention can be administered orally, intranasally, parenterally (e.g., intravenously), by intramuscular injection, by intraperitoneal injection, transdermally, extracorporeally, topically or the like. In the methods described herein which include the administration and uptake of exogenous DNA into the cells of a subject (i.e., gene transduction or transfection), the nucleic acids of the present invention can be in the form of naked DNA or the nucleic acids can be in a vector for delivering the nucleic acids to the cells for expression of the polypeptides and/or fragments of this invention. The vector can be a commercially available preparation or can be constructed in the laboratory according to methods well known in the art.

Delivery of a nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system, which can package a recombinant retroviral genome. The recombinant retrovirus can then be used to infect and thereby deliver to the infected cells nucleic acid encoding the polypeptide and/or fragment of this invention. The exact method of introducing the exogenous nucleic acid into mammalian cells is, of course, not limited to the use of retroviral vectors. Other techniques are widely available for this procedure including the use of adenoviral vectors, alphaviral vectors, adeno-associated viral (AAV) vectors, lentiviral vectors, pseudotyped retroviral vectors and vaccinia viral vectors, as well as any other viral vectors now known or developed in the future. Physical transduction techniques can also be used, such as liposome delivery and receptor-mediated and other endocytosis mechanisms. This invention can be used in conjunction with any of these or other commonly used gene transfer methods.

As one example, if the nucleic acid of this invention is delivered to the cells of a subject in an adenovirus vector, the dosage for administration of adenovirus to humans can range from about $10^7$ to $10^9$ plaque forming units (pfu) per injection, but can be as high as $10^{12}$, $10^{15}$ and/or $10^{20}$ pfu per injection.

In some embodiments, a subject will receive a single injection of a viral vector comprising a nucleic acid of this invention. If additional injections are necessary, they can be repeated at daily/weekly/monthly intervals for an indefinite period and/or until the efficacy of the treatment has been established. As set forth herein, the efficacy of treatment can be determined by evaluating the symptoms and clinical parameters described herein and/or by detecting a desired immunological response.

The exact amount of the nucleic acid or vector required will vary from subject to subject, depending on the species, age, weight and general condition of the subject, the particular nucleic acid or vector used, its mode of administration and the like. Thus, it is not possible to specify an exact amount for every nucleic acid or vector. However, an appropriate amount can be determined by one of ordinary skill in the art using only routine experimentation given the teachings herein.

Further provided are isolated nucleic acids comprising, consisting essentially of and/or consisting of nucleotide sequences that encode the proteins and fragments of this invention. In particular, the present invention provides a fusion protein comprising, consisting essentially of, and/or consisting of the amino acid sequence of SEQ ID NO:2

(Sema6D-Ig: primary amino acid sequence (886 aa)

(MGFLLLWFCVLFLLVSRLRAVSFPEDDEPLNTVDYHYSRQYPVFRGRPSGNESQHRL

DFQLMLKIRDTLYIAGRDQVYTVNLNEIPQTEVIPSKKLTWRSRQQDRENCAMKGKH

KDECHNFIKVFVPRNDEMVFVCGTNAFNPMCRYYRLRTLEYDGEEISGLARCPFDAR

QTNVALFADGKLYSATVADFLASDAVIYRSMGDGSALRTIKYDSKWIKEPHFLHAIE

YGNYVYFFFREIAVEHNNLGKAVYSRVARICKNDMGGSQRVLEKHWTSFLKARLNC

SVPGDSFFYFDVLQSITDIIQINGIPTVVGVFTTQLNSIPGSAVCAFSMDDIEKVFKGRF

KEQKTPDSVWTAVPEDKVPKPRPGCCAKHGLAEAYKTSIDFPDDTLAFIKSHPLMDS

AVPPIADEPWFTKTRVRYRLTAIEVDRSAGPYQNYTVIFVGSEAGVVLKVLAKTSPFS

LNDSVLLEEIEAYNPAKCSAESEEDRKVVSLQLDKDHHALYVAFSSCVVRIPLSRCER

YGSCKKSCIASRDPYCGWLSQGVCERVTLGMLPGGYEQDTEYGNTAHLGDCHDME

VSSSSVTTVASSPEITSKVIDTWRPKLTSSRKFVVQDDPNTSDFTDTISGIPKGVRWEV

QSGESNQMVHMNVLITCVFAA): Sema6D seq (652 aa)

(GSEPKSCDKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALHNHYTQK

SLSLSPGK): Ig seq

Additionally provided is a nucleic acid comprising, consisting essentially of, and/or consisting of a nucleotide sequence that encodes an amino acid sequence comprising, consisting essentially of, and/or consisting of the amino acid sequence or a biologically active fragment of the amino acid sequence of SEQ ID NO:2 above. In a particular embodiment, the nucleic acid of this invention comprises the nucleotide sequence of SEQ ID NO:1:

(GCCACCCATGGGGTTCC TTCTGCTTTG GTTCTGCGTG

CTGTTCCTTC TGGTCTCCAG GTTACGGGCGGTCAGCTTCC

CAGAAGACGA TGAGCCCCTC AACACGGTTG ACTATCACTA

TTCAAGGCAATATCCGGTTT TTAGAGGACG CCCTTCAGGC

AACGAATCGC AGCACAGGCT GGACTTTCAGCTGATGTTGA

AAATTCGAGA CACACTTTAT ATTGCTGGCA GGGATCAAGT

CTATACAGTGAACTTAAATG AAATCCCCCA AACAGAGGTG

ATACCAAGCA AGAAGCTGAC GTGGAGGTCCAGACAGCAGG

ATCGAGAAAATTGTGCTATG AAAGGCAAGC ATAAAGATGA

ATGCCACAACTTCATCAAAG TCTTTGTCCC AAGAAATGAT

GAGATGGTTT TTGTCTGTGG TACCAATGCTTTCAACCCGA

TGTGCAGATA CTATAGGTTG AGAACGTTAG AGTATGATGG

GGAAGAAATTAGTGGCCTGG CACGATGCCC GTTTGATGCC

CGACAAACCA ATGTCGCCCT CTTTGCTGATGGAAAACTCT

ATTCTGCCAC AGTGGCTGAT TTCCTGGCCA GTGATGCTGT

CATTTACAGAAGCATGGGAG ATGGATCTGC CCTTCGCACA

ATAAAATACG ATTCCAAGTG GATCAAAGAACCACACTTCC

TTCATGCCAT AGAATATGGA AACTATGTCT ATTTCTTCTT

CAGAGAAATCGCCGTGGAAC ATAATAACTT AGGCAAGGCT

GTGTATTCCC GCGTGGCTCG CATTTGTAAAAACGACATGG

GTGGCTCACA GCGGGTCCTG GAGAAACACT GGACTTCCTT

-continued
```
CCTTAAGGCTCGGCTGAACT GCTCCGTTCC TGGAGATTCC

TTTTTCTACT TCGACGTCCT GCAGTCTATAACAGACATAA

TCCAAATCAA TGGCATCCCC ACTGTGGTTG GGGTCTTCAC

CACACAGCTCAACAGCATTC CTGGTTCTGC AGTCTGTGCC

TTTAGCATGG ACGACATTGA GAAAGTGTTCAAAGGGCGGT

TCAAAGAGCA GAAAACCCCA GACTCTGTTT GGACAGCAGT

TCCCGAAGACAAAGTACCAA AACCAAGGCC TGGCTGTTGT

GCCAAACACG GCCTCGCAGA AGCTTACAAGACCTCCATCG

ACTTTCCAGA TGACACCCTG GCTTTCATCA AGTCCCACCC

GCTGATGGACTCTGCCGTCC CACCCATTGC CGATGAGCCC

TGGTTCACAA AGACACGGGT CAGGTACAGGTTGACAGCCA

TCGAAGTGGA CCGTTCAGCA GGGCCATACC AAAACTACAC

AGTCATCTTTGTTGGCTCTG AAGCTGGCGT GGTACTTAAA

GTTTTGGCAA AGACCAGTCC TTTCTCTCTGAATGACAGTG

TATTACTCGA AGAGATTGAA GCTTATAACC CAGCCAAGTG

CAGCGCCGAGAGTGAGGAGG ACAGAAAGGT GGTCTCATTA

CAGCTGGACA AGGATCACCA TGCTTTATACGTGGCCTTCT

CTAGCTGCGT GGTCCGCATC CCCCTCAGCC GCTGTGAGCG

CTACGGATCGTGTAAAAAGT CTTGCATTGC ATCACGTGAC

CCGTACTGTG GTTGGTTAAG CCAGGGAGTTTGTGAGAGAG

TGACCCTAGG GATGCTCCCT GGAGGATATG

AGCAGGACACGGAGTACGGCAACACAGCCC ACCTAGGGGA

CTGCCACGAC ATGGAGGTAT CCTCATCTTC

TGTTACCACTGTGGCAAGTA GCCCAGAAAT TACATCTAAA

GTGATTGATA CCTGGAGACC TAAACTGACGAGCTCCCGGA

AATTTGTAGT TCAAGATGAC CCAAATACTT CTGATTTTAC

TGATACTATATCAGGTATCC CAAAGGGTGT ACGGTGGGAA

GTCCAGTCTG GAGAATCCAA TCAGATGGTCCACATGAATG

TCCTCATCAC CTGCGTGTTT GCCGCTGGAT CCGAGCCCAA

ATCTTGTGACA AAACTCACAC ATGCCCACCG TGCCCAGCA

CTGAACTCCT GGGGGGACCG TCAGTCTTCC TCTTCCCCCC

AAAACCCAAG GACACCCTCA TGATCTCCCG GACCCCTGAG

GTCACATGCG TGGTGGTGGA CGTGAGCCAC

GAAGACCCTGAGGTCAAGTT CAACTGGTAC GTGGACGGCG

TGGAGGTGCA TAATGCCAAG ACAAAGCCGCGGGAGGAGCA

GTACAACAGC ACGTACCGTG TGGTCAGCGT CCTCACCGTC

CTGCACCAGGACTGGCTGAA TGGCAAGGAG TACAAGTGCA

AGGTCTCCAA CAAAGCCCTC CCAGCCCCCATCGAGAAAAC

CATCTCCAAA GCCAAAGGGC AGCCCCGAGA ACCACAGGTG

TACACCCTGCCCCCATCCCG GGATGAGCTG ACCAAGAACC

AGGTCAGCCT GACCTGCCTG GTCAAAGGCTTCTATCCCAG
```
-continued
```
     CGACATCGCC GTGGAGTGGG AGAGCAATGG GCAGCCGGAG

AACAACTACAAGACCACGCC TCCCGTGCTG GACTCCGACG

5   GCTCCTTCTT CCTCTACAGC AAGCTCACCGTGGACAAGAG

CAGGTGGCAG CAGGGGAACG TCTTCTCATG CTCCGTGATG

CATGAGGCTCTGCACAACCA CTACACGCAG AAGAGCCTCT

10   CCCTGTCTCC GGGTAAATGA).
```

Further provided herein is a nucleic acid that is the complement of each and any of the nucleic acids of this invention.

A variety of protocols for detecting the presence of and/or measuring the amount of Sema6D protein, using, e.g., polyclonal and/or monoclonal antibodies specific for the Sema6D protein, are known in the art. Examples of such protocols include, but are not limited to, enzyme immunoassays (EIA), agglutination assays, immunoblots (Western blot; dot/slot blot, etc.), radioimmunoassays (RIA), immunodiffusion assays, chemiluminescence assays, antibody library screens, expression arrays, enzyme-linked immunosorbent assays (ELISA), radioimmunoassays (RIA), immunoprecipitation, Western blotting, competitive binding assays, immunofluorescence, immunohistochemical staining precipitation/flocculation assays and fluorescence-activated cell sorting (FACS). These and other assays are described, among other places, in Hampton et al. (*Serological Methods, a Laboratory Manual*, APS Press, St Paul, Minn. (1990)) and Maddox et al. (*J. Exp. Med.* 158:1211-1216 (1993)).

Furthermore, a number of assays for identification, detection and/or amplification of nucleic acid sequences (e.g., Sema6D mRNA) are well known in the art. For example, various protocols can be employed in the methods of this invention to amplify nucleic acid. As used herein, the term "oligonucleotide-directed amplification procedure" refers to template-dependent processes that result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term "template dependent process" refers to nucleic acid synthesis of a RNA or a DNA molecule wherein the sequence of the newly synthesized strand of nucleic acid is dictated by the well-known rules of complementary base pairing. Typically, vector mediated methodologies involve the introduction of the nucleic acid fragment into a DNA or RNA vector, the clonal amplification of the vector, and the recovery of the amplified nucleic acid fragment. Examples of such methodologies are provided in U.S. Pat. No. 4,237,224 (incorporated herein by reference in its entirety). Nucleic acids, used as a template for amplification methods can be isolated from cells according to standard methodologies (Sambrook et al., 1989). The nucleic acid can be genomic DNA or fractionated or whole cell RNA. Where RNA is used, it may be desired to convert the RNA to a complementary DNA. In one embodiment, the RNA can be whole cell RNA and is used directly as the template for amplification.

Pairs of primers that selectively hybridize to nucleic acids corresponding to the Sema6D gene or coding sequence are contacted with the nucleic acid under conditions that permit selective hybridization. The term "primer," as defined herein, is meant to encompass any nucleic acid that is capable of priming the synthesis of a nascent nucleic acid in a template dependent process. Typically, primers are oligonucleotides from ten to twenty bases in length, but shorter (e.g., 6, 7, 8, or 9 bases) or longer (e.g., 21, 22, 23, 24, 25, 26, 27, 28, 29, 30, 35, 40, 45, 50 bases) sequences can be employed. Primers can in double-stranded or single-stranded form, although the single-stranded form is commonly used.

Once hybridized, the nucleic acid: primer hybridization complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In some embodiments, the detection can be performed by visual means. Alternatively, the detection can involve indirect identification of the product via chemiluminescence, radioactive scintigraphy of incorporated radiolabel or fluorescence or chemiluminescence label or even via a system using electrical or thermal impulse signals (e.g., Affymax technology).

A number of template dependent processes are available to amplify the sequences present in a given template sample. One of the best-known amplification methods is the polymerase chain reaction (referred to as PCR), which is described in detail in U.S. Pat. Nos. 4,683,195, 4,683,202 and 4,800,159, each incorporated herein by reference in its entirety.

Briefly, in PCR, two primer sequences are prepared that are complementary to regions on opposite complementary strands of the target sequence. An excess of deoxynucleoside triphosphates is added to a reaction mixture along with a DNA polymerase, e.g., a Taq polymerase. If the particular target sequence is present in a sample, the primers will bind to the target sequence and the polymerase will cause the primers to be extended along the sequence by adding on nucleotides. By raising and lowering the temperature of the reaction mixture, the extended primers will dissociate from the target sequence to form reaction products, excess primers will bind to the target sequence and to the reaction products and the process is repeated.

A reverse transcriptase PCR amplification procedure can be performed in order to quantify the amount of mRNA amplified. Methods of reverse transcribing RNA into cDNA are well known in the art (e.g., Sambrook et al., 1989). Alternative methods for reverse transcription employ thermostable, RNA-dependent DNA polymerases. These methods are described, for example, in PCT Publication No. WO 90/07641, filed Dec. 21, 1990, incorporated herein by reference in its entirety. Polymerase chain reaction methodologies are well known in the art.

Another method for nucleic acid amplification is the ligase chain reaction ("LCR"), disclosed in Eur. Pat. Appl. No. 320308, incorporated herein by reference in its entirety. In LCR, two complementary probe pairs are prepared and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 (incorporated by reference herein in its entirety) describes a method similar to LCR for binding probe pairs to a target sequence.

Qbeta replicase (QβR), described in PCT Application No. PCT/US87/00880, (incorporated herein by reference), can also be used as an amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]triphosphates in one strand of a restriction site may also be useful in the amplification of nucleic acids in the present invention.

Strand Displacement Amplification (SDA), described in U.S. Pat. Nos. 5,455,166, 5,648,211, 5,712,124 and 5,744,311, each incorporated herein by reference, is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present.

The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification method, as described in Intl. Pat. Appl. No. PCT/US89/01025, which is incorporated herein by reference in its entirety, may be used in accordance with the present invention. In one embodiment, "modified" primers are used in a PCR-like, template- and enzyme-dependent synthesis. The primers may be modified by labeling with a capture moiety (e.g., biotin) and/or a detectable moiety (e.g., enzyme). In another embodiment, an excess of labeled probes is added to a sample. In the presence of the target sequence, the probe binds and is cleaved catalytically. After cleavage, the target sequence is released intact, available to be bound by excess probe. Cleavage of the labeled probe signals the presence of the target sequence.

Other nucleic acid amplification procedures include transcription-based amplification systems (TAS), including nucleic acid sequence based amplification (NASBA) and 3 SR (PCT Publication No. WO 88/10315, incorporated herein by reference). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7, T3 or SP6. In an isothermal cyclic reaction, the RNAs are reverse transcribed into single stranded DNA, which is then converted to double-stranded DNA, and then transcribed once again with an RNA polymerase such as T7, T3 or SP6. The resulting products, whether truncated or complete, indicate target specific sequences.

European Pat. Appl. No. 329822 (incorporated herein by reference in its entirety) discloses a nucleic acid amplification process involving cyclically synthesizing single stranded RNA (ssRNA), ssDNA, and double-stranded DNA (dsDNA), which can be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA).

The resultant ssDNA is a template for a second primer, which also includes the sequences of an RNA polymerase promoter (exemplified by T7 RNA polymerase) 5' to its homology to the template. This primer is then extended by DNA polymerase (exemplified by the large Klenow fragment of E. coli DNA polymerase I), resulting in a double-stranded DNA (dsDNA) molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle, leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Application WO 89/06700 (incorporated herein by reference in its entirety) discloses a nucleic acid sequence amplification scheme based on the hybridization of a promoter/primer sequence to a target single-stranded DNA (ss-DNA), followed by transcription of many RNA copies of the sequence. This scheme is not cyclic, i.e., new templates are not produced from the resultant RNA transcripts. Other amplification methods include "RACE" and "one-sided PCR" (Frohman, 1990, incorporated by reference herein).

Methods based on ligation of two (or more) oligonucleotides in the presence of nucleic acid having the sequence of the resulting "di-oligonucleotide," thereby amplifying the dioligonucleotide, can also be used in the amplification step of the present invention.

Following any amplification, it is desirable to separate the amplification product from the template and the excess primer for the purpose of determining whether specific amplification has occurred. In one embodiment, amplification products can be separated by agarose, agarose-acrylamide or polyacrylamide gel electrophoresis using standard methods (e.g., Sambrook et al., 1989).

Alternatively, chromatographic techniques can be used to effect separation. There are many kinds of chromatography that can be used in the present invention: such as, for example, adsorption, partition, ion exchange and molecular sieve, as well as many specialized techniques for using them including column, paper, thin-layer and gas chromatography.

Amplification products must be visualized in order to confirm amplification of the target sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In some embodiments, visualization is achieved indirectly. Following separation of amplification products, a labeled, nucleic acid probe is brought into contact with the amplified target sequence. The probe preferably is conjugated to a chromophore but may be radiolabeled. In another embodiment, the probe is conjugated to a binding partner, such as an antibody or biotin, and the other member of the binding pair carries a detectable moiety.

In other embodiments, detection can be by Southern or Northern blotting and hybridization with a labeled probe. The techniques involved in Southern and Northern blotting are well known to those of skill in the art and can be found in many standard books on molecular protocols (e.g., Sambrook et al., 1989). Briefly, amplification products are separated by gel electrophoresis. The gel is then contacted with a membrane, such as nitrocellulose, permitting transfer of the nucleic acid and noncovalent binding. Subsequently, the membrane is incubated with a chromophore-conjugated probe that is capable of hybridizing with a target amplification product. Detection is by exposure of the membrane to x-ray film or ion-emitting detection devices. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel.

Additionally, a wide variety of labeling and conjugation techniques are known in the art that are used in various nucleic acid detection and amplification assays. Methods for producing labeled hybridization probes and/or PCR or other ligation primers for detecting and/or amplifying nucleic acid sequences can include, for example, oligolabeling, nick translation and end-labeling, as well as other well known methods. Alternatively, nucleic acid sequences encoding the polypeptides of this invention, and/or any functional fragment thereof, can be cloned into a plasmid or vector for detection and amplification. Such plasmids and vectors are well known in the art and are commercially available. It is also contemplated that the methods of this invention can be conducted using a variety of commercially available kits (e.g., Pharmacia & Upjohn; Promega; U.S. Biochemical Corp.). Suitable reporter molecules or labels, which can be used for ease of detection, include, for example, radionuclides, enzymes, fluorescence agents, chemiluminescence agents and chromogenic agents, as well as substrates, cofactors, inhibitors, magnetic particles and the like as are well known in the art.

The present invention further includes isolated polypeptides, peptides, proteins, fragments, domains and/or nucleic acid molecules that are substantially equivalent to those described for this invention. As used herein, "substantially equivalent" can refer both to nucleic acid and amino acid sequences, for example a mutant sequence, that varies from a reference sequence by one or more substitutions, deletions, or additions, the net effect of which does not result in an undesirable adverse functional dissimilarity between reference and subject sequences. In some embodiments, this invention can include substantially equivalent sequences that have an adverse functional dissimilarity. For purposes of the present invention, sequences having equivalent biological activity and equivalent expression characteristics are considered substantially equivalent.

The invention further provides homologs, as well as methods of obtaining homologs, of the polypeptides and/or fragments of this invention. As used herein, an amino acid sequence or protein is defined as a homolog of a polypeptide or fragment of the present invention if it shares significant homology to one of the polypeptides and/or fragments of the present invention. Significant homology means at least 60%, 65%, 75%, 80%, 85%, 90%, 95%, 98% and/or 100% homology with another amino acid sequence. Specifically, by using the nucleic acids disclosed herein as a probe or as primers, and techniques such as PCR amplification and colony/plaque hybridization, one skilled in the art can identify homologs of the polypeptides and/or fragments of this invention.

In further embodiments, the nucleic acids encoding the polypeptides and/or fragments of this invention can be part of a recombinant nucleic acid construct comprising any combination of restriction sites and/or functional elements as are well known in the art that facilitate molecular cloning and other recombinant DNA manipulations. Thus, the present invention further provides a recombinant nucleic acid construct comprising a nucleic acid encoding a polypeptide and/or biologically active fragment of this invention.

The present invention further provides a vector comprising a nucleic acid encoding a polypeptide and/or fragment of this invention. The vector can be an expression vector which contains all of the genetic components required for expression of the nucleic acid in cells into which the vector has been introduced, as are well known in the art. The expression vector can be a commercial expression vector or it can be constructed in the laboratory according to standard molecular biology protocols. The expression vector can comprise viral nucleic acid including, but not limited to, poxvirus, vaccinia virus, adenovirus, retrovirus and/or adeno-associated virus nucleic acid. The nucleic acid or vector of this invention can also be in a liposome or a delivery vehicle, which can be taken up by a cell via receptor-mediated or other type of endocytosis.

The nucleic acid of this invention can be in a cell, which can be a cell expressing the nucleic acid whereby a polypeptide and/or biologically active fragment of this invention is produced in the cell. In addition, the vector of this invention can be in a cell, which can be a cell expressing the nucleic acid of the vector whereby a polypeptide and/or biologically active fragment of this invention is produced in the cell. It is also contemplated that the nucleic acids and/or vectors of this invention can be present in a host animal (e.g., a transgenic animal), which expresses the nucleic acids of this invention and produces the polypeptides and/or fragments of this invention.

The nucleic acid encoding the polypeptide and/or fragment of this invention can be any nucleic acid that functionally encodes the polypeptides and/or fragments of this invention. To functionally encode the polypeptides and/or fragments (i.e., allow the nucleic acids to be expressed), the nucleic acid of this invention can include, for example, expression control sequences, such as an origin of replication, a promoter, an enhancer and necessary information processing sites, such as ribosome binding sites, RNA splice sites, polyadenylation sites and transcriptional terminator sequences.

Nonlimiting examples of expression control sequences that can be present in a nucleic acid of this invention include promoters derived from metallothionine genes, actin genes, immunoglobulin genes, CMV, SV40, adenovirus, bovine papilloma virus, etc. A nucleic acid encoding a selected polypeptide and/or fragment can readily be determined based upon the genetic code for the amino acid sequence of the selected polypeptide and/or fragment and many nucleic acids will encode any selected polypeptide and/or fragment. Modifications in the nucleic acid sequence encoding the polypeptide and/or fragment are also contemplated. Modifications that can be useful are modifications to the sequences controlling expression of the polypeptide and/or fragment to make production of the polypeptide and/or fragment inducible or repressible as controlled by the appropriate inducer or repressor. Such methods are standard in the art. The nucleic acid of this invention can be generated by means standard in the art, such as by recombinant nucleic acid techniques and/or by synthetic nucleic acid synthesis or in vitro enzymatic synthesis.

The nucleic acids and/or vectors of this invention can be transferred into a host cell (e.g., a prokaryotic or eukaryotic cell) by well-known methods, which vary depending on the type of cell host. For example, calcium chloride transfection is commonly used for prokaryotic cells, whereas calcium phosphate treatment, transduction and/or electroporation can be used for other cell hosts.

As used herein, "a" or "an" or "the" can mean one or more than one. For example, "a" cell can mean one cell or a plurality of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

A T cell of this invention includes but is not limited to CD4+ T cells, T regulatory cells, double positive (CD4+, CD8+) T cells and double negative (CD4−, CD8−) T cells. A B cell of this invention is, e.g., an antibody producing cell and can be for example, a plasma B cell, a memory B cell, a B-1 cell or a B-2 cell.

As used herein, "T cell activation" or "B cell activation" means a process or activity that causes T cells or B cells to exhibit a phenotype of an activated T cell or B cell, and "activated T cell" or "activated B cell" describes T cells or B cells that can exhibit some of the following phenotypes: T cell activation can be measured by methods not limited to the following: CD69, CD25, HLA-DR, CD62L and/or CD154 expression and/or the production of IL-2, calcium mobilization, ZAP-70 phosphorylation, LAT phosphorylation, Lck phosphorylation, NF-κB activation, MEK activation, NFAT activation, Ap-1 activation; T cell proliferation and cytotoxicity (defined as the ability to kill target cells). B cell activation can be measured by any methods known in the art to identify antigen-mediated activation, T cell dependent activation, T cell-independent activation, etc.

Nonlimiting examples of a Sema6D protein of this invention have an amino acid sequence as shown in the Sequence Listing. For example SEQ ID NOs: 22, 24, 26, 28, 30 and are examples of human isoforms of a Sema6D protein. Other Sema6D proteins as are known in the art and as described herein are also included in the present invention.

As used herein, "modulate," "modulates" or "modulation" refers to enhancement (e.g., an increase) or inhibition (e.g., diminished, reduced or suppressed) of the specified activity. The term "enhancement," "enhance," "enhances," or "enhancing" refers to an increase in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase) and/or an increase in the specified activity of at least about 5%, 10%, 25%, 35%, 40%, 50%, 60%, 75%, 80%, 90%, 95%, 97%, 98%, 99% or 100%. The term "inhibit," "diminish," "reduce" or "suppress" refers to a decrease in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more decrease) and/or a decrease or reduction in the specified activity of at least about 5%, 10%, 25%, 35%, 40%, 50%, 60%, 75%, 80%, 90%, 95%, 97%, 98%, 99% or 100%. In particular embodiments, the inhibition or reduction results in little or essentially no detectable activity (at most, an insignificant amount, e.g., less than about 10% or about 5%).

The term "overexpress," "overexpresses" or "overexpression" as used herein in connection with isolated nucleic acids encoding Sema6D refers to expression that results in higher levels of Sema6D polypeptide than exist in the cell in its native (control) state. Overexpression of Sema6D can result in levels that are 25%, 50%, 100%, 200%, 500%, 1000%, 2000% or higher in the cell. Further, nucleic acid encoding Sema6D can be introduced into a cell that does not produce the specified form of Sema6D (e.g., an isoform) encoded by the transgene or does so only at negligible levels.

The term "enhance," "enhances," "enhancing" or "enhancement" with respect to T cell or B cell activation refers to an increase in T cell or B cell activation (e.g., at least about a 1.5-fold, 2-fold, 3-fold, 4-fold, 5-fold, 6-fold, 8-fold, 10-fold, twelve-fold, or even fifteen-fold or more increase), for example, in response to a substance that enhances T cell or B cell activation. Alternatively, these terms can refer to increasing expression of nucleic acid encoding Sema6D in a cell or subject in response to an enhancer as compared with the amount of Sema6D nucleic acid expression in the absence of the enhancer.

A "fusion polypeptide" is a polypeptide produced when two heterologous nucleotide sequences or fragments thereof coding for two (or more) different polypeptides not found fused together in nature are fused together in the correct translational reading frame. Illustrative fusion polypeptides include, but are not limited to a fusion of the extracellular domain of Sema6D or active fragment thereof to an immunoglobulin fragment as described herein. Ig fragments from human, mouse, rat, goat, rabbit can all be used. In addition, mutations in the Fc binding sequence do not alter the function of the protein, and these can also be used. When used in animals, it is best to use the IgG fusion that is from the same species. For example, using human IgG fusion protein to perform in mice may cause immunogenicity in the long run, although for short term experiments, this is less of a concern.

As used herein, a "functional" or "active" polypeptide is one that retains at least one biological activity normally associated with that polypeptide. Preferably, a "functional" polypeptide retains all of the activities possessed by the unmodified peptide. By "retains" biological activity, it is meant that the polypeptide retains at least about 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits essentially no detectable biological activity normally associated with the polypeptide (e.g., at most, only an insignificant amount, e.g., less than about 10% or even 5%).

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 USPQ 461, 463 (CCPA 1976) (emphasis in the original); see also MPEP §2111.03. Thus, the term "consisting essentially of" when used in a claim of this invention is not intended to be interpreted to be equivalent to "comprising."

"Isolated" as used herein means the nucleic acid or protein or protein fragment of this invention is sufficiently free of contaminants or cell components with which nucleic acids or proteins normally occur. "Isolated" does not mean that the preparation is technically pure (homogeneous), but it is sufficiently pure to provide the nucleic acid or protein or protein fragment in a form in which it can be used therapeutically.

"Epitope" or "antigenic epitope" or "antigenic peptide" as used herein means a specific amino acid sequence which, when present in the proper conformation, provides a reactive site for an antibody or T cell receptor. The identification of epitopes on antigens can be carried out by immunology protocols that are well known in the art. Typically, an epitope or antigenic peptide can be 4, 5, 6, 7, 8, 9, 10, 12, 14, 16, 18, 20, 25, 30, 35, 40, 45 or 50 amino acids in length.

As used herein, the term "polypeptide" or "protein" is used to describe a chain of amino acids that correspond to those encoded by a nucleic acid. A polypeptide of this invention can be a peptide, which usually describes a chain of amino acids of from two to about 30 amino acids. The term polypeptide as used herein also describes a chain of amino acids having more than 30 amino acids and can be a fragment or domain of a protein or a full length protein. Furthermore, as used herein, the term polypeptide can refer to a linear chain of amino acids or it can refer to a chain of amino acids that has been processed and folded into a functional protein. It is understood, however, that 30 is an arbitrary number with regard to distinguishing peptides and polypeptides and the terms can be used interchangeably for a chain of amino acids. The polypeptides of the present invention are obtained by isolation and purification of the polypeptides from cells where they are produced naturally, by enzymatic (e.g., proteolytic) cleavage, and/or recombinantly by expression of nucleic acid encoding the polypeptides or fragments of this invention. The polypeptides and/or fragments of this invention can also be obtained by chemical synthesis or other known protocols for producing polypeptides and fragments.

The amino acid sequences disclosed herein are presented in the amino to carboxy direction, from left to right. Nucleotide sequences are presented herein in the 5' to 3' direction, from left to right. It is intended that the nucleic acids of this invention can be either single or double stranded (i.e., including the complementary nucleic acid). A nucleic acid of this invention can be the complement of a nucleic acid described herein.

A "biologically active fragment" or "active fragment" or "functional fragment" or "functionally active fragment" as used herein includes a polypeptide of this invention that comprises a sufficient number of amino acids to have one or more of the biological activities of the polypeptides of this invention. Such biological activities can include, but are not limited to, in any combination, binding activity, immunomodulating activity and/or immunogenic activity, as well as any other activity now known or later identified for the polypeptides and/or fragments of this invention. A fragment of a polypeptide of this invention can be produced by methods well known and routine in the art. Fragments of this invention can be produced, for example, by enzymatic or other cleavage of naturally occurring peptides or polypeptides or by synthetic protocols that are well known. Such fragments can be tested for one or more of the biological activities of this invention according to the methods described herein, which are routine methods for testing activities of polypeptides, and/or according to any art-known and routine methods for identifying such activities. Such production and testing to identify biologically active fragments of the polypeptides described herein would be well within the scope of one of ordinary skill in the art and would be routine.

Fragments of the polypeptides of this invention are preferably at least about ten amino acids in length and retain one or more of the biological activities (e.g., immunomodulating; binding) and/or the immunological activities of the proteins of this invention. Examples of the fragments of this invention include, but are not intended to be limited to, the following fragments identified by the amino acid number as shown in the Sequence Listing herein: Amino acids 1-10, 10-20, 20-30, 30-40, 40-50, 50-60, 60-70, 70-80, 80-90, 90-100, 110-120, 120-130, 130-140, 140-150, 150-160, 160-170, 170-180, 180-190, 190-200, 200-210, 210-220, 220-230, 230-240, 240-250, 1-25, 1-50, 1-67, 1-75, 1-100, 1-125, 1-135, 1-145, 1-150, 1-160, 1-170, 1-180, 1-190, 1-200, 1-250, 68-180, 183-223, 50-100, 100-200, 200-300, 300-400, 400-500, 500-600, 600-650, etc.

It is understood that this list is exemplary only and that a fragment of this invention can be any amino acid sequence containing any combination of contiguous amino acids that are numbered in the Sequence Listing as amino acids 1 through 652. even if that combination is not specifically recited as an example herein. It is also understood that these fragments can be combined in any order or amount. For example, fragment 1-10 can be combined with fragment 10-20 to produce a fragment of amino acids 1-20. As another example, fragment 1-20 can be combined with fragment 50-60 to produce a single fragment of this invention having 31 amino acids (AA 10-20 and AA 50-60). Also fragments can be present in multiple numbers and in any combination in a fragment of this invention. Thus, for example, fragment 1-150 can be combined with a second fragment 1-150 and/or combined with fragment 400-500 to produce a fragment of this invention.

The terms "homology," "identity" and "complementarity" as used herein refer to a degree of similarity between two or more sequences. There may be partial homology or complete homology (i.e., identity). A partially complementary sequence that at least partially inhibits an identical sequence from hybridizing to a target nucleic acid is referred to as "substantially homologous." The inhibition of hybridization of the completely complementary sequence to the target sequence can be examined using a hybridization assay (Southern or Northern blot, solution hybridization and the like) under conditions of low stringency. A substantially homologous sequence or hybridization probe will compete for and inhibit the binding of a completely homologous sequence to the target sequence under conditions of low stringency, as this term is known in the art. This is not to say that conditions of low stringency are such that non-specific binding is permitted; low stringency conditions require that the binding of two sequences to one another be a specific (i.e., selective) interaction. The absence of non-specific binding can be tested by the use of a second target sequence that lacks even a partial degree of complementarity (e.g., less than about 30% identity). In the absence of non-specific binding, the probe will not hybridize to the second non-complementary target sequence.

The term "hybridization" as used herein refers to any process by which a first strand of nucleic acid binds with a second strand of nucleic acid through base pairing. Nucleic acids encoding the polypeptides and/or fragments of this invention can be detected by DNA-DNA or DNA-RNA hybridization and/or amplification using probes, primers and/or fragments of polynucleotides encoding the polypeptides and/or fragments of this invention and/or designed to detect and/or amplify the nucleic acids of this invention.

The term "hybridization complex" as used herein refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells and/or nucleic acids have been fixed).

The term "nucleotide sequence" refers to a heteropolymer of nucleotides or the sequence of these nucleotides. The terms "nucleic acid," "oligonucleotide" and "polynucleotide" are also used interchangeably herein to refer to a heteropolymer of nucleotides. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene. Nucleic acids of this invention can comprise a nucleotide sequence that can be identical in sequence to the sequence which is naturally occurring or, due to the well-characterized degeneracy of the nucleic acid code, can include alternative codons that encode the same amino acid as that which is found in the naturally occurring sequence. Furthermore, nucleic acids of this invention can comprise nucleotide sequences that can include codons which represent conservative substitutions of amino acids as are well known in the art, such that the biological activity of the resulting polypeptide and/or fragment is retained.

The term "probe" or "primer" includes naturally occurring and/or recombinant and/or chemically synthesized single- and/or double-stranded nucleic acids. They can be labeled for detection by nick translation, Klenow fill-in reaction, PCR and/or other methods well known in the art. Probes and primers of the present invention, their preparation and/or labeling are described in Sambrook et al. 1989. *Molecular Cloning: A Laboratory Manual*, Cold Spring Harbor Laboratory, NY and Ausubel et al. 1989. *Current Protocols in Molecular Biology*, John Wiley & Sons, New York N.Y., both of which are incorporated herein by reference in their entirety for these teachings.

The term "stringent" as used herein refers to hybridization conditions that are commonly understood in the art to define the conditions of the hybridization procedure. Stringency conditions can be low, high or medium, as those terms are commonly know in the art and well recognized by one of ordinary skill. In various embodiments, stringent conditions can include, for example, highly stringent (i.e., high stringency) conditions (e.g., hybridization in 0.5 M $NaHPO_4$, 7% sodium dodecyl sulfate (SDS), 1 mM EDTA at 65° C., and washing in 0.1×SSC/0.1% SDS at about 68° C.), and/or moderately stringent (i.e., medium stringency) conditions (e.g., washing in 0.2×SSC/0.1% SDS at about 42° C.).

"Amplification" as used herein includes the production of multiple copies of a nucleic acid molecule and is generally carried out using polymerase chain reaction (PCR) and/or any other amplification technologies as are well known in the art (Dieffenbach and Dveksler. 1995. *PCR Primer, a Laboratory Manual*, Cold Spring Harbor Press, Plainview, N.Y.).

"Effective amount" as used herein refers to an amount of a compound, agent, substance or composition of this invention that is sufficient to produce a desired effect, which can be a therapeutic effect. The effective amount will vary with the age, general condition of the subject, the severity of the condition being treated, the particular compound, agent, substance or composition administered, the duration of the treatment, the nature of any concurrent treatment, the pharmaceutically acceptable carrier used if any, and like factors within the knowledge and expertise of those skilled in the art. As appropriate, an "effective amount" in any individual case can be determined by one of ordinary skill in the art by reference to the pertinent texts and literature and/or by using routine experimentation. (Remington, *The Science And Practice of Pharmacy* (20th ed. 2000)).

A "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components (e.g., pharmaceutically acceptable carriers) include any of the standard pharmaceutical carriers such as phosphate buffered saline solutions, water, emulsions such as oil/water emulsion, microemulsions and various types of wetting agents. In particular, it is intended that a pharmaceutically acceptable carrier be a sterile carrier that is formulated for administration to or delivery into a subject of this invention.

The compositions of the present invention can also include other medicinal agents, pharmaceutical agents, carriers, diluents, immunostimulatory cytokines, etc. and can be in a pharmaceutically acceptable carrier. Actual methods of preparing such dosage forms are known, or will be apparent, to those skilled in this art.

An "immunomodulatory molecule" of this invention can be, but is not limited to an immunostimulatory cytokine that can be, but is not limited to, GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules.

Additional examples of an immunomodulatory molecule of this invention include the adjuvants of this invention, including, for example, SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Suitable adjuvants also include an aluminum salt such as aluminum hydroxide gel (alum), aluminum phosphate, or algannmulin, but may also be a salt of calcium, iron or zinc, or may be an insoluble suspension of acylated tyrosine, or acylated sugars, cationically or anionically derivatized polysaccharides, or polyphosphazenes.

Other adjuvants are well known in the art and include QS-21, Freund's adjuvant (complete and incomplete), aluminum hydroxide, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

Additional adjuvants can include, for example, a combination of monophosphoryl lipid A, preferably 3-de-O-acylated monophosphoryl. lipid A (3D-MPL) together with an aluminum salt. An enhanced adjuvant system involves the combination of a monophosphoryl lipid A and a saponin derivative, particularly the combination of QS21 and 3D-MPL as disclosed in PCT publication number WO 94/00153 (the entire contents of which are incorporated herein by reference), or a less reactogenic composition where the QS21 is quenched with cholesterol as disclosed in PCT publication number WO 96/33739 (the entire contents of which are incorporated herein by reference). A particularly potent adjuvant formulation involving QS21 3D-MPL & tocopherol in an oil in water emulsion is described in PCT publication number WO 95/17210 (the entire contents of which are incorporated herein by reference). In addition, the nucleic acid of this invention can include an adjuvant by comprising a nucleotide sequence encoding a Sema6D protein or active fragment thereof of this invention and a nucleotide sequence that provides an adjuvant function, such as CpG sequences. Such CpG sequences, or motifs, are well known in the art. Other TLR agonists, such as Pam3Cys, Poly(I:C), single stranded RNA, as well as CATERPILLER (NOD-LRR) agonists, such as proteoglycan-derived products, are also included herein.

The terms "treat," "treating" or "treatment" include any type of action that imparts a modulating effect, which, for example, can be a beneficial effect, to a subject afflicted with a disorder, disease, condition or illness, including improvement in the disorder, disease, condition or illness of the subject (e.g., in one or more symptoms), delay in the progression of the disorder, disease, condition or illness, prevention or delay of the onset of the disorder, disease, condition or illness, and/or change in clinical parameters, disorder, disease, condition or illness status, etc., as would be well known in the art.

As used herein, the term "antibody" includes intact immunoglobulin molecules as well as fragments thereof that are capable of binding the epitopic determinant of an antigen (i.e., antigenic determinant). Antibodies that bind the polypeptides of this invention are prepared using intact polypeptides or fragments as the immunizing antigen. The polypeptide or fragment used to immunize an animal can be derived from enzymatic cleavage, recombinant expression, isolation from biological materials, synthesis, etc., and can be conjugated to a carrier protein, if desired. Commonly used carriers that are chemically coupled to peptides and proteins for the production of antibody include, but are not limited to, bovine serum albumin, thyroglobulin and keyhole limpet hemocyanin. The coupled peptide or protein is then used to immunize the animal (e.g., a mouse, rat, or rabbit). The polypeptide or peptide antigens can also be administered with an adjuvant, as described herein and as otherwise known in the art.

An antibody of this invention can be any type of immunoglobulin, including IgG, IgM, IgA, IgD, and/or IgE. The antibody can be monoclonal or polyclonal and can be of any species of origin, including, for example, mouse, rat, rabbit, horse, goat, sheep or human, or can be a chimeric or humanized antibody (e.g., Walker et al., *Molec. Immunol.* 26:403-11 (1989)). The antibodies can be recombinant monoclonal antibodies produced according to the methods disclosed in U.S. Pat. No. 4,474,893 or U.S. Pat. No. 4,816,567. The antibodies can also be chemically constructed according to methods disclosed in U.S. Pat. No. 4,676,980. The antibody can further be a single chain antibody (e.g., scFv) or bispecific antibody.

Antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) *Science* 254:1275-1281). Antibodies can also be obtained by phage display techniques known in the art or by immunizing a heterologous host with a cell containing an epitope of interest.

The polypeptide, fragment or antigenic epitope that is used as an immunogen can be modified or administered in an adjuvant in order to increase antigenicity. Methods of increasing the antigenicity of a protein or peptide are well known in the art and include, but are not limited to, coupling the antigen with a heterologous protein (such as globulin or β-galactosidase) or through the inclusion of an adjuvant during immunization.

For example, for the production of antibodies, various hosts including goats, rabbits, rats, mice, humans, and others, can be immunized by injection with the polypeptides and/or fragments of this invention, with or without a carrier protein. Additionally, various adjuvants may be used to increase the immunological response. Such adjuvants include, but are not limited to, Freund's complete and incomplete adjuvants, mineral gels such as aluminum hydroxide, and surface-active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

Monoclonal antibodies can be produced in a hybridoma cell line according to the technique of Kohler and Milstein (*Nature* 265:495-97 (1975)). Other techniques for the production of monoclonal antibodies include, but are not limited to, the human B-cell hybridoma technique, and the EBV-hybridoma technique (Kozbor et al. 1985. *J. Immunol. Methods* 81:31-42; Cote et al. 1983. *Proc. Natl. Acad. Sci.* 80:2026-2030; Cole et al. 1984. *Mol. Cell Biol.* 62:109-120).

For example, to produce monoclonal antibodies, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in a bacterial cell such as *E. coli* by recombinant techniques known to those skilled in the art (e.g., Huse. *Science* 246:1275-81 (1989)). Any one of a number of methods well known in the art can be used to identify the hybridoma cell, which produces an antibody with the desired characteristics. These include screening the hybridomas by ELISA assay, Western blot analysis, or radioimmunoassay. Hybridomas secreting the desired antibodies are cloned and the class and subclass are identified using standard procedures known in the art.

For polyclonal antibodies, antibody-containing serum is isolated from the immunized animal and is screened for the presence of antibodies with the desired specificity using any of the well known procedures as described herein.

The present invention further provides antibodies of this invention in detectably labeled form. Antibodies can be detectably labeled through the use of radioisotopes, affinity labels (such as biotin, avidin, etc.), enzymatic labels (such as horseradish peroxidase, alkaline phosphatase, etc.) fluorescence labels (such as FITC or rhodamine, etc.), paramagnetic atoms, gold beads, etc. Such labeling procedures are well-known in the art. The labeled antibodies of the present invention can be used for in vitro, in vivo, and in situ assays to identify a polypeptide and/or fragment of this invention in a sample.

In some embodiments, the present invention further provides the above-described antibodies immobilized on a solid support (e.g., beads, plates, slides or wells formed from materials such as latex or polystyrene). Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., *Handbook of Experimental Immunology* 4th Ed., Blackwell Scientific Publications, Oxford, England, Chapter 10 (1986)). Antibodies can likewise be conjugated to detectable groups such as radiolabels (e.g., $^{35}S$, $^{125}I$, $^{131}I$), enzyme labels (e.g., horseradish peroxidase, alkaline phosphatase), and fluorescence labels (e.g., fluorescein) in accordance with known techniques. Determination of the formation of an antibody/antigen complex in the methods of this invention can be by detection of, for example, precipitation, agglutination, flocculation, radioactivity, color development or change, fluorescence, luminescence, etc., as is well know in the art.

In addition, techniques developed for the production of chimeric antibodies or humanized antibodies by splicing mouse antibody genes to human antibody genes to obtain a molecule with appropriate antigen specificity and biological activity can be used (Morrison et al. 1984. *Proc. Natl. Acad. Sci.* 81:6851-6855; Neuberger et al. 1984. *Nature* 312:604-608; Takeda et al. 1985. *Nature* 314:452-454). Alternatively, techniques described for the production of single chain antibodies can be adapted, using methods known in the art, to produce single chain antibodies specific for the polypeptides and fragments of this invention. Antibodies with related specificity, but of distinct idiotypic composition, can be generated by chain shuffling from random combinatorial immunoglobulin libraries (Burton 1991. *Proc. Natl. Acad. Sci.* 88:11120-3).

Various immunoassays can be used for screening to identify antibodies having the desired specificity for the proteins and peptides of this invention. Numerous protocols for competitive binding or immunoradiometric assays using either polyclonal or monoclonal antibodies with established specificity are well known in the art. Such immunoassays typically involve the measurement of complex formation between an antigen and its specific antibody (e.g., antigen/antibody complex formation). For example, a two-site, monoclonal-based immunoassay utilizing monoclonal antibodies reactive to two non-interfering epitopes on the proteins or peptides of this invention can be used, as well as a competitive binding assay.

The present invention is more particularly described in the following examples, which are intended as illustrative only since numerous modifications and variations therein will be apparent to those skilled in the art.

EXAMPLES

I. The Semaphorin 6D Receptor on T Cells is Required for Activation of CD4$^+$ T Cells Mice.

All experiments were performed with 8-12 week old C57BL/6 mice from Jackson Labs. OT-II mice which express the OVA[323-339]-specific TCR transgene on the C57BL/6 background were generous gifts from M. Croft. All animal procedures were conducted in complete compliance with the NIH *Guide for the Care and Use of Laboratory Animals*, approved by the Institutional Animal Care and Use Committee of the University of North Carolina, Chapel Hill.

Cells.

Murine bone marrow derived dendritic cells (BMDCs) were isolated from bone marrow and grown in vitro for maturation. Briefly cells were grown in GM-CSF and IL-4 for 10 days before maturing with 20 ng/ml TNF-α for 2 additional days.

Magnetic Bead Isolation of TCR Tg OTII T Cells.

Splenic T cells were isolated from OTII mice based on expression of CD4. Magnetic bead purifications were performed according to the protocol provided by Miltenyi Biotec (Auburn, Calif.). Briefly, splenocytes isolated from B6 or OTII mice were incubated with anti-mouse CD4 antibody conjugated with PE (BD PharMingen, San Diego, Calif.). Spleen cell samples were then incubated with anti-PE antibody coated magnetic beads (Miltenyi Biotec, Auburn, Calif.) and cells positively selected by passage through LS columns attached to magnetic separators. Flow through and eluent fractions were collected following Miltenyi protocol guidelines.

SYBR Green Real-Time PCR.

SYBR Green qPCR Rox mix (Abgene) was used for all quantitative PCR experiments. The following cycle conditions were used: Stage 1) 50°, for 2 minutes; Stage 2) 95°, for 15 minutes; Stage 3) 95° for 15 seconds, 56-57° for 15-30 seconds, 72° for 15-30 seconds, repeat 40×; Stage 4) dissociation curve. The relative level of expression for each primer target was calculated via (ΔΔCT)×1000. Target genes were calculated in reference to β-actin for each sample. The β-actin primers used were: (Forward) 5'-agggctatgctctccctcac-3' (SEQ ID NO:3) and (Reverse) 5'-ctctcagctgtggtggtgaa-3' (SEQ ID NO:4). The Sema6D primers used were: (Forward) 5'-cagaagcatgggagatggat-3' (SEQ ID NO:5) and (Reverse) 5'-gccacccatgtcgttttac-3' (SEQ ID NO:6).

Cloning and Production of Mouse Semaphorin 6D-Ig Fusion Protein (Sema6D-Ig).

Sema6D cDNA was obtained via reverse transcription reaction, according to manufacturer's instruction, utilizing Superscript III (Invitrogen) and an RNA sample isolated from the brain of C57BL/6J mice. Sema6D has multiple isoforms that differ slightly in the extracellular region between the Sema domain and the trans-membrane domain. Thus, to obtain a full length cDNA of Sema6D, the forward primer (5'-atggggttcettctgattggtt) (SEQ ID NO:7) and reverse primer (3'-ctagtacgtgtacttgttcagtggtctg) (SEQ ID NO:8) were designed utilizing current mRNA sequence for Sema6D contained within the GenBank database. PCR utilizing heat-stable DNA polymerase LATaq (TAKARA) followed by 0.8% agarose gel electrophoresis, produced a band of approximately 3 kb. The 3 kb DNA band was isolated and cloned into the pCR2.1 TOPO vector (Invitrogen). Multiple sequencing reactions (UNC-CH genomics core facility) verified that the cloned DNA sequence was identical to the full-length sequence of Sema6D isoform 6 (Sema6D-6).

Isolation of a cDNA fragment encoding the extracellular region of mouse Sema6D-6 (amino acids 1-652) was obtained via PCR amplification utilizing the full length Sema6D-6 cloned into the pCR2.1 TOPO vector. The forward primer (5'-gcggatatcgccacccatggggttccttctgattggttct) (SEQ ID NO:9) was designed to include a HindIII restriction endonuclease and the reverse primer (5'-gcgggatccagcggcaaacacg-caggtgatgagga) (SEQ ID NO:10) was designed with a BamHI restriction endonuclease site. The PCR product was gel purified and digested by HindIII and BamHI restriction endonucleases (New England Biolabs). The digested fragment containing most of the extracellular region of Sema6D (Sema6DEC) was subcloned into a modified pcDNA3.1 vector (Invitrogen) containing a human IgG1 fragment (Hinge-CH2-CH3). For transient expression, the sequenced SEMA6DEC-Ig plasmid was transfected into the COS-7 cell line (ATCC CRL-1651) via a standard calcium phosphate transfection protocol. Serum containing DMEM medium was substituted with a serum-free DMEM medium at 48 hour post transfection. The supernatant containing SEMA6DEC-Ig protein was harvested at 48-72 hours after transfection and purified by protein A affinity chromatography. Expression and secretion of SEMA6DEC-Ig was verified by immunoprecipitation followed by western blot analysis. Five milliliters of the supernatant were removed from Sema6DEC-Ig-transfected COS-7 cells cultured in serum-free DMEM 48 hours post transfection, and incubated with protein A/G agarose beads (Promega). Subsequent western blotting using anti-human IgG-HRP indicated a clear band of approximately 100 kDa and no other major bands that might represent either degradation products or contaminating proteins.

Generation of stable expression cells was performed via co-transfection of SEMA6DEC-Ig plasmid and a mouse dihydrofolate reductase (DHFR) encoding expression vector pSV2-dhfr (ATCC 37146) into DHFR-Chinese hamster ovary cells (CHO/DG44, Invitrogen) at a 20:1 ratio (weight: weight) through electroporation technique (300V, 960 uF, Bio-rad). Stable Sema6D-Ig expressing CHO cell clones were selected in Excell 302 serum free CHO medium (JRH Biosciences) supplemented with L-glutamine (Invitrogen) and 100 nM methotrexate (MTX, Sigma). Sema6D-Ig produced by the CHO cells was harvested from large-scale cultures via protein A affinity chromatography followed by gel filtration chromatography purification (Biosilect 400, Bio-rad).

Semi-Quantitative RT-PCR of Type III Semaphorin Transcripts.

Total RNA was isolated from DO11.10 T cells with or without activation, 3B11 cells at day 0, day 3, day 5 and day 7 of maturation, and brain cells using TRIzol Reagent (Invitrogen). One microgram of RNA of each sample was reverse transcribed using MMLV reverse transcriptase (Invitrogen). Semaphorin 3A, 3B, 3C, 3D and 3E transcripts were assessed using Taq polymerase (Invitrogen) and semi-quantitative PCR (22 cycles). Standardization of cDNA amounts was analyzed via PCR for 18S RNA. Sequences of the primers for the class III semaphorins are as follows: Semaphorin 3A, (forward) 5'-CGGGACTTCGCTATCTTCAG-3' (SEQ ID NO:11) and (reverse) 5'-AGCATGAGTGGCTTTTCCAG-3' (SEQ ID NO:12); Semaphorin 3B, (forward) 5'-GCTGTCT-TCTCCACCTCCAG-3' (SEQ ID NO:13) and (reverse) 5'-GGTTCCGACCAAACTGGATA-3 (SEQ ID NO:14)'; Semaphorin 3C, (forward) 5'-TCGGCAGTGTGTGTG-TATCA-3' (SEQ ID NO:15) and (reverse) 5'-CCTTCTGTG-GATGGGGTAGA-3' (SEQ ID NO:16); Semaphorin 3D, (forward) 5'-ATGGCTGATATCCGAGCAGT-3' (SEQ ID NO:17) and (reverse) 5'-TTCTCTTGAAGGTCGGTGCT-3' (SEQ ID NO:18); and Semaphorin 3E, (forward) 5'-GAGGC-CATGCTGTATGTGTG-3' (SEQ ID NO:19) and (reverse) 5'-CGTCATCGGGTAATCTTTGG-3' (SEQ ID NO:20).

Flow Cytometry.

Following splenic or BM isolation, cells were suspended in ammonium chloride-Tris buffer (ACT) for 3 minutes at 37° C. to remove RBC. ACT treatment was performed with carboxyfluorescein diacetate succinimidyl ester (CFDAse, Molecular Probes, Eugene, Oreg.) labeled cells. Following ACT treatment, cells were washed and resuspended in 5% BCS in BSS and stained with the appropriate antibodies as described. For all studies, non-specific staining was reduced by addition of FcR blocking antibody and unlabeled Rat/Hamster Ig. Incubation with biotinylated antibodies was followed by incubation with Streptavidin-PE, PerCP or APC (BD PharMingen, San Diego, Calif.). Primary antibody incubations were for a minimum of 30 minutes at 4° C. followed by washing in BCS/BSS. Secondary antibody incubations were for a maximum of 15 minutes at 4° C. followed by washing in BCS/BSS. Stained cells were either analyzed immediately or fixed with 1% formaldehyde in 1.25×PBS. Staining was quantified with a Becton Dickinson FACSCalibur. A minimum of 50,000 events was collected and fluorescence signals detected via four-decade logarithmic amplification except for FSC and SSC which were detected via a linear scale. Spectral overlap compensation was made with single-color stained samples for each detection channel. For each experiment, data were analyzed using FlowJo software (Treestar, Calif.).

In Vitro CD3/CD28 Stimulation.

For stimulation of T cells, 5 µg/ml of anti-mouse CD3 and anti-mouse CD28 were added in PBS to cell culture plates for overnight coating at 4° C. For a 6 well plate, 1 ml/well was used. Following the overnight incubation, the plates were washed 3× with PBS or complete medium (cRPMI: RPMI+ serum). Primary T cells isolated from spleens were incubated at $1 \times 10^6$ cells/ml in 2 mls per well of a 6 well coated plate.

Ovalbumin (OVA) (Whole Protein or Peptide) Loading of DCs.

BMDCs, cultured for up to 10 days in cRPMI supplemented with GMCSF and IL4, were resuspended at a concentration of $1 \times 10^6$ cells in 1 ml of cRPMI with 10 µg/mL whole OVA protein or peptide. The cells were incubated for 12 hrs at 37° C. with rotation. Following the incubation, the cells were washed 2× in cRPMI.

Adoptive Transfer.

Following isolation of splenocytes or BMDCs from mice, RBCs were lysed via incubation with ACT. The percentage of Tg OTII T cells within a population was determined by staining $2 \times 10^5$ cells with anti-Vα2 and anti-Vβ5 in 5% BCS in BSS at 4° C. and analyzed via a Becton Dickinson FACSCalibur cell sorter. For each primary transfer, $3 \times 10^6$ T cells and BMDCs were injected via tail vein into B6 recipient mice. Typically, three mice were used per experimental group.

CFSE Labeling of T Cells.

T cells labeled with carboxyfluorescein diacetate succinimidyl ester (CFDAse or CFSE; Molecular Probes, Eugene, Oreg.) were incubated at 37° C. for 10 minutes in serum free RPMI. The final concentration of CFSE used was 15 µM in RPMI with 10-20 million cells per ml. Following incubation with CFSE, the T cells were washed in cRPMI. Experimental conditions permitting, cells utilized for CFSE labeling were not treated with ASC red blood cell lysis buffer at the time of isolation.

Activation of T Cells by Co-Culture with Ag-Loaded BMDCs.

For in vitro activation, OTII TCR Tg (OVA-specific) T cells were incubated with immature BMDCs at a ratio of 1:1 in RPMI. OTII T cells were isolated from the spleens of Tg mice and purified by negative selection with T enrichment columns (R&D systems). Isolated T cells were labeled with CFSE or unlabeled prior to culture. BMDCs were either unloaded or loaded with OVA antigen (Ag) prior to culture. Approximately $0.5 \times 10^6$ T cells and BMDCs were cultured in 1 ml per well of a 24 well plate. At the culture initiation, IL4 & GM-CSF were added at a concentration of 5 ηg/mL.

Use of Anti-Sema6D Antibody or the Sema6D-Ig Fusion Protein to Block the Functional Activation of T Cells.

Antibodies for blocking interactions between the T cells and BMDCs, such as anti-Sema6D Ab, were used at a final concentration of 10 µg/ml. The Sema6D-Ig fusion protein was used at a final concentration of 5 µg/ml. One day following initiation, cell cultures were supplemented with 1 ml of cRPMI. The cultured cells were analyzed by flow cytometry for indications of T cell activation via proliferation and expression of activation markers as described herein.

Activated $CD4^+$ T Cells Express Semaphorin 6D In Vitro.

$CD4^+$ T cells were isolated from splenocytes by magnetic bead separation and activated in vitro by anti-CD3 and anti-CD28 stimulation. Splenic $CD4^+$ T cells were isolated by magnetic bead selection to a purity of greater than 90%. Purified T cells were cultured with plate bound anti-CD3 and -CD28 antibodies for stimulation. RNA was isolated from cultures at 12, 24 and 48 hr post initiation and analyzed by qPCR for Semaphorin 6D (Sema6D) expression. Following 12 hrs of stimulation, expression of Sema6D mRNA was increased as measured by qPCR, and this enhancement continued until at least 48 hrs post activation. Protein expression of Sema6D on activated $CD4^+$ T cells was also examined by flow cytometry. Following 96 hrs of anti-CD3 and anti-CD28 stimulation, enhanced expression of CD25 and CD44 was detected on $CD3^+CD4^+$ T cells, indicative of their activation. Concurrently, upregulation of Sema6D was observed on $CD3^+CD4^+$ T cells following 96 hrs of stimulation. Isotype-matched control Ig showed no such increase. Thus, activation of $CD4^+$ T cells via stimulation of CD3 and CD28 results in an upregulated expression of Sema6D at the cell surface. In contrast, measurements of Semaphorin 3A to 3F by the highly sensitive RT-PCR failed to detect any signals in resting or activated T cells. Semi-quantitative RT-PCR analysis revealed that OTII T cells did not express detectable levels of any type 3 semaphorins, including Sema 3A-E. Semaphorin 3 expression was detected in brain samples, used as positive controls.

DC Mediated Activation of Tg OTII T Cells Results in Sema6D Expression In Vivo.

Although expression of Sema6D in vitro via anti-CD3 and -CD28 stimulation was observed, it remained uncertain whether this result reflected the physiological reality of in vivo T cell activation. To examine the in vivo situation, the TCR transgenic (Tg) mouse line, OTII, whose $CD4^+$ T cells express a TCR specific for the OVA antigen, was used. OTII Tg T cells were isolated from splenocytes and adoptively transferred to recipient mice with either OVA-loaded DCs (immune) or un-loaded DCs (naïve). The recipient mouse splenocytes were harvested at days 2, 3 and 4 post adoptive transfer and the cells were analyzed by flow cytometry. The activation and expansion of the OTII T cells were visualized as an expansion of the population of T cells expressing the Tg TCR Vα2 and Vβ5 chains. Proliferation of the OTII T cells was observed in vivo by day 2 and peaked at day 4, representing an approximately 5-fold expansion in immune vs. naïve mice. Concurrently, on day 4, the expression of CD25 was upregulated on OTII T cells from immune mice vs. naïve mice. This was accompanied by an upregulation of Sema6D on activated OTII T cells in vivo vs. naïve mice. Thus, in a physiologically relevant system of in vivo antigen presenting cell mediated T stimulation, enhanced expression of Sema6D on activated $CD4^+$ T cells was observed, confirming the induction of Sema6D during T cell activation.

Blocking Sema6D Antibody Inhibits DC Mediated OTII T Cell Proliferation and Activation.

To examine the functional consequence of Sema6D expression on T cells, an in vitro DC-mediated T cell activation assay was used. Tg OTII T cells were cultured with OVA loaded BMDCs (OVA-BMDC) or unloaded BMDCs (BMDC). Following isolation but prior to co-culture, the OTII T cells were labeled with CFSE to enable monitoring of activation-induced proliferation. At days 2, 6 and 7 post culture initiation, cultured cells were collected and analyzed by flow cytometry. Activation is associated with proliferation, which results in a serial dilution of CFSE staining intensity with each cell division. Thus a pattern of serially diluted CFSE staining is indicative of T cell activation. OTII T cells cultured control exhibited little change, while OTII T cells incubated with OVA-BMDC cells displayed activation-induced proliferation as measured by a dilution of CFSE intensity. Initially, a small amount of proliferation was observed on day 2 post-culture of V$\beta$5$^+$ (OTII) T cells with OVA-BMDC but not control BMDC (0.94% V$\beta$5$^+$CFSE$^{low}$ vs. 0.064%). By day 7 of co-culture, the OTII T cells incubated with OVA-BMDC proliferated greatly compared with those cultured with control BMDC, representing a greater than 11 fold induction. The proliferating cells observed on day 7 were TCR$^+$CD4$^+$CD8$^-$ T cells, indicative of the OTII Tg T cell phenotype.

Significantly, when OTII T cells were cultured with OVA-BMDC in the presence of an antibody to block Sema6D (Sema6D Ab), the proliferation of the T cells was abrogated. While proliferation on day 6 and 7 was markedly reduced, the initial level of proliferation observed on day 2 was comparable to cultures with a control antibody (Ctrl Ab). Thus, while early survival may be unaffected, optimal proliferation and homeostasis of the V$\beta$5$^+$ OTII T cells were inhibited by Sema6D blockade at both days 6 and 7.

The expression of Sema6D on in vitro activated OTII T cells was also examined and expression on both unactivated and activated T cells by day 7 was observed. BMDCs that were loaded (OVA-BMDC) or unloaded (BMDC) with whole OVA protein were cultured with purified OTII T cells in vitro. Prior to culture initiation, OTII T cells were labeled with CFSE. Antigen positive cultures were also treated with either a Sema6D blocking antibody or a control antibody. As expected, addition of blocking antibody significantly inhibited the detection of Sema6D expression compared with control antibody or unactivated cultures.

Finally, the ability of blocking Sema6D Ab to inhibit the appearance of an activated T cell phenotype was examined. Expression levels of CD25, CD62L, CD69, CD154 and CD44 were analyzed. For all the phenotypic markers analyzed, blocking Sema6D antibody inhibited the accumulation or appearance of activated OTII Tg T cells while isotype-control antibody did not. The low number of cells displaying an activated phenotype in the Sema6D Ab treated group may reflect an initial activation and proliferation that occurs in the presence of Sema6D Ab. Moreover, there does not appear to be reduced viability of CFSE$^{bright}$ T cells lacking activation makers, suggesting that Sema6D Ab affects only stimulated T cells. These data indicate that Sema6D regulates DC mediated T cell proliferation, activation and survival.

Sema6D-Ig Inhibits BMDC Mediated T Cell Activation.

To further characterize the function of Sema6D, a hybrid of a cDNA fragment encoding the extracellular region of mouse Sema6D-6 (amino acids 1-652) and a human IgG1 fragment (hinge-CH2-CH3) was produced, resulting in a Sema6D-Ig fusion protein. This fusion protein was used along with the anti-Sema6D antibody in an experimental procedure as described herein. BMDCs that were loaded (OVA-BMDC) or unloaded (BMDC) with whole OVA protein were cultured with purified OTII T cells in vitro. Prior to culture initiation, OTII T cells were labeled with CFSE. Antigen positive cultures were also treated with a control antibody, a MHC class II blocking antibody, a Sema6D blocking antibody or the Sema6D-Ig fusion protein. At day 5 post culture initiation, the proliferation of CD4$^+$ T cells was analyzed. Utilizing Sema6D-Ig as a blocking reagent administered to in vitro cultures, inhibition of BMDC mediated T cell proliferation was observed, as compared to a control antibody treated group (5.15% CFSE$^{low}$CD4$^+$ vs. 29%). The level of inhibition with the Sema6D-Ig fusion protein was comparable to inhibition via the anti-Sema6D Ab. As a control, treatment with a blocking antibody for MHC II resulted in complete inhibition of T cell activation.

These studies demonstrate that activated T cells express high levels of Semaphorin 6D both in vitro and in vivo and that inhibition of Sema6D, via treatment with a blocking Ab or Sema6D-Ig, significantly inhibits dendritic cell mediated T cell activation. These data demonstrate that Sema6D represents an important novel receptor for the regulation of T cell immunity.

These studies further indicate that Sema6D inhibitors may reduce the survival of activated T cells only and do not appear to function as general inhibitors of T cell survival. In Sema6D Ab treated cultures (OVA-BMDC+Sema6D), the viability of non-dividing CFSE$^{bright}$ and TCR$^+$ or CD4$^+$ cells did not appear to be affected when compared with T cells from naïve (BMDC) cultures (72.5 vs. 72.4%; and 66.1 vs. 67.2% respectively). Thus, in the case of autoimmunity, blocking Sema6D would allow for the specific targeting of activated autoimmune T cells while allowing unactivated, non-auotimmune T cells to persist. A similar method could be applied to transplant patients to induce a tolerizing effect on rejecting T cells. Alternatively, stimulating activated T cells via agonist ligand binding of Sema6D, could lead to enhanced vaccine efficacy or even enhanced tumor rejection via stimulation of anti-tumor T cells.

II. Blocking Sema6D with the Sema6D Ig Fusion Protein Caused a Delayed Inhibition of T Cell Activation This was tested by assaying the phosphorylation of three T cell activating molecules, CrkL, LAT and CD3$\zeta$. CD3$\zeta$ phosphorylation is an early event in T cell activation that occurs proximal to the T cell receptor. Its activation as indicated by phosphorylation is not altered by Sema6D-Ig inhibition. In the studies conducted, Sema6D was shown to regulate endogenous T cell signaling during late-stage activation. OTII T cells were co-cultured with DCs loaded with OVA antigen (OVA-DC) or unloaded DCs (DC). Antigen positive cultures were treated with Sema6D-Ig (S6D-Ig) or human IgG1 (hIgG1). OTII T cells co-cultured with DCs were analyzed by phosphor-specific flow cytometry for endogenous signaling pathways. FACS analysis of phosphorylated CrkL in TCR$^+$ OTII T cells was carried out at days 3 and 6 of co-culture with DCs. FACS analysis of phosphorylated LAT in TCR$^+$ OTII T cells was also carried out at days 3 and 6. FACS analysis of phosphorylated CD3$\zeta$ in TCR$^+$ OTII T cells was also carried out at days 3 and 6 of co-culture.

Phosphorylation of CrkL is an indication of c-Abl activation, and it was inhibited by Sema6D-Ig inhibition but only at a late time point (day 6 but not day 3). LAT phosphorylation which lies downstream of c-Abl phosphorylation was inhibited by Sema6D-Ig at a late time point (day 6 but not day 3).

These results indicate that Sema6D signaling is most relevant late during T cell activation. Further it lies upstream of c-Abl, CrkL and LAT phosphorylation but does not affect CD3ζ phosphorylation. Thus blocking Sema6D-Ig is a mechanism to block late T cell activation, which provides a different intervening point from most immune clinical biologics used in the market.

III. Expression of Sema6D on B Cells

This is of particular interest as recently anti-B cell antibodies have been effective in both reducing autoimmunity in people, and reducing B lymphoma growth. Sema6D was found to be expressed by B cells to a similar extent as T cells, in both mouse and human (FIGS. 1a,b). Furthermore, expression was shown in four different types of leukemia (FIG. 1c). Blocking Sema6D was shown to reduce T cell proliferation and B cell proliferation. This indicates that blocking Sema6D can reduce lymphocyte survival, which is important in the control of autoimmunity, but also in the control of transformed B and T lymphomas/leukemia.

Expression of Sema6D Protein in B Cells is Enhanced During an Immune Response.

To explore if the expression of Sema6D is enhanced during B cell activation (a state similar to auto-activated B cells implicated in autoimmune diseases such as systemic lupus and arthritis, and transformed B cells found in leukemia and lymphomas), B cells activated in vivo were tested with antigens and antigen presenting cells. DCs matured for 8 days in vitro were loaded with whole OVA protein and then transferred by i.v. injection with OTII TCR transgenic (OVA specific) T cells to recipient B6 mice. At day 4 post-transfer, recipient mouse splenocytes were isolated and analyzed by flow cytometry for the expression of Sema6D. Splenocytes were incubated with anti-CD45, -B220 and -Sema6D antibodies. B220$^+$ CD45$^+$ splenocytes were gated and analyzed for expression of Sema6D. The percentage of B220$^+$ Sema6D$^+$ cells was displayed for splenocytes from naïve and immune animals. These studies showed that in vivo activated B cells expressed significantly higher levels of Sema6D. In these experiments, B cells were marked with B220, and they showed elevated Sema6D after antigen stimulation. This suggests that Sema6D-Ig molecules might selectively target activated B cells and transformed B cells, but not naïve resting B cells.

Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents and publications in their entireties are hereby incorporated by reference into this application in order to more fully describe the state of the art to which this invention pertains.

The foregoing is illustrative of the present invention, and is not to be construed as limiting thereof. The invention is defined by the following claims, with equivalents of the claims to be included therein.

REFERENCES

1. Keir, M. E., and A. H. Sharpe. 2005. The B7/CD28 costimulatory family in autoimmunity. *Immunol Rev* 204: 128.
2. Greenwald, R. J., G. J. Freeman, and A. H. Sharpe. 2005. The B7 family revisited. *Annu Rev Immunol* 23:515.
3. Girvin, A. M., M. C. Dal Canto, L. Rhee, B. Salomon, A. Sharpe, J. A. Bluestone, and S. D. Miller. 2000. A critical role for B7/CD28 costimulation in experimental autoimmune encephalomyelitis: a comparative study using costimulatory molecule-deficient mice and monoclonal antibody blockade. *J Immunol* 164:136.
4. Salomon, B., and J. A. Bluestone. 2001. Complexities of CD28/B7: CTLA-4 costimulatory pathways in autoimmunity and transplantation. *Annu Rev Immunol* 19:225.
5. Feldmann, M., and L. Steinman. 2005. Design of effective immunotherapy for human autoimmunity. *Nature* 435:612,
6. Quezada, S. A., L. Z. Jarvinen, E. F. Lind, and R. J. Noelle. 2004. CD40/CD154 interactions at the interface of tolerance and immunity. *Annu Rev Immunol* 22:307.
7. Watts, T. H. 2005. TNF/TNFR family members in costimulation of T cell responses. *Annu Rev Immunol* 23:23.
8. Wong, A. W., W. J. Brickey, D. J. Taxman, H. W. van Deventer, W. Reed, J. X. Gao, P. Zheng, Y. Liu, P. Li, J. S. Blum, K. P. McKinnon, and J. P. Ting. 2003. CIITA-regulated plexin-A1 affects T-cell-dendritic cell interactions. *Nat Immunol* 4:891.
9. Tamagnone, L., S. Artigiani, H. Chen, Z. He, G. I. Ming, H. Song, A. Chedotal, M. L. Winberg, C. S. Goodman, M. Poo, M. Tessier-Lavigne, and P. M. Comoglio. 1999. Plexins are a large family of receptors for transmembrane, secreted, and GPI-anchored semaphorins in vertebrates. *Cell* 99:71.
10. Castellani, V., and G. Rougon. 2002. Control of semaphorin signaling. *Curr Opin Neurobiol* 12:532.
11. Kikutani, H., and A. Kumanogoh, 2003. Semaphorins in interactions between T cells and antigen-presenting cells. *Nat Rev Immunol* 3:159.
12. Kumanogoh, A., and H. Kikutani. 2003. Immune semaphorins: a new area of semaphorin research. *J Cell Sci* 116:3463.
13. Liu, B. P., and S. M. Strittmatter. 2001. Semaphorin-mediated axonal guidance via Rho-related G proteins. *Curr Opin Cell Biol* 13:619.
14. Tamagnone, L., and P. M. Comoglio. 2004. To move or not to move? Semaphorin signalling in cell migration. *EMBO Rep* 5:356.
15. Toyofuku, T., H. Zhang, A. Kumanogoh, N. Takegahara, M. Yabuki, K. Harada, M. Hori, and H. Kikutani. 2004. Guidance of myocardial patterning in cardiac development by Sema6D reverse signalling. *Nat Cell Biol* 6:1204.
16. Toyofuku, T., H. Zhang, A. Kumanogoh, N. Takegahara, F. Suto, J. Kamei, K. Aoki, M. Yabuki, M. Hori, H. Fujisawa, and H. Kikutani. 2004. Dual roles of Sema6D in cardiac morphogenesis through region-specific association of its receptor, Plexin-A1, with off-track and vascular endothelial growth factor receptor type 2. *Genes Dev* 18:435.
17. Turner, L. J., S. Nicholls, and A. Hall. 2004. The activity of the plexin-A1 receptor is regulated by Rac. *J Biol Chem* 279:33199.
18. Zanata, S. M., I. Hovatta, B. Rohm, and A. W. Puschel. 2002. Antagonistic effects of Rnd1 and RhoD GTPases regulate receptor activity in Semaphorin 3A-induced cytoskeletal collapse. *J Neurosci* 22:471.
19. Zipfel, P. A., W. Zhang, M. Quiroz, and A. M. Pendergast. 2004. Requirement for Abl kinases in T cell receptor signaling. *Curr Biol* 14:1222.

TABLE 1

Nucleotide and amino acid sequences of the Sema6D protein of the invention and a fusion protein of the invention.

| Accession No. | Organism | Definition | SEQ ID NO: |
|---|---|---|---|
| NM_020858 | Homo sapiens | Homo sapiens sema domain, transmembrane domain (TM), and cytoplasmic domain, (semaphorin) 6D (SEMA6D), transcript variant 1, mRNA. | 21 |
| NP_065909 | Homo sapiens | semaphorin 6D isoform 1 precursor | 22 |
| NM_153616 | Homo sapiens | Homo sapiens sema domain, transmembrane domain (TM), and cytoplasmic domain, (semaphorin) 6D (SEMA6D), transcript variant 2, mRNA | 23 |
| NP_705869 | Homo sapiens | semaphorin 6D isoform 2 precursor | 24 |
| NM_153617 | Homo sapiens | Homo sapiens sema domain, transmembrane domain (TM), and cytoplasmic domain, (semaphorin) 6D (SEMA6D), transcript variant 3, mRNA | 25 |
| NP_705870 | Homo sapiens | semaphorin 6D isoform 3 precursor | 26 |
| NM_153618 | Homo sapiens | Homo sapiens sema domain, transmembrane domain (TM), and cytoplasmic domain, (semaphorin) 6D (SEMA6D), transcript variant 4, mRNA | 27 |
| NP_705871 | Homo sapiens | semaphorin 6D isoform 4 precursor | 28 |
| NM_153619 | Homo sapiens | Homo sapiens sema domain, transmembrane domain (TM), and cytoplasmic domain, (semaphorin) 6D (SEMA6D), transcript variant 5, mRNA | 29 |
| NP_705872 | Homo sapiens | semaphorin 6D isoform 5 precursor | 30 |
| NM_024966 | Homo sapiens | Homo sapiens sema domain, transmembrane domain (TM), and cytoplasmic domain, (semaphorin) 6D (SEMA6D), transcript variant 6, mRNA | 31 |
| NP_079242 | Homo sapiens | semaphorin 6D isoform 6 precursor | 32 |
| NM_172537 | Mus musculus | Mus musculus sema domain, transmembrane domain (TM), and cytoplasmic domain, (semaphorin) 6D (Sema6d), transcript variant 1, mRNA | 33 |
| n/a | Mus musculus | CDS of NM_172537 | 34 |
| NP_766125 | Mus musculus | sema domain, transmembrane domain (TM), and cytoplasmic domain, (semaphorin) 6D isoform 1 | 35 |
| n/a | Mus musculus | CDS of NM_199238 | 36 |
| NP_954708 | Mus musculus | sema domain, transmembrane domain (TM), and cytoplasmic domain, (semaphorin) 6D isoform 2 | 37 |
| n/a | Mus musculus | CDS of NM_199241 | 38 |
| NP_954711 | Mus musculus | sema domain, transmembrane domain (TM), and cytoplasmic domain, (semaphorin) 6D isoform 4 | 39 |
| n/a | Mus musculus | CDS of NM_199239 | 47 |
| NP_954709 | Mus musculus | sema domain, transmembrane domain (TM), and cytoplasmic domain, (semaphorin) 6D isoform 5 | 48 |
| n/a | Mus musculus | CDS of NM_199240 | 49 |
| NP_954710 | Mus musculus | sema domain, transmembrane domain (TM), and cytoplasmic domain, (semaphorin) 6D isoform 6 | 50 |
| n/a | Mus musculus | CDS of Sema6D-6 | 51 |
| BC098887 | Danio rerio | Danio rerio sema domain, transmembrane domain (TM), and cytoplasmic domain, (semaphorin) 6D, mRNA | 52 |
| AAH98887 | Danio rerio | Sema domain, transmembrane domain (TM), and cytoplasmic domain, (semaphorin) 6D | 53 |
| XM_230583 | Rattus norvegius | PREDICTED: Rattus norvegicus sema domain, transmembrane domain (TM), and cytoplasmic domain, (semaphorin) 6D (predicted) (Sema6d_predicted), mRNA | 54 |
| XP_230583 | Rattus norvegius | PREDICTED: similar to sema domain, transmembrane domain (TM), and cytoplasmic domain, (semaphorin) 6D isoform 4 | 55 |
| XM_596649 | Bos taurus | PREDICTED: Bos taurus similar to semaphorin 6D, transcript variant 5 (LOC518458), mRNA | 56 |

TABLE 1-continued

Nucleotide and amino acid sequences of the Sema6D protein of the invention and a fusion protein of the invention.

| Accession No. | Organism | Definition | SEQ ID NO: |
|---|---|---|---|
| XP_596649 | Bos taurus | PREDICTED: similar to semaphorin 6D isoform 5 | 57 |
| n/a | Artificial | CDS of Murine sema6D-Ig fusion protein | 58 |

TABLE 2

| PCR and Sequencing primers | |
|---|---|
| Primer sequence | SEQ ID NO: |
| ATGGGGTTCCTTCTGCTTTGGTT (offset: 1; 23 nt) | 7 |
| CTAGTACGTGTACTTGTTCAGTGGTCTG (offset: 2997; 28 nt) | 8 |
| AAAGCAGAAGGAACCCCATGGTT (Rev. -838) | 40 |
| ACCAGGTAGCTAAGTGGGACTTCTG (For. 761-) | 41 |
| TGACACCCTGGCTTTCATCAAGT (For. 1161-) | 42 |
| AAAGTCTTGCATTGCATCACGTGAC (For. 1566-) | 43 |
| CCAATCAGATGGTCCACATGAA (For. 1964-) | 44 |
| ATGAAGAGCCACTCTGAGAAGGC (For. 2362-) | 45 |
| TAACCGGGAGGCATCTCTATAC (For. 2769-) | 46 |

What is claimed is:

1. A fusion protein comprising the amino acid sequence of SEQ ID NO:2.

2. A nucleic acid molecule comprising a nucleotide sequence encoding the fusion protein of claim 1.

3. A nucleic acid molecule comprising the nucleotide sequence of SEQ ID NO:1.

4. A composition comprising the fusion protein of claim 1 in a pharmaceutically acceptable carrier.

5. A composition comprising the nucleic acid molecule of claim 2 in a pharmaceutically acceptable carrier.

6. A composition comprising the nucleic acid molecule of claim 3 in a pharmaceutically acceptable carrier.

* * * * *